US009145392B2

(12) United States Patent
Lan et al.

(10) Patent No.: US 9,145,392 B2
(45) Date of Patent: Sep. 29, 2015

(54) IMIDAZOLE AMINES AS MODULATORS OF KINASE ACTIVITY

(75) Inventors: Ruoxi Lan, Waltham, MA (US); Bayard R. Huck, Sudbury, MA (US); Yufang Xiao, Lexington, MA (US); Xiaoling Chen, Chestnut Hill, MA (US); Lizbeth Celeste Deselm, Melrose, MA (US); Hui Qiu, Acton, MA (US); Constantin Neagu, Belmont, MA (US); Donald Bankston, Dracut, MA (US); Christopher Charles Victor Jones, Arlington, MA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/237,075

(22) PCT Filed: Sep. 12, 2012

(86) PCT No.: PCT/US2012/054900
§ 371 (c)(1),
(2), (4) Date: Apr. 14, 2014

(87) PCT Pub. No.: WO2013/040059
PCT Pub. Date: Mar. 21, 2013

(65) Prior Publication Data
US 2014/0343029 A1 Nov. 20, 2014

Related U.S. Application Data

(60) Provisional application No. 61/533,601, filed on Sep. 12, 2011.

(51) Int. Cl.
*C07D 401/14* (2006.01)
*A61K 31/4545* (2006.01)
*A61K 31/506* (2006.01)
*A61K 31/5377* (2006.01)
*C07D 409/14* (2006.01)
*C07D 413/14* (2006.01)
*C07D 417/14* (2006.01)
*C07D 491/107* (2006.01)

(52) U.S. Cl.
CPC .......... *C07D 401/14* (2013.01); *A61K 31/4545* (2013.01); *A61K 31/506* (2013.01); *A61K 31/5377* (2013.01); *C07D 409/14* (2013.01); *C07D 413/14* (2013.01); *C07D 417/14* (2013.01); *C07D 491/107* (2013.01)

(58) Field of Classification Search
CPC .......................... C07D 401/14; A61K 31/4545
See application file for complete search history.

(56) References Cited

FOREIGN PATENT DOCUMENTS

| WO | 03064397 A1 | 8/2003 |
|---|---|---|
| WO | 2004/092154 A1 | 10/2004 |
| WO | 2005/033086 A1 | 4/2005 |
| WO | 2005/039506 A2 | 5/2005 |
| WO | 2005/054237 A1 | 6/2005 |
| WO | 2005/056014 A1 | 6/2005 |
| WO | 2005/117909 A2 | 12/2005 |
| WO | 2006/071819 A1 | 7/2006 |
| WO | 2006/078992 A2 | 7/2006 |
| WO | 2006/120573 A2 | 11/2006 |
| WO | 2006/131835 A2 | 12/2006 |
| WO | 2006/136821 A1 | 12/2006 |
| WO | 2008/140947 A1 | 11/2008 |
| WO | 2010/056563 A1 | 5/2010 |
| WO | 2010/093419 A1 | 8/2010 |
| WO | 2012/013282 A1 | 2/2012 |
| WO | 2012/016001 A1 | 2/2012 |
| WO | 2012/069146 A1 | 5/2012 |

OTHER PUBLICATIONS

Banker, G.S. et al, "Modern Pharmaceutics, 3ed.", Marcel Dekker, New York, 1996, pp. 451 and 596.*
Wolff, Manfred E. "Burger's Medicinal Chemistry, 5ed, Part I", John Wiley & Sons, 1995, pp. 975-977.*
Barlund et al., Multiple Genes at 17q23 Undergo Amplification and Overexpression in Breast Cancer, Cancer Res., 2000, 60:5340-5346.
Couch et al., Localization of PS6K to Chromosomal Region 17q23 and Determination of Its Amplification in Breast Cancer, Cancer Res., 1999, 59:1408-11.
Garcia-Bustos J. et al., PIK1, an essential phosphatidylinositol 4-kinase associated with the yeast nucleus, EMBO J., 1994, 13(10):2352-2361.
Hanks, S.K. and Hunter T., the eukaryotic protein kinase superfamily: Kinase (catalytic) domain structure and classification, FASEB J., 1995, 9:576-596.
Hardie and Hanks, The Protein Kinase Facts Book. I and II, 1995, Academic Press, San Diego, CA.
Hiles I. et al., Phosphatidylinositol 3-Kinase: Structure and Expression of the 110 kd Catalytic Subunit, Cell, 1992, 70:419-429.
Knighton D. et al., Crystal Structure of the Catalytic Subunit of Cyclic Adenosine Monophosphate-Dependent Protein Kinase, Science, 1991, 253:407-414.

(Continued)

*Primary Examiner* — David K O Dell

(74) *Attorney, Agent, or Firm* — Dwight D. Kim; EMD Serono Research and Development Institute

(57) ABSTRACT

The invention provides novel imidazole amine compounds according to Formula (I) and Formula (II) their manufacture and use for the treatment of hyperproliferative diseases, such as cancer.

26 Claims, No Drawings

(56) References Cited

OTHER PUBLICATIONS

Kunz J. et al., Target of Rapamycin in Yeast, TOR2, Is an Essential Phosphatidylinositol Kinase Homolog Required for G1 Progression, Cell, 1993, 73:585-596.

Wu et al., 17q23 Amplifications in Breast Cancer Involve the PAT1, RAD51C, PS6K, and SIGMA1B Genes, Cancer Res. (2000): 60:5371-5375.

Preliminary Report on Patentability, dated Mar. 12, 2014, pp. 1-5.

* cited by examiner

IMIDAZOLE AMINES AS MODULATORS OF KINASE ACTIVITY

RELATED APPLICATIONS

This application is a U.S. national stage application of PCT international application PCT/US2012/054900, filed on Sep. 12, 2012, which claims the benefit of U.S. provisional application USSN 61/533,601, filed on Sep. 12, 2011. The entire contents of the aforementioned applications are hereby incorporated by reference.

FIELD OF THE INVENTION

The invention relates to a series of imidazole amine compounds that are useful in the treatment of hyperproliferative diseases, such as cancer, in mammals. Also encompassed by the present invention is the use of such compounds in the treatment of hyperproliferative diseases in mammals, especially humans, and pharmaceutical compositions containing such compounds.

SUMMARY OF THE RELATED ART

Protein kinases constitute a large family of structurally related enzymes that are responsible for the control of a wide variety of signal transduction processes within the cell (Hardie, G. and Hanks, S. (1995) The Protein Kinase Facts Book. I and II, Academic Press, San Diego, Calif.). The kinases may be categorized into families by the substrates they phosphorylate (e.g., protein-tyrosine, protein-serine/threonine, lipids, etc.). Sequence motifs have been identified that generally correspond to each of these kinase families (e.g., Hanks, S. K., Hunter, T., FASEB J., 9:576-596 (1995); Knighton, et al., Science, 253:407-414 (1991); Hiles, et al., Cell, 70:419-429 (1992); Kunz, et al., Cell, 73:585-596 (1993); Garcia-Bustos, et al., EMBO J., 13:2352-2361 (1994)). Protein kinases may be characterized by their regulation mechanisms. These mechanisms include, for example, autophosphorylation, transphosphorylation by other kinases, protein-protein interactions, protein-lipid interactions, and protein-polynucleotide interactions. An individual protein kinase may be regulated by more than one mechanism.

Kinases regulate many different cell processes including, but not limited to, proliferation, differentiation, apoptosis, motility, transcription, translation and other signalling processes, by adding phosphate groups to target proteins. These phosphorylation events act as molecular on/off switches that can modulate or regulate the target protein biological function. Phosphorylation of target proteins occurs in response to a variety of extracellular signals (hormones, neurotransmitters, growth and differentiation factors, etc.), cell cycle events, environmental or nutritional stresses, etc. The appropriate protein kinase functions in signalling pathways to activate or inactivate (either directly or indirectly), for example, a metabolic enzyme, regulatory protein, receptor, cytoskeletal protein, ion channel or pump, or transcription factor. Uncontrolled signalling due to defective control of protein phosphorylation has been implicated in a number of diseases, including, for example, inflammation, cancer, allergy/asthma, diseases and conditions of the immune system, diseases and conditions of the central nervous system, and angiogenesis.

Protein kinase 70S6K, the 70 kDa ribosomal protein kinase p70S6K (also known as SK6, p70/p85 S6 kinase, p70/p85 ribosomal S6 kinase and p70S6K), is a member of the AGC subfamily of protein kinases. p70S6K is a serine-threonine kinase that is a component of the phosphatidylinositol 3 kinase (PI3K)/AKT pathway. p70S6K is downstream of PI3K, and activation occurs through phosphorylation at a number of sites in response to numerous mitogens, hormones and growth factors. p70S6K activity is also under the control of a mTOR-containing complex (TORC1) since rapamycin acts to inhibit p70S6K activity. p70S6K is regulated by PI3K downstream targets AKT and PKCξ. Akt directly phosphorylates and inactivates TSC2, thereby activating mTOR. In addition, studies with mutant alleles of p70S6K that inhibited by Wortmannin but not by rapamycin suggest that the PI3K pathway can exhibit effects on p70S6K independent of the regulation of mTOR activity.

The enzyme p70S6K modulates protein synthesis by phosphorylation of the S6 ribosomal protein. S6 phosphorylation correlates with increased translation of mRNAs encoding components of the translational apparatus, including ribosomal proteins and translational elongation factors whose increased expression is essential for cell growth and proliferation. These mRNAs contain an oligopyrimidine tract at their 5' transcriptional start (termed 5'TOP), which has been shown to be essential for their regulation at the translational level.

In addition to its involvement in translation, p70S6K activation has also been implicated in cell cycle control, neuronal cell differentiation, regulation of cell motility and a cellular response that is important in tumor metastases, the immune response and tissue repair. Antibodies to p70S6K abolish the mitogenic response driven entry of rat fibroblasts into S phase, indication that p70S6K function is essential for the progression from G1 to S phase in the cell cycle. Furthermore, inhibition of cell cycle proliferation at the G1 to S phase of the cell cycle by rapamycin has been identified as a consequence of inhibition of the production of the hyperphosphorylated, activated form of p70S6K.

A role for p70S6K in tumor cell proliferation and protection of cells from apoptosis is supported based on it participation in growth factor receptor signal transduction, overexpression and activation in tumor tissues. For example, Northern and Western analyses revealed that amplification of the PS6K gene was accompanied by corresponding increases in mRNA and protein expression, respectively (Cancer Res. (1999) 59: 1408-11-Localization of PS6K to Chromosomal Region 17q23 and Determination of Its Amplification in Breast Cancer).

Chromosome 17q23 is amplified in up to 20% of primary breast tumors, in 87% of breast tumors containing BRCA2 mutations and in 50% of tumors containing BRCA1 mutations, as well as other cancer types such as pancreatic, bladder and neuroblastoma (see M. Barlund, O. Monni, J. Kononen, R. Cornelison, J. Torhorst, G. Sauter, O.-P. Kallioniemi and Kallioniemi A., Cancer Res., 2000, 60:5340-5346). It has been shown that 17q23 amplifications in breast cancer involve the PAT1, RAD51C, PS6K, and SIGMA1B genes (Cancer Res. (2000): 60, pp. 5371-5375).

The p70S6K gene has been identified as a target of amplification and overexpression in this region, and statistically significant association between amplification and poor prognosis has been observed. Clinical inhibition of p70S6K activation was observed in renal carcinoma patients treated with CCI-779 (rapamycin ester), an inhibitor of the upstream kinase mTOR. A significant linear association between disease progression and inhibition of p70S6K activity was reported. In response to energy stress, the tumor suppressor LKB1 activates AMPK which phosphorylates the TSC1/2 complex and enables it to inactivate the mTOR/p70S6K pathway. Mutations in LKB1 cause Peutz-Jeghers syndrome (PJS), where patients with PJS are 15 times more likely to develop cancer than the general population. In addition, ⅓ of lung adenocarcinomas harbor inactivating LKB1 mutations. P70S6K has been implicated in metabolic diseases and disorders. It was reported that the absence of p70S6K protects against age- and diet-induced obesity while enhancing insulin sensitivity. A role for p70S6K in metabolic diseases and disorders such as obesity, diabetes, metabolic syndrome, insulin resistance, hyperglycemia, hyperaminoacidemia, and hyperlipidmia is supported based upon the findings.

Compounds described as suitable for p70S6K inhibition are disclosed in WO 03/064397, WO 04/092154, WO 05/054237, WO 05/056014, WO 05/033086, WO 05/117909, WO 05/039506, WO 06/120573, WO 06/136821, WO 06/071819, WO 06/131835, WO 08/140,947, WO 10/056, 563, WO 10/093,419, WO 12/013,282, WO 12/016,001 and WO 12/069,146.

DESCRIPTION OF THE INVENTION

It is the object of the present invention to provide novel compounds that modulate kinase activity. This protein kinase modulation includes, but is not limited to, p70S6K inhibition and Akt inhibition useful in the treatment of hyperproliferative diseases, especially those related to the hyperactivity of the above mentioned protein kinases, such as cancer in mammals, with superior pharmacological properties both with respect to their activities as well as their solubility, metabolic clearance and bioavailability characteristics.

As a result, this invention provides novel, heterocyclic pyrimidinyl and pyridinyl amine compounds and pharmaceutically acceptable salts, solvates or prodrugs thereof, that are kinase inhibitors and useful in the treatment of the above mentioned diseases.

The compounds are defined by Formula (I):

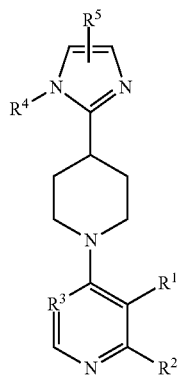

(I)

and pharmaceutically acceptable salts, solvates, solvates of salts, or prodrugs thereof, wherein:

$R^1$ is Hal, LA, OH, O(LA), $NH_2$ and/or NH(LA), $N(LA)_2$, $NO_2$, CN, OCN, SCN, COOH, COO(LA), $CONH_2$, CONH(LA), $CON(LA)_2$, NHCO(LA), NHCONH(LA), $NHCONH_2$, $NHSO_2$(LA), CHO, CO(LA), $SO_2NH_2$, $SO_2$(LA), or a mono- or bicyclic, aliphatic or aromatic homo- or heterocycle having 0, 1, 2, 3 or 4 N, S and/or O atoms and 4, 5 or 6, 7, 8, 9, or 10 skeleton atoms which may be unsubstituted or, independently of one another, mono-, di- or trisubstituted by Hal, LA, OH, O(LA), $NH_2$ and/or NH(LA), $N(LA)_2$, $NO_2$, CN, OCN, SCN, COOH, COO(LA), $CONH_2$, CONH(LA), $CON(LA)_2$, NHCO(LA), NHCONH(LA), $NHCONH_2$, $NHSO_2$(LA), CHO, CO(LA), $SO_2NH_2$, $SO_2$(LA) and/or $SO_2$Hal or an unbranched or branched linear or cyclic alkyl having 1, 2, 3, 4, 5, 6, 7 or 8 C atoms, in which one or two $CH_2$ groups may be replaced by an O atom and/or by an —NH—, NH(LA), —CO—, —NHCO— or —CH═CH— group, and/or in which a CH group may be replaced by —N—;

$R^2$ is H, $NH_2$, NH(LA), $N(LA)_2$ or NHCO(LA);

$R^3$ is N or CH;

$R^4$ is H, an unbranched or branched linear or mono- or bicyclic alkyl group having 1, 2, 3, 4, 5, 6, 7, 8 or 9 C atoms, in which one or two $CH_2$ groups may be replaced by an —O—, —NH—, group, and/or in which one or two CH groups may be replaced by —N—, and/or in which 1, 2 or 3 H atoms may be replaced by Hal or OH, $R^5$ is a monocyclic aromatic or aliphatic homo- or heterocycle having 0, 1 or 2 N, S and/or O atoms and 5 or 6 skeleton atoms which may be unsubstituted or, independently of one another, mono-, di- or trisubstituted by Hal, LA, OH, O(LA), $NH_2$ and/or NH(LA), $N(LA)_2$, $NO_2$, CN, OCN, SCN, COOH, COO(LA), $CONH_2$, CONH(LA), $CON(LA)_2$, NHCO(LA), NHCONH(LA), $NHCONH_2$, $NHSO_2$(LA), CHO, CO(LA), $SO_2NH_2$, $SO_2$(LA);

Hal is F, Cl, Br or I, and

LA is an unbranched or branched, saturated or partially unsaturated, linear hydrocarbon chain having 1, 2, 3 or 4 C atoms, wherein 1, 2 or 3 H atoms may be replaced by Hal.

In a preferred embodiment the compounds of the invention conform to Formula (II) in which all substituents have the meanings indicated for Formula (I):

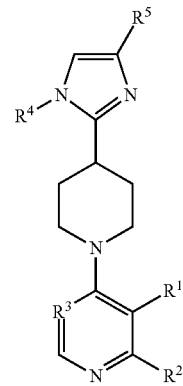

(II)

In a further preferred embodiment the compounds of the invention conform to Subformulae 1 to 19 of Formulae (I) or (II), wherein:

in Subformula 1

$R^1$ is Hal, LA, O(LA), CN, $CONH_2$, or a monocyclic aliphatic or aromatic homo- or heterocycle having 0, 1 or 2 N or O atoms and 5 or 6 skeleton atoms, in Subformula 2

$R^2$ is $NH_2$, in Subformula 3

$R^3$ is N, in Subformula 4

$R^4$ is unbranched or branched, linear or monocyclic alkyl having 1, 2, 3, 4, 5, 6, 7, 8 or 9 C atoms, in which one or two $CH_2$ groups may be replaced by —O— or —NH—, and/or in which one or two CH groups may be replaced by —N—, in Subformula 5

$R^5$ is cyclohexyl, phenyl or pyridyl, which is unsubstituted or mono- or disubstituted by Hal or LA, in Subformula 6

$R^1$ is Hal, LA, O(LA), CN, CONH$_2$, or a monocyclic aliphatic or aromatic homo- or heterocycle having 0, 1 or 2 N or O atoms and 5 or 6 skeleton atoms, $R^2$ is NH$_2$, $R^3$ is N, in Subformula 7

$R^2$ is NH$_2$, $R^3$ is N, $R^4$ is unbranched or branched, linear or monocyclic alkyl having 1, 2, 3, 4, 5, 6, 7, 8 or 9 C atoms, in which one or two CH$_2$ groups may be replaced by an —O—, —NH—, group, and/or in which one or two CH groups may be replaced by —N—, in Subformula 8

$R^2$ is NH$_2$, $R^3$ is N, $R^5$ is cyclohexyl, phenyl or pyridyl, which is unsubstituted or mono- or disubstituted by Hal or LA, in Subformula 9

$R^1$ is Hal, LA, O(LA), CN, CONH$_2$, or a monocyclic aliphatic or aromatic homo- or heterocycle having 0, 1 or 2 N or O atoms and 5 or 6 skeleton atoms, $R^2$ is NH$_2$, $R^3$ is N, $R^5$ is cyclohexyl, phenyl or pyridyl, which is unsubstituted or mono- or disubstituted by Hal or LA, in Subformula 10

$R^1$ is Hal, LA, O(LA), CN, CONH$_2$, or a monocyclic aliphatic or aromatic homo- or heterocycle having 0, 1 or 2 N or O atoms and 5 or 6 skeleton atoms, $R^2$ is NH$_2$, $R^3$ is N, $R^4$ is unbranched or branched, linear or monocyclic alkyl having 1, 2, 3, 4, 5, 6, 7, 8 or 9 C atoms, in which one or two CH$_2$ groups may be replaced by an by —O— or —NH—, and/or in which one or two CH groups may be replaced by —N—, in Subformula 11

$R^2$ is NH$_2$, $R^3$ is N, $R^4$ is unbranched or branched, linear or monocyclic alkyl having 1, 2, 3, 4, 5, 6, 7, 8 or 9 C atoms, in which one or two CH$_2$ groups may be replaced by —O— or —NH—, and/or in which one or two CH groups may be replaced by —N—, $R^5$ is cyclohexyl, phenyl or pyridyl, which is unsubstituted or mono- or disubstituted by Hal or LA, in Subformula 12

$R^1$ is Hal, LA, O(LA), CN, CONH$_2$, or a monocyclic aliphatic or aromatic homo- or heterocycle having 0, 1 or 2 N or O atoms and 5 or 6 skeleton atoms, $R^2$ is NH$_2$, $R^3$ is N, $R^4$ is unbranched or branched, linear or monocyclic alkyl having 1, 2, 3, 4, 5, 6, 7, 8 or 9 C atoms, in which one or two CH$_2$ groups may be replaced by —O— or —NH—, and/or in which one or two CH groups may be replaced by —N—, $R^5$ is cyclohexyl, phenyl or pyridyl, which is unsubstituted or mono- or disubstituted by Hal or LA, in Subformula 13

$R^1$ is Cl, CN, CONH$_2$, isopropyl, isopropyloxy, ethyl, ethenyl, ethyloxy, $R^2$ is NH$_2$, $R^3$ is N, in Subformula 14

$R^2$ is NH$_2$, $R^3$ is N, $R^4$ is branched monocyclic alkyl having 5, 6 or 7 C atoms, of which 3 or 4 C atoms are ring atoms, and in which one CH$_2$ group may be replaced by —O— or NH—, and/or in which one CH group may be replaced by —N—, or unbranched or branched linear alkyl having 5, 6 or 7 C atoms, in which one CH$_2$ group may be replaced by —O— or NH—, and/or in which one CH group may be replaced by —N—, in Subformula 15

$R^2$ is NH$_2$, $R^3$ is N, $R^5$ is phenyl or pyridyl, which is para-substituted by Hal and/or meta-substituted by Hal or LA, in Subformula 16

$R^1$ is Cl, CN, CONH$_2$, isopropyl, isopropyloxy, ethyl, ethenyl, ethyloxy, $R^2$ is NH$_2$, $R^3$ is N, $R^4$ is branched monocyclic alkyl having 5, 6 or 7 C atoms, of which 3 or 4 C atoms are ring atoms, and in which one CH$_2$ group may be replaced by —O— or NH—, and/or in which one CH group may be replaced by —N—, or unbranched or branched linear alkyl having 5, 6 or 7 C atoms, in which one CH$_2$ group may be replaced by —O— or NH—, and/or in which one CH group may be replaced by —N—, in Subformula 17

$R^1$ is Cl, CN, CONH$_2$, isopropyl, isopropyloxy, ethyl, ethenyl, ethyloxy, $R^2$ is NH$_2$, $R^3$ is N, $R^5$ is phenyl or pyridyl, which is para-substituted by Hal and/or meta-substituted by Hal or LA, in Subformula 18

$R^2$ is NH$_2$, $R^3$ is N, $R^4$ is branched monocyclic alkyl having 5, 6 or 7 C atoms, of which 3 or 4 C atoms are ring atoms, and in which one CH$_2$ group may be replaced by —O— or NH—, and/or in which one CH group may be replaced by —N—, or unbranched or branched linear alkyl having 5, 6 or 7 C atoms, in which one CH$_2$ group may be replaced by —O— or NH—, and/or in which one CH group may be replaced by —N—, $R^5$ is phenyl or pyridyl, which is para-substituted by Hal and/or meta-substituted by Hal or LA, in Subformula 19

$R^1$ is Cl, CN, CONH$_2$, isopropyl, isopropyloxy, ethyl, ethenyl, ethyloxy, $R^2$ is NH$_2$, $R^3$ is N, $R^4$ is branched monocyclic alkyl having 5, 6 or 7 C atoms, of which 3 or 4 C atoms are ring atoms, and in which one CH$_2$ group may be replaced by —O— or NH—, and/or in which one CH group may be replaced by —N—, or unbranched or branched linear alkyl having 5, 6 or 7 C atoms, in which one CH$_2$ group may be replaced by —O— or NH—, and/or in which one CH group may be replaced by —N—, $R^5$ is phenyl or pyridyl, which is para-substituted by Hal and/or meta-substituted by Hal or LA, and pharmaceutically acceptable salts, solvates, solvates of salts, or prodrugs thereof.

In even more preferred embodiments, the substituents designated $R^1$, $R^4$ and $R^5$ in Formula (I), above, are defined as follows [with the unmodified substituents of Formula (I) remaining as defined above]:

$R^1$ is formamide; ethyl; isopropyl, Hal; ethoxy, isopropoxy, vinyl; carbonitrile; 1H-pyrazol-4-yl; 2,2,2-trifluoroethoxy; 4-fluorophenyl; 4-methoxyphenyl; 5-isoxazol-4-yl; methoxy; 1H-pyrrol-3-yl; 5-isoxazol-4-yl; cyclobutyl; cyclopropyl; 5-cyclopent-1-enyl; isopropenyl; hydroxymethyl, 3,4-difluorophenyl; 3-fluorophenyl; 2-fluorophenyl; pyridin-4-yl; 6-aminopyridin-3-yl; 2-methyl-thiazol-5-yl; 6-methylpyridin-3-yl; pyridin-3-yl; 4-hydroxymethylphenyl; (E)-2-ethoxy-vinyl and methyl;

$R^4$ is 2-azetidin-1-yl-ethyl; 2-dimethylaminoethyl; 2-methylaminoethyl; 2-ethylaminoethyl; 2-isopropylaminoethyl; 2-cyclopropylmethylaminoethyl; 2-methoxyethylaminoethyl; 2-cyclopropylaminoethyl; 2-aminoethyl; 2-cyclopentylaminoethyl; 1-piperidin-4-yl; 1-pyrrolidin-3-yl; 1-azetidin-3-ylmethyl; 1-methyl-azetidin-3-ylmethyl; 2-pyrrolidin-1-yl-ethyl; 2-tert-butylaminoethyl; 2-cyclopropylaminoethyl; 2-ethylisopropylaminoethyl; 2-diethylaminoethyl; 2-isobutylaminoethyl; 2-(1,1-dimethylpropylamino)-ethyl; 2-(isopropylmethylamino)-ethyl; 1-pyrrolidin-2-ylmethyl; 1-azetidin-2-ylmethyl; azetidin-3-yl; 2-(2-dimethylaminoethyl-methylamino)ethyl; 2-(2-methoxyethyl-methylamino)-ethyl; 2-piperidin-1-yl-ethyl; 2-(2-oxa-6-aza-spiro [3,4]oct-6-yl)-ethyl; 2-(6-oxa-1-aza-spiro[3.3]hept-1-yl)-ethyl; 2-(2-oxa-6-aza-spiro [3.3]hept-6-yl)-ethyl; 2-(3-fluoroazetidin-1-yl)-ethyl; 2-(3,3-difluoroazetidin-1-yl and 2-(3-methylazetidin-1-yl)-ethyl;

$R^5$ is 4-fluoro-3-trifluoromethylphenyl; 4-fluoro-3-methylphenyl; 2-trifluoromethylpyridin-4-yl; 2-isopropylpyridin-4-yl; 3-chloro-4-fluorophenyl; cyclohexyl; 3-trifluoromethylphenyl; 3-chloro-4-methoxyphenyl; 3-chloro-4-methylphenyl; 3-fluoro-4-methoxyphenyl; 3-fluoro-4-methylphenyl; 2-tert-butylpyridin-4-yl; 2-cyclopropylpyridin-4-yl; 2-ethylpyridin-4-yl; 4-methyl-3-trifluoromethylphenyl; 3-difluoromethoxy-4-fluorophenyl; 1H-pyrazol-4-yl; isoxazol-4-yl; 4-difluoromethoxyphenyl; phenyl; thiophen-3-yl; furan-3-yl; 6-chloropyridin-2-yl; 2-fluoropyridin-4-yl; 6-trifluoromethylpyridin-2-yl; 3-chloroophenyl; 3-fluorophenyl; 4-fluoro-3-methoxyphenyl; 3,4-difluorophenyl; 4-fluorophenyl; 4-chlorophenyl; 2-fluorophenyl; 5-chloro-6-fluoropyridin-3-yl; 2-methylpyridin-4-yl and 3-trifluoromethoxyphenyl.

In other preferred embodiments the substituents designated $R^1$, in Formula (I), are set out in Table 1.

TABLE 1

Preferred substituents for $R^1$ in Formula (I):

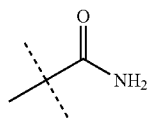

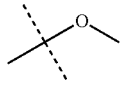

TABLE 1-continued

Preferred substituents for $R^1$ in Formula (I):

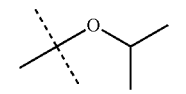

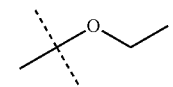

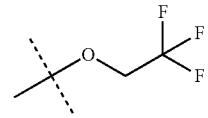

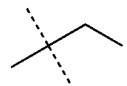

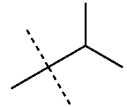

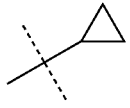

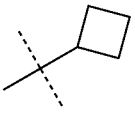

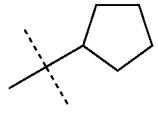

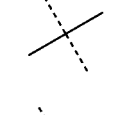

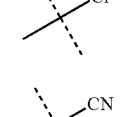

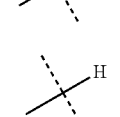

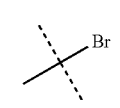

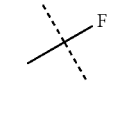

TABLE 1-continued
Preferred substituents for $R^1$ in Formula (I):
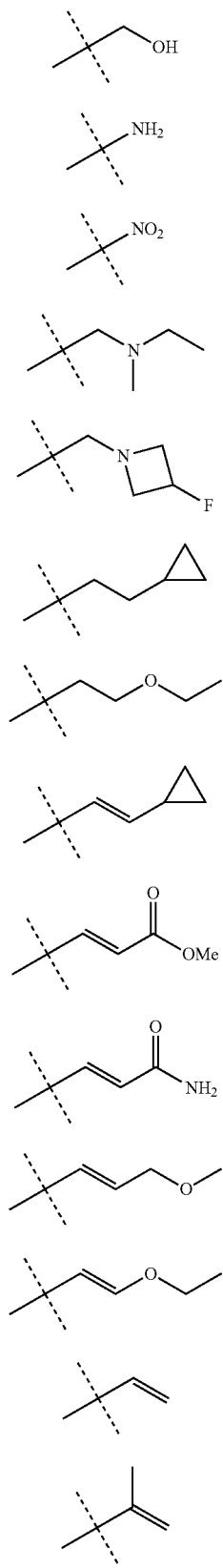
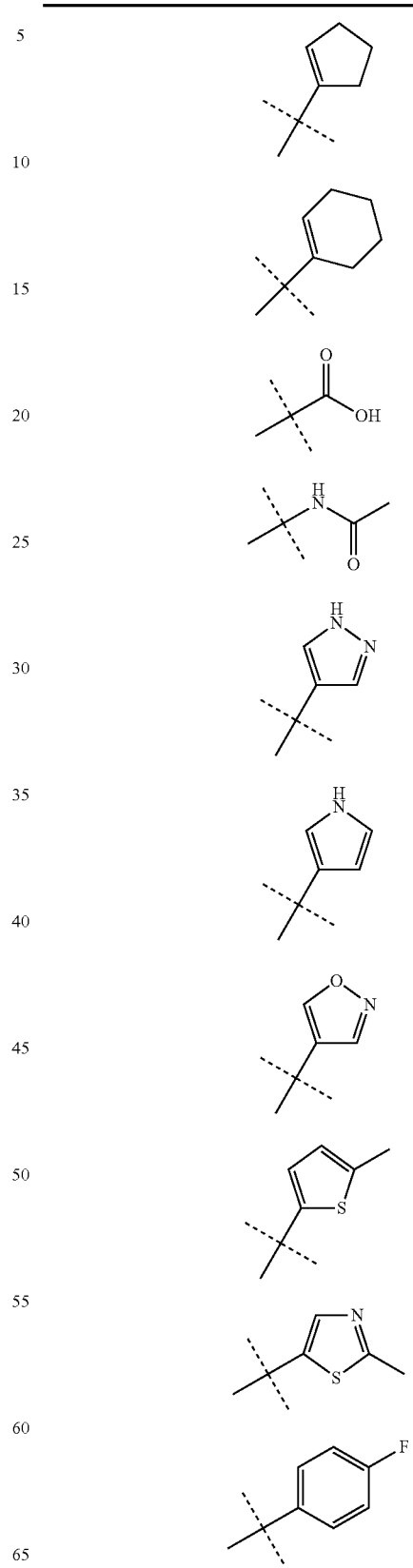

TABLE 1-continued
Preferred substituents for $R^1$ in Formula (I):
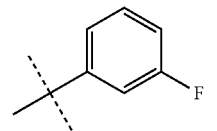
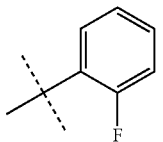
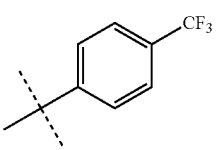
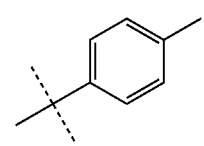
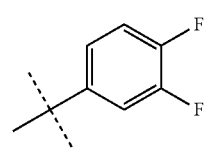
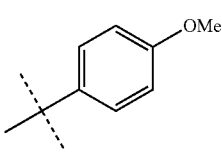
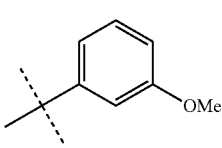
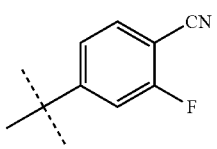
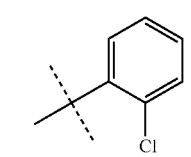
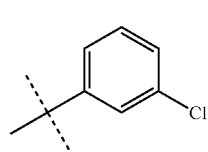
TABLE 1-continued
Preferred substituents for $R^1$ in Formula (I):
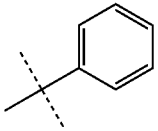
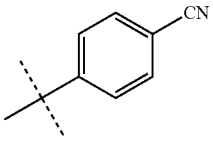
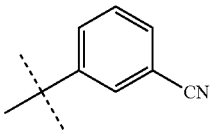
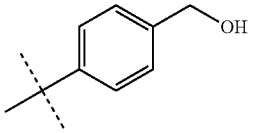
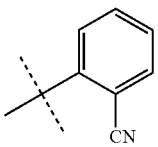
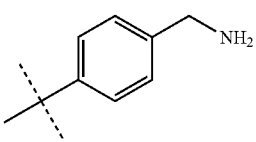
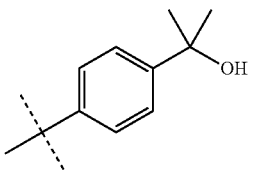
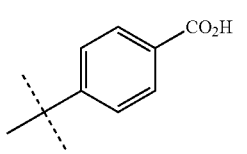
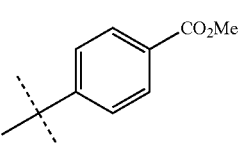
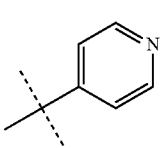

TABLE 1-continued
Preferred substituents for $R^1$ in Formula (I):
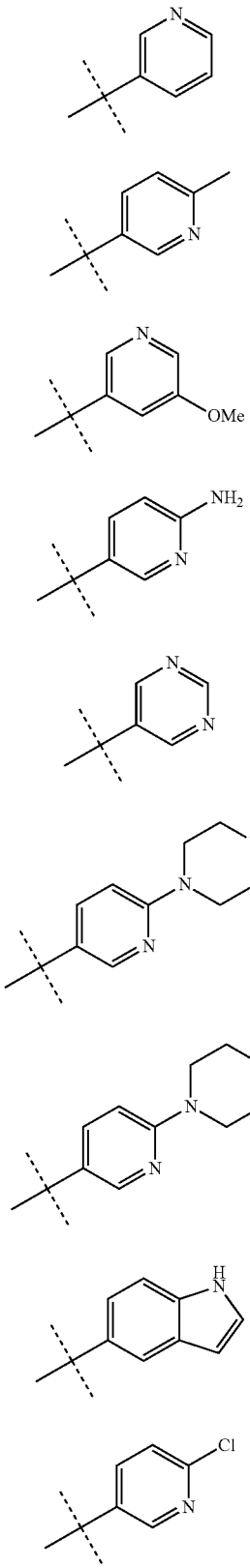
TABLE 1-continued
Preferred substituents for $R^1$ in Formula (I):
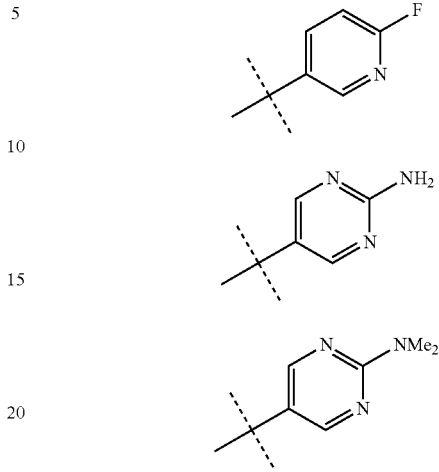
In other preferred embodiments the substituents designated $R^4$, in Formula (I), are set out in Table 2.
TABLE 2
Preferred substituents for $R^4$ in Formula (I):
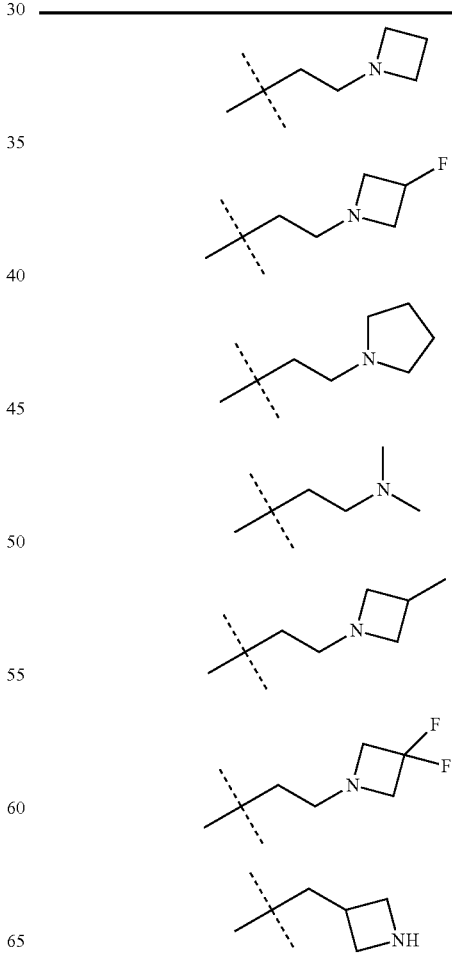

TABLE 2-continued
Preferred substituents for $R^4$ in Formula (I):
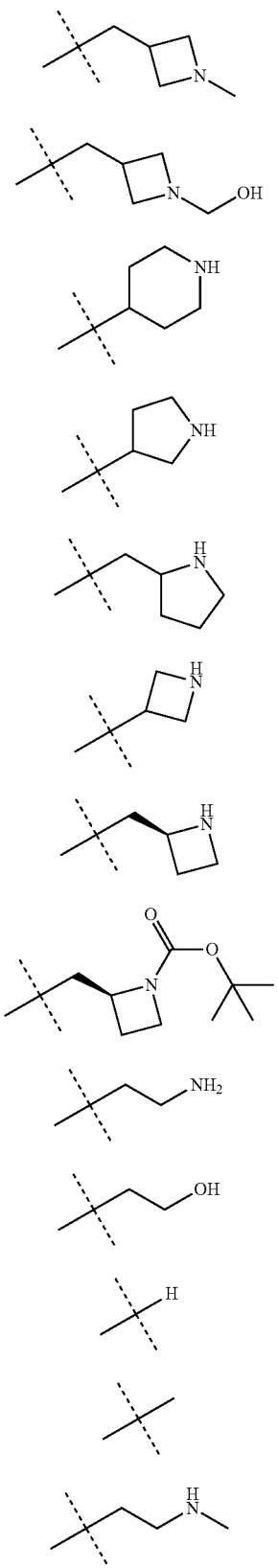
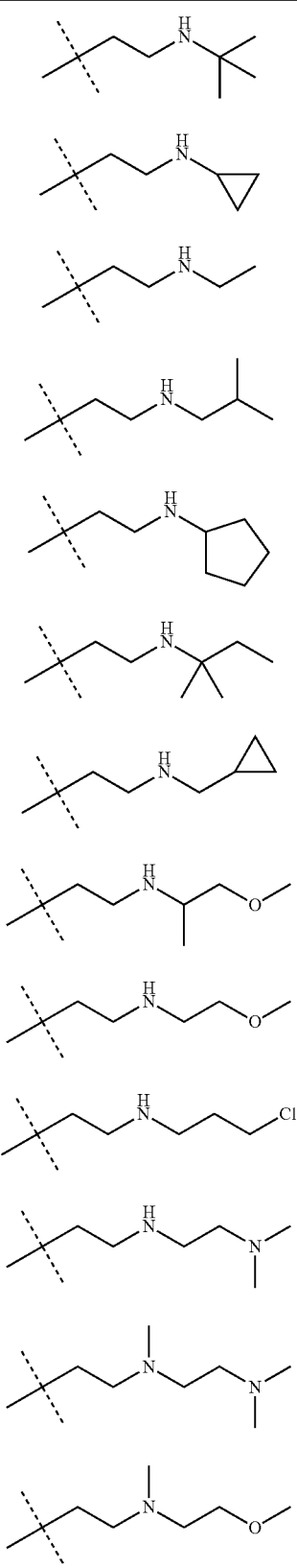

TABLE 2-continued
Preferred substituents for $R^4$ in Formula (I):
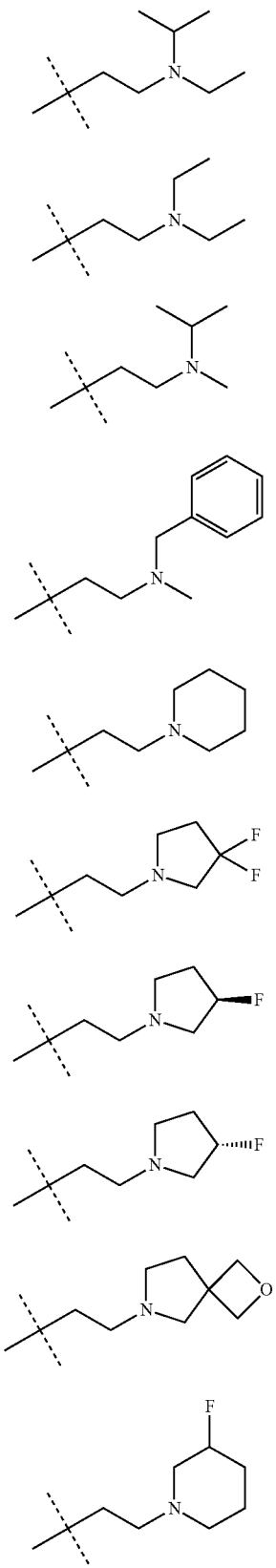
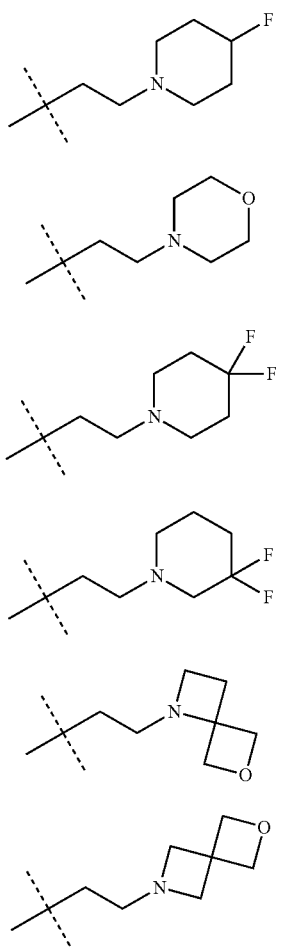
In other preferred embodiments the substituents designated R5, in Formula (I), are set out in Table 3.
TABLE 3
Preferred substituents for $R^5$ in Formula (I):
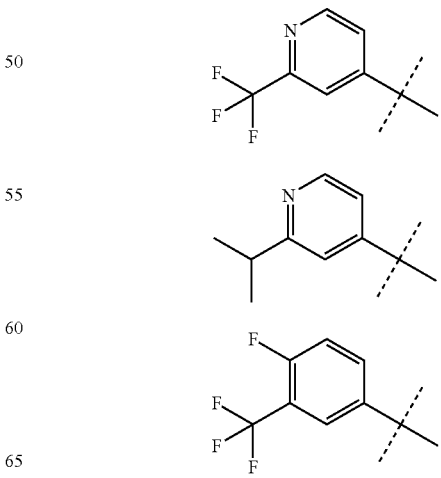

TABLE 3-continued
Preferred substituents for $R^5$ in Formula (I):
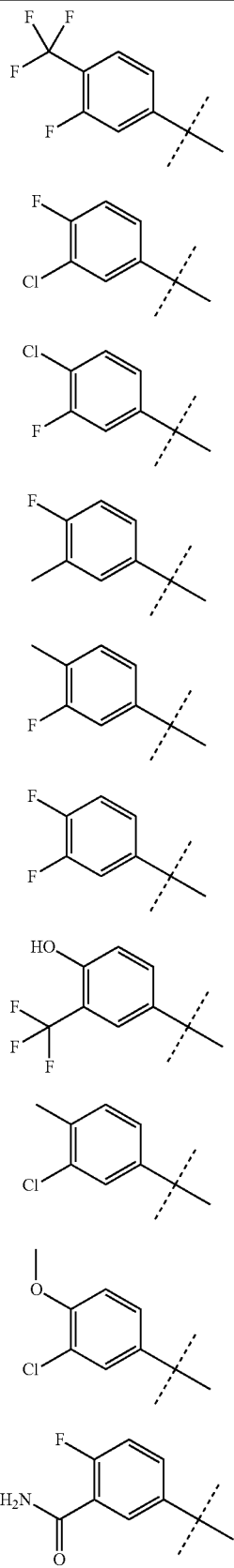
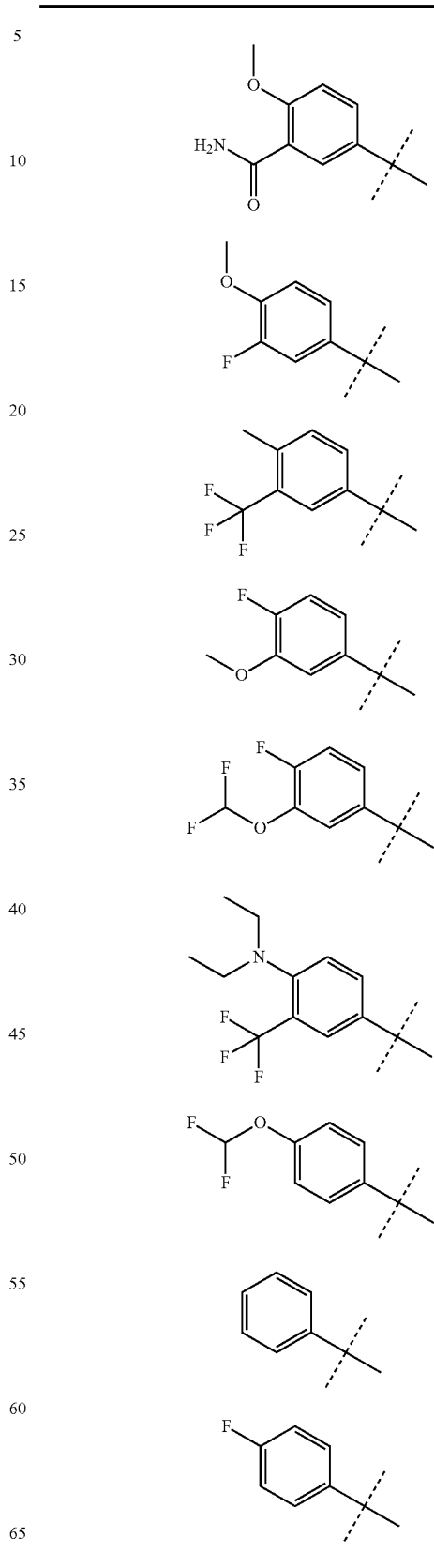

TABLE 3-continued
Preferred substituents for $R^5$ in Formula (I):
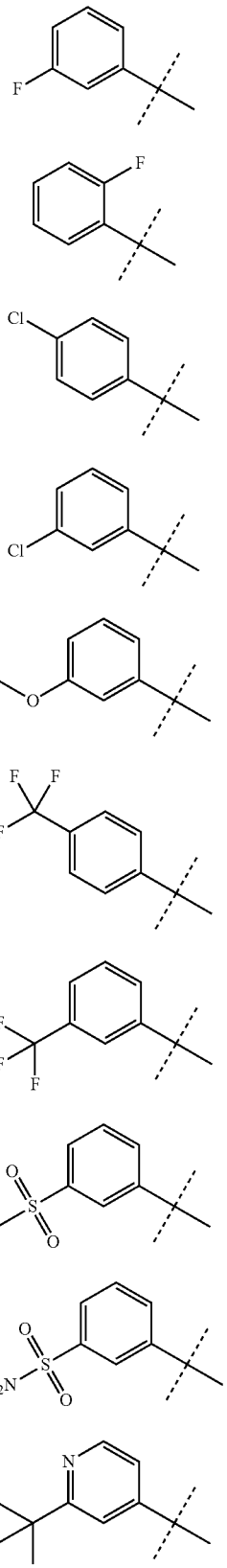
TABLE 3-continued
Preferred substituents for $R^5$ in Formula (I):
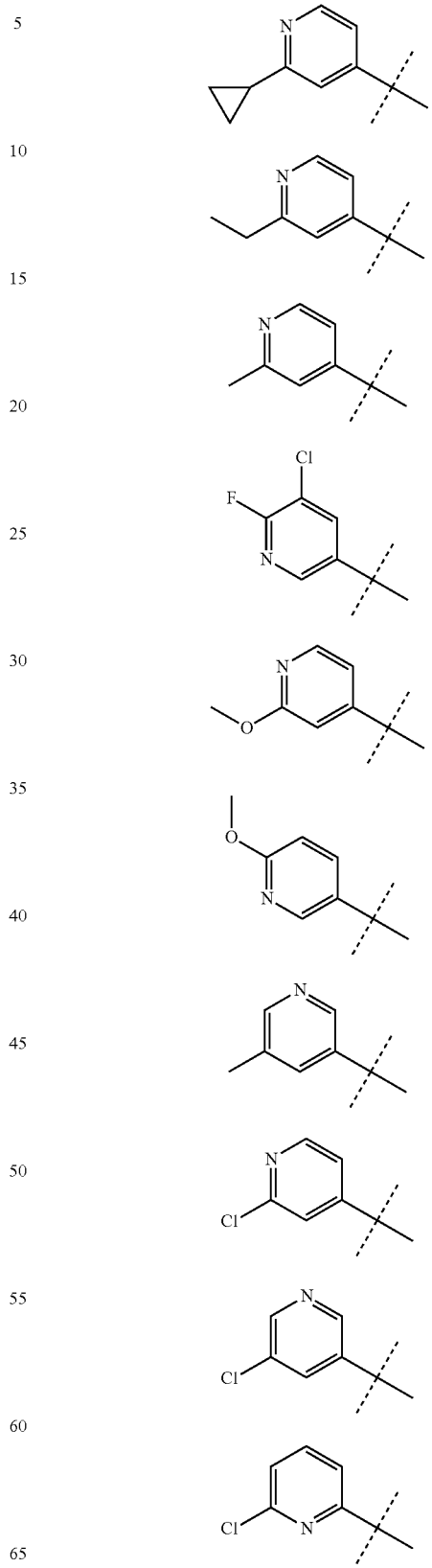

TABLE 3-continued

Preferred substituents for $R^5$ in Formula (I):

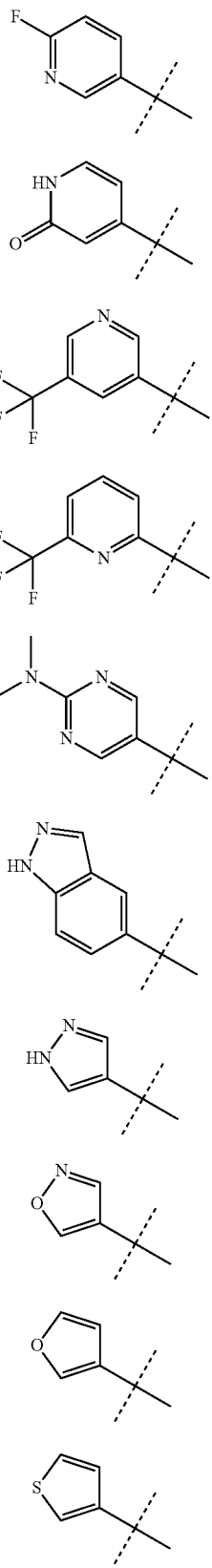

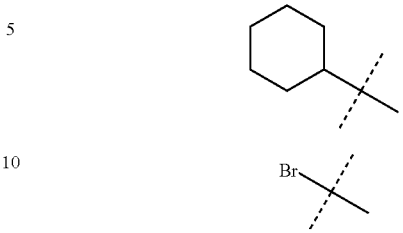

In general, all residues which occur more than once may be identical or different, i.e. are independent of one another.

The compounds of the present invention can be in the form of a prodrug compound. "Prodrug compound" means a derivative that is converted into a biologically active compound according to the present invention under physiological conditions in the living body, e.g., by oxidation, reduction, hydrolysis or the like, each of which is carried out enzymatically, or without enzyme involvement. Examples of prodrugs are compounds, wherein the amino group in a compound of the present invention is acylated, alkylated or phosphorylated, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated, or wherein a sulfhydryl group forms a disulfide bridge with a carrier molecule, e.g. a peptide, that delivers the drug selectively to a target and/or to the cytosol of a cell. These compounds can be produced from compounds of the present invention according to well-known methods. Other examples of prodrugs are compounds, wherein the carboxylate in a compound of the present invention is for example converted into an alkyl-, aryl-, choline-, amino, acyloxymethylester, linolenoyl-ester.

Metabolites of compounds of the present invention are also within the scope of the present invention.

Where tautomerism, e.g., keto-enol tautomerism, of compounds of the present invention or their prodrugs may occur, the individual forms, e.g., the keto or the enol form, are claimed separately and together as mixtures in any ratio. The same applies for stereoisomers, e.g., enantiomers, cis/trans isomers, conformers and the like. If desired, isomers can be separated by methods well known in the art, e.g. by liquid chromatography. The same applies for enantiomers, e.g., by using chiral stationary phases. Additionally, enantiomers may be isolated by converting them into diastereomers, i.e., coupling with an enantiomerically pure auxiliary compound, subsequent separation of the resulting diastereomers and cleavage of the auxiliary residue. Alternatively, any enantiomer of a compound of the present invention may be obtained from stereoselective synthesis using optically pure starting materials.

The compounds of the present invention can be in the form of a pharmaceutically acceptable salt or a solvate. The term "pharmaceutically acceptable salts" refers to salts prepared from pharmaceutically acceptable non-toxic bases or acids, including inorganic bases or acids and organic bases or acids. In cases where the compounds of the present invention contain one or more acidic or basic groups, the invention also comprises their corresponding pharmaceutically or toxicologically acceptable salts, in particular their pharmaceutically utilizable salts. Thus, the compounds of the present invention which contain acidic groups can be present in salt form, and can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the present invention which contain one or more basic groups, i.e. groups which can be protonated, can be present in salt form, and can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to a person skilled in the art, for example by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

The term "substituted" preferably relates to the substitution by the above-mentioned substituents, where a plurality of different degrees of substitution are possible, unless indicated otherwise.

All physiologically acceptable salts, derivatives, solvates, solvates of salts, and stereoisomers of these compounds, including mixtures thereof in all ratios, are also in accordance with the invention.

The compounds of Formula (I) and Formula (II) may have one or more centres of chirality. They may accordingly occur in various enantiomeric forms and be in racemic or optically active form. The invention therefore also relates to the optically active forms (stereoisomers), the enantiomers, the racemates, the diastereomers and hydrates and solvates of these compounds.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isoprpanol/acetonitrile, for example in the ratio 82:15:3. A method for the resolution of racemates containing ester groups (for example acetyl esters) is the use of enzymes, in particular esterases.

Furthermore, the present invention relates to pharmaceutical compositions comprising a compound of the present invention, or a prodrug compound thereof, or a pharmaceutically acceptable salt or solvate thereof as an active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

A pharmaceutical composition of the present invention may additionally comprise one or more other compounds as active ingredients, such as one or more additional compounds of the present invention, or a prodrug compound or other p70S6K inhibitors. The pharmaceutical compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In one embodiment, said compounds and pharmaceutical composition are for the treatment of cancer such as brain, lung, colon, epidermoid, squamous cell, bladder, gastric, pancreatic, breast, head, neck, renal, kidney, liver, ovarian, prostate, colorectal, uterine, rectal, oesophageal, testicular, gynecological, thyroid cancer, melanoma, hematologic malignancies such as acute myelogenous leukemia, multiple myeloma, chronic myelogenous leukemia, myeloid cell leukemia, glioma, Kaposi's sarcoma, or any other type of solid or liquid tumors. Preferably, the cancer to be treated is chosen from breast, colorectal, lung, prostate or pancreatic cancer or glioblastoma.

The invention also relates to the use of compounds according to the invention for the preparation of a medicament for the treatment of hyperproliferative diseases related to the hyperactivity of p70S6K as well as diseases modulated by the p70S6K cascade in mammals, or disorders mediated by aberrant proliferation, such as cancer and inflammation.

The invention also relates to a compound or pharmaceutical composition for treating a disease related to vasculogenesis or angiogenesis in a mammal which comprises a therapeutically effective amount of a compound of the present invention, or a pharmaceutically acceptable salt, prodrug or hydrate thereof, and a pharmaceutically acceptable carrier.

In one embodiment, said compound or pharmaceutical composition is for treating a disease selected from the group consisting of tumor angiogenesis, chronic inflammatory disease such as rheumatoid arthritis, inflammatory bowel disease, atherosclerosis, skin diseases such as psoriasis, eczema, and sclerodema, diabetes, diabetic retinopathy, retinopathy of prematurity and age-related macular degeneration.

This invention also relates to a compound or pharmaceutical composition for inhibiting abnormal cell growth in a mammal which comprises an amount of a compound of the present invention, or a pharmaceutically acceptable salt or solvate or prodrug thereof, in combination with an amount of another anti-cancer therapeutic, wherein the amounts of the compound, salt, solvate, or prodrug, and of the chemotherapeutic are together effective in inhibiting abnormal cell growth. Many anti-cancer therapeutics are presently known in the art. In one embodiment, the anti-cancer therapeutic is a chemotherapeutic selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. In another embodiment the anti-cancer therapeutic is an antibody selected from the group consisting of bevacizumab, CD40-specific antibodies, chTNT-1/B, denosumab, zanolimumab, IGF1R-specific antibodies, lintuzumab, edrecolomab, WX G250, rituximab, ticilimumab, trastuzumab and cetuximab. In yet another embodiment the anti-cancer therapeutic is an inhibitor of another protein kinase, such as Akt, Axl, Aurora A, Aurora B, dyrk2, epha2, fgfr3, igf1r, IKK2, JNK3, Vegfr1, Vegfr2, Vegfr3 (also known as Flt-4), KDR, MEK, MET, Plk1, RSK1, Src, TrkA, Zap70, cKit, bRaf, EGFR, Jak2, PI3K, NPM-Alk, c-Abl, BTK, FAK, PDGFR, TAK1, LimK, Flt-3, PDK1 and Erk.

This invention further relates to a method for inhibiting abnormal cell growth in a mammal or treating a hyperproliferative disorder that comprises administering to the mammal an amount of a compound of the present invention, or a pharmaceutically acceptable salt or solvate or prodrug thereof, in combination with radiation therapy, wherein the amounts of the compound, salt, solvate, or prodrug, is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of a compound of the invention in this combination therapy can be determined as described herein. It is believed that the compounds of the present invention can render abnormal cells more sensitive to treatment with radiation for purposes of killing and/or inhibiting the growth of such cells.

Accordingly, this invention further relates to a method for sensitizing abnormal cells in a mammal to treatment with radiation which comprises administering to the mammal an amount of a compound of the present invention or pharmaceutically acceptable salt or solvate or prodrug thereof, which amount is effective is sensitizing abnormal cells to treatment with radiation. The amount of the compound, salt, or solvate in this method can be determined according to the means for ascertaining effective amounts of such compounds described herein. The invention also relates to a method for inhibiting abnormal cell growth in a mammal that comprises an amount of a compound of the present invention, or a pharmaceutically acceptable salt or solvate thereof, a prodrug thereof, or an isotopically-labeled derivative thereof, and an amount of one or more substances selected from anti-angiogenesis agents, signal transduction inhibitors, and antiproliferative agents.

In practical use, the compounds of the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like. In the case of oral liquid preparations, any of the usual pharmaceutical media may be employed, such as, for example, suspensions, elixirs and solutions; or carriers such as starches, sugars, microcrystalline cellulose, diluents, granulating agents, lubricants, binders, disintegrating agents and the like. In the case of oral solid preparations the composition may take forms such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed.

Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing cancer, inflammation or other proliferative diseases for which compounds of the present invention are indicated, generally satisfactory results are obtained when the compounds of the present invention are administered at a daily dosage of from about 0.01 milligram to about 100 milligram per kilogram of animal body weight, preferably given as a single daily dose. For most large mammals, the total daily dosage is from about 0.2 milligrams to about 2000 milligrams, preferably from about 0.5 milligram to about 1000 milligrams. In the case of a 70 kg adult human, the total daily dose will generally be from about 0.5 milligrams to about 1000 milligrams. These aforementioned dosage regimens may be adjusted to provide the optimal therapeutic response.

The invention also relates to a set (kit) consisting of separate packs of a) an effective amount of a compound according to the invention or a physiologically acceptable salt, solvate or prodrug thereof, and b) an effective amount of a further medicament active ingredient.

The set comprises suitable containers, such as boxes, individual bottles, bags or ampoules. The set may, for example, comprise separate ampoules, each containing an effective amount of a compound according to the invention and/or pharmaceutically usable derivatives, solvates and stereoisomers thereof, including mixtures thereof in all ratios, and an effective amount of a further medicament active ingredient in dissolved or lyophilised form.

Experimental Section

Some abbreviations that may appear in this application are as follows:

| Abbreviations | |
|---|---|
| Designation | |
| ACN | acetonitrile |
| ATP | Adenosine triphosphate |
| b | Broad peak |
| d | Doublet |
| DMSO | dimethylsulfoxide |
| DIEA | N,N-Diisopropylethylamine |
| DTT | dithiothreitol |
| EDTA | Ethylenediaminetetraacetic acid |
| equiv. | equivalents |
| Et | ethyl |
| h | hour |
| HEPES | 4-(2-hydroxyethyl)-1-piperazineethanesulfonic acid |
| HPLC | High pressure liquid chromatography |
| LC/MS | Liquid chromatography coupled to mass spectrometry |
| m | multiplet |
| M | Molecular ion |
| m/z | Mass-to-charge ratio |
| Me | methyl |
| min | minute |
| MS | Mass spectrometry |
| N | Normal (unit of concentration) |
| NMO | 4-methylmorpholine N-oxide |
| NMR | Nuclear Magnetic Resonance |
| PG | Protecting group |

-continued

| Abbreviations | |
|---|---|
| Designation | |
| psi | Pounds per square inch |
| q | Quartette (or quartet) |
| Rf | Retention factor |
| RT | Room temperature |
| Rt. | Retention time |
| s | Singlet |
| Tert | Tertiary |
| TEA | Triethylamine |
| TFA | Trifluoroacetic acid |
| THAB | Tetrahexylammonium bromide |
| THF | Tetrahydrofuran |
| UV | ultraviolet |
| VIS | visible |

The compounds of the present invention can be prepared according to the procedures of the following Schemes and Examples, using appropriate materials and are further exemplified by the following specific examples.

Moreover, by utilizing the procedures described herein, in conjunction with ordinary skills in the art, additional compounds of the present invention claimed herein can be readily prepared. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The instant compounds are generally isolated in the form of their pharmaceutically acceptable salts, such as those described above. The amine-free bases corresponding to the isolated salts can be generated by neutralization with a suitable base, such as aqueous sodium hydrogencarbonate, sodium carbonate, sodium hydroxide and potassium hydroxide, and extraction of the liberated amine-free base into an organic solvent, followed by evaporation. The amine-free base, isolated in this manner, can be further converted into another pharmaceutically acceptable salt by dissolution in an organic solvent, followed by addition of the appropriate acid and subsequent evaporation, precipitation or crystallization.

The invention will be illustrated, but not limited, by reference to the specific embodiments described in the following schemes and examples. Unless otherwise indicated in the schemes, the variables have the same meaning as described above. Unless otherwise specified, all starting materials are obtained from commercially suppliers and used without further purifications. Unless otherwise specified, all temperatures are expressed in ° C. and all reactions are conducted at room temperature. Compounds were purified by either silica chromatography or preparative HPLC.

The present invention also relates to processes for manufacturing the compounds of Formula (I) and Formula (II) according to the hereinafter described schemes and working examples.

Synthetic Schemes Describing Intermediate and End Product Compounds

Aminopyrimidine chloride intermediates were either commercially available or prepared according to the synthetic routes outlined in Scheme 1, Scheme 2 and Scheme 3.

Scheme 1

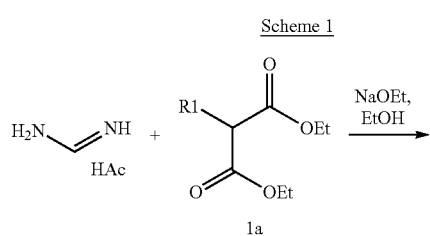

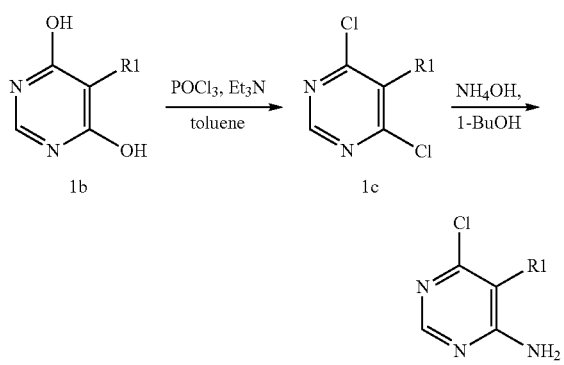

Formamidine acetate was reacted with 1a in the presence of sodium ethoxide in dry ethanol to yield 1b, which was converted to 1c by POCl3 in the presence of TEA in toluene. 1c was then reacted with aqueous ammonia in n-butanol at 100° C. to afford 1d.

Scheme 2

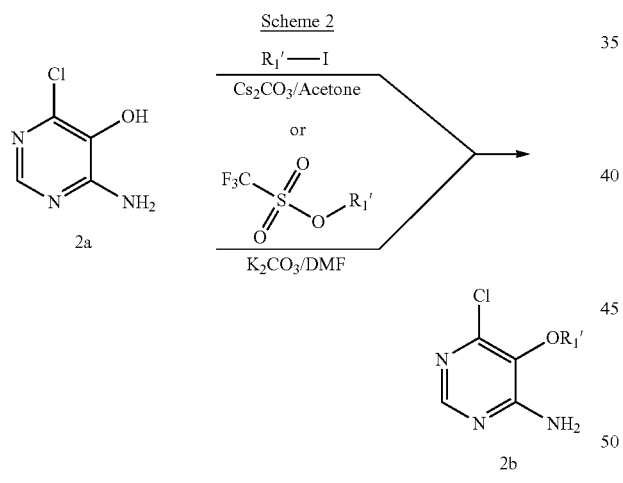

4-amino-6-chloropyrimidin-5-ol 2a was reacted with alkylated regents to provide the desired aminopyrimidine chloride intermediates 2b.

Scheme 3

4,5,6-trichloropyrimidine 3a was reacted with aqueous methylamine in 2-propanol to afford 5,6-dichloro-N-methylpyrimidin-4-amine 3b.

4-Imidazol-2-yl-piperidine intermediates were prepared according to the synthestic routes outlined in Scheme 4, Scheme 5 and Scheme 6.

Scheme 4

33

-continued

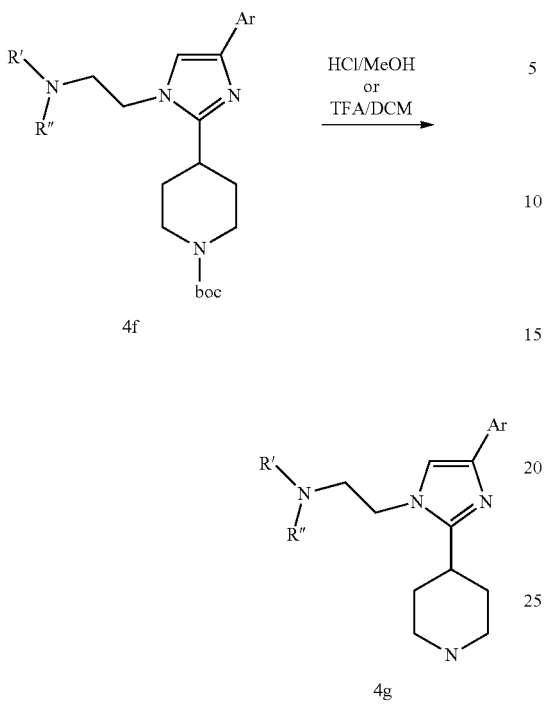

34

-continued

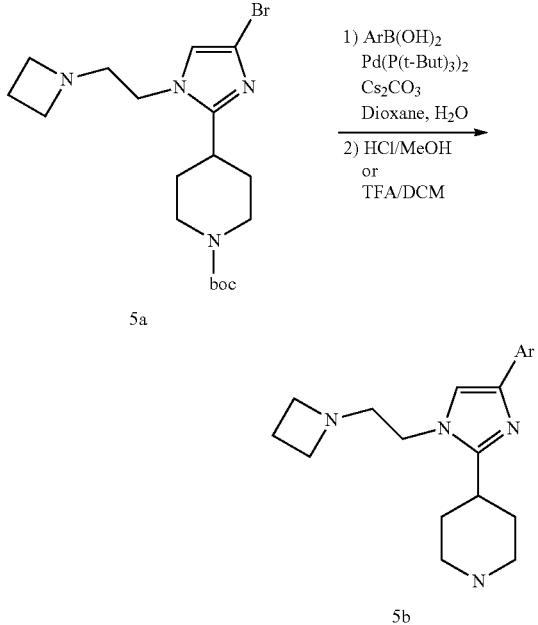

tert-butyl 4-(4-bromo-1-(2-hydroxyethyl)-1H-imidazol-2-yl)piperidine-1-carboxylate 4d was converted to tert-butyl 4-(1-(2-(azetidin-1-yl)ethyl)-4-bromo-1H-imidazol-2-yl)piperidine-1-carboxylate 5a. Suzuki coupling was performed with bromide intermediate 5a, followed by de-Boc under acidic condition to afford 4-(4-Ar-1-(2-(azetidin-1-yl)ethyl)-1H-imidazol-2-yl)piperidine 5b.

tert-butyl 4-formylpiperidine-1-carboxylate 4a was reacted with aqueous glyoxal in the presence of aqueous ammonium hydroxide in methanol to give tert-butyl 4-(1H-imidazol-2-yl)piperidine-1-carboxylate 4b, which was bromined to afford tert-butyl 4-(4-bromo-1H-imidazol-2-yl)piperidine-1-carboxylate 4c. 4c was alkylated with 2-(2-bromoethoxy)tetrahydro-2H-pyran, followed by removal of THP group under acidic condition to yield tert-butyl 4-(4-bromo-1-(2-hydroxyethyl)-1H-imidazol-2-yl)piperidine-1-carboxylate 4d. Suzuki coupling was performed with bromide intermediate 4d to afford 4e. 4e was reacted with methanesulfonyl chloride or 4-methylbenzenesulfonyl chloride, followed by quenching with amine afforded 4f, which was treated with hydrogen chloride in methanol or trifluoroacetic acid in DCM to provide the amine intermediates 4g.

Scheme 6

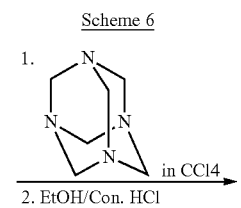

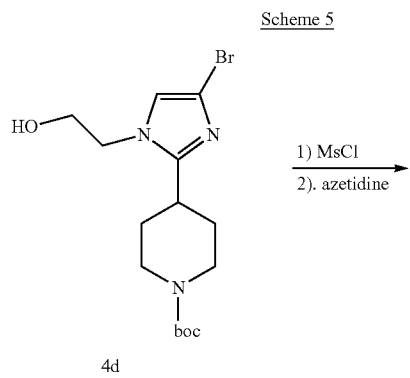

Scheme 5

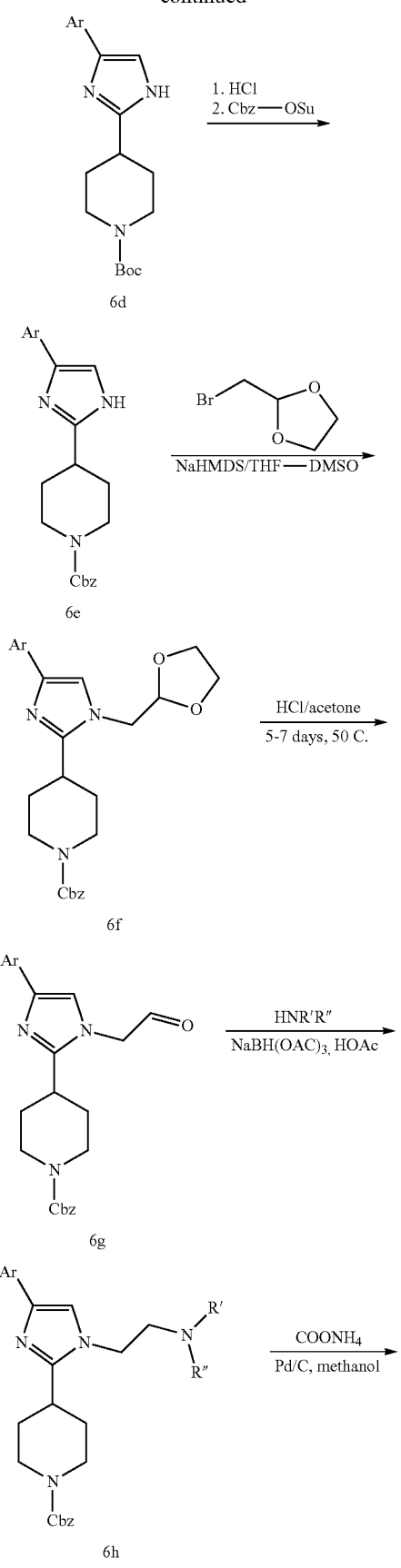

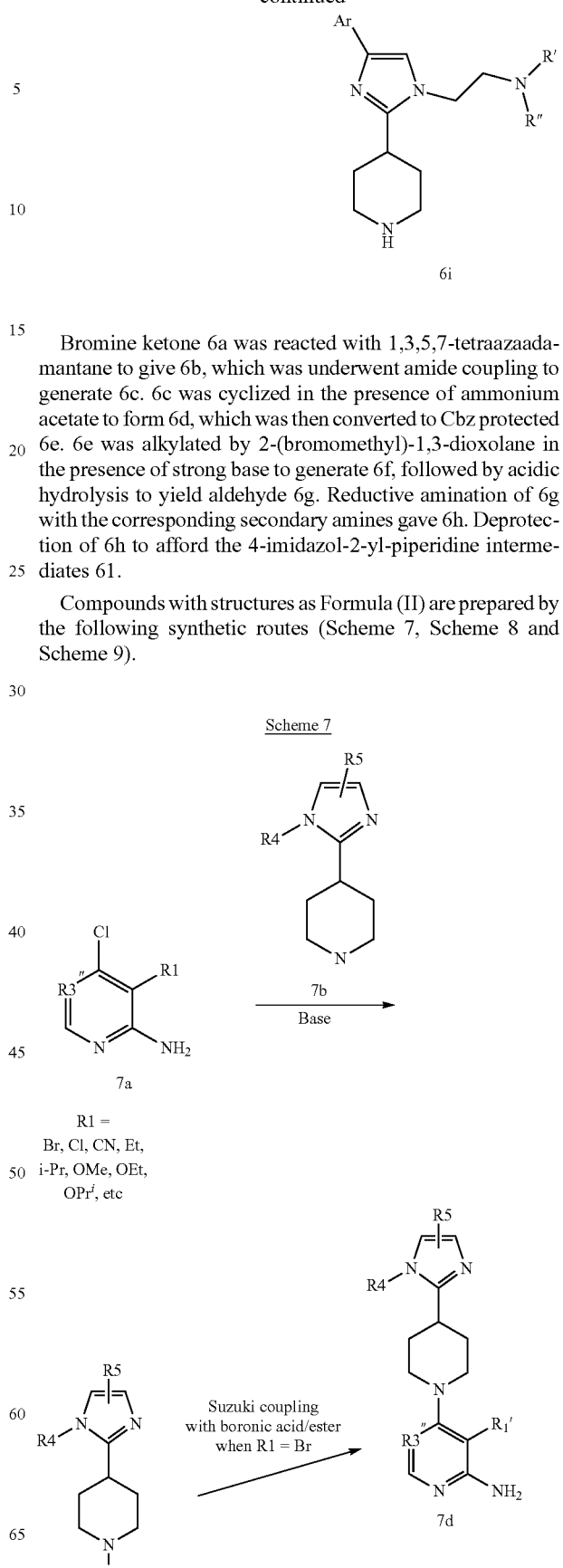

Bromine ketone 6a was reacted with 1,3,5,7-tetraazaadamantane to give 6b, which was underwent amide coupling to generate 6c. 6c was cyclized in the presence of ammonium acetate to form 6d, which was then converted to Cbz protected 6e. 6e was alkylated by 2-(bromomethyl)-1,3-dioxolane in the presence of strong base to generate 6f, followed by acidic hydrolysis to yield aldehyde 6g. Reductive amination of 6g with the corresponding secondary amines gave 6h. Deprotection of 6h to afford the 4-imidazol-2-yl-piperidine intermediates 6I.

Compounds with structures as Formula (II) are prepared by the following synthetic routes (Scheme 7, Scheme 8 and Scheme 9).

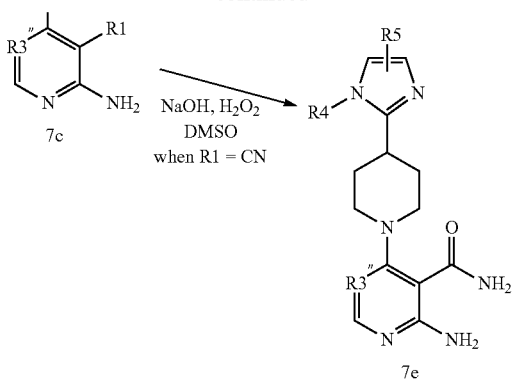

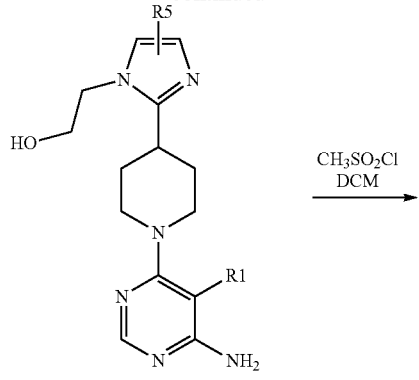

The aminopyrimidine chlorides 7a (commercially available or prepared according to Scheme 1, Scheme 2 and Scheme 3) were reacted with secondary amine 7b (prepared according to Scheme 4, Scheme 5 and Scheme 6) in the presence of base to provide compounds 7c. A Suzuki coupling was then performed with compounds 7c while R1 is bromide and boronic acid or ester to yield compounds 7d. Hydrolysis of the compounds 7c while R1 is nitrile provides compounds 7e.

In some embodiments of the present invention the aminopyrimidine chlorides 7a may be more generically represented as:

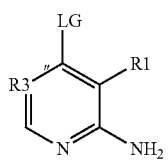

wherein "LG" is any leaving group typically used in nucleophilic substitutions, more preferably HAL, such as Cl or Br.

Scheme 8

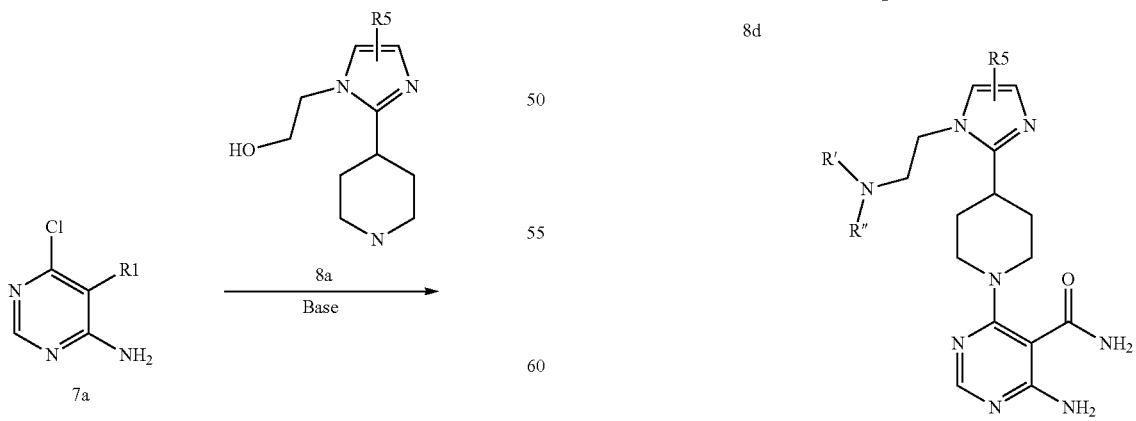

The aminopyrimidine chlorides 7a (commercially available or prepared according to Scheme 1, Scheme 2 and Scheme 3) were reacted with amines 8a (prepared by de-boc of the intermediates 4e (Scheme 4)) in the presence of base to provide compounds 8b. A mesylation reaction was performed on compounds 8b to form compounds 8c which was concentrated then alkylated by the desired amine to give compounds 8d. Hydrolysis of the compounds 8d while R1 is nitrile provides compounds 8e.

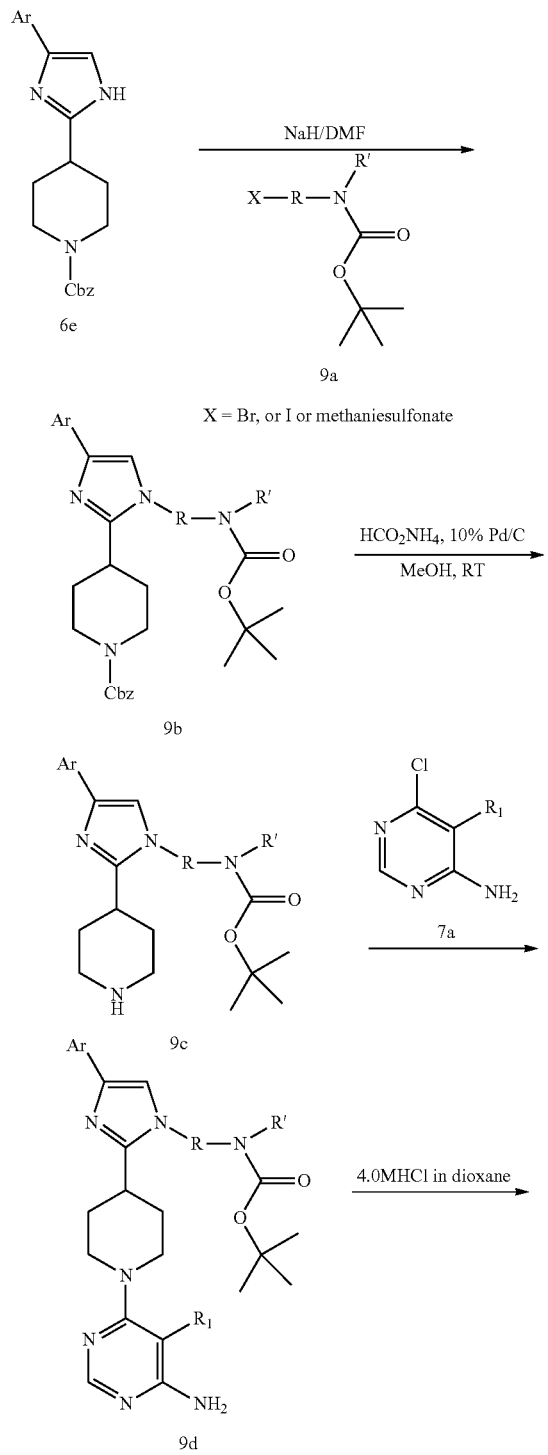

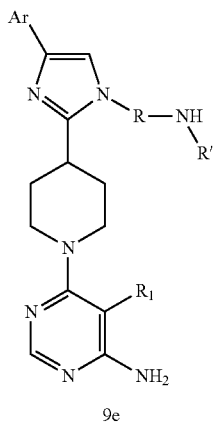

Intermediates 6e were treated with NaH and then coupled with alkyl reagents 9a, to generate 9b. Cbz group of 9b was removed by catalytic hydrogenation to give 9c. Aminopyrimidine chlorides 7a were coupled with 9c to afford 9d, Deprotection of Boc of 9d to produce 9e.

Analytical Methodology

Analytical LC/MS was Performed Using the Following Three Methods:

Method A: A Discovery $C^{18}$, 5 μm, 3×30 mm column was used at a flow rate of 400 μL/min, sample loop 5 μL, mobile phase: (A) water with 0.1% formic acid, mobile phase, (B) methanol with 0.1% formic acid; retention times are given in minutes. Method details: (I) runs on a Quaternary Pump G1311A (Agilent) with UV/VIS diode array detector G1315B (Agilent) and Finnigan LCQ Duo MS detector in ESI+modus with UV-detection at 254 and 280 nm with a gradient of 15-95% (B) in a 3.2 min linear gradient (II) hold for 1.4 min at 95% (B) (III) decrease from 95-15% (B) in a 0.1 min linear gradient (IV) hold for 2.3 min at 15% (B).

Method B: A Waters Symmetry $C^{18}$, 3.5 μm, 4.6×75 mm column at a flow rate of 1 mL/min, sample loop 10 μL, mobile phase (A) is water with 0.05% TFA, mobile phase (B) is ACN with 0.05% TFA; retention times are given in minutes. Methods details: (I) runs on a Binary Pump G1312A (Agilent) with UV/Vis diode array detector G1315B (Agilent) and Agilent G1956B (SL) MS detector in ESI+mode with UV-detection at 254 and 280 nm with a gradient of 20-85% (B) in a 10 min linear gradient (II) hold for 1 min at 85% (B) (III) decrease from 20-85% (B) in a 0.2 min linear gradient (IV) hold for 3.8 min at 20% (B).

Method C: Gradient: 4.2 min/Flow: 2 ml/min 99:01-0:100 Water+0.1% (Vol.) TFA; Acetonitril+0.1% (Vol.) TFA; 0.0 to 0.2 min: 99:01; 0.2 to 3.8 min: 99:01→0:100; 3.8 to 4.2 min: 0:100; Column: Chromolith Performance RP18e; 100 mm long, 3 mm diameter; Wavelength: 220 nm.

Analytical Chiral HPLC

Analytical chiral HPLC was performed using a ChiralPak AD-H column (250×4.6 mm) from Daicel Chemical Industries, Ltd. on an Agilent 1100 Series system. The method used a 5.0 μL injection volume, with a flow rate of 1 mL/min of 100% methanol for 15 min at 25° C., and UV-detection at 254 and 280 nm.

Preparative HPLC

Preparative HPLC was performed using either a Waters Atlantis $dC_{18}$ OBD™ 10 μM (30×250 mm) column or a Waters Sunfire Prep $O_{18}$ OBD 10 μM (30×250 mm) column. The columns were used at a flow rate of 60 mL/min on a Waters Prep LC 4000 System equipped with a sample loop (10 mL) and an ISCO UA-6 UV/Vis detector. The mobile phase was drawn from two solvent reservoirs containing (A) water and (B) HPLC-grade acetonitrile. A typical preparative run used a linear gradient (e.g., 0-60% solvent B over 60 min).

EXAMPLES

The working examples presented below are intended to illustrate particular embodiments of the invention, and are not intended to limit the scope of the specification or the claims in any way.

Preparation of the Intermediates

Representative Synthesis of Intermediate A (Scheme 1)

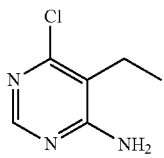

6-Chloro-5-ethylpyrimidin-4-amine

Step 1: 5-Ethylpyrimidine-4,6-diol

To a stirred solution of sodium ethoxide (21% in ethanol, 349 mL, 1.06 mol) in dry ethanol (500 mL) was added formamidine acetate (30.4 g, 0.29 mol) in lots at 0° C. under nitrogen. The reaction mixture was stirred at this temperature for 15 min and then added a solution of diethyl-ethylmalonate (50.0 g, 0.26 mol) in ethanol (200 mL) in drops at 0° C. under nitrogen. The reaction mixture was stirred at RT for 14 h. After completion of the reaction, the reaction mixture was concentrated under reduced pressure. The crude residue was dissolved in water (250 mL) and acidified (pH ~3 to 4) with aqueous solution HCl (1.5 N, 100 mL). The resulting solid was filtered off, washed with water (100 mL) and dried under vacuum to afford the titled compound (27.0 g, 72.5%) as white solid. LCMS: Mass found (M+, 141.0), $^1$H NMR (400 MHz, DMSO-d6) 11.54 (bs, 2H), 7.86 (s, 1H), 2.28-2.22 (m, 2H), 0.95-0.91 (m, 3H).

Step 2: 4,6-Dichloro-5-ethylpyrimidine

To a suspension of 5-ethylpyrimidine-4,6-diol (20.0 g, 0.14 mol) in dry toluene (200 mL) was added triethylamine (20.0 mL, 0.004 mol) at RT under nitrogen. The reaction mixture was heated to 115° C. and then POCl$_3$ (52.3 mL, 0.57 mol) was added in drops. The reaction mixture was stirred at same temperature for 3 h. After completion of the reaction, the reaction mixture was cooled to 0° C. and quenched with ice cold water (50 mL). The organic layer was separated, washed with saturated sodium bicarbonate (100 mL) and dried over sodium sulphate. The organic layer was concentrated under vacuum to afford the titled compound (22.5 g, 89%) as yellow liquid. $^1$H NMR (400 MHz, CDCl$_3$) 8.61 (bs, 1H), 2.95-2.89 (m, 2H), 1.25-1.22 (m, 3H).

Step 3: 6-Chloro-5-ethylpyrimidin-4-amine

To a mixture of 4,6-Dichloro-5-ethylpyrimidine (22.5 g, 0.12 mol) in 1-butanol (70 mL) in a 1L glass pressure tube was added aqueous ammonia (26%, 150 mL) at RT. The vessel was sealed and heated to 100° C. for 12 h. The reaction mixture was cooled to RT, the resulted solid was filtered, washed with water (50 mL) and dried under vacuum to afford the titled compound (11.0 g, 55%) as white solid. LCMS: Mass found (M+, 158.0). $^1$H NMR (400 MHz, CDCl3) 8.02 (s, 1H), 7.10 (bs, 2H), 2.57-2.50 (m, 2H), 1.03-0.99 (m, 3H).

Representative Synthesis of Intermediate B (Scheme 2)

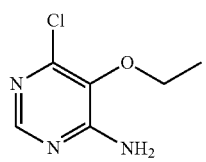

6-chloro-5-ethoxypyrimidin-4-amine

A reaction mixture of 4-amino-6-chloro-pyrimidin-5-ol (1000.0 mg; 6.8 mmol; 1.0 eq.), cesium carbonate (2686.3 mg; 8.24 mmol; 1.2 eq.), and iodoethane (1285.9 mg; 8.24 mmol; 1.2 eq.) in acetone (10 ml) was stirred at 50° C. overnight. The reaction solution was diluted with ethyl acetate (50 ml), washed with water, then brine, dried and concentrated. The residue was treated with ether, stirred for 30 min, filtered, collected white off solid as title compound (1165 mg in yield 98%).

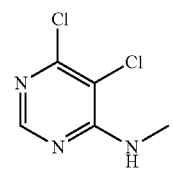

Intermediate C 5,6-dichloro-N-methylpyrimidin-4-amine (scheme 3)

To a stirred suspending solution of 4,5,6-trichloro-pyrimidine (300.00 mg; 1.00 eq.) in isoprpanol (1 ml), added 40% methylamine aq 1.0 ml and stirred at RT for 1 hr. The title compound was collected by filtration and washed with water (175 mg, yield 60%)

Representative Synthesis of Intermediate D (Scheme 4)

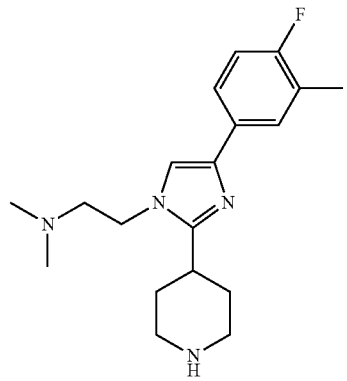

2-[4-(4-Fluoro-3-methylphenyl)-2-piperidin-4-yl-imidazol-1-yl]-ethyl-dimethylamine Step 1: tert-butyl 4-(1H-imidazol-2-yl)piperidine-1-carboxylate A solution of tert-butyl 4-formylpiperidine-1-carboxylate (99.0 g, 464.20 mmol) methanol (200 mL) was treated with 30% aqueous ammonium hydroxide (500 mL, 3.85 mol), followed by 40% aqueous glyoxal (53.50 mL, 466.42 mmol). The contents were allowed to stir at room temp for 1 h before it rotary evaporated to remove methanol. The remains were treated with brine (500 mL) and extracted with dichloromethane (1500 mL). The organics were dried over sodium sulfate and concentrated to a yellow oil. The oil was seeded with authentic material to afford an off-white solid as the title compound that was dried under vacuum for 6 h (110.37 g, 439.16 mmol, 95%).

Step 2: tert-butyl 4-(4-bromo-1H-imidazol-2-yl)piperidine-1-carboxylate

A solution of tert-butyl 4-(1H-imidazol-2-yl)piperidine-1-carboxylate (20.04 g, 79.74 mmol) in THF (450 mL) was cooled to −46 C (bath) before the flask was charged with NBS (14.27 g) in equal portions (10-min apart). LCMS data indicated complete reaction after 15 min, so the contents were concentrated to a yellow, solid foam that was further dried under vacuum overnight. The crude material (monobromide:dibromide=40:27) was purified by chromatography to give pure white solid (8.08 g, 24.47 mmol, 31%) as the title compound.

Step 3: tert-butyl 4-(4-bromo-1-(2-hydroxyethyl)-1H-imidazol-2-yl)piperidine-1-carboxylate A suspension of tert-butyl 4-(4-bromo-1H-imidazol-2-yl)piperidine-1-carboxylate (36.0 g, 109.02 mmol) in dry DMSO (400 mL) was treated with KOH (36.0 g, 641.60 mmol, 4.5 eq), and the contents became a clear-yellow solution after 20-30 min. After 90 min, the solution was treated with 2-(2-bromoethoxy)terahydropyran (36.0 g, 172.18 mmol, 1.2 eq). The reaction was deemed complete after 4 h by LCMS data, so the contents were diluted with ethyl acetate (800 mL) and washed with brine (3×800 mL). The organics were dried over sodium sulfate and concentrated to an oil with an approximate 8:1 ratio of regioisomers and the major isomer is the desired one. The oil was redissolved in methanol (400 mL) and treated with p-toluenesulfonic acid monohydrate (32.11 g, 168.80 mmol, 1.5 eq). The contents were stirred at room temp for 20 min, poured into ethyl acetate (500 mL) and washed with aqueous potassium carbonate (400 mL), followed by brine (2×400 mL). The organics were dried over sodium sulfate and concentrated to a colorless oil that was further dried under vacuum for 60 min. The resultant, thick oil was suspended in diethyl ether (200 mL) and rolled in an ice-water-salt bath for 90 min. A white solid precipitated, which was filtered and dried under vacuum for 30 min to give the title compound (25.15 g, 67.20 mmol, 62%, >96% by NMR and LCMS data).

Step 4: 4-[4-(4-Fluoro-3-methylphenyl)-1-(2-hydroxy-ethyl)-1H-imidazol-2-yl]-piperidine-1-carboxylic acid tert-butyl ester A mixture of 4-[4-bromo-1-(2-hydroxyethyl)-1H-imidazol-2-yl]-piperidine-1-carboxylic acid tert-butyl ester (1600.00 mg; 4.27 mmol; 1.00 eq.), 3-fluoro-4-methyl phenyl boronic acid (855.55 mg; 5.56 mmol; 1.30 eq.), palladium bis(tributylphosphine) (436.95 mg; 0.85 mmol; 0.20 eq.) and Cesium carbonate (4178.60 mg; 12.82 mmol; 3.00 eq.) in 1,4-Dioxane (10.0 mL) and water (1.50 mL) in the sealed vial was stirred at 70° C. for 5 hours. The crude was purified through flash chromatography (EtOAc in Hexanes 30% to 80%) to provide the title compound (1.2 g, 70%).

Step 5: 2-[4-(4-Fluoro-3-methylphenyl)-2-piperidin-4-yl-imidazol-1-yl]-ethyl-dimethylamine To a solution of 4-[4-(4-fluoro-3-methylphenyl)-1-(2-hydroxy-ethyl)-1H-imidazol-2-yl]-piperidine-1-carboxylic acid tert-butyl ester (1500.00 mg; 3.72 mmol; 1.00 eq.) in DCM (15 mL) at −78° C., were added 4-methylbenzenesulfonyl chloride (850.50 mg; 4.46 mmol; 1.20 eq.) and TEA (1128.54 mg; 11.15 mmol; 3.00 eq.). The mixture was stirred at −78° C. for 1 hour and was allowed to warm to room temperature and stirred overnight. DCM was removed and the residue was dissolved in Ether. The ether solution was washed with water twice, dried over MgSO4 and concentrated. The crude product was used for the next reaction without purification.

The mixture of above intermediate and dimethylamine (3352.05 mg; 74.35 mmol; 20.00 eq, 2.0M in THF) in the sealed vial was stirred for several hours. LC/MS and HPLC was used to monitor the reaction progress. After reaction was complete, the solvent was removed. The mixture was stirred for 20 minutes with TFA to remove the Boc group. The tittle compound was obtained through prep HPLC purification.

Representative Synthesis of Intermediate E (Scheme 5)

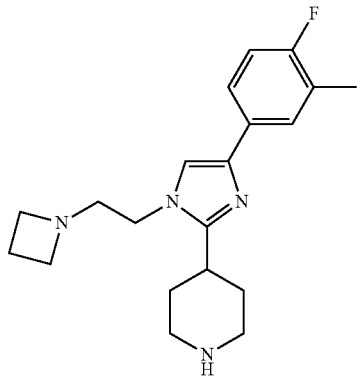 [SMILES: Cc1cc(-c2cn(CCN3CCC3)c(C3CCNCC3)n2)ccc1F]

4-(1-(2-(azetidin-1-yl)ethyl)-4-(4-fluoro-3-methylphenyl)-1H-imidazol-2-yl)piperidine Step 1: tert-butyl 4-(1-(2-(azetidin-1-yl)ethyl)-4-bromo-1H-imidazol-2-yl)piperidine-1-carboxylate A solution of tert-butyl 4-(4-bromo-1-(2-hydroxyethyl)-1H-imidazol-2-yl)piperidine-1-carboxylate (22.0 g) and Et₃N (24.5 ml) in DCM (250 ml) and cool to 0° C. Mesyl chloride (6.8 ml) was added dropwisely and the resulting mixture was stirred for 1 h. The reaction was quenched with saturated aqueous NaHCO₃ and extracted with DCM. The organic layer was concentrated to give tert-butyl 4-(4-bromo-1-(2-((methylsulfonyl)oxy)ethyl)-1H-imidazol-2-yl)piperidine-1-carboxylate (28.0 g).

A reaction mixture of tert-butyl 4-(4-bromo-1-(2-((methylsulfonyl)oxy)ethyl)-1H-imidazol-2-yl)piperidine-1-carboxylate (28.0 g) and azetidine (11 ml) in to DMF (200 ml) was stirred at 50° C. overnight. The reaction was diluted with EA, washed with water followed by saturated aqueous sodium chloride, dried and concentrated. The residue was purified by column chromatography to give tert-butyl 4-(1-(2-(azetidin-1-yl)ethyl)-4-bromo-1H-imidazol-2-yl)piperidine-1-carboxylate as off-white solid. (17.2 g).

Step 2: 4-(1-(2-(azetidin-1-yl)ethyl)-4-(4-fluoro-3-methylphenyl)-1H-imidazol-2-yl)piperidine A mixture of 4-[1-(2-Azetidin-1-yl-ethyl)-4-bromo-1H-imidazol-2-yl]-piperidine-1-carboxylic acid tert-butyl ester (8800.00 mg; 21.29 mmol; 1.00 eq.), 4-fluoro-3-methylphenylboronic acid (3932.91 mg; 25.55 mmol; 1.20 eq.) and Cs2CO3 (13872.97 mg; 42.58 mmol; 2.00 eq.) in doxane (80 ml) and water (8 ml) was purged by argon for 10 min, then Bis(tri-t-butylphosphine)palladium(0) (435.20 mg; 0.85 mmol; 0.04 eq.) was added under argon flow and purged by argon for 1 min. The resulting mixture was stirred at 50 C overnight. The reaction solution was diluted with ethyl acetate 250 ml, washed with brine-100 ml×2. The organic layer was dried and concentrated to afford the crude product which is purified by biotage Ki-Sil column to yield 4-[1-(2-azetidin-1-yl-ethyl)-4-(4-fluoro-3-methyl-phenyl)-1H-imidazol-2-yl]-piperidine-1-carboxylic acid tert-butyl ester (9370.00 mg; 99% yield).

To a solution of 4-[1-(2-azetidin-1-yl-ethyl)-4-(4-fluoro-3-methyl-phenyl)-1H-imidazol-2-yl]-piperidine-1-carboxylic acid tert-butyl ester in 55 ml of methanol, 4.0M HCl in dioxane (52.87 ml; 211.49 mmol; 10.00 eq.) was added slowly. the reaction mixture was stirred at RT for 4 hrs. LCMS showed the reaction was done. Off-white precipitate formed after 1 h stirring. The solid was collected by filtration and washed with ether 3 times to yield a white solid (8.78 g) as the pure title compound. The mother liquid was concentrated to dryness and added ether (30 mL) and ~5 ml of methanol. The solid was collected by filtration and washed with ether 3 time to provide another 0.82 g of the title compound as off-white solid (total yield: 100%)

Representative Synthesis of Intermediate F (Scheme 6)

4-(4-(4-fluoro-3-(trifluoromethyl)phenyl)-1-(2-(3-fluoroazetidin-1-yl)ethyl)-1H-imidazol-2-yl)piperidine

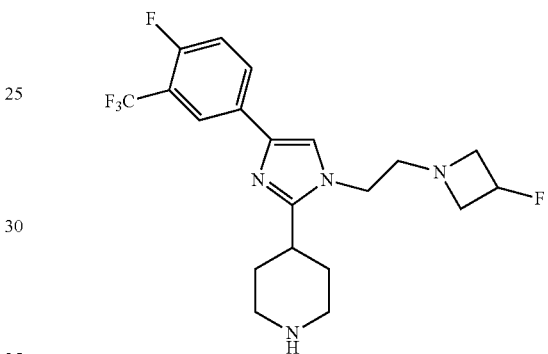

Step 1: 2-amino-1-(4-fluoro-3-(trifluoromethyl)phenyl)ethanone hydrochloride

2-Bromo-1-(4-fluoro-3-trifluoromethyl-phenyl)-ethanone (10.00 g; 35.08 mmol; 1.00 eq.) was added to a solution of 1,3,5,7-tetraaza-tricyclo[3.3.1.13,7]decane (5.80 g; 41.37 mmol; 1.18 eq.) in CCl4 100 ml, stirred overnight. The prepcipate was filtered and collected as a white solid.

The above solid was added ethanol 100 ml, and then 28 ml concentrated 36.5% HCl (aq) and stirred at RT over weekend, filtered off the solid. The filtrate was concentrated and solid came out. 10 ml of isoprpanol (contained 1% HCl) was added, filtered and collected white solid as the title compound 5.22 g, 57.8%

Step 2: tert-butyl 4-((2-(4-fluoro-3-(trifluoromethyl)phenyl)-2-oxoethyl)carbamoyl)piperidine-1-carboxylate To a solution of piperidine-1,4-dicarboxylic acid mono-tert-butyl ester (9611.92 mg; 41.92 mmol; 1.08 eq.) in THF 100 ml, added 4-methyl-morpholine (14.51 ml; 131.98 mmol; 3.40 eq.), The reaction mixture was cooled to −10° C., 3-methyl-butyryl chloride (5.03 ml; 38.82 mmol; 1.00 eq.) was add dropwise and maintaining the temperature below −5° C. after stirring for 30 mins at from −5° C. to 10° C., 2-(4-Fluoro-3-trifluoromethyl-phenyl)-2-oxo-ethyl-ammonium chloride (10.00 g; 38.82 mmol; 1.00 eq.) was added at −5° C. and stirred the mixture for 20 mins and then RT for 1 h. Added brine, extracted with EA, washed with brine, dried and concentrated. The crude oil was treated with ether. The white solid was collected as the title compound (12 g, yield 71.5%).

Step 3: tert-butyl 4-(4-(4-fluoro-3-(trifluoromethyl)phenyl)-1H-imidazol-2-yl)piperidine-1-carboxylate A mixture of 4-[2-(4-Fluoro-3-trifluoromethyl-phenyl)-2-oxo-ethylcarbamoyl]-piperidine-1-carboxylic acid tert-butyl ester (2900.00 mg; 6.71 mmol; 1.00 eq.), triethylamine (0.94 ml; 6.71 mmol; 1.00 eq.), and ammonium acetate (3618.76 mg; 46.95 mmol; 7.00 eq.) in 20 ml of n-butanol was placed in microwave (150° C.) for 20 min. after cooling to rt, the reaction mixture was diluted with 150 ml of ethyl acetate and washed with water, 5% NaHCO₃aq, then brine and concentrated. The residue was treated with ether and collected whit solid as title compound (1500 mg, 54% yield).

Step 4: benzyl 4-(4-(4-fluoro-3-(trifluoromethyl)phenyl)-1H-imidazol-2-yl)piperidine-1-carboxylate To 4-[4-(4-fluoro-3-trifluoromethyl-phenyl)-1H-imidazol-2-yl]-piperidine-1-carboxylic acid tert-butyl ester (6.00 g; 14.51 mmol; 1.00 eq.) in 10 ml of methanol 4.0 MHCl in dioxane 15 ml was added. The reaction mixture was stirred at RT overnight and concentrated to yield 4-(4-(4-fluoro-3-(trifluoromethyl)phenyl)-1H-imidazol-2-yl)piperidine hydrochloride salt as a white solid.

To 4-(4-(4-fluoro-3-(trifluoromethyl)phenyl)-1H-imidazol-2-yl)piperidine hydrochloride salt (1510.00 mg; 3.91 mmol; 1.00 eq.) in DCM was added Ethyldiisopropylamine (2.81 ml; 15.64 mmol; 4.00 eq.) and stirred for 5 mins. N-(Benzyloxycarbonyloxy) succinimide (1169.26 mg; 4.69 mmol; 1.20 eq.) was then added. The reaction mixture was stirred at RT overnight. The reaction mixture was diluted with DCM, washed with water, 5% NaHCO₃ aq and brine. The organic layer was dried and concentrated. The residue was subjected to SNAP column (100 g), eluted with 20-80% EA in hexane to afford the title compound (1310 mg, yield 74.9%).

Step 5: Benzyl 4-(1-((1,3-dioxolan-2-yl)methyl)-4-(4-fluoro-3-(trifluoromethyl)phenyl)-1H-imidazol-2-yl)piperidine-1-carboxylate The solution of 4-[4-(4-fluoro-3-trifluoromethyl-phenyl)-1H-imidazol-2-yl]-piperidine-1-carboxylic acid benzyl ester (1100.00 mg; 2.46 mmol; 1.00 eq.) in 2.0 ml of THF was cooled to −20° C., NaHMDS (541.00 mg; 2.95 mmol; 1.20 eq.) was added dropwise and the resulting mixture was stirred at RT for 30 mins. 2-Bromomethyl-[1,3]dioxolane (0.76 ml; 7.38 mmol; 3.00 eq.) was added and stirred at RT for 5 min. DMSO (10 ml) was added and the mixture was placed in microwave at 100° C. for 2 hr. The reaction mixture was cooled and diluted with water and extracted with EA. The organic layer was washed with brine, separated, dried and concentrated. The residue was subjected to snap column (100 g), eluted with 20%-80% EA in hexane to give the title compound (1000 mg, yield 76.2%).

Step 6: Benzyl 4-(4-(4-fluoro-3-(trifluoromethyl)phenyl)-1-(2-oxoethyl)-1H-imidazol-2-yl)piperidine-1-carboxylate The reaction mixture of benzyl 4-(1-((1,3-dioxolan-2-yl)methyl)-4-(4-fluoro-3-(trifluoromethyl)phenyl)-1H-imidazol-2-yl)piperidine-1-carboxylate (1450.00 mg; 2.72 mmol; 1.00 eq.) and toluene-4-sulfonic acid monohydrate (5169.79 mg; 27.18 mmol; 10.00 eq.) in 30 ml of acetone and 2.5 ml of water was stirred at 50° C. for one week. LC-MS showed some a mixture of the desired product, ~30% of starting material and some by products. The reaction mixture was concentrated and added 50 ml water, extracted with EA. The combined organic layers were washed with brine, dried and concentrated. The residue was subjected to SNAP column (100 g), eluted with 0-100% EA in hexane, then eluted with 10% methanol in DCM to afford the tile compound as yellow oil (480 mg, yield 36%) with a recovery of some starting material.

Step 7: Benzyl 4-(4-(4-fluoro-3-(trifluoromethyl)phenyl)-1-(2-(3-fluoroazetidin-1-yl)ethyl)-1H-imidazol-2-yl)piperidine-1-carboxylate 3-fluoro-azetidine hydrochloride (66.99 mg; 0.45 mmol; 1.05 eq.) in 1 ml of DCE was added ethyldiisopropylamine (0.15 ml; 0.86 mmol; 2.00 eq.). After stirring at RT for 10 mins, 4-[4-(4-fFluoro-3-trifluoromethyl-phenyl)-1-(2-oxo-ethyl)-1H-imidazol-2-yl]-piperidine-1-carboxylic acid benzyl ester (211.00 mg; 0.43 mmol; 1.00 eq.) was added, followed by sodium triacetoxyborohydride (274.09 mg; 1.29 mmol; 3.00 eq.). The resulting mixture was stirred overnight at RT. After workup, the title compound was obtained by pre-PLC purification.

Step 8: 4-(4-(4-Fluoro-3-(trifluoromethyl)phenyl)-1-(2-(3-fluoroazetidin-1-yl)ethyl)-1H-imidazol-2-yl)piperidine To 4-[1-[2-(3-f-azetidin-1-yl)-ethyl]-4-(4-fluoro-3-trifluoromethyl-phenyl)-1H-imidazol-2-yl]-piperidine-1-carboxylic acid benzyl ester (200.00 mg; 0.36 mmol; 1.00 eq.) in 10 ml of methanol was added ammonium format (229.90 mg; 3.65 mmol; 10.00 eq.) and 10% Pd/C (wet) 200 mg. The mixture was stirred at RT for 1 hr. Filtered off Pd/C. The filtrate was concentrated and then dissolved in EtOAc, washed with 5% NaHCO3, then brine, dried and concentrated. The crude title compound (138 mg, yield 91.3%) was directly used for the next step reaction without purification.

Example Compounds according to Formula (I) and Formula (II)

5-Bromo-6-{4-[4-(4-fluoro-3-trifluoromethyl-phenyl)-1-methyl-1H-imidazol-2-yl]-piperidin-1-yl}-pyrimidin-4-ylamine ("1")

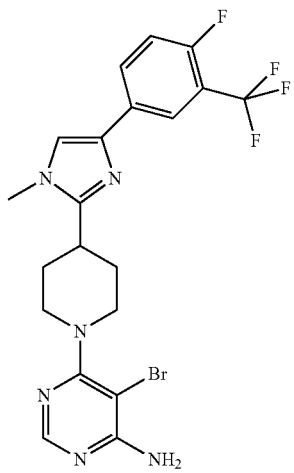 [SMILES: Cn1cc(-c2ccc(F)c(C(F)(F)F)c2)nc1C1CCN(c2ncnc(N)c2Br)CC1]

A mixture of 5-bromo-6-chloropyrimidin-4-amine (357.2 mg; 1.71 mmol; 1.02 eq.), 4-[4-(4-fluoro-3-trifluoromethyl-phenyl)-1-methyl-1h-imidazol-2-yl]-piperidine (550.00 mg; 1.68 mmol; 1.0 eq.), potassium carbonate (464.4 mg; 3.36 mmol; 2.0 eq.) in DMSO (6.0 ml) was stirred at 60° C. overnight. The reaction mixture was poured into water. The precipitate was filtered, washed with water and dried under vacuum to afford the title compound in 86% yield. LC-MS: (M+1=499, obsd.=499).

5-Bromo-6-{4-[5-(4-fluoro-3-trifluoromethyl-phenyl)-1-methyl-1H-imidazol-2-yl]-piperidin-1-yl}-pyrimidin-4-ylamine ("2")

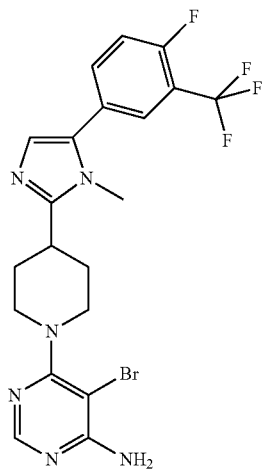 [SMILES: Cn1c(-c2ccc(F)c(C(F)(F)F)c2)cnc1C1CCN(c2ncnc(N)c2Br)CC1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[5-(4-fluoro-3-trifluoromethyl-phenyl)-1-methyl-1h-imidazol-2-yl]-piperidine instead of 4-[4-(4-fluoro-3-trifluoromethyl-phenyl)-1-methyl-1h-imidazol-2-yl]-piperidine. LC-MS: (M+1=499, obsd.=499).

5-Bromo-6-{4-[4-(3-trifluoromethyl-phenyl)-1H-imidazol-2-yl]-piperidin-1-yl}-pyrimidin-4-ylamine ("3")

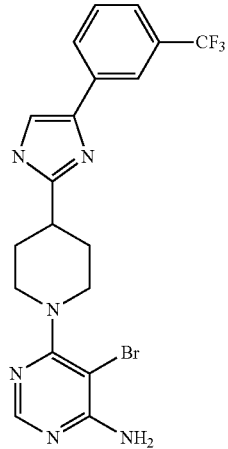 [SMILES: Nc1ncnc(N2CCC(c3nc(-c4cccc(C(F)(F)F)c4)c[nH]3)CC2)c1Br]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(3-trifluoromethyl-phenyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=467, obsd.=467).

5-Bromo-4-{4-[4-(3-trifluoromethyl-phenyl)-1H-imidazol-2-yl]-piperidin-1-yl}-pyrimidine ("4")

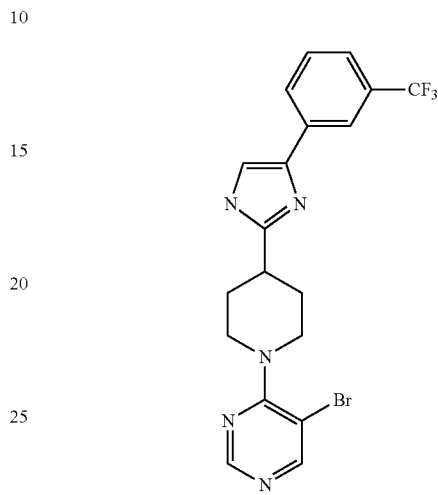

The title compound was prepared in an analogous manner as 5-Bromo-6-{4-[4-(3-trifluoromethyl-phenyl)-1H-imidazol-2-yl]-piperidin-1-yl}-pyrimidin-4-ylamine using 5-bromo-4-chloropyrimidine instead of 5-bromo-6-chloropyrimidin-4-amine. LC-MS: (M+1=452, obsd.=452).

3-bromo-4-(4-{4-[3-(trifluoromethyl)phenyl]-1H-imidazol-2-yl}piperidin-1-yl)pyridine ("5")

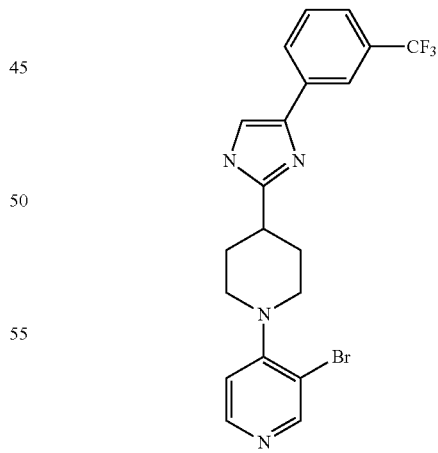

A mixture of 3-bromo-4-chloropyridine (100.0 mg; 0.52 mmol; 1.0 eq.), 4-[4-(3-trifluoromethyl-phenyl)-1h-imidazol-2-yl]-piperidine (153.4 mg; 0.52 mmol; 1.0 eq.), N,N-diisopropylethylamine (0.26 ml; 1.56 mmol; 3.0 eq.) in NMP (2.0 ml) in a microwave vial was heated at 160° C. for 4 h. The reaction mixture was poured into water. The precipitate was filtered, washed with water and dried under vacuum to afford the title compound in 64% yield. LC-MS: (M+1=451, obsd.=451).

4-Amino-6-{4-[4-(4-fluoro-3-trifluoromethyl-phenyl)-1-methyl-1H-imidazol-2-yl]-piperidin-1-yl}-pyrimidine-5-carbaldehyde ("6")

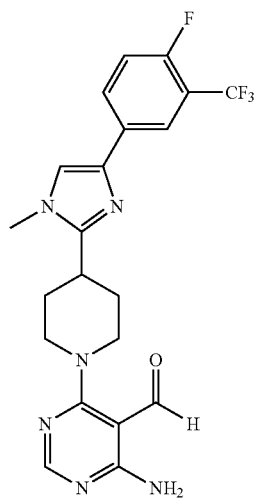 [SMILES: Cn1cc(-c2ccc(F)c(C(F)(F)F)c2)nc1C1CCN(c2ncnc(N)c2C=O)CC1]

A mixture of 4-[4-(4-fluoro-3-trifluoromethyl-phenyl)-1-methyl-1h-imidazol-2-yl]-piperidine (600.00 mg; 1.83 mmol; 1.0 eq.), 4-amino-6-chloropyrimidine-5-carbaldehyde (303.25 mg; 1.92 mmol; 1.05 eq.), DIEA (0.95 ml; 5.5 mmol; 3.0 eq.) in acetonitrile (10.0 ml) was heated at 40° C. for 1 h. The reaction mixture was poured into water. The precipitate was filtered, washed with water and dried under vacuum to afford the title compound in 85% yield. LC-MS: (M+1=449, obsd.=449).

4-Amino-6-{4-[4-(4-fluoro-3-trifluoromethyl-phenyl)-1-methyl-1H-imidazol-2-yl]-piperidin-1-yl}-pyrimidine-5-carbonitrile ("7")

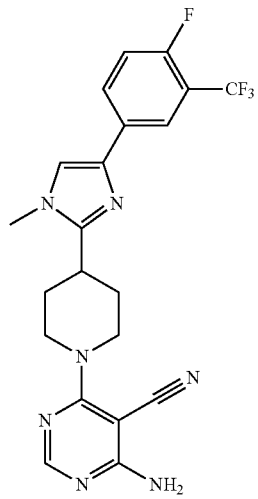 [SMILES: Cn1cc(-c2ccc(F)c(C(F)(F)F)c2)nc1C1CCN(c2ncnc(N)c2C#N)CC1]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carbaldehyde using 4-amino-6-chloropyrimidine-5-carbonitrile instead of 4-amino-6-chloropyrimidine-5-carbaldehyde. LC-MS: (M+1=446, obsd.=446).

4-Amino-6-{4-[1-(2-dimethylamino-ethyl)-4-(4-fluoro-3-trifluoromethyl-phenyl)-1H-imidazol-2-yl]-piperidin-1-yl}-pyrimidine-5-carbonitrile ("8")

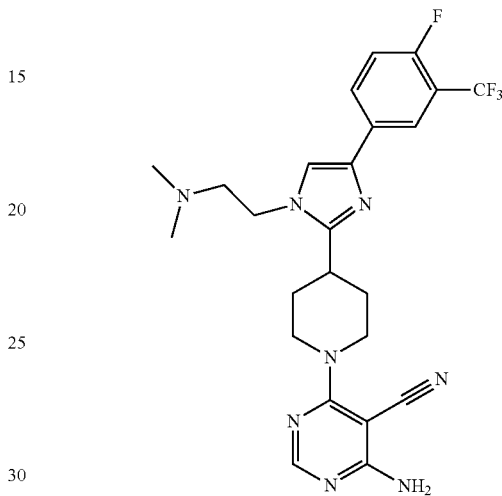

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carbonitrile using 2-(4-(4-fluoro-3-(trifluoromethyl)phenyl)-2-(piperidin-4-yl)-1H-imidazol-1-yl)-N,N-dimethylethanamine instead of 4-[4-(4-fluoro-3-trifluoromethyl-phenyl)-1-methyl-1h-imidazol-2-yl]-piperidine. LC-MS: (M+1=503, obsd.=503).

6-{4-[4-(4-Fluoro-3-trifluoromethyl-phenyl)-1-methyl-1H-imidazol-2-yl]-piperidin-1-yl}-5-methoxy-pyrimidin-4-ylamine ("9")

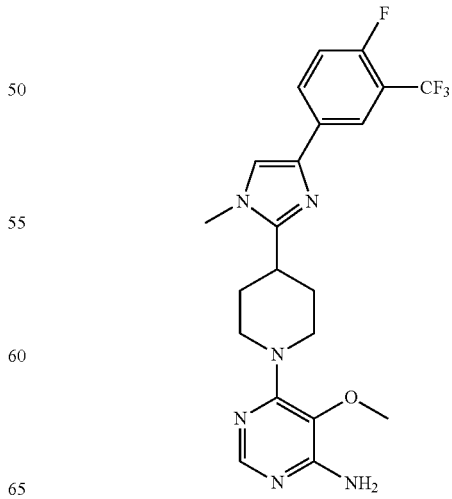

A mixture of 4-[4-(4-fluoro-3-trifluoromethyl-phenyl)-1-methyl-1h-imidazol-2-yl]-piperidine (40.00 mg; 0.12 mmol; 1.0 eq.), 6-chloro-5-methoxypyrimidin-4-amine (20.48 mg; 0.13 mmol; 1.05 eq.), potassium carbonate (33.78 mg; 0.24 mmol; 2.0 eq.) in DMSO (1.00 ml) in a microwave vial was heated at 150° C. for 2 h. LC-MS show ~40% conversion and product eluted closely to the amine starting material. The reaction mixture was workup and the crude was purified by reverse phase pre-HPLC (Waters, acetonitrile/0.1% TFA in water) to yield desired product in 22% yield. LC-MS: (M+1=451, obsd.=451).

5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine ("10")

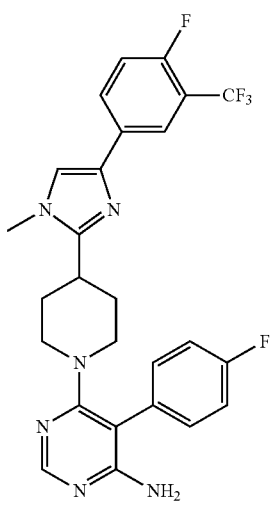 [SMILES: Cn1cc(-c2ccc(F)c(C(F)(F)F)c2)nc1C1CCN(c2ncnc(N)c2-c2ccc(F)cc2)CC1]

A mixture of 5-bromo-6-(4-{4-[4-fluoro-3-(trifluoromethyl)phenyl]-1-methyl-1H-imidazol-2-yl}piperidin-1-yl)pyrimidin-4-amine (100.0 mg; 0.2 mmol; 1.0 eq.), (4-fluorophenyl)boronic acid (56.0 mg; 0.4 mmol; 2.0 eq.), palladium(II) acetate (2.25 mg; 0.01 mmol; 0.05 eq.), dicyclohexyl(2',6'-dimethoxybiphenyl-2-yl)phosphine (8.22 mg; 0.02 mmol; 0.1 eq.) and cesium carbonate (195.7 mg; 0.6 mmol; 3.0 eq.) in dioxane (4 ml) and water (0.5 ml) in the microwave vial was heated at 100° C. for 30 min. The reaction mixture was workup and the crude was purified by reverse phase chromatography (Yamazen, acetonitrile/0.1% NH4OH in water). The pure fractions were concentrated to dryness under vacuum. The white solid was dissolved in water and acetonitrile, 200 µL of 0.5 N HCl was added. The excess of HCl was removed by concentrating under vacuum for 20 min. The resulting solution was then lyophilized to afford the title compound as HCl salt in 74% yield. LC-MS: (M+1=515, obsd.=515).

6-{4-[4-(4-Fluoro-3-trifluoromethyl-phenyl)-1-methyl-1H-imidazol-2-yl]-piperidin-1-yl}-5-(4-methoxy-phenyl)-pyrimidin-4-ylamine ("11")

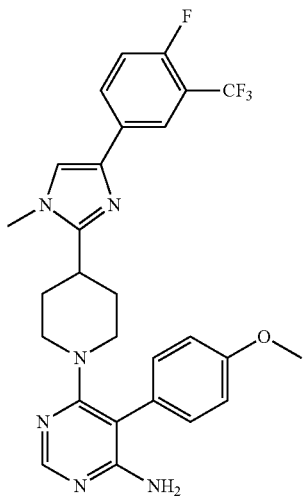

The title compound was prepared in an analogous manner as 5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine using 4-methoxyphenylboronic acid instead of 4-fluorophenylboronic acid. LC-MS: (M+1=527, obsd.=527).

6-{4-[4-(4-Fluoro-3-trifluoromethyl-phenyl)-1-methyl-1H-imidazol-2-yl]-piperidin-1-yl}-pyrimidin-4-ylamine ("12")

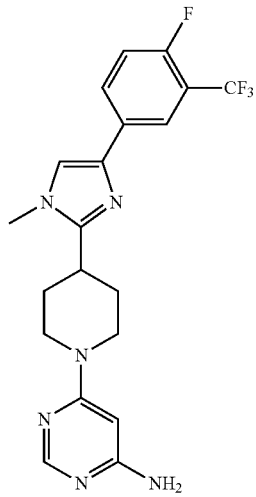 [SMILES: Cn1cc(-c2ccc(F)c(C(F)(F)F)c2)nc1C1CCN(c2cc(N)ncn2)CC1]

The title compound was obtained as the de-brominating by-product during the preparation of 6-{4-[4-(4-Fluoro-3-trifluoromethyl-phenyl)-1-methyl-1H-imidazol-2-yl]-piperidin-1-yl}-5-(4-methoxy-phenyl)-pyrimidin-4-ylamine. LC-MS: (M+1=421, obsd.=421).

6-{4-[4-(4-Fluoro-3-trifluoromethyl-phenyl)-1-methyl-1H-imidazol-2-yl]-piperidin-1-yl}-5-p-tolyl-pyrimidin-4-ylamine ("13")

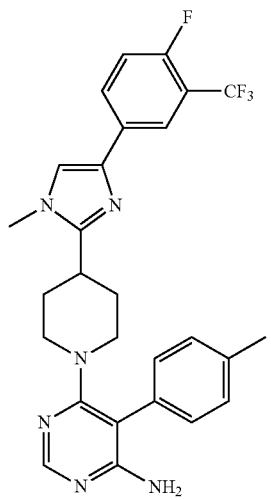

The title compound was prepared in an analogous manner as 5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine using 4-methylphenylboronic acid instead of 4-fluorophenylboronic acid. LC-MS: (M+1=511, obsd.=511).

[4-(4-Amino-6-{4-[4-(4-fluoro-3-trifluoromethyl-phenyl)-1-methyl-1H-imidazol-2-yl]-piperidin-1-yl}-pyrimidin-5-yl)-phenyl]-methanol ("14")

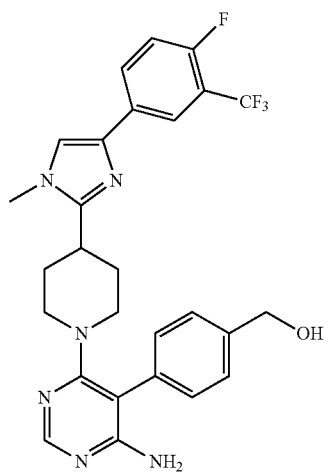 [SMILES: Cn1cc(-c2ccc(F)c(C(F)(F)F)c2)nc1C1CCN(c2ncnc(N)c2-c2ccc(CO)cc2)CC1]

The title compound was prepared in an analogous manner as 5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine using 4-(hydroxymethyl)benzeneboronic acid pinacol ester instead of 4-fluorophenylboronic acid. LC-MS: (M+1=527, obsd.=527).

3-(4-Amino-6-{4-[4-(4-fluoro-3-trifluoromethyl-phenyl)-1-methyl-1H-imidazol-2-yl]-piperidin-1-yl}-pyrimidin-5-yl)-benzonitrile ("15")

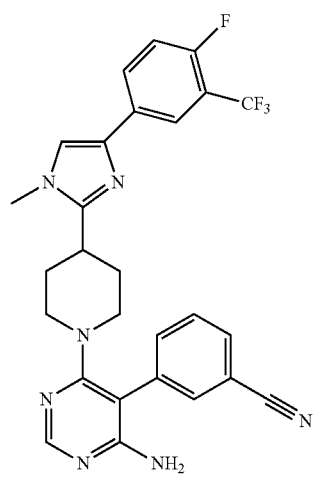 [SMILES: Cn1cc(-c2ccc(F)c(C(F)(F)F)c2)nc1C1CCN(c2ncnc(N)c2-c2cccc(C#N)c2)CC1]

The title compound was prepared in an analogous manner as 5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine using 3-cyanophenylboronic acid instead of 4-fluorophenylboronic acid. LC-MS: (M+1=522, obsd.=522).

6-{4-[4-(4-Fluoro-3-trifluoromethyl-phenyl)-1-methyl-1H-imidazol-2-yl]-piperidin-1-yl}-5-(4-trifluoromethyl-phenyl)-pyrimidin-4-ylamine ("16")

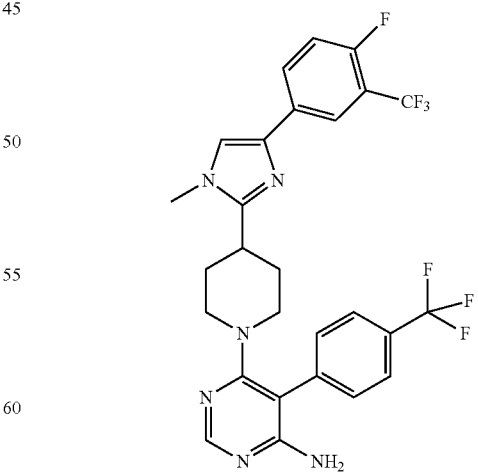

The title compound was prepared in an analogous manner as 5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine using (4-trifluoromethyl)phenylboronic acid instead of 4-fluorophenylboronic acid. LC-MS: (M+1=565, obsd.=565).

4-(4-Amino-6-{4-[4-(4-fluoro-3-trifluoromethyl-phenyl)-1-methyl-1H-imidazol-2-yl]-piperidin-1-yl}-pyrimidin-5-yl)-benzonitrile ("17")

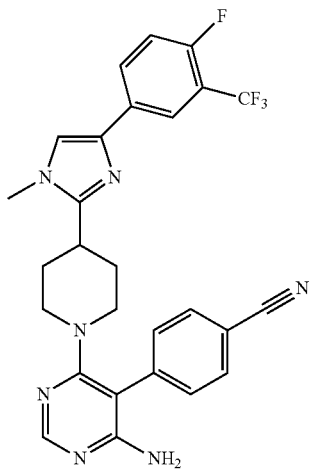 [SMILES: Cn1cc(-c2ccc(F)c(C(F)(F)F)c2)nc1C1CCN(c2ncnc(N)c2-c2ccc(C#N)cc2)CC1]

The title compound was prepared in an analogous manner as 5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine using 4-cyanophenylboronic acid instead of 4-fluorophenylboronic acid. LC-MS: (M+1=522, obsd.=522).

2-(4-Amino-6-{4-[4-(4-fluoro-3-trifluoromethyl-phenyl)-1-methyl-1H-imidazol-2-yl]-piperidin-1-yl}-pyrimidin-5-yl)-benzonitrile ("18")

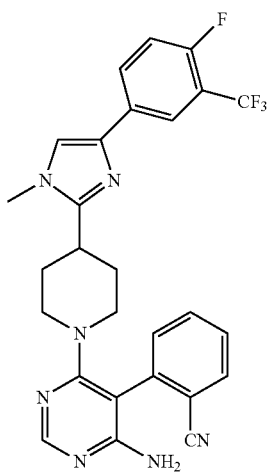 [SMILES: Cn1cc(-c2ccc(F)c(C(F)(F)F)c2)nc1C1CCN(c2ncnc(N)c2-c2ccccc2C#N)CC1]

The title compound was prepared in an analogous manner as 5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine using 2-cyanophenylboronic acid instead of 4-fluorophenylboronic acid. LC-MS: (M+1=522, obsd.=522).

6-{4-[4-(4-Fluoro-3-trifluoromethyl-phenyl)-1-methyl-1H-imidazol-2-yl]-piperidin-1-yl}-5-(6-methyl-pyridin-3-yl)-pyrimidin-4-ylamine ("19")

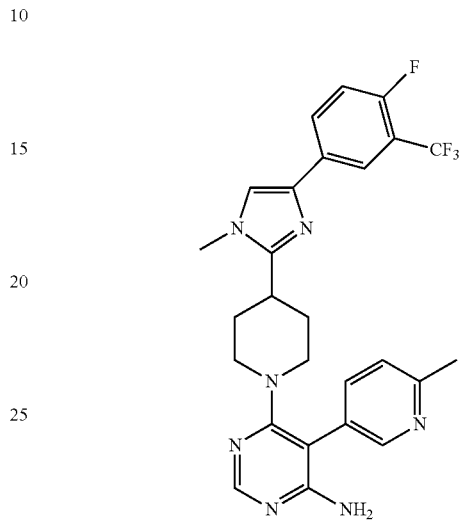

The title compound was prepared in an analogous manner as 5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine using 6-methylpyridin-3-yl)boronic acid instead of 4-fluorophenylboronic acid. LC-MS: (M+1=512, obsd.=512).

6-{4-[4-(4-Fluoro-3-trifluoromethyl-phenyl)-1-methyl-1H-imidazol-2-yl]-piperidin-1-yl}-5-(5-methyl-thiophen-2-yl)-pyrimidin-4-ylamine ("20")

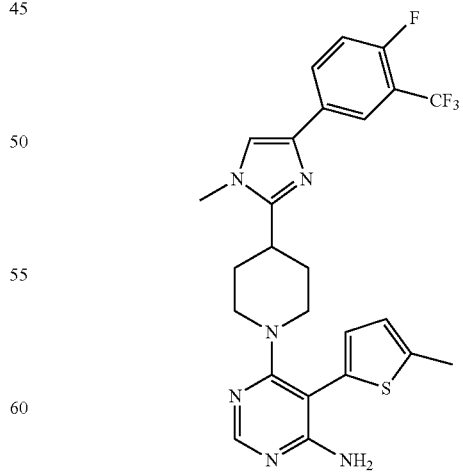

The title compound was prepared in an analogous manner as 5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine using 5-methylthiophene-2-boronic acid pinacol ester instead of 4-fluorophenylboronic acid. LC-MS: (M+1=517, obsd.=517).

6-{4-[4-(4-Fluoro-3-trifluoromethyl-phenyl)-1-methyl-1H-imidazol-2-yl]-piperidin-1-yl}-5-phenyl-pyrimidin-4-ylamine ("21")

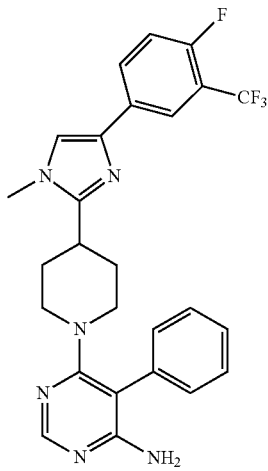 [SMILES: Cn1cc(-c2ccc(F)c(C(F)(F)F)c2)nc1C1CCN(c2ncnc(N)c2-c2ccccc2)CC1]

The title compound was prepared in an analogous manner as 5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine using phenylboronic acid instead of 4-fluorophenylboronic acid. LC-MS: (M+1=497, obsd.=497).

5-(3-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine ("22")

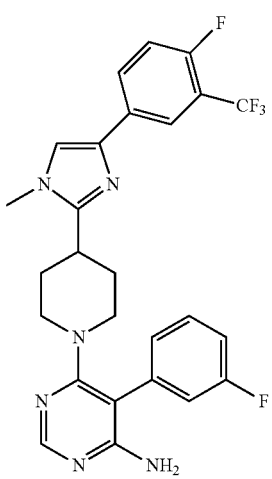 [SMILES: Cn1cc(-c2ccc(F)c(C(F)(F)F)c2)nc1C1CCN(c2ncnc(N)c2-c2cccc(F)c2)CC1]

The title compound was prepared in an analogous manner as 5-(4-fluoro-phenyl)-6-{4-[4-(4-fluoro-3-trifluoromethyl-phenyl)-1-methyl-1H-imidazol-2-yl]-piperidin-1-yl}-pyrimidin-4-ylamine using 3-fluorophenylboronic acid instead of 4-fluorophenylboronic acid. LC-MS: (M+1=515, obsd.=515).

5-(2-Fluorophenyl)-6-{4-[4-(4-fluoro-3-trifluoromethyl-phenyl)-1-methyl-1H-imidazol-2-yl]-piperidin-1-yl}-pyrimidin-4-ylamine ("23")

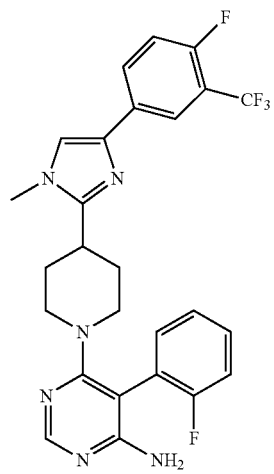 [SMILES: Cn1cc(-c2ccc(F)c(C(F)(F)F)c2)nc1C1CCN(c2ncnc(N)c2-c2ccccc2F)CC1]

The title compound was prepared in an analogous manner as 5-(4-fluoro-phenyl)-6-{4-[4-(4-fluoro-3-trifluoromethyl-phenyl)-1-methyl-1H-imidazol-2-yl]-piperidin-1-yl}-pyrimidin-4-ylamine using 2-fluorophenylboronic acid instead of 4-fluorophenylboronic acid. LC-MS: (M+1=515, obsd.=515).

5-(2-Chlorophenyl)-6-{4-[4-(4-fluoro-3-trifluoromethyl-phenyl)-1-methyl-1H-imidazol-2-yl]-piperidin-1-yl}-pyrimidin-4-ylamine ("24")

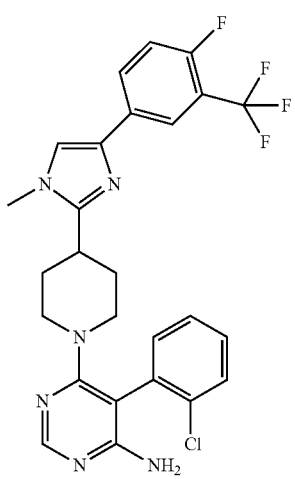 [SMILES: Cn1cc(-c2ccc(F)c(C(F)(F)F)c2)nc1C1CCN(c2ncnc(N)c2-c2ccccc2Cl)CC1]

The title compound was prepared in an analogous manner as 5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine using 2-chlorophenylboronic acid instead of 4-fluorophenylboronic acid. LC-MS: (M+1=531, obsd.=531).

6-{4-[4-(4-Fluoro-3-trifluoromethyl-phenyl)-1-methyl-1H-imidazol-2-yl]-piperidin-1-yl}-5-(6-morpholin-4-yl-pyridin-3-yl)-pyrimidin-4-ylamine ("25")

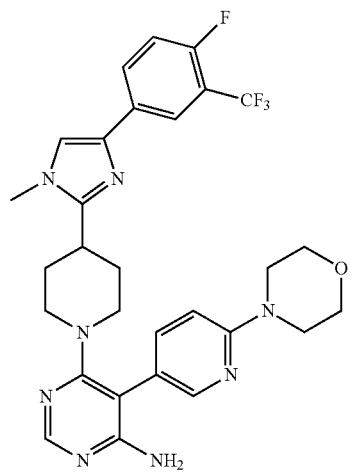 [SMILES: Cn1cc(-c2ccc(F)c(C(F)(F)F)c2)nc1C1CCN(c2ncnc(N)c2-c2ccc(N3CCOCC3)nc2)CC1]

The title compound was prepared in an analogous manner as 5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine using (6-morpholinopyridin-3-yl)boronic acid instead of 4-fluorophenylboronic acid. LC-MS: (M+1=583, obsd.=583).

6-{4-[4-(4-Fluoro-3-trifluoromethyl-phenyl)-1-methyl-1H-imidazol-2-yl]-piperidin-1-yl}-5-(6-piperazin-1-yl-pyridin-3-yl)-pyrimidin-4-ylamine ("26")

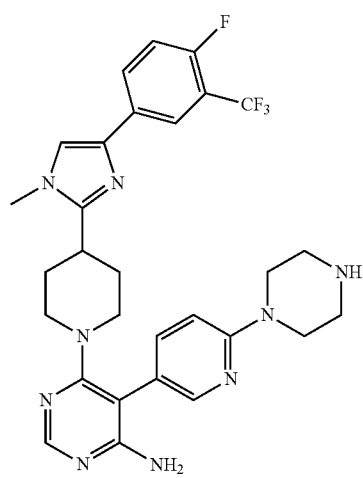 [SMILES: Cn1cc(-c2ccc(F)c(C(F)(F)F)c2)nc1C1CCN(c2ncnc(N)c2-c2ccc(N3CCNCC3)nc2)CC1]

The title compound was prepared in an analogous manner as 5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine using (6-(piperazin-1-yl)pyridin-3-yl)boronic acid instead of 4-fluorophenylboronic acid. LC-MS: (M+1=582, obsd.=582).

5-(6-Fluoro-pyridin-3-yl)-6-{4-[4-(4-fluoro-3-trifluoromethyl-phenyl)-1-methyl-1H-imidazol-2-yl]-piperidin-1-yl}-pyrimidin-4-ylamine ("27")

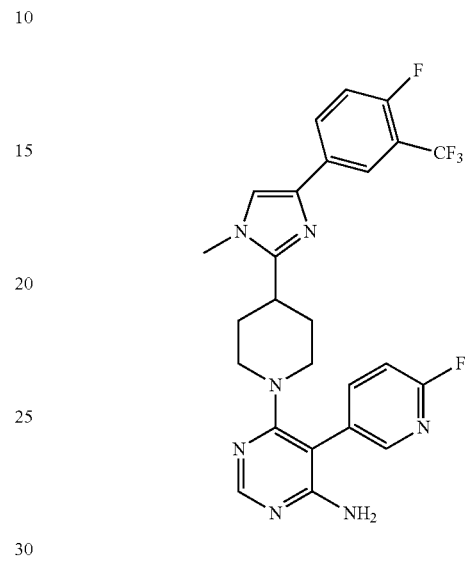

The title compound was prepared in an analogous manner as 5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine using (6-fluoropyridin-3-yl)boronic acid pinacol ester instead of 4-fluorophenylboronic acid. LC-MS: (M+1=516, obsd.=516).

6'-{4-[4-(4-Fluoro-3-trifluoromethyl-phenyl)-1-methyl-1H-imidazol-2-yl]-piperidin-1-yl}-[5,5']bipyrimidinyl-2,4'-diamine ("28")

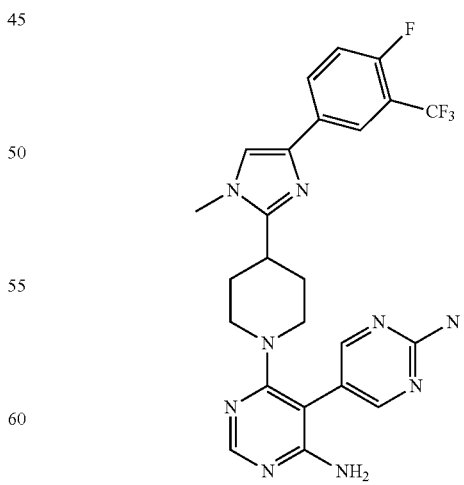

The title compound was prepared in an analogous manner as 5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine using (2-aminopyrimidin-5-yl)boronic acid pinacol ester instead of 4-fluorophenylboronic acid. LC-MS: (M+1=514, obsd.=514).

6-{4-[4-(4-Fluoro-3-trifluoromethyl-phenyl)-1-methyl-1H-imidazol-2-yl]-piperidin-1-yl}-5-(3-methoxyphenyl)-pyrimidin-4-ylamine ("29")

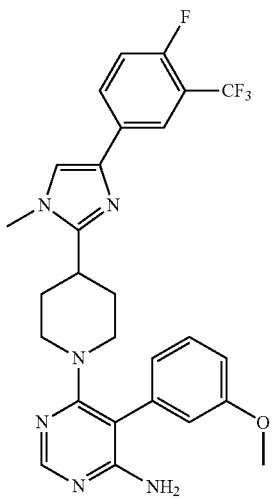

The title compound was prepared in an analogous manner as 5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine using 3-methoxyphenylboronic acid instead of 4-fluorophenylboronic acid. LC-MS: (M+1=527, obsd.=527).

5-(3,4-Difluoro-phenyl)-6-{4-[4-(4-fluoro-3-trifluoromethyl-phenyl)-1-methyl-1H-imidazol-2-yl]-piperidin-1-yl}-pyrimidin-4-ylamine ("30")

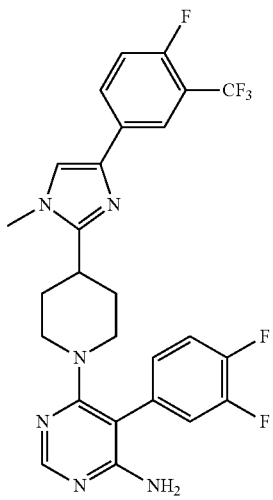 [SMILES: Cn1cc(-c2ccc(F)c(C(F)(F)F)c2)nc1C1CCN(c2ncnc(N)c2-c2ccc(F)c(F)c2)CC1]

The title compound was prepared in an analogous manner as 5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine using 3,4-difluorophenylboronic acid instead of 4-fluorophenylboronic acid. LC-MS: (M+1=533, obsd.=533).

6'-{4-[4-(4-Fluoro-3-trifluoromethyl-phenyl)-1-methyl-1H-imidazol-2-yl]-piperidin-1-yl}-N2,N2-dimethyl-[5,5]bipyrimidinyl-2,4'-diamine ("31")

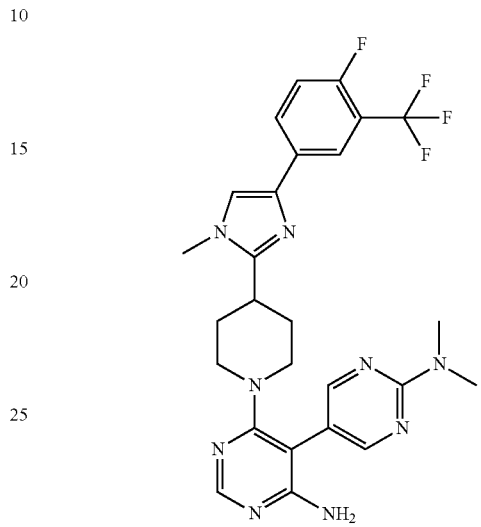

The title compound was prepared in an analogous manner as 5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine using (2-(dimethylamino)pyrimidin-5-yl)boronic acid instead of 4-fluorophenylboronic acid. LC-MS: (M+1=542, obsd.=542).

5-(4-Aminomethyl-phenyl)-6-{4-[4-(4-fluoro-3-trifluoromethyl-phenyl)-1-methyl-1H-imidazol-2-yl]-piperidin-1-yl}-pyrimidin-4-ylamine ("32")

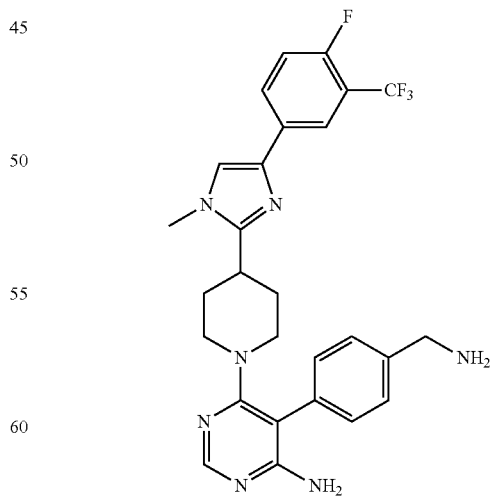

The title compound was prepared in an analogous manner as 5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine using (4-(aminomethyl)phenyl)boronic acid instead of 4-fluorophenylboronic acid. LC-MS: (M+1=526, obsd.=526).

5-(4-Methoxy-phenyl)-6-{4-[4-(3-trifluoromethyl-phenyl)-1H-imidazol-2-yl]-piperidin-1-yl}-pyrimidin-4-ylamine ("33")

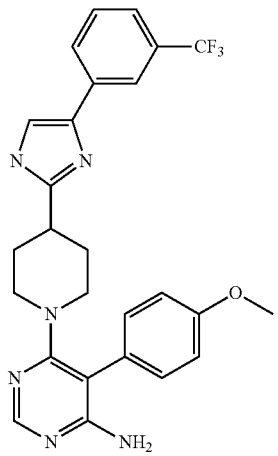 [SMILES: COc1ccc(-c2c(N)ncnc2N2CCC(c3nc(-c4cccc(C(F)(F)F)c4)c[nH]3)CC2)cc1]

The title compound was prepared in an analogous manner as 6-{4-[4-(4-Fluoro-3-trifluoromethyl-phenyl)-1-methyl-1H-imidazol-2-yl]-piperidin-1-yl}-5-(4-methoxy-phenyl)-pyrimidin-4-ylamine using 5-Bromo-6-{4-[4-(3-trifluoromethyl-phenyl)-1H-imidazol-2-yl]-piperidin-1-yl}-pyrimidin-4-ylamine instead of 5-bromo-6-(4-{4-[4-fluoro-3-(trifluoromethyl)phenyl]-1-methyl-1H-imidazol-2-yl}piperidin-1-yl)pyrimidin-4-amine. LC-MS: (M+1=495, obsd.=495).

5-(4-Methoxy-phenyl)-4-{4-[4-(3-trifluoromethyl-phenyl)-1H-imidazol-2-yl]-piperidin-1-yl}-pyrimidine ("34")

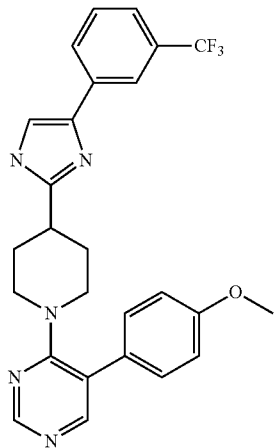 [SMILES: COc1ccc(-c2cncnc2N2CCC(c3nc(-c4cccc(C(F)(F)F)c4)c[nH]3)CC2)cc1]

The title compound was prepared in an analogous manner as 6-{4-[4-(4-Fluoro-3-trifluoromethyl-phenyl)-1-methyl-1H-imidazol-2-yl]-piperidin-1-yl}-5-(4-methoxy-phenyl)-pyrimidin-4-ylamine using 5-Bromo-4-{4-[4-(3-trifluoromethyl-ethyl-phenyl)-1H-imidazol-2-yl]-piperidin-1-yl}-pyrimidine instead of 5-bromo-6-(4-{4-[4-fluoro-3-(trifluoromethyl)phenyl]-1-methyl-1H-imidazol-2-yl}piperidin-1-yl)pyrimidin-4-amine. LC-MS: (M+1=480, obsd.=480).

3-(4-methoxyphenyl)-4-(4-{4-[3-(trifluoromethyl)phenyl]-1H-imidazol-2-yl}piperidin-1-yl)pyridine ("35")

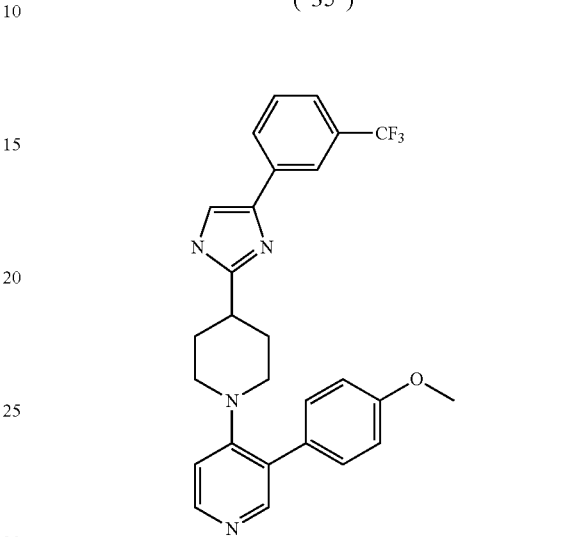

The title compound was prepared in an analogous manner as 6-{4-[4-(4-Fluoro-3-trifluoromethyl-phenyl)-1-methyl-1H-imidazol-2-yl]-piperidin-1-yl}-5-(4-methoxy-phenyl)-pyrimidin-4-ylamine using 3-bromo-4-(4-{4-[3-(trifluoromethyl)phenyl]-1H-imidazol-2-yl}piperidin-1-yl)pyridine instead of 5-bromo-6-(4-{4-[4-fluoro-3-(trifluoromethyl)phenyl]-1-methyl-1H-imidazol-2-yl}piperidin-1-yl)pyrimidin-4-amine. LC-MS: (M+1=479, obsd.=479).

(4-Amino-6-{4-[4-(4-fluoro-3-trifluoromethyl-phenyl)-1-methyl-1H-imidazol-2-yl]-piperidin-1-yl}-pyrimidin-5-yl)-methanol ("36")

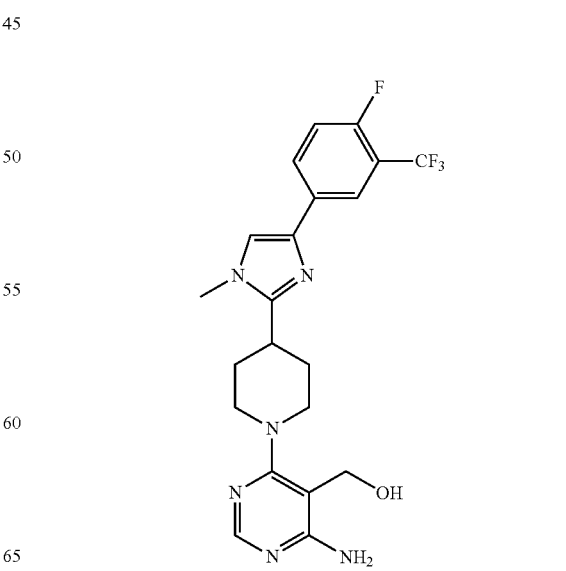

The reaction mixture of 4-amino-6-(4-{4-[4-fluoro-3-(trifluoromethyl)phenyl]-1-methyl-1H-imidazol-2-yl}piperidin-1-yl)pyrimidine-5-carbaldehyde (23.00 mg; 0.05 mmol; 1.0 eq.) and sodium borohydride (7.8 mg; 0.21 mmol; 4.0 eq.) in EtOH (2.00 ml) was stirred at room temperature over weekend. The reaction mixture was workup and purified by reverse phase chromatography (Yamazen, acetonitrile/0.1% NH4OH in water). The pure fractions were lyophilized to afford the title compound in 65% yield. LC-MS: (M+1=451, obsd.=451).

4-Amino-6-{4-[4-(4-fluoro-3-trifluoromethyl-phenyl)-1-methyl-1H-imidazol-2-yl]-piperidin-1-yl}-pyrimidine-5-carboxamide ("37")

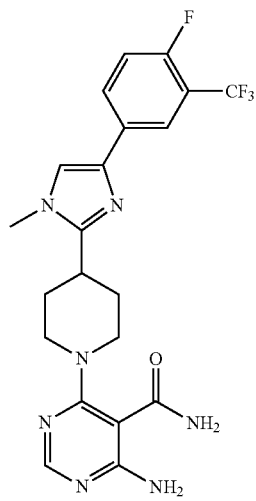

Hydrogen peroxide (0.40 ml; 4.49 mmol; 40.0 eq.) was added dropwise to the mixture of 4-amino-6-(4-{4-[4-fluoro-3-(trifluoromethyl)phenyl]-1-methyl-1H-imidazol-2-yl}piperidin-1-yl)pyrimidine-5-carbonitrile (50.0 mg; 0.11 mmol; 1.0 eq.) and potassium carbonate (124.1 mg; 0.9 mmol; 8.0 eq.) in DMSO (3.0 ml) at room temperature. The resulting mixture was then stirred at 40° C. for 5 hours. The reaction mixture was poured into water, filtered and washed with water. The crude was purified by reverse phase chromatography (Yamazen, acetonitrile/0.1% NH4OH in water). The fractions were evaporated to dryness under vacuum. The white solid was dissolved in water and acetonitrile, 200 □L of 0.5N HCl was added. The clear solution was then evaporated under vacuum for 10 min to remove excess of HCl. The solution was then lyophilized to yield the title compound as HCl salt in 88% yield. LC-MS: (M+1=464, obsd.=464).

4-Amino-6-{4-[1-(2-dimethylamino-ethyl)-4-(4-fluoro-3-trifluoromethyl-phenyl)-1H-imidazol-2-yl]-piperidin-1-yl}-pyrimidine-5-carboxylic acid amide ("38")

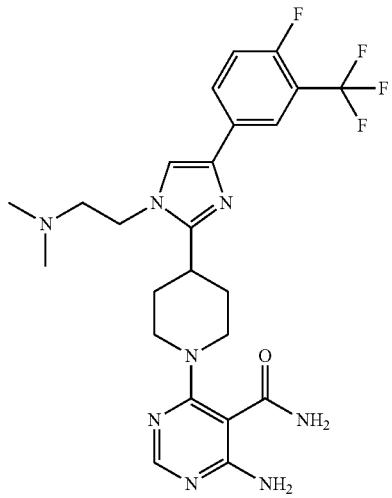 [SMILES: CN(C)CCn1cc(-c2ccc(F)c(C(F)(F)F)c2)nc1C1CCN(c2ncnc(N)c2C(N)=O)CC1]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-{4-[1-(2-dimethylamino-ethyl)-4-(4-fluoro-3-trifluoromethyl-phenyl)-1H-imidazol-2-yl]-piperidin-1-yl}-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=521, obsd.=521).

6-{4-[4-(4-Fluoro-3-trifluoromethyl-phenyl)-1-methyl-1H-imidazol-2-yl]-piperidin-1-yl}-5-pyridin-4-yl-pyrimidin-4-ylamine ("39")

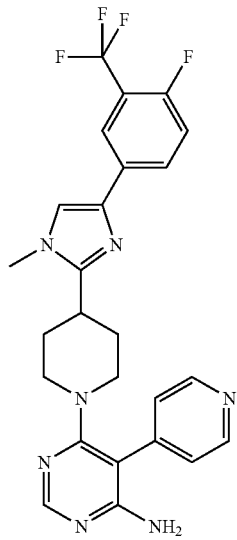 [SMILES: Cn1cc(-c2ccc(F)c(C(F)(F)F)c2)nc1C1CCN(c2ncnc(N)c2-c2ccncc2)CC1]

The title compound was prepared in an analogous manner as 5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine using 4-pyridylboronic acid pinacol ester instead of 4-fluorophenylboronic acid. LC-MS: (M+1=498, obsd.=498).

5-(6-Amino-pyridin-3-yl)-6-{4-[4-(4-fluoro-3-trifluoromethyl-phenyl)-1-methyl-1H-imidazol-2-yl]-piperidin-1-yl}-pyrimidin-4-ylamine ("40")

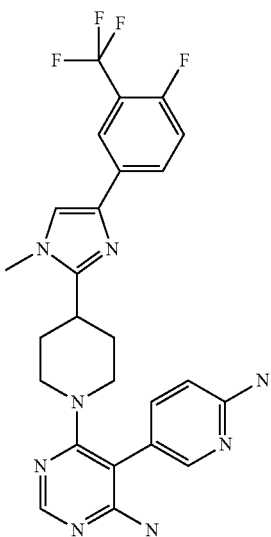 [SMILES: Cn1cc(-c2ccc(F)c(C(F)(F)F)c2)nc1C1CCN(c2ncnc(N)c2-c2ccc(N)nc2)CC1]

The title compound was prepared in an analogous manner as 5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine using 2-aminopyridine-5-boronic acid pinacol ester instead of 4-fluorophenylboronic acid. LC-MS: (M+1=513, obsd.=513).

5-Bromo-4-{4-[4-(4-fluoro-3-trifluoromethyl-phenyl)-1-methyl-1H-imidazol-2-yl]-piperidin-1-yl}-pyrimidine ("41")

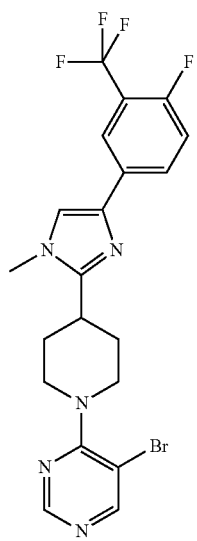 [SMILES: Cn1cc(-c2ccc(F)c(C(F)(F)F)c2)nc1C1CCN(c2ncncc2Br)CC1]

The title compound was prepared in an analogous manner as 5-Bromo-6-{4-[4-(3-trifluoromethyl-phenyl)-1H-imidazol-2-yl]-piperidin-1-yl}-pyrimidin-4-ylamine using 5-bromo-4-chloropyrimidine instead of 5-bromo-6-chloro-pyrimidin-4-amine. LC-MS: (M+1=484, obsd.=484).

5-(4-Fluoro-phenyl)-4-{4-[4-(4-fluoro-3-trifluoromethyl-phenyl)-1-methyl-1H-imidazol-2-yl]-piperidin-1-yl}-pyrimidine ("42")

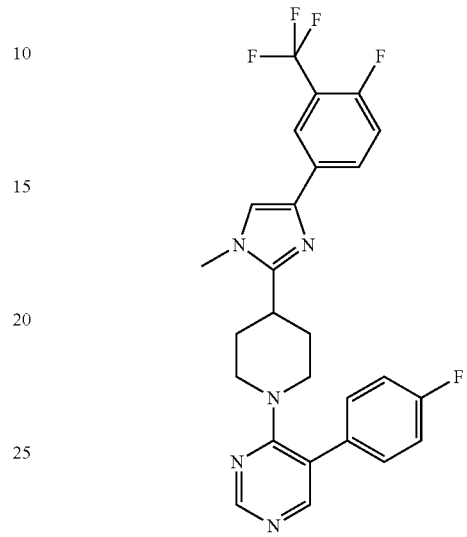

The title compound was prepared in an analogous manner as 5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine using 5-bromo-4-{4-[4-(4-fluoro-3-trifluoromethyl-phenyl)-1-methyl-1H-imidazol-2-yl]-piperidin-1-yl}-pyrimidine instead of 5-Bromo-6-{4-[4-(4-fluoro-3-trifluoromethyl-phenyl)-1-methyl-1H-imidazol-2-yl]-piperidin-1-yl}-pyrimidin-4-ylamine. LC-MS: (M+1=500, obsd.=500).

5-Bromo-6-{4-[4-(4-fluoro-3-trifluoromethyl-phenyl)-1H-imidazol-2-yl]-piperidin-1-yl}-pyrimidin-4-ylamine ("43")

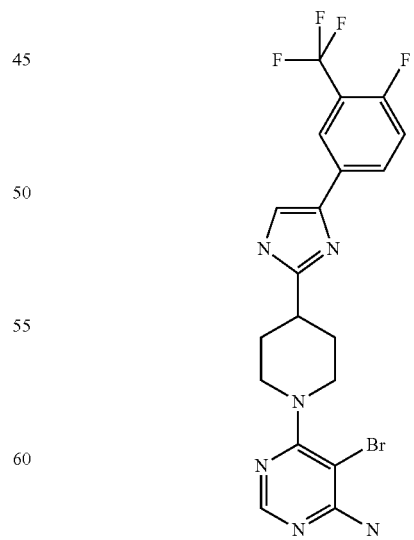

The title compound was prepared in an analogous manner as 5-bromo-6-{4-[4-(3-trifluoromethyl-phenyl)-1H-imidazol-2-yl]-piperidin-1-yl}-pyrimidin-4-ylamine using 4-{4-

[4-fluoro-3-(trifluoromethyl)phenyl]-1H-imidazol-2-yl}piperidine instead of 4-[4-(4-fluoro-3-trifluoromethylphenyl)-1-methyl-1h-imidazol-2-yl]-piperidine. LC-MS: (M+1=485, obsd.=485).

5-(4-Fluoro-phenyl)-6-{4-[4-(4-fluoro-3-trifluoromethyl-phenyl)-1H-imidazol-2-yl]-piperidin-1-yl}-pyrimidin-4-ylamine ("44")

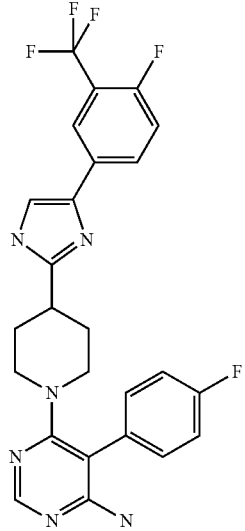 [SMILES: Nc1ncnc(N2CCC(c3nc(-c4ccc(F)c(C(F)(F)F)c4)c[nH]3)CC2)c1-c1ccc(F)cc1]

The title compound was prepared in an analogous manner as 5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine using 5-bromo-4-{4-[4-(4-fluoro-3-trifluoromethyl-phenyl)-1H-imidazol-2-yl]-piperidin-1-yl}-pyrimidine instead of 5-Bromo-6-{4-[4-(4-fluoro-3-trifluoromethyl-phenyl)-1-methyl-1H-imidazol-2-yl]-piperidin-1-yl}-pyrimidin-4-ylamine. LC-MS: (M+1=501, obsd.=501).

(E)-3-(4-Amino-6-{4-[4-(4-fluoro-3-trifluoromethyl-phenyl)-1-methyl-1H-imidazol-2-yl]-piperidin-1-yl}-pyrimidin-5-yl)-acrylic acid methyl ester ("45")

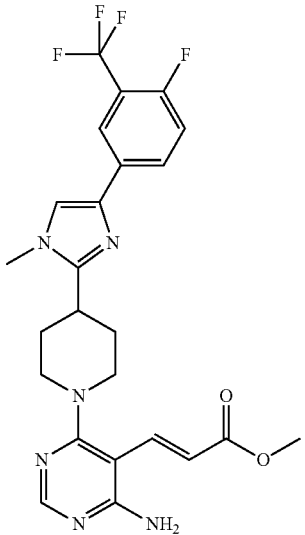

To a mixture of 4-amino-6-(4-{4-[fluoro-3-(trifluoromethyl)phenyl]-1-methyl-1H-imidazol-2-yl}piperidin-1-yl)pyrimidine-5-carbaldehyde (100 mg; 0.22 mmol; 1.0 eq.) in DMSO (2 mL), methyl (triphenylphosphoranylidene)acetate (82.0 mg; 0.25 mmol; 1.1 eq.), lithium chloride (19.1 mg; 0.45 mmol; 2.0 eq.) and triethylamine (0.04 ml; 0.27 mmol; 1.2 eq.) were added. The resulting suspension was stirred at 60° C. overnight. The crude was purified by pre-HPLC (Waters, basic condition) to afford the title compound in 72% yield. LC-MS: (M+1=505, obsd.=505).

(E)-3-(4-Amino-6-{4-[4-(4-fluoro-3-trifluoromethyl-phenyl)-1-methyl-1H-imidazol-2-yl]-piperidin-1-yl}-pyrimidin-5-yl)-acrylamide ("46")

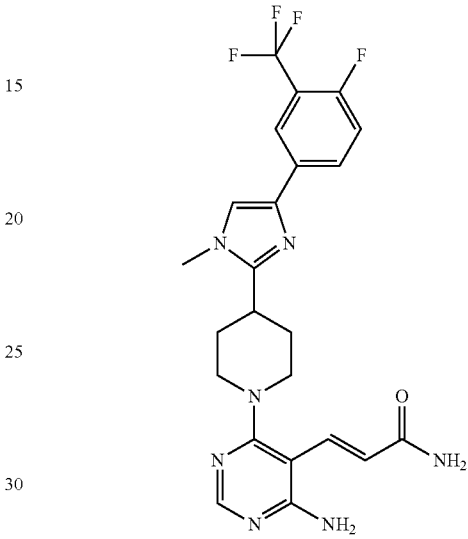

A mixture of E)-3-(4-Amino-6-{4-[4-(4-fluoro-3-trifluoromethyl-phenyl)-1-methyl-1H-imidazol-2-yl]-piperidin-1-yl}-pyrimidin-5-yl)-acrylic acid methyl ester (15.0 mg; 0.03 mmol; 1.0 eq.) in 7M ammonia in MeOH (2.1 ml; 14.8 mmol; 500 eq.) was stirred at 70° C. overnight. The crude reaction mixture was purified by reverse phase chromatography (Waters, with acetonitrile/water under basic condition). The fractions were concentrated to dryness and then redissolved in water and acetonitrile. 200 μL of 0.5N HCl was added and the excess of HCl was removed under vacuum and then lyophilized to afford the title compound as HCl salt. LC-MS: (M+1=490, obsd.=490).

6-{4-[4-(4-Fluoro-3-trifluoromethyl-phenyl)-1-methyl-1H-imidazol-2-yl]-piperidin-1-yl}-5-(5-methoxy-pyridin-3-yl)-pyrimidin-4-ylamine ("47")

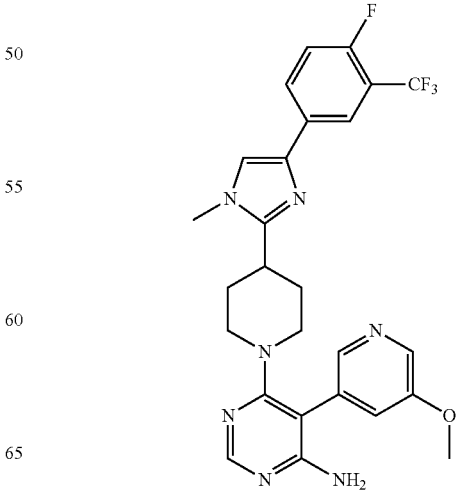

The title compound was prepared in an analogous manner as 5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine using (5-methoxypyridin-3-yl)boronic acid instead of 4-fluorophenylboronic acid. LC-MS: (M+1=528, obsd.=528).

6-{4-[4-(4-Fluoro-3-trifluoromethyl-phenyl)-1-methyl-1H-imidazol-2-yl]-piperidin-1-yl}-[5,5']bipyrimidinyl-4-ylamine ("48")

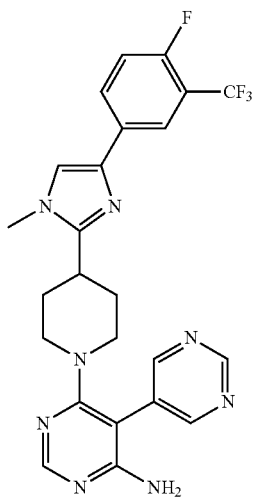 [SMILES: Cn1cc(-c2ccc(F)c(C(F)(F)F)c2)nc1C1CCN(c2ncnc(N)c2-c2cncnc2)CC1]

The title compound was prepared in an analogous manner as 5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine using pyrimidin-5-ylboronic acid instead of 4-fluorophenylboronic acid. LC-MS: (M+1=499, obsd.=499).

6-{4-[4-(4-Fluoro-3-trifluoromethyl-phenyl)-1-methyl-1H-imidazol-2-yl]-piperidin-1-yl}-5-(1H-indol-5-yl)-pyrimidin-4-ylamine ("49")

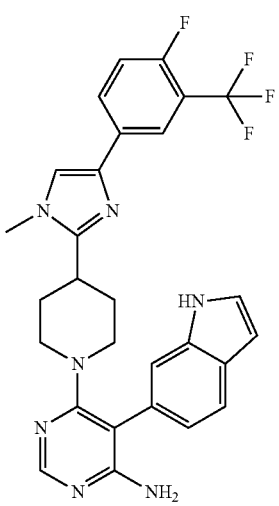 [SMILES: Cn1cc(-c2ccc(F)c(C(F)(F)F)c2)nc1C1CCN(c2ncnc(N)c2-c2ccc3cc[nH]c3c2)CC1]

The title compound was prepared in an analogous manner as 5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine using (1H-indol-5-yl)boronic acid pinacol ester instead of 4-fluorophenylboronic acid. LC-MS: (M+1=536, obsd.=536).

5-(6-Chloro-pyridin-3-yl)-6-{4-[4-(4-fluoro-3-trifluoromethyl-phenyl)-1-methyl-1H-imidazol-2-yl]-piperidin-1-yl}-pyrimidin-4-ylamine ("50")

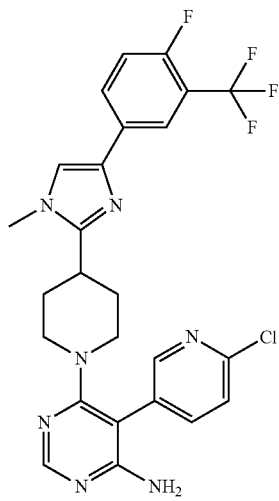 [SMILES: Cn1cc(-c2ccc(F)c(C(F)(F)F)c2)nc1C1CCN(c2ncnc(N)c2-c2ccc(Cl)nc2)CC1]

The title compound was prepared in an analogous manner as 5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine using (1H-indol-5-yl)boronic acid pinacol ester instead of 4-fluorophenylboronic acid. LC-MS: (M+1=532, obsd.=532).

5-(3-Chloro-phenyl)-6-{4-[4-(4-fluoro-3-trifluoromethyl-phenyl)-1-methyl-1H-imidazol-2-yl]-piperidin-1-yl}-pyrimidin-4-ylamine ("51")

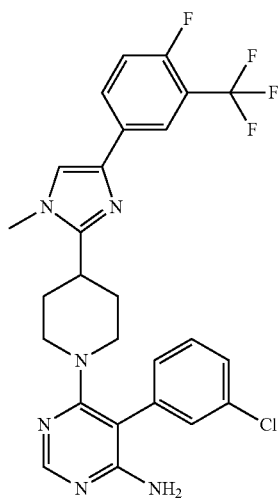 [SMILES: Cn1cc(-c2ccc(F)c(C(F)(F)F)c2)nc1C1CCN(c2ncnc(N)c2-c2cccc(Cl)c2)CC1]

The title compound was prepared in an analogous manner as 5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine using 3-chlorophenylboronic acid instead of 4-fluorophenylboronic acid. LC-MS: (M+1=531, obsd.=531).

4-(4-Amino-6-{4-[4-(4-fluoro-3-trifluoromethyl-phenyl)-1-methyl-1H-imidazol-2-yl]-piperidin-1-yl}-pyrimidin-5-yl)-2-fluoro-benzonitrile ("52")

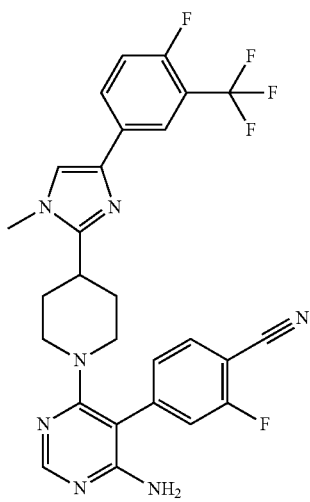 [SMILES: Cn1cc(-c2ccc(F)c(C(F)(F)F)c2)nc1C1CCN(c2ncnc(N)c2-c2ccc(C#N)c(F)c2)CC1]

The title compound was prepared in an analogous manner as 5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine using 4-cyano-3-fluorophenylboronic acid instead of 4-fluorophenylboronic acid. LC-MS: (M+1=540, obsd.=540).

6-{4-[4-(4-Fluoro-3-trifluoromethyl-phenyl)-1-methyl-1H-imidazol-2-yl]-piperidin-1-yl}-5-pyridin-3-yl-pyrimidin-4-ylamine ("53")

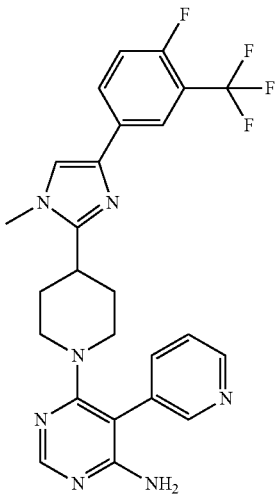 [SMILES: Cn1cc(-c2ccc(F)c(C(F)(F)F)c2)nc1C1CCN(c2ncnc(N)c2-c2cccnc2)CC1]

The title compound was prepared in an analogous manner as 5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine using 4-cyano-3-fluorophenylboronic acid instead of 4-fluorophenylboronic acid. LC-MS: (M+1=498, obsd.=498).

6-{4-[4-(4-Fluoro-3-trifluoromethyl-phenyl)-1-methyl-1H-imidazol-2-yl]-piperidin-1-yl}-5-((E)-3-methoxy-propenyl)-pyrimidin-4-ylamine ("54")

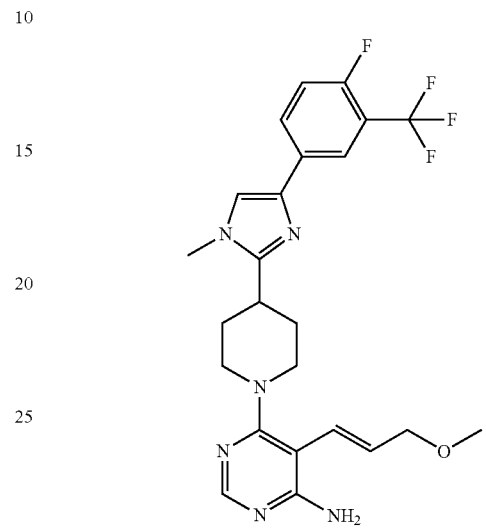

The title compound was prepared in an analogous manner as 5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine using (E)-2-(3-methoxypropen-1-yl)boronic acid pinacol ester instead of 4-fluorophenylboronic acid. LC-MS: (M+1=491, obsd.=491).

6-{4-[4-(4-Fluoro-3-trifluoromethyl-phenyl)-1-methyl-1H-imidazol-2-yl]-piperidin-1-yl}-5-(2-methyl-thiazol-5-yl)-pyrimidin-4-ylamine ("55")

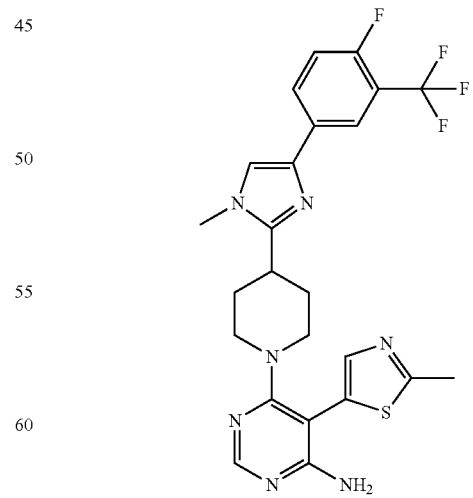

The title compound was prepared in an analogous manner as 5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine using (2-methylthiazol-5-yl)boronic acid pinacol ester instead of 4-fluorophenylboronic acid. LC-MS: (M+1=518, obsd.=518).

5-Bromo-6{4-(4-fluoro-3-trifluoromethyl-phenyl)-1-2-pyrrolidin-1-yl-ethyl)-1H-imidazol-2-yl]-piperidin-1-yl}-pyrimidin-4-ylamine ("56")

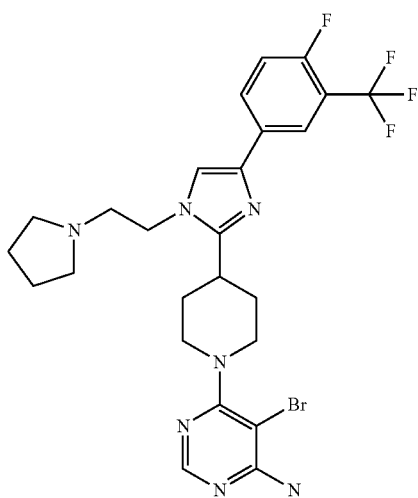 [SMILES: Nc1ncnc(N2CCC(c3nc(-c4ccc(F)c(C(F)(F)F)c4)cn3CCN3CCCC3)CC2)c1Br]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-trifluoromethyl-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=582, obsd.=582).

5-(4-Fluorophenyl)-6{4-(4-fluoro-3-trifluoromethyl-phenyl)-1-2-pyrrolidin-1-yl-ethyl)-1H-imidazol-2-yl]-piperidin-1-yl}-pyrimidin-4-ylamine ("57")

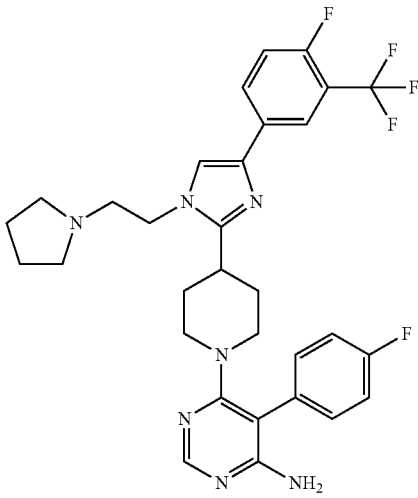 [SMILES: Nc1ncnc(N2CCC(c3nc(-c4ccc(F)c(C(F)(F)F)c4)cn3CCN3CCCC3)CC2)c1-c1ccc(F)cc1]

The title compound was prepared in an analogous manner as 5-(4-fluoro-phenyl)-6-{4-[4-(4-fluoro-3-trifluoromethyl-phenyl)-1-methyl-1H-imidazol-2-yl]-piperidin-1-yl}-pyrimidin-4-ylamine using 5-Bromo-6{4-(4-fluoro-3-trifluoromethyl-phenyl)-1-2-pyrrolidin-1-yl-ethyl)-1H-imidazol-2-yl]-piperidin-1-yl}-pyrimidin-4-ylamine instead of 5-bromo-6-{4-[4-(4-fluoro-3-trifluoromethyl-phenyl)-1-methyl-1H-imidazol-2-yl]-piperidin-1-yl}-pyrimidin-4-ylamine. LC-MS: (M+1=612, obsd.=612).

5-(2-Fluorophenyl)-6{4-(4-fluoro-3-trifluoromethyl-phenyl)-1-2-pyrrolidin-1-yl-ethyl)-1H-imidazol-2-yl]-piperidin-1-yl}-pyrimidin-4-ylamine ("58")

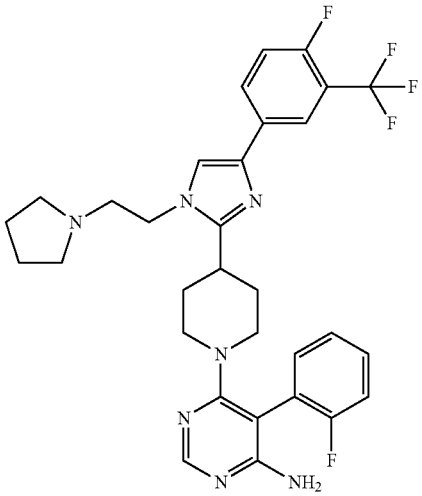 [SMILES: Nc1ncnc(N2CCC(c3nc(-c4ccc(F)c(C(F)(F)F)c4)cn3CCN3CCCC3)CC2)c1-c1ccccc1F]

The title compound was prepared in an analogous manner as 5-(4-Fluorophenyl)-6{4-(4-fluoro-3-trifluoromethyl-phenyl)-1-2-pyrrolidin-1-yl-ethyl)-1H-imidazol-2-yl]-piperidin-1-yl}-pyrimidin-4-ylamine using 2-fluorophenylboronic acid instead of 4-fluorophenylboronic acid. LC-MS: (M+1=598, obsd.=598).

5-(3,4-Difluorophenyl)-6{4-(4-fluoro-3-trifluoromethyl-phenyl)-1-2-pyrrolidin-1-yl-ethyl)-1H-imidazol-2-yl]-piperidin-1-yl}-pyrimidin-4-ylamine ("59")

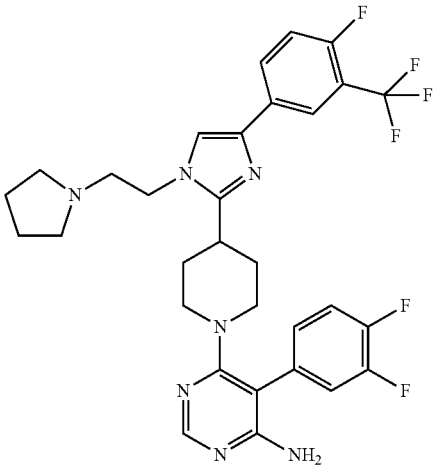 [SMILES: Nc1ncnc(N2CCC(c3nc(-c4ccc(F)c(C(F)(F)F)c4)cn3CCN3CCCC3)CC2)c1-c1ccc(F)c(F)c1]

The title compound was prepared in an analogous manner as 6-{4-[1-(2-Dimethylamino-ethyl)-4-(4-fluoro-3-trifluoromethyl-phenyl)-1H-imidazol-2-yl]-piperidin-1-yl}-5-(4-fluoro-phenyl)-pyrimidin-4-ylamine using 3,4-difluorophenylboronic acid instead of 4-fluorophenylboronic acid. LC-MS: (M+1=616, obsd.=616).

6-{4-(4-fluoro-3-trifluoromethyl-phenyl)-1-2-pyrrolidin-1-yl-ethyl)-1H-imidazol-2-yl]-piperidin-1-yl}-5-vinyl-pyrimidin-4-ylamine ("60")

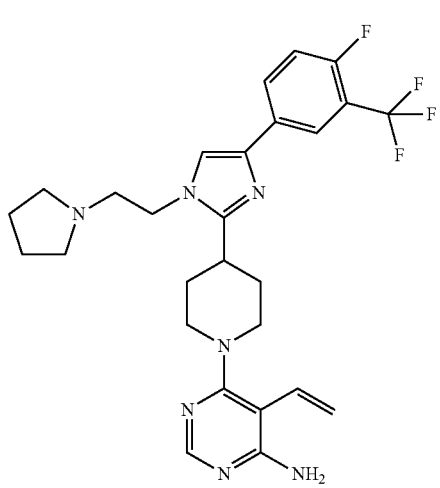 [SMILES: C=Cc1c(N)ncnc1N1CCC(c2nc(-c3ccc(F)c(C(F)(F)F)c3)cn2CCN2CCCC2)CC1]

The title compound was prepared in an analogous manner as 6-{4-[1-(2-Dimethylamino-ethyl)-4-(4-fluoro-3-trifluoromethyl-phenyl)-1H-imidazol-2-yl]-piperidin-1-yl}-5-(4-fluoro-phenyl)-pyrimidin-4-ylamine using vinylboronic acid pinacol ester instead of 4-fluorophenylboronic acid. LC-MS: (M+1=530, obsd.=530).

5-Bromo-6-{4-[4-(4-fluoro-3-trifluoromethyl-phenyl)-1-(2-piperidin-1-yl-ethyl)-1H-imidazol-2-yl]-piperidin-1-yl}-pyrimidin-4-ylamine ("61")

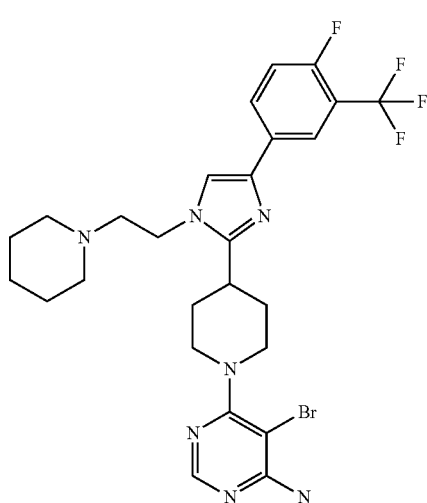 [SMILES: Nc1ncnc(N2CCC(c3nc(-c4ccc(F)c(C(F)(F)F)c4)cn3CCN3CCCCC3)CC2)c1Br]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 1-(2-(4-(4-fluoro-3-(trifluoromethyl)phenyl)-2-(piperidin-4-yl)-1H-imidazol-1-yl)ethyl)piperidine instead of 4-[4-(4-fluoro-3-trifluoromethyl-phenyl)-1-methyl-1h-imidazol-2-yl]-piperidine. LC-MS: (M+1=596, obsd.=596).

5-(4-Fluorophenyl)-6{4-(4-fluoro-3-trifluoromethyl-phenyl)-1-2-piperidin-1-yl-ethyl)-1H-imidazol-2-yl]-piperidin-1-yl}-pyrimidin-4-ylamine ("62")

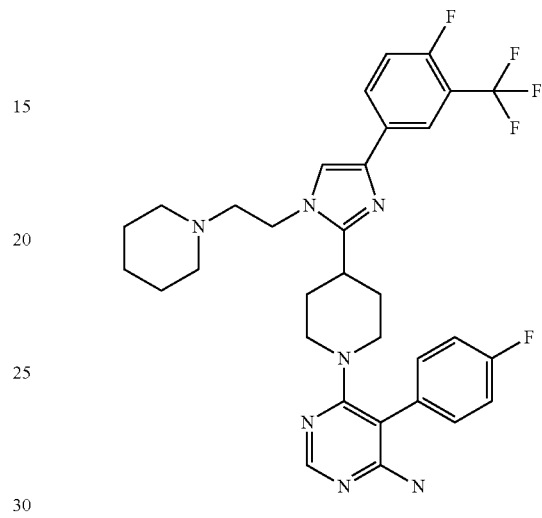

The title compound was prepared in an analogous manner as 5-(4-fluoro-phenyl)-6-{4-[4-(4-fluoro-3-trifluoromethyl-phenyl)-1-methyl-1H-imidazol-2-yl]-piperidin-1-yl}-pyrimidin-4-ylamine using 5-bromo-6-{4-[4-(4-fluoro-3-trifluoromethyl-phenyl)-1-(2-piperidin-1-yl-ethyl)-1H-imidazol-2-yl]-piperidin-1-yl}-pyrimidin-4-ylamine instead of 5-bromo-6-{4-[4-(4-fluoro-3-trifluoromethyl-phenyl)-1-methyl-1H-imidazol-2-yl]-piperidin-1-yl}-pyrimidin-4-ylamine. LC-MS: (M+1=612, obsd.=612).

5-(2-Fluorophenyl)-6{4-(4-fluoro-3-trifluoromethyl-phenyl)-1-2-piperidin-1-yl-ethyl)-1H-imidazol-2-yl]-piperidin-1-yl}-pyrimidin-4-ylamine ("63")

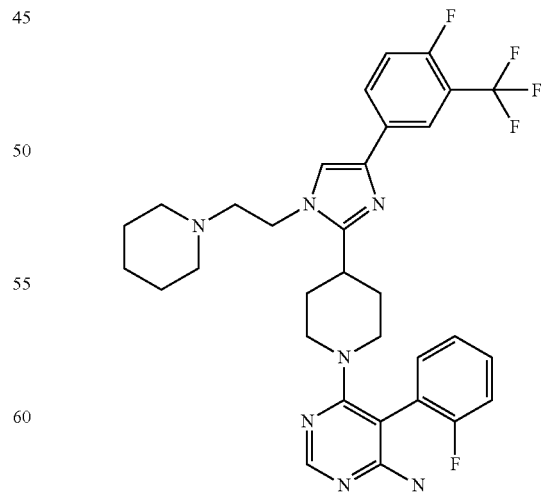

The title compound was prepared in an analogous manner as 5-(4-fluorophenyl)-6{4-(4-fluoro-3-trifluoromethyl-phenyl)-1-2-piperidin-1-yl-ethyl)-1H-imidazol-2-yl]-piperidin- 1-yl}-pyrimidin-4-ylamine using 2-fluorophenylboronic acid instead of 4-fluorophenylboronic acid. LC-MS: (M+1=612, obsd.=612).

5-(3-Fluorophenyl)-6{4-(4-fluoro-3-trifluoromethyl-phenyl)-1-2-piperidin-1-yl-ethyl)-1H-imidazol-2-yl]-piperidin-1-yl}-pyrimidin-4-ylamine ("64")

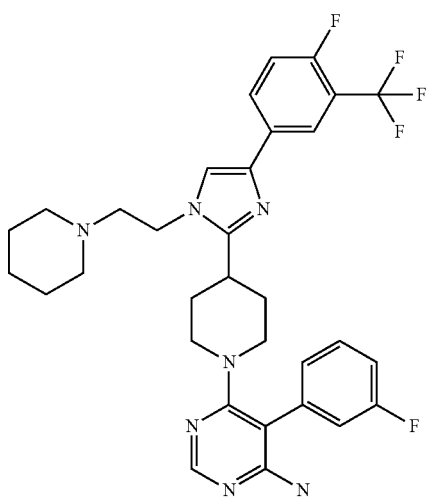 [SMILES: Nc1ncnc(N2CCC(c3nc(-c4ccc(F)c(C(F)(F)F)c4)cn3CCN3CCCCC3)CC2)c1-c1cccc(F)c1]

The title compound was prepared in an analogous manner as 5-(4-fluorophenyl)-6{4-(4-fluoro-3-trifluoromethyl-phenyl)-1-2-piperidin-1-yl-ethyl)-1H-imidazol-2-yl]-piperidin-1-yl}-pyrimidin-4-ylamine using 3-fluorophenylboronic acid instead of 4-fluorophenylboronic acid. LC-MS: (M+1=612, obsd.=612).

6-{4-[4-(4-Fluoro-3-trifluoromethyl-phenyl)-1-(2-piperidin-1-yl-ethyl)-1H-imidazol-2-yl]-piperidin-1-yl}-5-vinyl-pyrimidin-4-ylamine ("65")

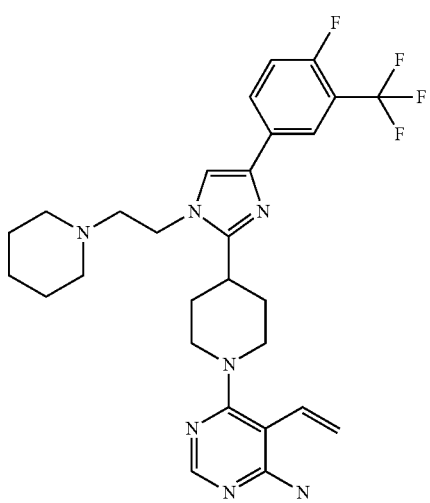 [SMILES: C=Cc1c(N)ncnc1N1CCC(c2nc(-c3ccc(F)c(C(F)(F)F)c3)cn2CCN2CCCCC2)CC1]

The title compound was prepared in an analogous manner as 5-(4-fluorophenyl)-6{4-(4-fluoro-3-trifluoromethyl-phenyl)-1-2-piperidin-1-yl-ethyl)-1H-imidazol-2-yl]-piperidin- 1-yl}-pyrimidin-4-ylamine using vinylboronic acid pinacol ester instead of 4-fluorophenylboronic acid. LC-MS: (M+1=544, obsd.=544).

6{4-(4-fluoro-3-trifluoromethyl-phenyl)-1-2-piperidin-1-yl-ethyl)-1H-imidazol-2-yl]-piperidin-1-yl}-pyrimidin-4-ylamine ("66")

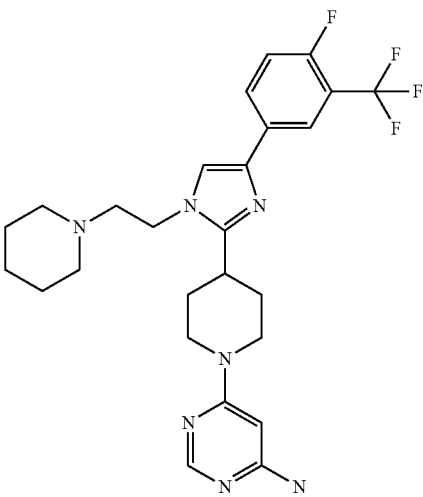 [SMILES: Nc1cc(N2CCC(c3nc(-c4ccc(F)c(C(F)(F)F)c4)cn3CCN3CCCCC3)CC2)ncn1]

The title compound was prepared in an analogous manner as 5-Bromo-6-{4-[4-(4-fluoro-3-trifluoromethyl-phenyl)-1-(2-piperidin-1-yl-ethyl)-1H-imidazol-2-yl]-piperidin-1-yl}-pyrimidin-4-ylamine using 6-chloropyrimidin-4-amine instead of 5-bromo-6-chloropyrimidin-4-amine. LC-MS: (M+1=518, obsd.=518).

5-Bromo-6-{4-[1-(2-dimethylamino-ethyl)-4-(4-fluoro-3-trifluoromethyl-phenyl)-1H-imidazol-2-yl]-piperidin-1-yl}-pyrimidin-4-ylamine ("67")

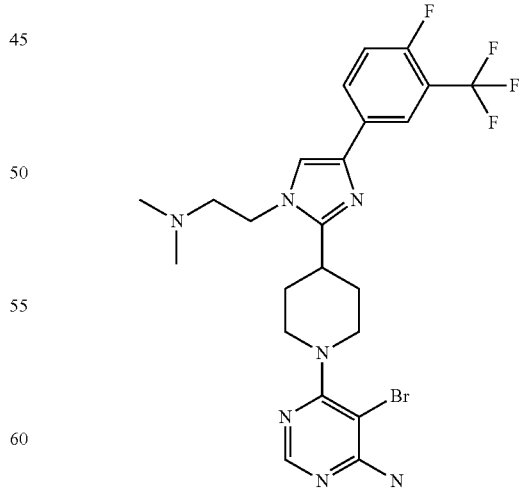

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 2-(4-(4-fluoro-3-(trifluoromethyl)phenyl)-2-

(piperidin-4-yl)-1H-imidazol-1-yl)-N,N-dimethylethanamine instead of 4-[4-(4-fluoro-3-trifluoromethyl-phenyl)-1-methyl-1h-imidazol-2-yl]-piperidine. LC-MS: (M+1=556, obsd.=556).

6-{4-[1-(2-Dimethylamino-ethyl)-4-(4-fluoro-3-trifluoromethyl-phenyl)-1H-imidazol-2-yl]-piperidin-1-yl}-5-(4-fluoro-phenyl)-pyrimidin-4-ylamine ("68")

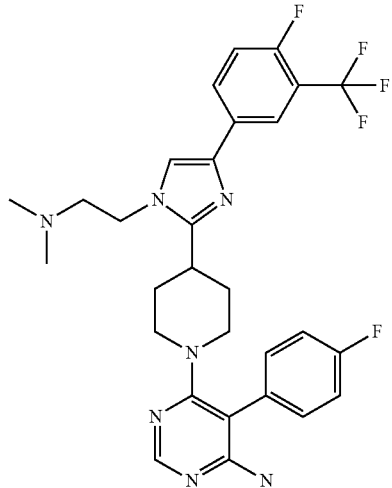 [SMILES: CN(C)CCn1cc(-c2ccc(F)c(C(F)(F)F)c2)nc1C1CCN(c2ncnc(N)c2-c2ccc(F)cc2)CC1]

The title compound was prepared in an analogous manner as 5-(4-fluoro-phenyl)-6-{4-[4-(4-fluoro-3-trifluoromethyl-phenyl)-1-methyl-1H-imidazol-2-yl]-piperidin-1-yl}-pyrimidin-4-ylamine using 5-Bromo-6-{4-[1-(2-dimethylamino-ethyl)-4-(4-fluoro-3-trifluoromethyl-phenyl)-1H-imidazol-2-yl]-piperidin-1-yl}-pyrimidin-4-ylamine instead of 5-Bromo-6-{4-[4-(4-fluoro-3-trifluoromethyl-phenyl)-1-methyl-1H-imidazol-2-yl]-piperidin-1-yl}-pyrimidin-4-ylamine. LC-MS: (M+1=572, obsd.=572).

6-{4-[1-(2-Dimethylamino-ethyl)-4-(4-fluoro-3-trifluoromethyl-phenyl)-1H-imidazol-2-yl]-piperidin-1-yl}-5-pyridin-4-yl-pyrimidin-4-ylamine ("69")

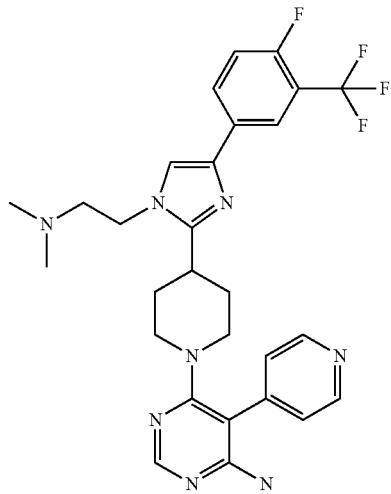 [SMILES: CN(C)CCn1cc(-c2ccc(F)c(C(F)(F)F)c2)nc1C1CCN(c2ncnc(N)c2-c2ccncc2)CC1]

The title compound was prepared in an analogous manner as 6-{4-[1-(2-Dimethylamino-ethyl)-4-(4-fluoro-3-trifluoromethyl-phenyl)-1H-imidazol-2-yl]-piperidin-1-yl}-5-(4-fluoro-phenyl)-pyrimidin-4-ylamine using 4-pyridinylboronic acid pinacol ester instead of 4-fluorophenylboronic acid. LC-MS: (M+1=555, obsd.=555).

6-{4-[1-(2-Dimethylamino-ethyl)-4-(4-fluoro-3-trifluoromethyl-phenyl)-1H-imidazol-2-yl]-piperidin-1-yl}-5-pyridin-4-yl-pyrimidin-4-ylamine ("70")

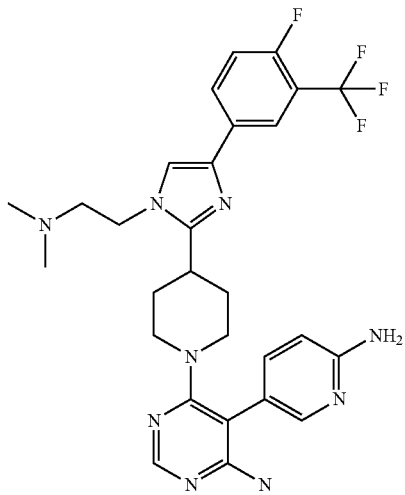 [SMILES: CN(C)CCn1cc(-c2ccc(F)c(C(F)(F)F)c2)nc1C1CCN(c2ncnc(N)c2-c2ccc(N)nc2)CC1]

The title compound was prepared in an analogous manner as 6-{4-[1-(2-Dimethylamino-ethyl)-4-(4-fluoro-3-trifluoromethyl-phenyl)-1H-imidazol-2-yl]-piperidin-1-yl}-5-(4-fluoro-phenyl)-pyrimidin-4-ylamine 2-aminopyridine-5-boronic acid pinacol ester instead of 4-fluorophenylboronic acid. LC-MS: (M+1=570, obsd.=570).

6'-{4-[1-(2-Dimethylamino-ethyl)-4-(4-fluoro-3-trifluoromethyl-phenyl)-1H-imidazol-2-yl]-piperidin-1-yl}-[5,5']bipyrimidinyl-2,4'-diamine ("71")

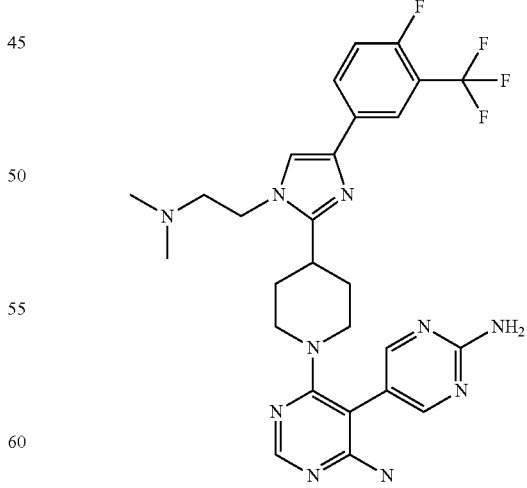

The title compound was prepared in an analogous manner as 6-{4-[1-(2-Dimethylamino-ethyl)-4-(4-fluoro-3-trifluoromethyl-phenyl)-1H-imidazol-2-yl]-piperidin-1-yl}-5-(4-fluoro-phenyl)-pyrimidin-4-ylamine 2-aminopyridine-5-boronic acid pinacol ester instead of 4-fluorophenylboronic acid. LC-MS: (M+1=571, obsd.=571).

6-{4-[1-(2-Dimethylamino-ethyl)-4-(4-fluoro-3-trifluoromethyl-phenyl)-1H-imidazol-2-yl]-piperidin-1-yl}-5-isopropenyl-pyrimidin-4-ylamine ("72")

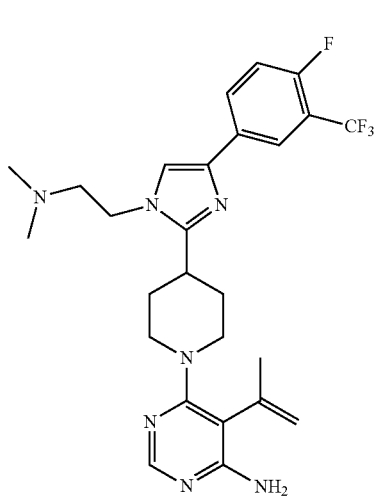 [SMILES: C=C(C)c1c(N)ncnc1N1CCC(c2nc(-c3ccc(F)c(C(F)(F)F)c3)cn2CCN(C)C)CC1]

The title compound was prepared in an analogous manner as 6-{4-[1-(2-Dimethylamino-ethyl)-4-(4-fluoro-3-trifluoromethyl-phenyl)-1H-imidazol-2-yl]-piperidin-1-yl}-5-(4-fluoro-phenyl)-pyrimidin-4-ylamine using 2-Isopropenyl boronic acid pinacol ester instead of 4-fluorophenylboronic acid. LC-MS: (M+1=518, obsd.=518).

6-{4-[1-(2-Dimethylamino-ethyl)-4-(4-fluoro-3-trifluoromethyl-phenyl)-1H-imidazol-2-yl]-piperidin-1-yl}-5-vinyl-pyrimidin-4-ylamine ("73")

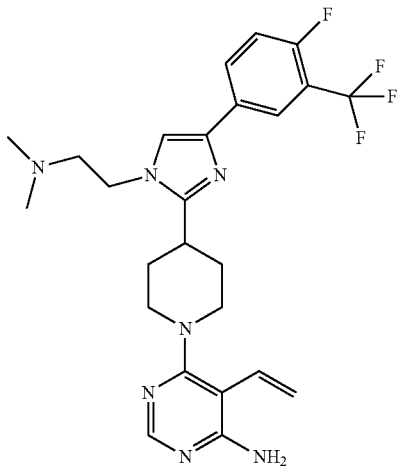 [SMILES: C=Cc1c(N)ncnc1N1CCC(c2nc(-c3ccc(F)c(C(F)(F)F)c3)cn2CCN(C)C)CC1]

The title compound was prepared in an analogous manner as 6-{4-[1-(2-Dimethylamino-ethyl)-4-(4-fluoro-3-trifluoromethyl-phenyl)-1H-imidazol-2-yl]-piperidin-1-yl}-5-(4-fluoro-phenyl)-pyrimidin-4-ylamine using vinylboronic acid pinacol ester instead of 4-fluorophenylboronic acid. LC-MS: (M+1=504, obsd.=504).

4-Amino-6-{4-[1-(2-azetidin-1-yl-ethyl)-4-(4-fluoro-3-trifluoromethyl-phenyl)-1H-imidazol-2-yl]-piperidin-1-yl}-pyrimidine-5-carbonitrile ("74")

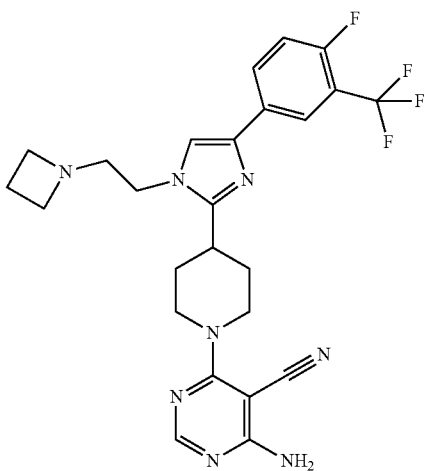 [SMILES: N#Cc1c(N)ncnc1N1CCC(c2nc(-c3ccc(F)c(C(F)(F)F)c3)cn2CCN2CCC2)CC1]

The title compound was prepared in an analogous manner as 4-amino-6-{4-[4-(4-fluoro-3-trifluoromethyl-phenyl)-1-methyl-1H-imidazol-2-yl]-piperidin-1-yl}-pyrimidine-5-carbonitrile using 4-[1-(2-azetidin-1-yl-ethyl)-4-(4-fluoro-3-trifluoromethyl-phenyl)-1H-imidazol-2-yl]-piperidine trifluoroacetate instead of 4-[4-(4-fluoro-3-trifluoromethyl-phenyl)-1-methyl-1h-imidazol-2-yl]-piperidine. LC-MS: (M+1=515, obsd.=515).

4-Amino-6-{4-[1-(2-azetidin-1-yl-ethyl)-4-(3-chloro-4-fluoro-phenyl)-1H-imidazol-2-yl]-piperidin-1-yl}-pyrimidine-5-carbonitrile ("75")

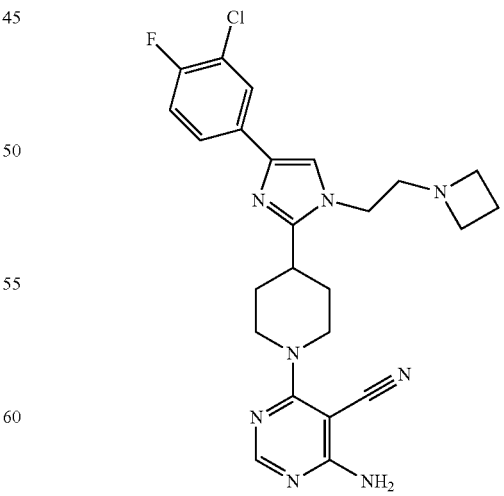

The title compound was prepared in an analogous manner as 4-amino-6-{4-[4-(4-fluoro-3-trifluoromethyl-phenyl)-1-methyl-1H-imidazol-2-yl]-piperidin-1-yl}-pyrimidine-5- carbonitrile using 4-[1-(2-Azetidin-1-yl-ethyl)-4-(3-chloro-4-fluoro-phenyl)-1H-imidazol-2-yl]-piperidine hydrochloride instead of 4-[4-(4-fluoro-3-trifluoromethyl-phenyl)-1-methyl-1h-imidazol-2-yl]-piperidine. LC-MS: (M+1=481, obsd.=481).

4-Amino-6-{4-[1-(2-azetidin-1-yl-ethyl)-4-(4-difluoromethoxy-phenyl)-1H-imidazol-2-yl]-piperidin-1-yl}-pyrimidine-5-carbonitrile ("76")

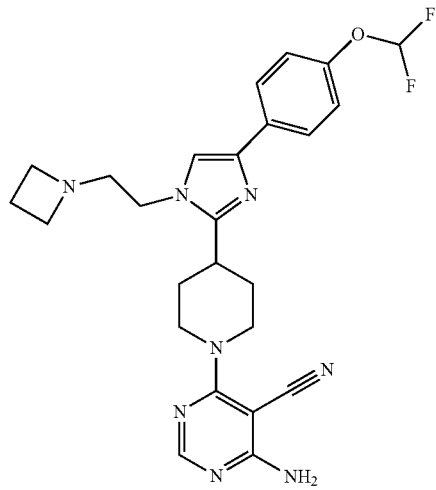 [SMILES: N#Cc1c(N)ncnc1N1CCC(c2nc(-c3ccc(OC(F)F)cc3)cn2CCN2CCC2)CC1]

The title compound was prepared in an analogous manner as 4-amino-6-{4-[4-(4-fluoro-3-trifluoromethyl-phenyl)-1-methyl-1H-imidazol-2-yl]-piperidin-1-yl}-pyrimidine-5-carbonitrile using 4-[1-(2-Azetidin-1-yl-ethyl)-4-(4-difluoromethoxy-phenyl)-1H-imidazol-2-yl]-piperidine trifluoroacetate instead of 4-[4-(4-fluoro-3-trifluoromethyl-phenyl)-1-methyl-1h-imidazol-2-yl]-piperidine. LC-MS: (M+1=495, obsd.=495).

4-Amino-6-{4-[1-(2-azetidin-1-yl-ethyl)-4-cyclohexyl-1H-imidazol-2-yl]-piperidin-1-yl}-pyrimidine-5-carbonitrile ("77")

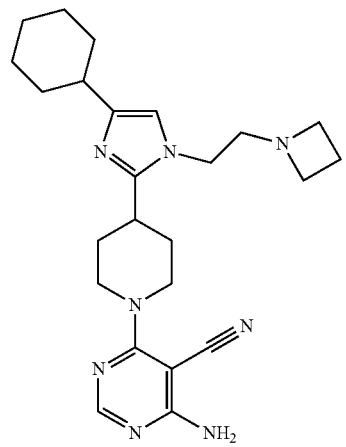 [SMILES: N#Cc1c(N)ncnc1N1CCC(c2nc(C3CCCCC3)cn2CCN2CCC2)CC1]

The title compound was prepared in an analogous manner as 4-amino-6-{4-[4-(4-fluoro-3-trifluoromethyl-phenyl)-1-methyl-1H-imidazol-2-yl]-piperidin-1-yl}-pyrimidine-5-carbonitrile using 4-[1-(2-azetidin-1-yl-ethyl)-4-cyclohexyl-1h-imidazol-2-yl]-piperidine trifluoroacetate instead of 4-[4-(4-fluoro-3-trifluoromethyl-phenyl)-1-methyl-1h-imidazol-2-yl]-piperidine. LC-MS: (M+1=435, obsd.=435).

4-Amino-6-{4-[1-(2-azetidin-1-yl-ethyl)-4-(4-fluoro-3-trifluoromethyl-phenyl)-1H-imidazol-2-yl]-piperidin-1-yl}-pyrimidine-5-carboxylic acid amide ("78")

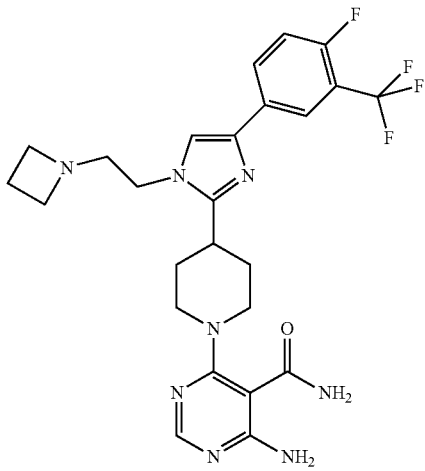 [SMILES: NC(=O)c1c(N)ncnc1N1CCC(c2nc(-c3ccc(F)c(C(F)(F)F)c3)cn2CCN2CCC2)CC1]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-{4-[1-(2-azetidin-1-yl-ethyl)-4-(4-fluoro-3-trifluoromethyl-phenyl)-1H-imidazol-2-yl]-piperidin-1-yl}-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=533, obsd.=533).

4-Amino-6-{4-[1-(2-azetidin-1-yl-ethyl)-4-(3-chloro-4-fluoro-phenyl)-1H-imidazol-2-yl]-piperidin-1-yl}-pyrimidine-5-carboxylic acid amide ("79")

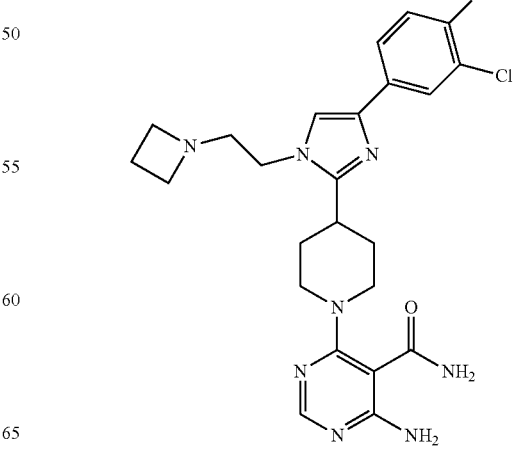

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-{4-[1-(2-azetidin-1-yl-ethyl)-4-(3-chloro-4-fluorophenyl)-1H-imidazol-2-yl]-piperidin-1-yl}-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=499, obsd.=499).

4-Amino-6-{4-[1-(2-azetidin-1-yl-ethyl)-4-cyclohexyl-1H-imidazol-2-yl]-piperidin-1-yl}-pyrimidine-5-carboxylic acid amide ("80")

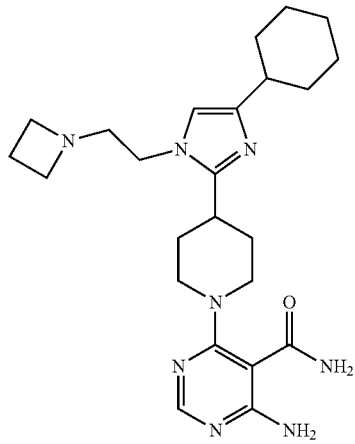 [SMILES: NC(=O)c1c(N)ncnc1N1CCC(c2nc(C3CCCCC3)cn2CCN2CCC2)CC1]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-{4-[1-(2-azetidin-1-yl-ethyl)-4-cyclohexyl-1H-imidazol-2-yl]-piperidin-1-yl}-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=453, obsd.=453).

4-Amino-6-{4-[1-(2-azetidin-1-yl-ethyl)-4-(4-difluoromethoxy-phenyl)-1H-imidazol-2-yl]-piperidin-1-yl}-pyrimidine-5-carboxylic acid amide ("81")

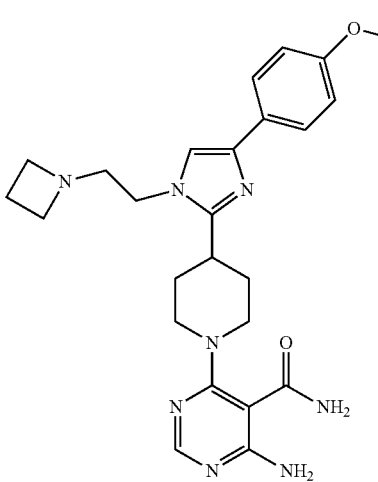

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-{4-[1-(2-azetidin-1-yl-ethyl)-4-(4-difluoromethoxy-phenyl)-1H-imidazol-2-yl]-piperidin-1-yl}-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=513, obsd.=513).

6-(4-(1-(2-(Dimethylamino)ethyl)-4-(4-fluoro-3-(trifluoromethyl)phenyl)-1H-imidazol-2-yl)piperidin-1-yl)-5-ethylpyrimidin-4-amine ("82")

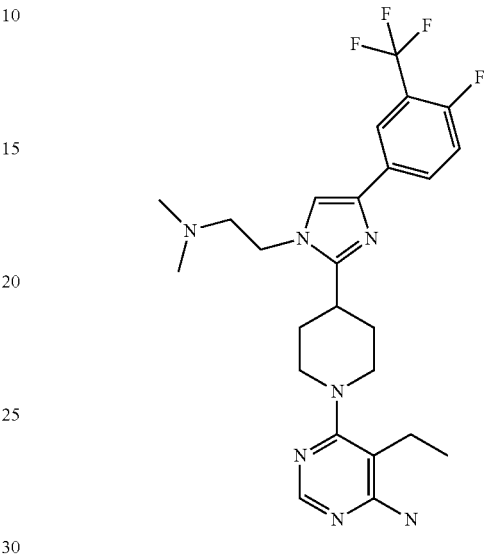

In a 10 mL round-bottom flask containing 6-{4-[1-(2-dimethylamino-ethyl)-4-(4-fluoro-3-trifluoromethyl-phenyl)-1H-imidazol-2-yl]-piperidin-1-yl}-5-vinyl-pyrimidin-4-ylamine; compound with trifluoro-acetic acid (25.00 mg; 0.04 mmol; 1.00 eq.) in methanol (2.00 ml; 49.37 mmol; 1231.95 eq.) under argon was slowly poured 10% Pd/C (80.00 mg; 0.75 mmol; 18.76 eq.). The round-bottom flask was vacuumed and then filled with H₂. The procedure was repeated for 4 more times before the mixture was stirred at rt for O/N under H₂ (balloon). The obtained mixture was filtered and then purified with Waters pre-HPLC. LC-MS: (M+1=506, obsd.=506).

5-(2-Cyclopropylethyl)-6-(4-(1-(2-(dimethylamino)ethyl)-4-(4-fluoro-3-(trifluoromethyl)phenyl)-1H-imidazol-2-yl)piperidin-1-yl)pyrimidin-4-amine ("83")

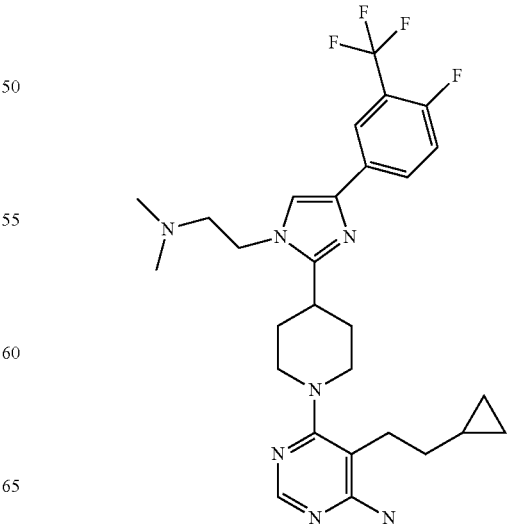

The title compound was prepared in an analogous manner as 6-(4-(1-(2-(dimethylamino)ethyl)-4-(4-fluoro-3-(trifluoromethyl)phenyl)-1H-imidazol-2-yl)piperidin-1-yl)-5-ethylpyrimidin-4-amine using (E)-5-(2-cyclopropylvinyl)-6-(4-(1-(2-(dimethylamino)ethyl)-4-(4-fluoro-3-(trifluoromethyl)phenyl)-1H-imidazol-2-yl)piperidin-1-yl)pyrimidin-4-amine. LC-MS: (M+1=546, obsd.=546).

6-(4-(1-(2-(Dimethylamino)ethyl)-4-(4-fluoro-3-(trifluoromethyl)phenyl)-1H-imidazol-2-yl)piperidin-1-yl)-5-(2-ethoxyethyl)pyrimidin-4-amine ("84")

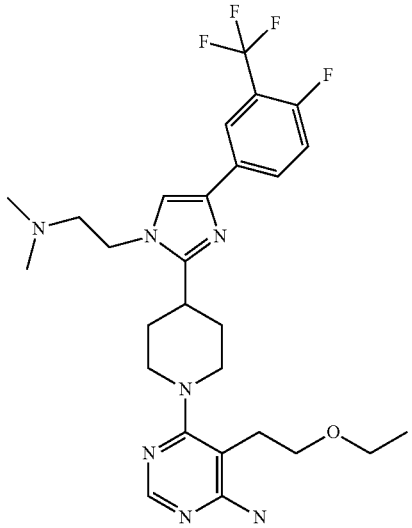 [SMILES: CCOCCc1c(N)ncnc1N1CCC(c2nc(-c3ccc(F)c(C(F)(F)F)c3)cn2CCN(C)C)CC1]

The title compound was prepared in an analogous manner as 6-(4-(1-(2-(dimethylamino)ethyl)-4-(4-fluoro-3-(trifluoromethyl)phenyl)-1H-imidazol-2-yl)piperidin-1-yl)-5-ethylpyrimidin-4-amine using (E)-6-(4-(1-(2-(dimethylamino)ethyl)-4-(4-fluoro-3-(trifluoromethyl)phenyl)-1H-imidazol-2-yl)piperidin-1-yl)-5-(2-ethoxyvinyl)pyrimidin-4-amine. LC-MS: (M+1=550, obsd.=550).

(E)-5-(2-Cyclopropylvinyl)-6-(4-(1-(2-(dimethylamino)ethyl)-4-(4-fluoro-3-(trifluoromethyl)phenyl)-1H-imidazol-2-yl)piperidin-1-yl)pyrimidin-4-amine ("85")

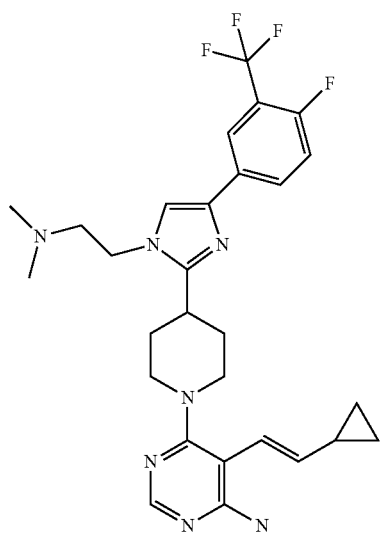 [SMILES: CN(C)CCn1cc(-c2ccc(F)c(C(F)(F)F)c2)nc1C1CCN(c2ncnc(N)c2/C=C/C2CC2)CC1]

The title compound was prepared in an analogous manner as 6-(4-(1-(2-(dimethylamino)ethyl)-4-(4-fluoro-3-(trifluoromethyl)phenyl)-1H-imidazol-2-yl)piperidin-1-yl)-5-(4-fluorophenyl)pyrimidin-4-amine using (E)-2-(2-cyclopropylvinyl)-4,4,5,5-tetramethyl-1,3,2-dioxaborolane instead of 4-fluorophenyl boronic acid. LC-MS: (M+1=544, obsd.=544).

(E)-6-(4-(1-(2-(Dimethylamino)ethyl)-4-(4-fluoro-3-(trifluoromethyl)phenyl)-1H-imidazol-2-yl)piperidin-1-yl)-5-(2-ethoxyvinyl)pyrimidin-4-amine ("86")

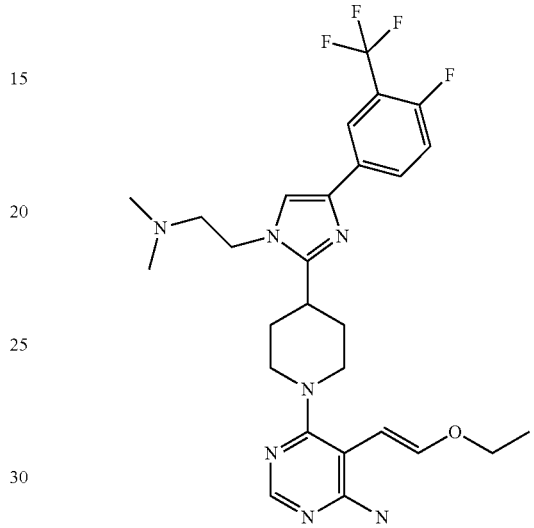

The title compound was prepared in an analogous manner as 6-(4-(1-(2-(dimethylamino)ethyl)-4-(4-fluoro-3-(trifluoromethyl)phenyl)-1H-imidazol-2-yl)piperidin-1-yl)-5-(4-fluorophenyl)pyrimidin-4-amine using (E)-2-(2-ethoxyvinyl)-4,4,5,5-tetramethyl-1,3,2-dioxaborolane instead of 4-fluorophenyl boronic acid. LC-MS: (M+1=548, obsd.=548).

2-(4-(4-Amino-6-(4-(1-(2-(dimethylamino)ethyl)-4-(4-fluoro-3-(trifluoromethyl)phenyl)-1H-imidazol-2-yl)piperidin-1-yl)pyrimidin-5-yl)phenyl)propan-2-ol ("87")

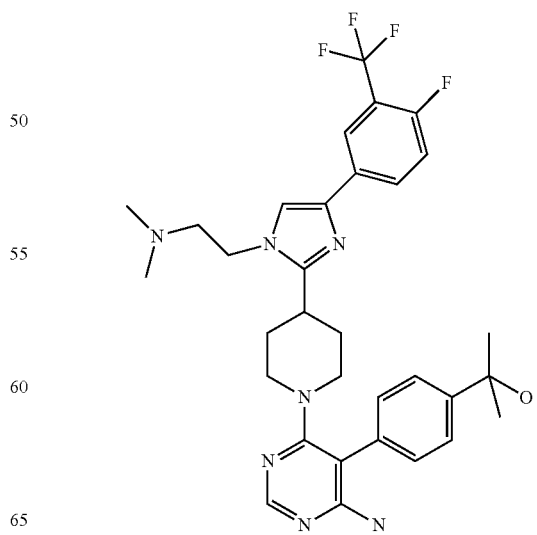

The title compound was prepared in an analogous manner as 6-(4-(1-(2-(dimethylamino)ethyl)-4-(4-fluoro-3-(trifluoromethyl)phenyl)-1H-imidazol-2-yl)piperidin-1-yl)-5-(4-fluorophenyl)pyrimidin-4-amine using 2-(4-(4,4,5,5-tetramethyl-1,3,2-dioxaborolan-2-yl)phenyl)propan-2-ol instead of 4-fluorophenyl boronic acid. LC-MS: (M+1=612, obsd.=612).

Methyl 4-(4-amino-6-(4-(1-(2-(dimethylamino)ethyl)-4-(4-fluoro-3-(trifluoromethyl)phenyl)-1H-imidazol-2-yl)piperidin-1-yl)pyrimidin-5-yl)benzoate ("88")

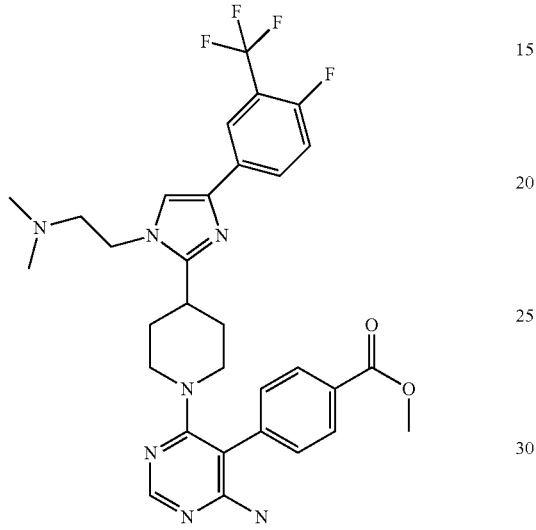

The title compound was prepared in an analogous manner as 6-(4-(1-(2-(dimethylamino)ethyl)-4-(4-fluoro-3-(trifluoromethyl)phenyl)-1H-imidazol-2-yl)piperidin-1-yl)-5-(4-fluorophenyl)pyrimidin-4-amine using methyl 4-(4,4,5,5-tetramethyl-1,3,2-dioxaborolan-2-yl)benzoate instead of 4-fluorophenyl boronic acid. LC-MS: (M+1=612, obsd.=612).

4-(4-Amino-6-(4-(1-(2-(dimethylamino)ethyl)-4-(4-fluoro-3-(trifluoromethyl)phenyl-1H-imidazol-2-yl)piperidin-1-yl)pyrimidin-5-yl)benzoic acid ("89")

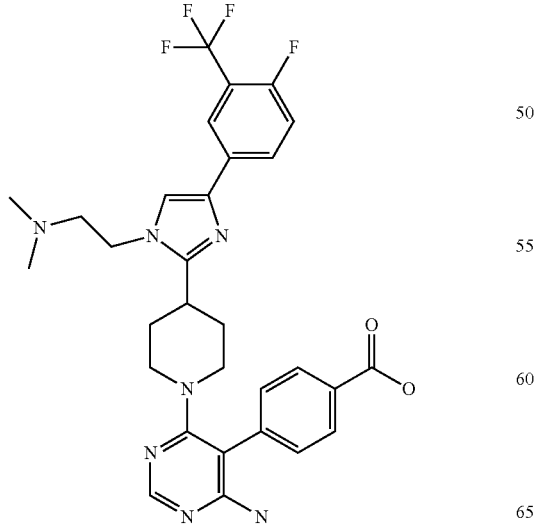

In a round-bottom flask containing 4-(4-Amino-6-{4-[1-(2-dimethylamino-ethyl)-4-(4-fluoro-3-trifluoromethyl-phenyl)-1H-imidazol-2-yl]-piperidin-1-yl}-pyrimidin-5-yl)-benzoic acid methyl ester (25.70 mg; 0.04 mmol; 1.00 eq.) was added 1 N lithium hydroxide monohydrate (0.08 mg; 0.00 mmol; 0.05 eq.) water solution followed by THF (2.00 ml; 24.69 mmol; 593.43 eq.). The mixture was stirred at rt for 4 h before it was concentrated and purified with waters pre-HPLC. LC-MS: (M+1=598, obsd.=598).

5-(Cyclopent-1-en-1-yl)-6-(4-(1-(2-(dimethylamino)ethyl)-4-(4-fluoro-3-(trifluoromethyl)phenyl-1H-imidazol-2-yl)piperidin-1-yl)pyrimidin-4-amine ("90")

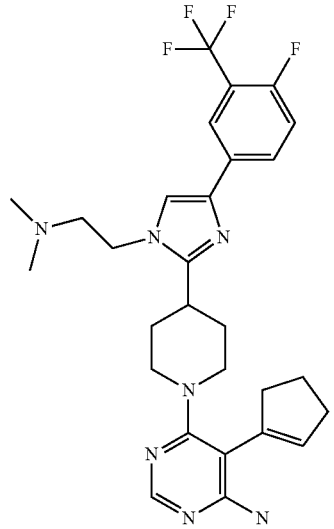 [SMILES: CN(C)CCn1cc(-c2ccc(F)c(C(F)(F)F)c2)nc1C1CCN(c2ncnc(N)c2C2=CCCC2)CC1]

The title compound was prepared in an analogous manner as 6-(4-(1-(2-(dimethylamino)ethyl)-4-(4-fluoro-3-(trifluoromethyl)phenyl)-1H-imidazol-2-yl)piperidin-1-yl)-5-(4-fluorophenyl)pyrimidin-4-amine using 2-(cyclopent-1-en-1-yl)-4,4,5,5-tetramethyl-1,3,2-dioxaborolane instead of 4-fluorophenyl boronic acid. LC-MS: (M+1=612, obsd.=612). LC-MS: (M+1=544, obsd.=544).

5-Cyclopropyl-6-(4-(1-(2-(dimethylamino)ethyl)-4-(4-fluoro-3-(trifluoromethyl)phenyl)-1H-imidazol-2-yl)piperidin-1-yl)pyrimidin-4-amine ("91")

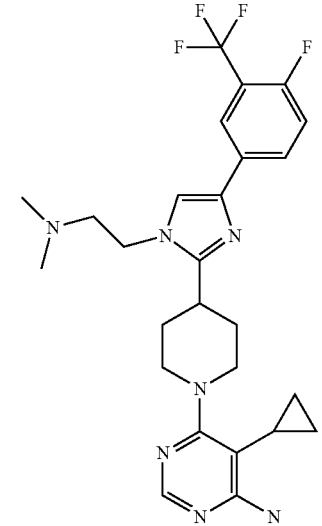 [SMILES: CN(C)CCn1cc(-c2ccc(F)c(C(F)(F)F)c2)nc1C1CCN(c2ncnc(N)c2C2CC2)CC1]

In a microwave vial containing 5-bromo-6-{4-[1-(2-dimethylamino-ethyl)-4-(4-fluoro-3-trifluoromethyl-phenyl)-1H-imidazol-2-yl]-piperidin-1-yl}-pyrimidin-4-ylamine (70.00 mg; 0.13 mmol; 1.00 eq.) in Toluene (3.50 ml) and water (0.35 ml) was added 2-cyclopropyl-4,4,5,5-tetramethyl-[1,3,2]dioxaborolane (0.09 ml; 0.50 mmol; 4.00 eq.), Palladium acetate (4.24 mg; 0.02 mmol; 0.15 eq.), Tricyclohexyl-phosphane (10.58 mg; 0.04 mmol; 0.30 eq.) and Potassium phosphonate (112.16 mg; 0.53 mmol; 4.20 eq.). The mixture was stirred at 100° C. for 5 h before the reaction mixture was filtered, concentrated and purified via waters pre-HPLC. LC-MS: (M+1=518, obsd.=518).

5-ethyl-6-(4-(4-(4-fluoro-3-(trifluoromethyl)phenyl)-1-(2-(3-fluoroazetidin-1-yl)ethyl)-1H-imidazol-2-yl)piperidin-1-yl)pyrimidin-4-amine ("92")

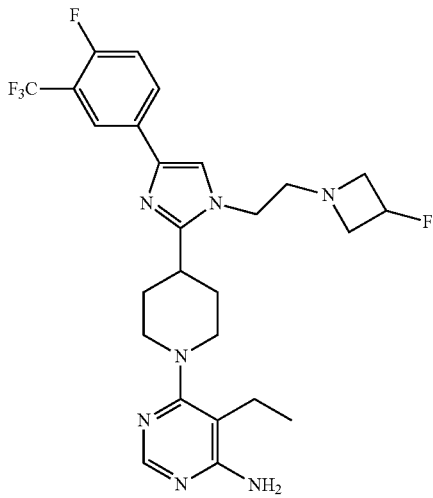

The reaction mixture of 6-chloro-5-ethyl-pyrimidin-4-ylamine (50.00 mg; 0.32 mmol; 1.00 eq.), 4-(4-(4-fluoro-3-(trifluoromethyl)phenyl)-1-(2-(3-fluoroazetidin-1-yl)ethyl)-1H-imidazol-2-yl)piperidine (138.05 mg; 0.33 mmol; 1.05 eq.) and DIEA (65.77 mg; 0.48 mmol; 1.50 eq.) in DMSO (1.5 ml) was placed in microwave at 125° C. for 1 hr. found small amount desired, mostly was sm, 140° C. for another 1 hr, more product formed, 150° C. for another 1 hr, purified the product by HPLC, collected title compound 33 mg, yield 16%. LC-MS (M+1=536, obsd.=536).

5-ethyl-6-(4-(4-(4-fluoro-3-(trifluoromethyl)phenyl)-1-(2-(3-methylazetidin-1-yl)ethyl)-1H-imidazol-2-yl)piperidin-1-yl)pyrimidin-4-amine ("93")

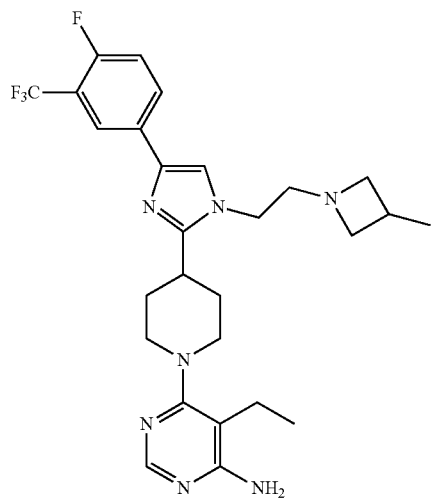 [SMILES: CCc1c(N)ncnc1N1CCC(c2nc(-c3ccc(F)c(C(F)(F)F)c3)cn2CCN2CC(F)C2)CC1]

The title compound was prepared in an analogous manner as 5-ethyl-6-(4-(4-(4-fluoro-3-(trifluoromethyl)phenyl)-1-(2-(3-fluoroazetidin-1-yl)ethyl)-1H-imidazol-2-yl)piperidin-1-yl)pyrimidin-4-amine using 4-(4-(4-fluoro-3-(trifluoromethyl)phenyl)-1-(2-(3-methylazetidin-1-yl)ethyl)-1H-imidazol-2-yl)piperidine instead of 4-[1-[2-(3-Fluoro-azetidin-1-yl)-ethyl]-4-(4-fluoro-3-trifluoromethyl-phenyl)-1H-imidazol-2-yl]-piperidine. LC-MS: (M+1=532, obsd.=532).

6-(4-(1-(2-(3,3-difluoroazetidin-1-yl)ethyl)-4-(4-fluoro-3-(trifluoromethyl)phenyl)-1H-imidazol-2-yl)piperidin-1-yl)-5-ethylpyrimidin-4-amine ("94")

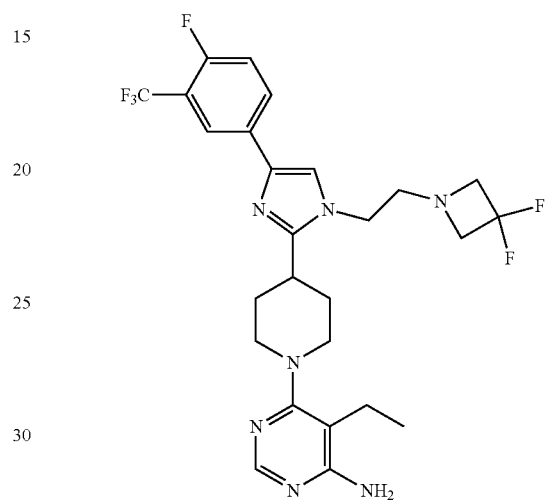

The title compound was prepared in an analogous manner as 5-ethyl-6-(4-(4-(4-fluoro-3-(trifluoromethyl)phenyl)-1-(2-(3-fluoroazetidin-1-yl)ethyl)-1H-imidazol-2-yl)piperidin-1-yl)pyrimidin-4-amine using 4-(1-(2-(3,3-difluoroazetidin-1-yl)ethyl)-4-(4-fluoro-3-(trifluoromethyl)phenyl)-1H-imidazol-2-yl)piperidine instead of 4-[1-[2-(3-Fluoro-azetidin-1-yl)-ethyl]-4-(4-fluoro-3-trifluoromethyl-phenyl)-1H-imidazol-2-yl]-piperidine.
LC-MS: (M+1=554, obsd.=554).

6-(4-(1-(2-(dimethylamino)ethyl)-4-(4-fluoro-3-(trifluoromethyl)phenyl)-1H-imidazol-2-yl)piperidin-1-yl)-5-(((ethyl(methyl)amino)methyl)pyrimidin-4-amine ("95")

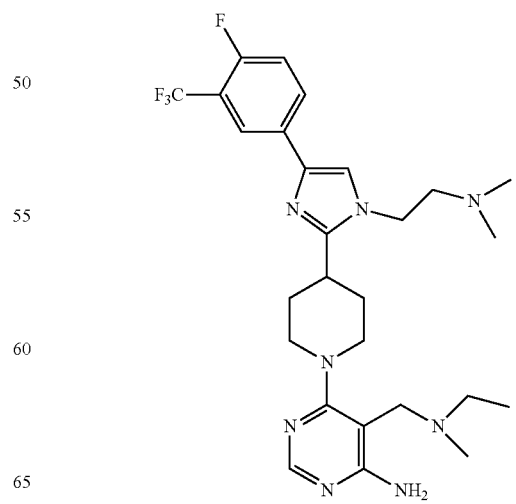

Step 1: 4-amino-6-(4-(1-(2-(dimethylamino)ethyl)-4-(4-fluoro-3-(trifluoromethyl)phenyl)-1H-imidazol-2-yl)piperidin-1-yl)pyrimidine-5-carbaldehyde The reaction mixture of 4-Amino-6-chloro-pyrimidine-5-carbaldehyde (150.00 mg; 0.95 mmol; 1.00 eq.), 4-[1-(2-Azetidin-1-yl-ethyl)-4-(4-fluoro-3-trifluoromethyl-phenyl)-1H-imidazol-2-yl]-piperidine trifluoroacetate (2) (594.52 mg; 0.95 mmol; 1.00 eq.) and Triethyl-amine (0.80 ml; 5.71 mmol; 6.00 eq.) in MeCN 4 ml were stirred at RT for 2 hr, lc-ms showed desired as major. Filtrate, collected white solid as 4-amino-6-(4-(1-(2-(dimethylamino)ethyl)-4-(4-fluoro-3-(trifluoromethyl)phenyl)-1H-imidazol-2-yl)piperidin-1-yl)pyrimidine-5-carbaldehyde, 277 mg, yield 56.2%. LC-MS: (M+1=506, obsd.=506).

Step 2: 6-(4-(1-(2-(dimethylamino)ethyl)-4-(4-fluoro-3-(trifluoromethyl)phenyl)-1H-imidazol-2-yl)piperidin-1-yl)-5-((ethyl(methyl)amino)methyl)pyrimidin-4-amine To a solution of 4-Amino-6-{4-[1-(2-dimethylamino-ethyl)-4-(4-fluoro-3-trifluoromethyl-phenyl)-1H-imidazol-2-yl]-piperidin-1-yl}-pyrimidine-5-carbaldehyde (90.00 mg; 0.18 mmol; 1.00 eq.) in 1 ml DCE added ethyl-methyl-amine (0.02 ml; 0.19 mmol; 1.05 eq.) and sodium p-triacetoxyborohydride (113.20 mg; 0.53 mmol; 3.00 eq.), stirred for overnight at RT, lc-ms showed desired (<30%, major ms 618/619), purified by prep HPLC, collected title compound. LC-MS: (M+1=549, obsd.=549).

6-(4-(1-(2-(azetidin-1-yl)ethyl)-4-(4-fluoro-3-(trifluoromethyl)phenyl)-1H-imidazol-2-yl)piperidin-1-yl)-5-isopropoxypyrimidin-4-amine ("96")

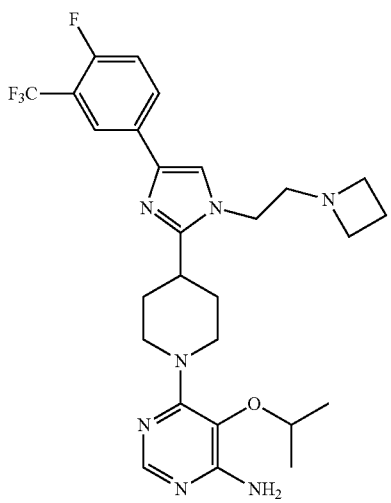 [SMILES: CC(C)Oc1c(N)ncnc1N1CCC(c2nc(-c3ccc(F)c(C(F)(F)F)c3)cn2CCN2CCC2)CC1]

Step 1: 6-chloro-5-isopropoxypyrimidin-4-amine

A reaction mixture of 4-Amino-6-chloro-pyrimidin-5-ol (500.00 mg; 3.44 mmol; 1.00 eq.), Cs2CO3 (2238.59 mg; 6.87 mmol; 2.00 eq.), and 2-Iodo-propane (1167.95 mg; 6.87 mmol; 2.00 eq.) in acetone 10 ml was stirred at 65° C. for 3 hr, desired as major, also found dialkylation by product, removed off solvent, treated with ethyl acetate, solid came out, filtered, washed with ether, collected product 6-chloro-5-isopropoxy-pyrimidin-4-amine 160 mg, yield 24.8%

Step 2: 6-(4-(1-(2-(azetidin-1-yl)ethyl)-4-(4-fluoro-3-(trifluoromethyl)phenyl)-1H-imidazol-2-yl)piperidin-1-yl)-5-isopropoxypyrimidin-4-amine A reaction mixture of 6-Chloro-5-isopropoxy-pyrimidin-4-ylamine (40.00 mg; 0.21 mmol; 1.00 eq.), 4-[1-(2-Azetidin-1-yl-ethyl)-4-(4-fluoro-3-trifluoromethyl-phenyl)-1H-imidazol-2-yl]-piperidine trifluoroacetate (2) (133.13 mg; 0.21 mmol; 1.00 eq.), and Cs2CO3 (277.84 mg; 0.85 mmol; 4.00 eq.) in DMSO 5.0 ml was stirred at 120° C. for 2 days, purified the product by HPLC, collected title compound 64 mg, yield 45.5%. LC-MS: (M+1=548, obsd.=548).

6-(4-(1-(2-(azetidin-1-yl)ethyl)-4-(4-fluoro-3-(trifluoromethyl)phenyl)-1H-imidazol-2-yl)piperidin-1-yl)-5-methoxypyrimidin-4-amine ("97")

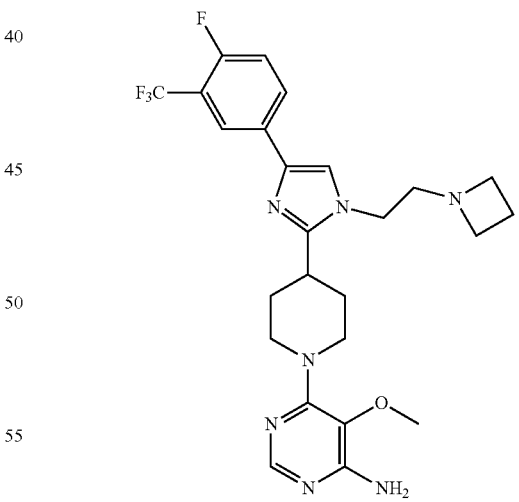

The title compound was prepared in an analogous manner as 6-(4-(1-(2-(azetidin-1-yl)ethyl)-4-(4-fluoro-3-(trifluoromethyl)phenyl)-1H-imidazol-2-yl)piperidin-1-yl)-5-isopropoxypyrimidin-4-amine using 6-chloro-5-methoxypyrimidin-4-amine Instead 6-chloro-5-isopropoxypyrimidin-4-amine LC-MS (M+1=520, obsd.=520).

6-(4-(1-(2-(azetidin-1-yl)ethyl)-4-(4-fluoro-3-(trifluoromethyl)phenyl)-1H-imidazol-2-yl)piperidin-1-yl)-5-(1H-pyrazol-4-yl)pyrimidin-4-amine ("98")

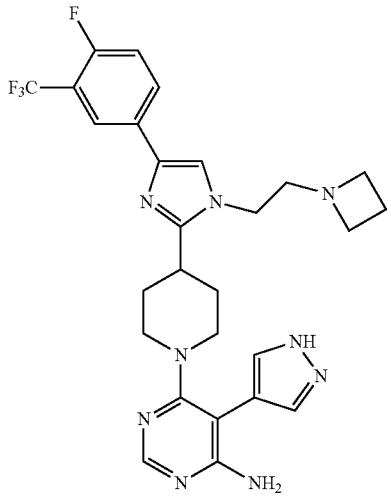 [SMILES: Nc1ncnc(N2CCC(c3nc(-c4ccc(F)c(C(F)(F)F)c4)cn3CCN3CCC3)CC2)c1-c1cn[nH]c1]

A mixture of 6-{4-[1-(2-Azetidin-1-yl-ethyl)-4-(4-fluoro-3-trifluoromethyl-phenyl)-1H-imidazol-2-yl]-piperidin-1-yl}-5-bromo-pyrimidin-4-ylamine (100.00 mg; 0.18 mmol; 1.00 eq.), 4-(4,4,5,5-Tetramethyl-[1,3,2]dioxaborolan-2-yl)-pyrazole-1-carboxylic acid tert-butyl ester (77.63 mg; 0.26 mmol; 1.50 eq.), and in dioxane 2 ml and water 0.15 ml was degas, added Pd(t-Bu$_3$)$_2$ 13 mg, stirred at 50° C. for overnight. Added methanol 5 ml, 4.0M HCl in dioxane 5 ml, stirred at RT for 4 hr, removed off solvent and purified by prep HPLC, collected title compound 15 mg, yield 12.7%. LC-MS: (M+1=556, obsd.=556).

6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine ("99")

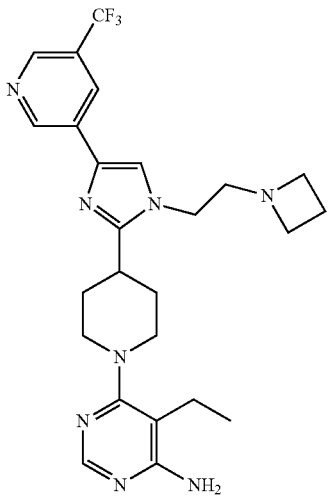

Step 1: 3-(1-(2-(azetidin-1-yl)ethyl)-2-(piperidin-4-yl)-1H-imidazol-4-yl)-5-(trifluoromethyl)pyridine-Hydrochloride salt A mixture of 4-[1-(2-Azetidin-1-yl-ethyl)-4-bromo-1H-imidazol-2-yl]-piperidine-1-carboxylic acid tert-butyl ester (880.00 mg; 2.13 mmol; 1.00 eq.), and 4-(4,4,5,5-tetramethyl-[1,3,2]dioxaborolan-2-yl)-2-trifluoromethyl-pyridine (609.67 mg; 3.19 mmol; 1.50 eq.) in dioxane 8 ml and water 0.6 ml, was added Cs2CO3 (1387.30 mg; 4.26 mmol; 2.00 eq.), purged with argon, then added Pd(t-Bu$_3$P)$_2$ (108.80 mg; 0.21 mmol; 0.10 eq.), stirred at 50° C. for overnight. Lc-ms showed desired as major.

Purified the product by prepHPLC, collected desired 700 mg. yield 68.6 LC-MS: (M+1=380, obsd.=380).

Above product 700 mg was added methanol 3 ml, 4.0 MHCl in dioxane 3 ml, stirred at RT for 4 hr. lc-ms showed desired, filtered, collected white solid as title compound 650 mg, yield 58%.

Step 2: 6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine A reaction mixture of 6-Chloro-5-ethyl-pyrimidin-4-ylamine (50.00 mg; 0.32 mmol; 1.00 eq.), 3-[1-(2-Azetidin-1-yl-ethyl)-2-piperidin-4-yl-1H-imidazol-4-yl]-5-trifluoromethyl-pyridine hydrochloride (3) (155.08 mg; 0.32 mmol; 1.00 eq.), and Cs2CO3 (206.74 mg; 0.63 mmol; 4.00 eq.) in DMSO 1.0 ml was stirred at 120° C. for 2 days, purified by HPLC, title compound 81 mg, 41.5%. LC-MS: (M+1=501, obsd.=501).

6-(4-(1-(2-(azetidin-1-yl)ethyl)-4-(3-(trifluoromethoxy)phenyl)-1H-imidazol-2-yl)piperidin-1-yl)-5-ethylpyrimidin-4-amine ("100")

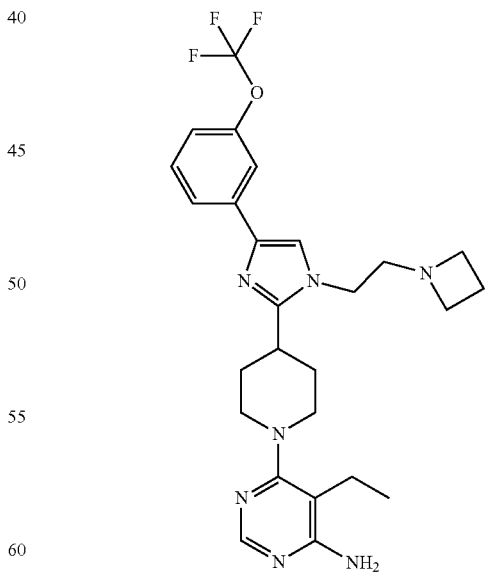

The title compound was prepared in an analogous manner as 6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine of using 4-(1-(2-(azetidin-1-yl)ethyl)-4-(3-(trifluoromethoxy)phenyl)-1H-imidazol-2-yl)piperidine instead of 3-(1-(2-(azetidin-1-yl)ethyl)-2-(piperidin-4-yl)-1H-imidazol-4-yl)-5-(trifluoromethyl)pyridine hydrochloride salt. LC-MS: (M+1=516, obsd.=516).

6-(4-(1-(2-(azetidin-1-yl)ethyl)-4-(5-chloropyridin-3-yl)-1H-imidazol-2-yl)piperidin-1-yl)-5-ethylpyrimidin-4-amine ("101")

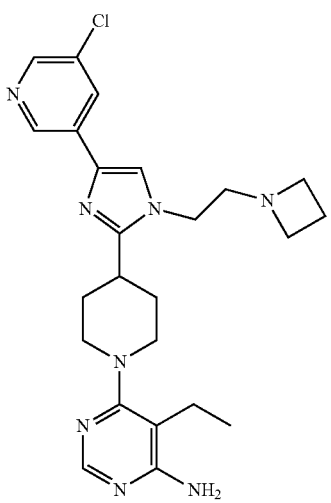 [SMILES: CCc1c(N)ncnc1N1CCC(c2nc(-c3cncc(Cl)c3)cn2CCN2CCC2)CC1]

The title compound was prepared in an analogous manner as 6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine of using 3-(1-(2-(azetidin-1-yl)ethyl)-2-(piperidin-4-yl)-1H-imidazol-4-yl)-5-chloropyridine instead of 3-(1-(2-(azetidin-1-yl)ethyl)-2-(piperidin-4-yl)-1H-imidazol-4-yl)-5-(trifluoromethyl)pyridine hydrochloride salt. LC-MS: (M+1=467, obsd.=467).

6-(4-(1-(2-(azetidin-1-yl)ethyl)-4-(4-fluoro-3-(trifluoromethyl)phenyl)-1H-imidazol-2-yl)piperidin-1-yl)-5-ethoxypyrimidin-4-amine ("102")

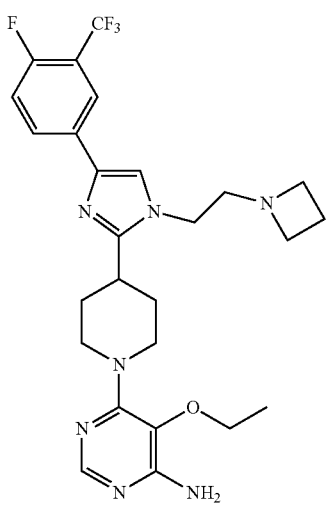 [SMILES: CCOc1c(N)ncnc1N1CCC(c2nc(-c3ccc(F)c(C(F)(F)F)c3)cn2CCN2CCC2)CC1]

A reaction mixture of 6-Chloro-5-ethoxy-pyrimidin-4-ylamine (30.00 mg; 0.17 mmol; 1.00 eq.), 4-[1-(2-Azetidin-1-yl-ethyl)-4-(4-fluoro-3-trifluoromethyl-phenyl)-1H-imidazol-2-yl]-piperidine trifluoroacetate (2) (107.92 mg; 0.17 mmol; 1.00 eq.), and Cs2CO3 (225.22 mg; 0.69 mmol; 4.00 eq.) in DMSO 1.0 ml was stirred at 120° C. for overnight. Purified the product by prep HPLC, collected title compound 27 mg, yield 24%. LC-MS: (M+1=534, obsd.=534).

6-(4-(1-(2-(azetidin-1-yl)ethyl)-4-(4-fluoro-3-(trifluoromethyl)phenyl)-1H-imidazol-2-yl)piperidin-1-yl)-5-(2,2,2-trifluoroethoxy)pyrimidin-4-amine ("103")

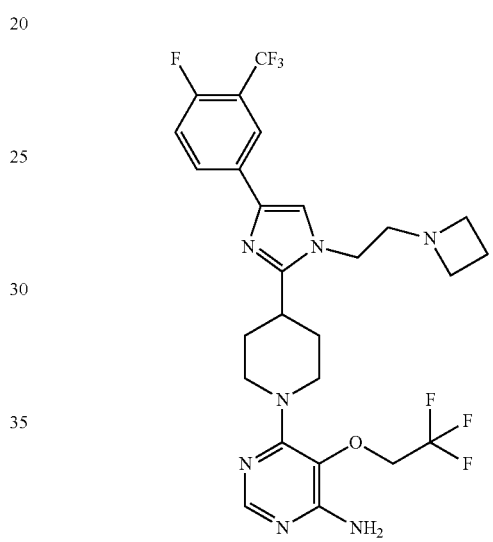

Step 1: 6-chloro-5-(2,2,2-trifluoroethoxy)pyrimidin-4-amine

A reaction mixture of 4-Amino-6-chloro-pyrimidin-5-ol (500.00 mg; 3.44 mmol; 1.00 eq.), Cs2CO3 (1343.15 mg; 4.12 mmol; 1.20 eq.), and Trifluoro-methanesulfonic acid 2,2,2-trifluoro-ethyl ester (0.59 ml; 4.12 mmol; 1.20 eq.) in DMF 2 ml was stirred at RT for overnight. lc-ms showed clean desired, worked up, purified by HPLC, collected title compound 610 mg, yield 78%.

Step 2: 6-(4-(1-(2-(azetidin-1-yl)ethyl)-4-(4-fluoro-3-(trifluoromethyl)phenyl)-1H-imidazol-2-yl)piperidin-1-yl)-5-(2,2,2-trifluoroethoxy)pyrimidin-4-amine A reaction mixture of 6-Chloro-5-(2,2,2-trifluoro-ethoxy)-pyrimidin-4-ylamine (45.00 mg; 0.20 mmol; 1.00 eq.), 4-[1-(2-Azetidin-1-yl-ethyl)-4-(4-fluoro-3-trifluoromethyl-phenyl)-1H-imidazol-2-yl]-piperidine trifluoroacetate (2) (123.48 mg; 0.20 mmol; 1.00 eq.), and Cs2CO3 (257.71 mg; 0.79 mmol; 4.00 eq.) in DMSO 1.0 ml was stirred at 120° C. for 5 days. Purified by HPLC, collected title product 54 mg, yield 39.8%. LC-MS: (M+1=588, obsd.=588).

6-(4-(1-(2-(azetidin-1-yl)ethyl)-4-(2-chloropyridin-4-yl)-1H-imidazol-2-yl)piperidin-1-yl)-5-ethylpyrimidin-4-amine ("104")

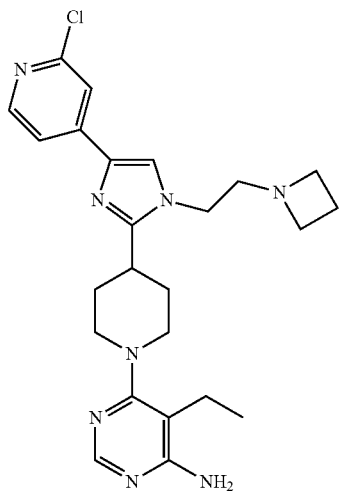 [SMILES: CCc1c(N)ncnc1N1CCC(c2nc(-c3ccnc(Cl)c3)cn2CCN2CCC2)CC1]

The title compound was prepared in an analogous manner as 6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine of using 4-(1-(2-(azetidin-1-yl)ethyl)-2-(piperidin-4-yl)-1H-imidazol-4-yl)-2-chloropyridine instead of 3-(1-(2-(azetidin-1-yl)ethyl)-2-(piperidin-4-yl)-1H-imidazol-4-yl)-5-(trifluoromethyl)pyridine hydrochloride salt. LC-MS: (M+1=467, obsd.=467).

6-(4-(1-(2-(azetidin-1-yl)ethyl)-4-(2-(trifluoromethyl)pyridin-4-yl)-1H-imidazol-2-yl)piperidin-1-yl)-5-ethylpyrimidin-4-amine ("105")

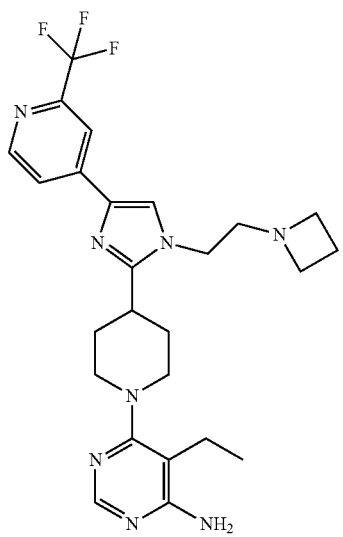

The title compound was prepared in an analogous manner as 6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine of using 4-(1-(2-(azetidin-1-yl)ethyl)-2-(piperidin-4-yl)-1H-imidazol-4-yl)-2-(trifluoromethyl)pyridine instead of 3-(1-(2-(azetidin-1-yl)ethyl)-2-(piperidin-4-yl)-1H-imidazol-4-yl)-5-(trifluoromethyl)pyridine hydrochloride salt. LC-MS: (M+1=501, obsd.=501).

5-(2-(1-(6-amino-5-ethylpyrimidin-4-yl)piperidin-4-yl)-1-(2-(azetidin-1-yl)ethyl)-1H-imidazol-4-yl)-2-fluorobenzamide ("106")

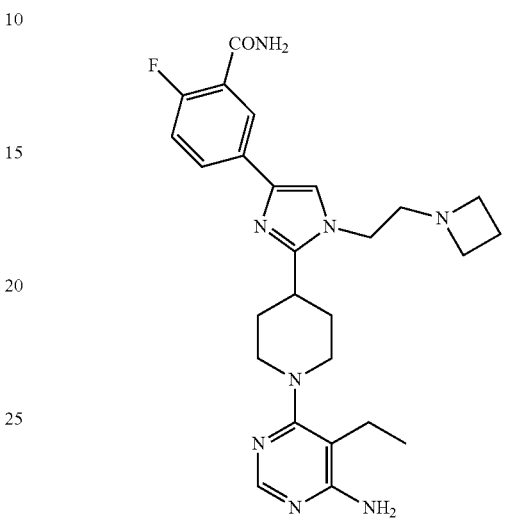

The title compound was prepared in an analogous manner as 6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine of using 5-(1-(2-(azetidin-1-yl)ethyl)-2-(piperidin-4-yl)-1H-imidazol-4-yl)-2-fluorobenzamide instead of 3-(1-(2-(azetidin-1-yl)ethyl)-2-(piperidin-4-yl)-1H-imidazol-4-yl)-5-(trifluoromethyl)pyridine hydrochloride salt. LC-MS: (M+1=493, obsd.=493).

5-(2-(1-(6-amino-5-ethylpyrimidin-4-yl)piperidin-4-yl)-1-(2-(azetidin-1-yl)ethyl)-1H-imidazol-4-yl)-2-methoxybenzamide ("107")

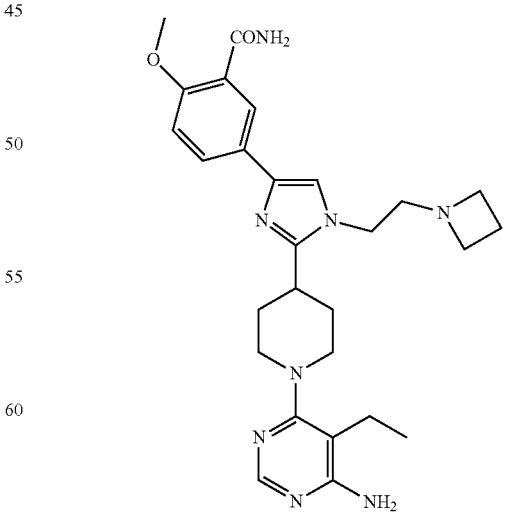

The title compound was obtained when prepared 5-(2-(1-(6-amino-5-ethylpyrimidin-4-yl)piperidin-4-yl)-1-(2-(azetidin-1-yl)ethyl)-1H-imidazol-4-yl)-2-fluorobenzamide as a by product. LC-MS: (M+1=505, obsd.=505).

6-(4-(1-(2-(azetidin-1-yl)ethyl)-4-(4-fluoro-3-methoxyphenyl)-1H-imidazol-2-yl)piperidin-1-yl)-5-ethylpyrimidin-4-amine ("108")

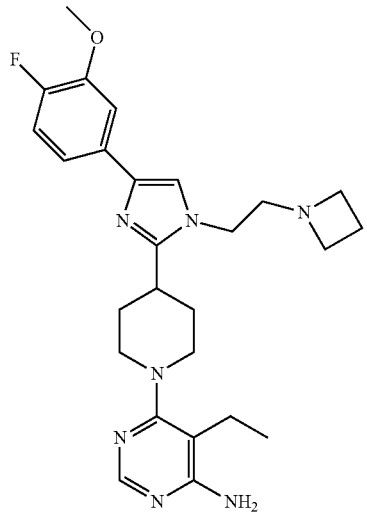 [SMILES: CCc1c(N)ncnc1N1CCC(c2nc(-c3ccc(F)c(OC)c3)cn2CCN2CCC2)CC1]

The title compound was prepared in an analogous manner as 6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine of using 4-(1-(2-(azetidin-1-yl)ethyl)-4-(4-fluoro-3-methoxyphenyl)-1H-imidazol-2-yl)piperidine instead of 3-(1-(2-(azetidin-1-yl)ethyl)-2-(piperidin-4-yl)-1H-imidazol-4-yl)-5-(trifluoromethyl)pyridine hydrochloride salt. LC-MS: (M+1=480, obsd.=480).

6-(4-(1-(2-(azetidin-1-yl)ethyl)-4-(4-fluoro-3-(trifluoromethyl)phenyl)-1H-imidazol-2-yl)piperidin-1-yl)-5-(isoxazol-4-yl)pyrimidin-4-amine ("109")

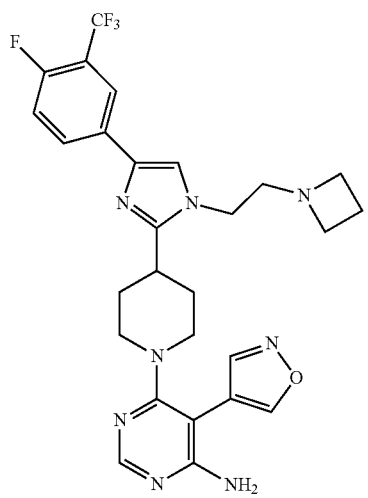 [SMILES: Nc1ncnc(N2CCC(c3nc(-c4ccc(F)c(C(F)(F)F)c4)cn3CCN3CCC3)CC2)c1-c1cnoc1]

The title compound was prepared in an analogous manner as 6-(4-(1-(2-(azetidin-1-yl)ethyl)-4-(4-fluoro-3-(trifluoromethyl)phenyl)-1H-imidazol-2-yl)piperidin-1-yl)-5-(1H-pyrazol-4-yl)pyrimidin-4-amine of using isoxazol-4-ylboronic acid instead tert-butyl 4-(4,4,5,5-tetramethyl-1,3,2-dioxaborolan-2-yl)-1H-pyrazole-1-carboxylate. LC-MS: (M+1=557, obsd.=557).

6-(4-(1-(2-(azetidin-1-yl)ethyl)-4-(4-fluoro-3-(trifluoromethyl)phenyl)-1H-imidazol-2-yl)piperidin-1-yl)-5-(1H-pyrrol-3-yl)pyrimidin-4-amine ("110")

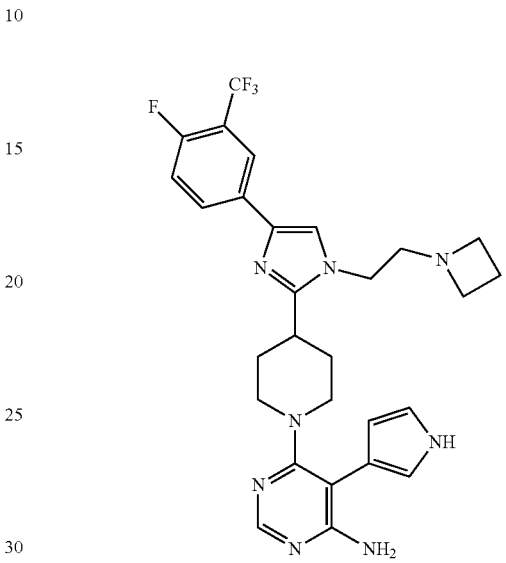

The title compound was prepared in an analogous manner as 6-(4-(1-(2-(azetidin-1-yl)ethyl)-4-(4-fluoro-3-(trifluoromethyl)phenyl)-1H-imidazol-2-yl)piperidin-1-yl)-5-(1H-pyrazol-4-yl)pyrimidin-4-amine of using (1H-pyrrol-3-yl) boronic acid instead tert-butyl 4-(4,4,5,5-tetramethyl-1,3,2-dioxaborolan-2-yl)-1H-pyrazole-1-carboxylate. LC-MS: (M+1=555, obsd.=555).

6-(4-(1-(2-(azetidin-1-yl)ethyl)-4-(2-methylpyridin-4-yl)-1H-imidazol-2-yl)piperidin-1-yl)-5-ethylpyrimidin-4-amine ("111")

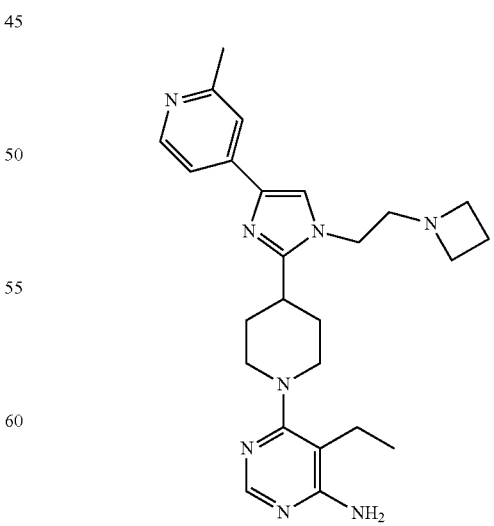

The title compound was prepared in an analogous manner as 6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine of using 4-(1-(2-(azetidin-1-yl)ethyl)-2-(piperidin-4-yl)-1H-imidazol-4-yl)-2-methylpyridine instead of 3-(1-(2-(azetidin-1-yl)ethyl)-2-(piperidin-4-yl)-1H-imidazol-4-yl)-5-(trifluoromethyl)pyridine hydrochloride salt. LC-MS: (M+1=447, obsd.=447).

6-(4-(1-(2-(azetidin-1-yl)ethyl)-4-(2-methoxypyridin-4-yl)-1H-imidazol-2-yl)piperidin-1-yl)-5-ethylpyrimidin-4-amine ("112")

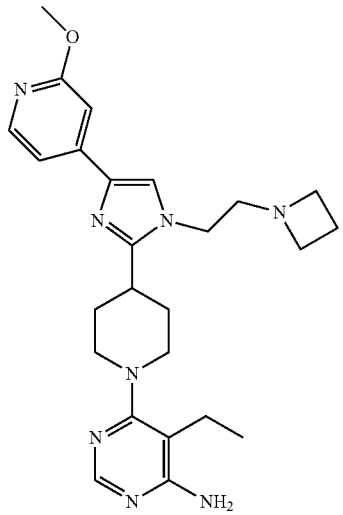 [SMILES: CCc1c(N)ncnc1N1CCC(c2nc(-c3ccnc(OC)c3)cn2CCN2CCC2)CC1]

The title compound was prepared in an analogous manner as 6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine of using 4-(1-(2-(azetidin-1-yl)ethyl)-2-(piperidin-4-yl)-1H-imidazol-4-yl)-2-methoxypyridine instead of 3-(1-(2-(azetidin-1-yl)ethyl)-2-(piperidin-4-yl)-1H-imidazol-4-yl)-5-(trifluoromethyl)pyridine hydrochloride salt. LC-MS: (M+1=463, obsd.=463).

6-(4-(1-(2-(azetidin-1-yl)ethyl)-4-(5-methylpyridin-3-yl)-1H-imidazol-2-yl)piperidin-1-yl)-5-ethylpyrimidin-4-amine ("113")

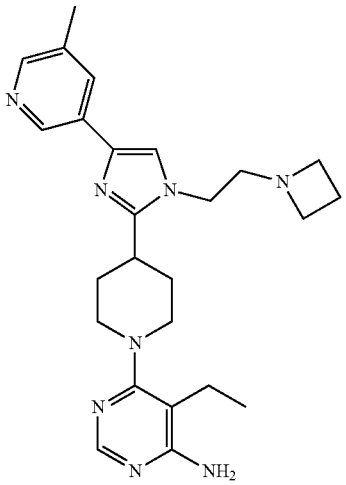 [SMILES: CCc1c(N)ncnc1N1CCC(c2nc(-c3cncc(C)c3)cn2CCN2CCC2)CC1]

The title compound was prepared in an analogous manner as 6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine of using 3-(1-(2-(azetidin-1-yl)ethyl)-2-(piperidin-4-yl)-1H-imidazol-4-yl)-5-methylpyridine instead of 3-(1-(2-(azetidin-1-yl)ethyl)-2-(piperidin-4-yl)-1H-imidazol-4-yl)-5-(trifluoromethyl)pyridine hydrochloride salt. LC-MS: (M+1=447, obsd.=447).

6-(4-(1-(2-(azetidin-1-yl)ethyl)-4-(4-fluoro-3-(trifluoromethyl)phenyl)-1H-imidazol-2-yl)piperidin-1-yl)-5-isopropylpyrimidin-4-amine ("114")

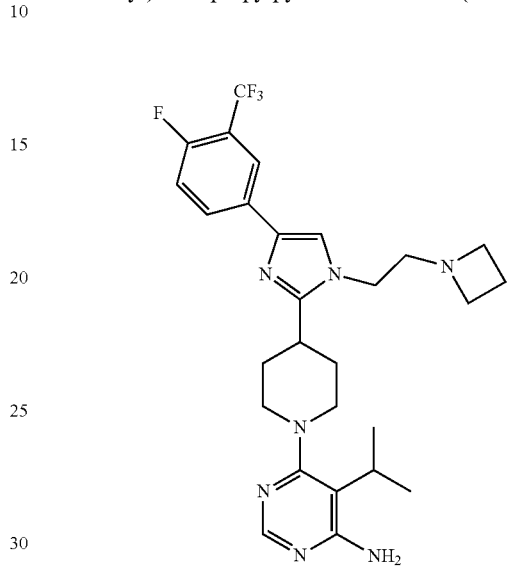

A reaction mixture of 6-Chloro-5-isopropyl-pyrimidin-4-ylamine (30.00 mg; 0.17 mmol; 1.00 eq.), 4-[1-(2-Azetidin-1-yl-ethyl)-4-(4-fluoro-3-trifluoromethyl-phenyl)-1H-imidazol-2-yl]-piperidine trifluoroacetate (2) (109.16 mg; 0.17 mmol; 1.00 eq.), and Cs2CO3 (227.81 mg; 0.70 mmol; 4.00 eq.) in DMSO 1.0 ml was stirred at 120° C. for 4 days, purified by prep HPLC, collected title compound 31 mg, yield 27.7%. LC-MS: (M+1=532, obsd.=532).

6-(4-(1-(2-(azetidin-1-yl)ethyl)-4-(2-(trifluoromethyl)pyridin-4-yl)-1H-imidazol-2-yl)piperidin-1-yl)-5-methoxypyrimidin-4-amine ("115")

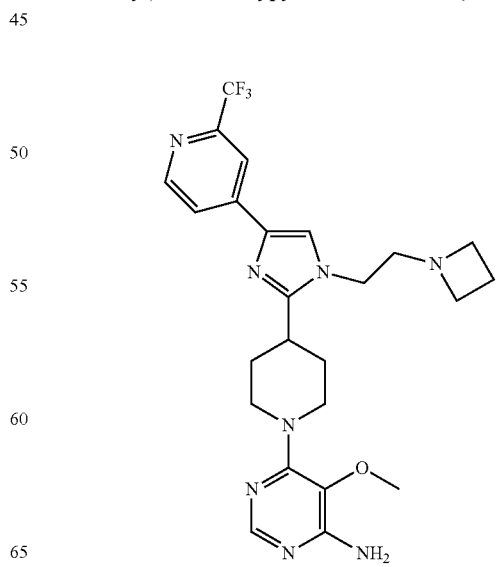

A reaction mixture of 6-Chloro-5-methoxy-pyrimidin-4-ylamine (45.00 mg; 0.28 mmol; 1.00 eq.), 4-[1-(2-Azetidin-1-yl-ethyl)-2-piperidin-4-yl-1H-imidazol-4-yl]-2-trifluoromethyl-pyridine hydrochloride (4) (148.13 mg; 0.28 mmol; 1.00 eq.), and Cs2CO3 (367.53 mg; 1.13 mmol; 4.00 eq.) in DMSO 1.0 ml was stirred at 120° C. for 2 days, purified by HPLC collected title compound 17 mg. LC-MS: (M+1=503, obsd.=503).

6-(4-(1-(2-(azetidin-1-yl)ethyl)-4-(2-(trifluoromethyl)pyridin-4-yl)-1H-imidazol-2-yl)piperidin-1-yl)-5-ethoxypyrimidin-4-amine ("116")

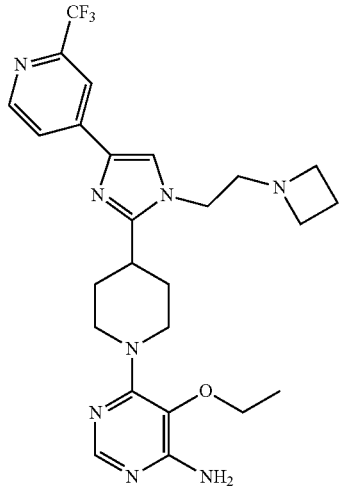 [SMILES: CCOc1c(N)ncnc1N1CCC(c2nc(-c3ccnc(C(F)(F)F)c3)cn2CCN2CCC2)CC1]

The title compound was prepared in an analogous manner as 6-(4-(1-(2-(azetidin-1-yl)ethyl)-4-(2-(trifluoromethyl)pyridin-4-yl)-1H-imidazol-2-yl)piperidin-1-yl)-5-methoxypyrimidin-4-amine using 6-Chloro-5-ethoxy-pyrimidin-4-ylamine instead of 6-Chloro-5-methoxy-pyrimidin-4-ylamine. LC-MS: (M+1=517, obsd.=517).

6-(4-(1-(2-(azetidin-1-yl)ethyl)-4-(2-(trifluoromethyl)pyridin-4-yl)-1H-imidazol-2-yl)piperidin-1-yl)-5-isopropoxypyrimidin-4-amine ("117")

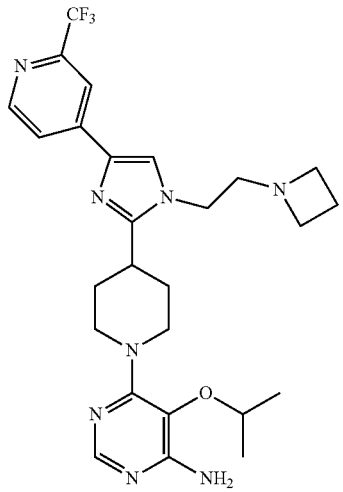 [SMILES: CC(C)Oc1c(N)ncnc1N1CCC(c2nc(-c3ccnc(C(F)(F)F)c3)cn2CCN2CCC2)CC1]

The title compound was prepared in an analogous manner as 6-(4-(1-(2-(azetidin-1-yl)ethyl)-4-(2-(trifluoromethyl)pyridin-4-yl)-1H-imidazol-2-yl)piperidin-1-yl)-5-methoxypyrimidin-4-amine using 6-chloro-5-isopropoxypyrimidin-4-amine instead of 6-Chloro-5-methoxy-pyrimidin-4-ylamine. LC-MS: (M+1=531, obsd.=531).

6-(4-(1-(2-(azetidin-1-yl)ethyl)-4-(2-(trifluoromethyl)pyridin-4-yl)-1H-imidazol-2-yl)piperidin-1-yl)-5-(2,2,2-trifluoroethoxy)pyrimidin-4-amine ("118")

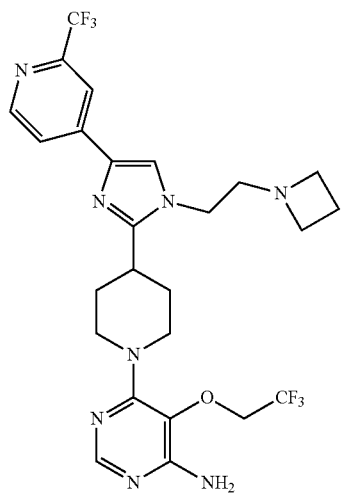 [SMILES: Nc1ncnc(N2CCC(c3nc(-c4ccnc(C(F)(F)F)c4)cn3CCN3CCC3)CC2)c1OCC(F)(F)F]

The title compound was prepared in an analogous manner as 6-(4-(1-(2-(azetidin-1-yl)ethyl)-4-(2-(trifluoromethyl)pyridin-4-yl)-1H-imidazol-2-yl)piperidin-1-yl)-5-methoxypyrimidin-4-amine using 6-chloro-5-(2,2,2-trifluoroethoxy)pyrimidin-4-amine instead of 6-Chloro-5-methoxy-pyrimidin-4-ylamine. LC-MS: (M+1=571, obsd.=571).

6-(4-(1-(2-(azetidin-1-yl)ethyl)-4-(6-(trifluoromethyl)pyridin-2-yl)-1H-imidazol-2-yl)piperidin-1-yl)-5-ethylpyrimidin-4-amine ("119")

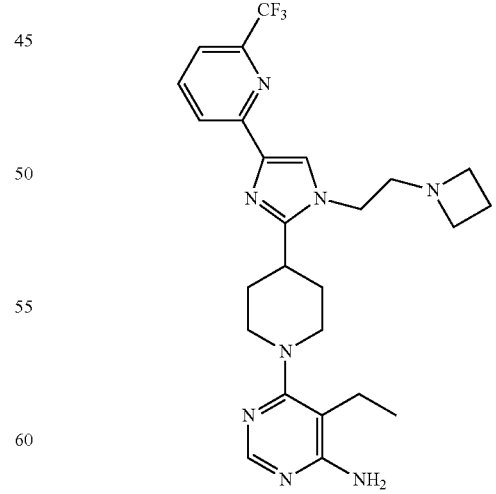

A reaction mixture of 6-Chloro-5-ethyl-pyrimidin-4-ylamine (30.00 mg; 0.19 mmol; 1.00 eq.), 2-[1-(2-Azetidin-1-yl-ethyl)-2-piperidin-4-yl-1H-imidazol-4-yl]-6-trifluoromethyl-pyridine hydrochloride (4) (99.99 mg; 0.19 mmol;

1.00 eq.), and CS$_2$CO$_3$ (248.09 mg; 0.76 mmol; 4.00 eq.) in DMSO 1.0 ml was stirred at 120° C. for over weekend. Purified by HPLC (basic) to afford the title compound 38 mg, yield 32.7%. LC-MS (M+1=501, obsd.=501).

4-amino-6-(4-(1-(2-(azetidin-1-yl)ethyl)-4-(4-fluoro-3-methoxyphenyl)-1H-imidazol-2-yl)piperidin-1-yl) pyrimidine-5-carbonitrile ("120")

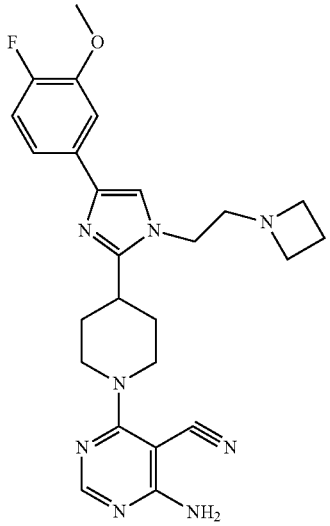 [SMILES: COc1cc(-c2cn(CCN3CCC3)c(C3CCN(c4ncnc(N)c4C#N)CC3)n2)ccc1F]

A reaction mixture of 4-Amino-6-chloro-pyrimidine-5-carbonitrile (52.00 mg; 0.36 mmol; 1.00 eq.), 4-[1-(2-Azetidin-1-yl-ethyl)-4-(4-fluoro-3-methoxy-phenyl)-1H-imidazol-2-yl]-piperidine hydrochloride (4) (179.46 mg; 0.36 mmol; 1.00 eq.), and Ethyl-diisopropyl-amine (0.26 ml; 1.42 mmol; 4.00 eq.) in acetonitrile 2 ml was stirred at RT for overnight, all starting material was converted to desired monitored by lc-MS, filtered, collected white solid as title compound, 106 mg, yield 62.5%. LC-MS (M+1=477, obsd.=477).

4-amino-6-(4-(1-(2-(azetidin-1-yl)ethyl)-4-(4-fluoro-3-methoxyphenyl)-1H-imidazol-2-yl)piperidin-1-yl) pyrimidine-5-carboxamide ("121")

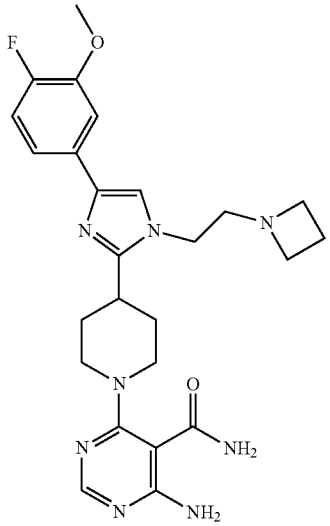 [SMILES: COc1cc(-c2cn(CCN3CCC3)c(C3CCN(c4ncnc(N)c4C(N)=O)CC3)n2)ccc1F]

A reaction mixture of 4-Amino-6-{4-[1-(2-azetidin-1-yl-ethyl)-4-(4-fluoro-3-methoxy-phenyl)-1H-imidazol-2-yl]-piperidin-1-yl}-pyrimidine-5-carbonitrile (100.00 mg; 0.21 mmol; 1.00 eq.), DMSO 8 ml was stirred at RT added H$_2$O$_2$ (0.20 ml; 2.10 mmol; 10.00 eq.) and 2.0M NaOH.2.0MNaOH aq (1.05 ml; 2.10 mmol; 10.00 eq.), stirred at RT for 2 hr, got desired as major detected by lc-ms, purified the product by prep HPLC (basic), title compound 66 mg, 63%. LC-MS (M+1=495, obsd.=495).

4-amino-6-(4-(1-(2-(azetidin-1-yl)ethyl)-4-(4-fluoro-3-methylphenyl)-1H-imidazol-2-yl)piperidin-1-yl) pyrimidine-5-carbonitrile ("122")

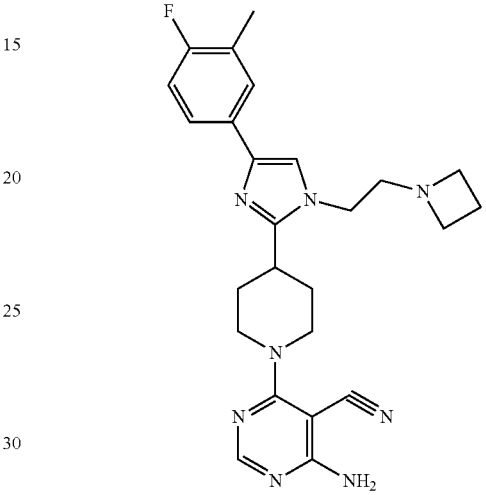

The title compound was prepared in an analogous manner as 4-amino-6-(4-(1-(2-(azetidin-1-yl)ethyl)-4-(4-fluoro-3-methoxyphenyl)-1H-imidazol-2-yl)piperidin-1-yl)pyrimidine-5-carbonitrile of using 4-(1-(2-(azetidin-1-yl)ethyl)-4-(4-fluoro-3-methylphenyl)-1H-imidazol-2-yl)piperidine instead 4-[1-(2-Azetidin-1-yl-ethyl)-4-(4-fluoro-3-methoxy-phenyl)-1H-imidazol-2-yl]-piperidine hydrochloride.
LC-MS: (M+1=461, obsd.=461).

6-(4-(1-(2-(azetidin-1-yl)ethyl)-4-(6-chloropyridin-2-yl)-1H-imidazol-2-yl)piperidin-1-yl)-5-ethylpyrimidin-4-amine ("123")

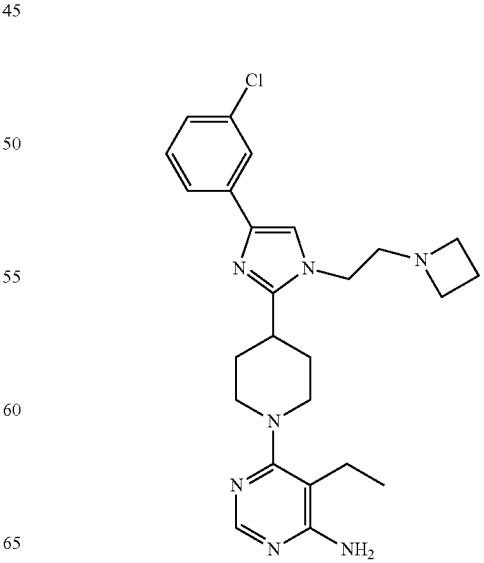

A reaction mixture of 6-Chloro-5-ethyl-pyrimidin-4-ylamine (45.00 mg; 0.29 mmol; 1.00 eq.), 2-[1-(2-Azetidin-1-yl-ethyl)-2-piperidin-4-yl-1H-imidazol-4-yl]-6-chloropyridine hydrochloride (4) (140.40 mg; 0.29 mmol; 1.00 eq.), and Cs2CO3 (372.13 mg; 1.14 mmol; 4.00 eq.) in DMSO 1.0 ml was stirred at 120° C. for 2 days, purified by HPLC, collected title compound 36 mg. LC-MS (M+1=467, obsd.=467).

4-amino-6-(4-(1-(2-(azetidin-1-yl)ethyl)-4-(4-fluoro-3-methylphenyl)-1H-imidazol-2-yl)piperidin-1-yl)pyrimidine-5-carboxamide ("124")

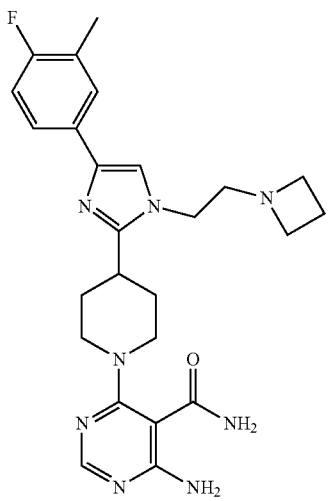 [SMILES: Cc1cc(-c2cn(CCN3CCC3)c(C3CCN(c4ncnc(N)c4C(N)=O)CC3)n2)ccc1F]

The title compound was prepared in an analogous manner as 4-amino-6-(4-(1-(2-(azetidin-1-yl)ethyl)-4-(4-fluoro-3-methoxyphenyl)-1H-imidazol-2-yl)piperidin-1-yl)pyrimidine-5-carboxamide. LC-MS: (M+1=479, obsd.=479).

4-amino-6-(4-(1-(2-(azetidin-1-yl)ethyl)-4-(2-(trifluoromethyl)pyridin-4-yl)-1H-imidazol-2-yl)piperidin-1-yl)pyrimidine-5-carbonitrile ("125")

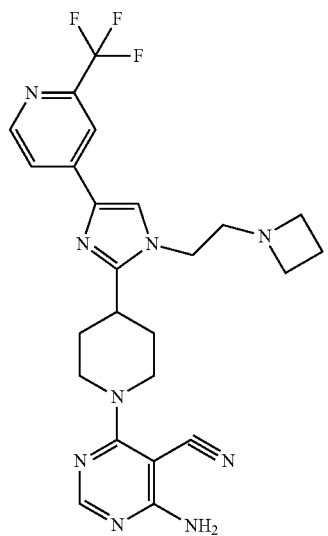 [SMILES: N#Cc1c(N)ncnc1N1CCC(c2nc(-c3ccnc(C(F)(F)F)c3)cn2CCN2CCC2)CC1]

The title compound was prepared in an analogous manner as 4-amino-6-(4-(1-(2-(azetidin-1-yl)ethyl)-4-(4-fluoro-3-methylphenyl)-1H-imidazol-2-yl)piperidin-1-yl)pyrimidine-5-carbonitrile. LC-MS: (M+1=498, obsd.=498).

6-(4-(1-(2-(azetidin-1-yl)ethyl)-4-(2-(trifluoromethyl)pyridin-4-yl)-1H-imidazol-2-yl)piperidin-1-yl)-5-bromopyrimidin-4-amine ("126")

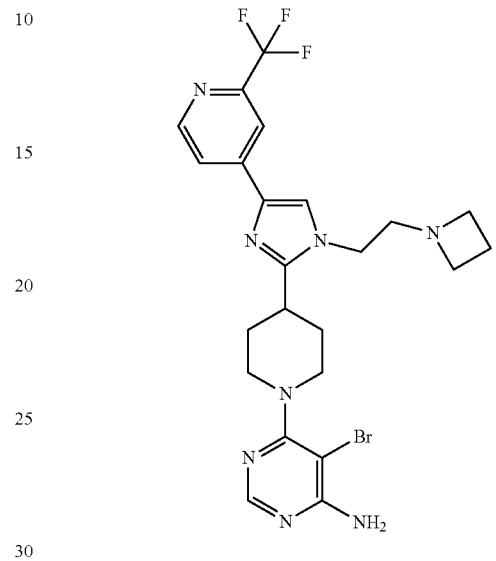

A reaction mixture of 5-Bromo-6-chloro-pyrimidin-4-ylamine (53.00 mg; 0.25 mmol; 1.00 eq.), 4-[1-(2-azetidin-1-yl-ethyl)-2-piperidin-4-yl-1H-imidazol-4-yl]-2-trifluoromethyl-pyridine hydrochloride (4) (133.56 mg; 0.25 mmol; 1.00 eq.), and ethyl-diisopropyl-amine (0.23 ml; 1.27 mmol; 5.00 eq.) in ACN 3 ml was stirred at 80° C. for overnight. Purified by HPLC (basic), collected title compound, 30 mg, yield, 21%. LC-MS: (M+1=551, obsd.=551).

5-bromo-6-(4-(1-(2-((3-chloropropyl)amino)ethyl)-4-(2-(trifluoromethyl)pyridin-4-yl)-1H-imidazol-2-yl)piperidin-1-yl)pyrimidin-4-amine ("127")

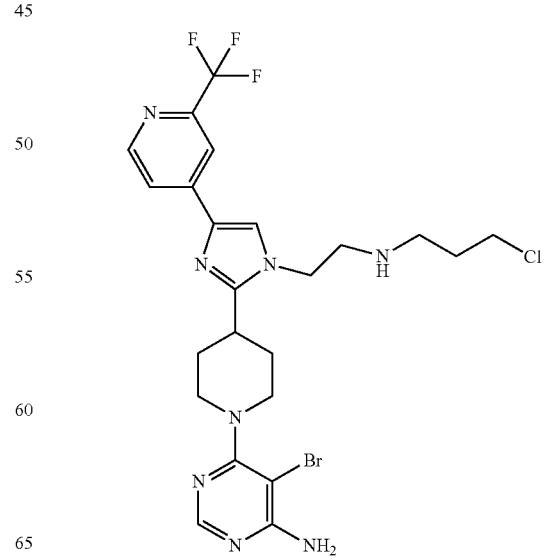

The title compound was prepared in an analogous manner as 6-(4-(1-(2-(azetidin-1-yl)ethyl)-4-(2-(trifluoromethyl)pyridin-4-yl)-1H-imidazol-2-yl)piperidin-1-yl)-5-bromopyrimidin-4-amine. LC-MS: (M+1=588, obsd.=588).

4-amino-6-(4-(1-(2-aminoethyl)-4-(2-(trifluoromethyl)pyridin-4-yl)-1H-imidazol-2-yl)piperidin-1-yl)pyrimidine-5-carboxylic acid ("128")

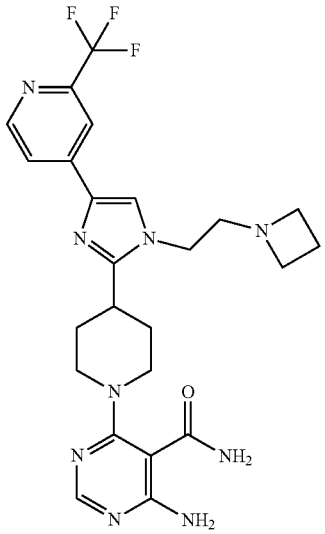 [SMILES: NC(=O)c1c(N)ncnc1N1CCC(c2nc(-c3ccnc(C(F)(F)F)c3)cn2CCN2CCC2)CC1]

The title compound was prepared in an analogous manner as 4-amino-6-(4-(1-(2-(azetidin-1-yl)ethyl)-4-(4-fluoro-3-methoxyphenyl)-1H-imidazol-2-yl)piperidin-1-yl)pyrimidine-5-carboxamide. LC-MS: (M+1=516, obsd.=516).

4-amino-6-(4-(1-(2-(azetidin-1-yl)ethyl)-4-(furan-3-yl)-1H-imidazol-2-yl)piperidin-1-yl)pyrimidine-5-carbonitrile ("129")

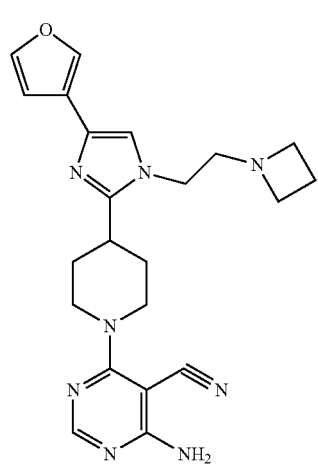 [SMILES: N#Cc1c(N)ncnc1N1CCC(c2nc(-c3ccoc3)cn2CCN2CCC2)CC1]

The title compound was prepared in an analogous manner as 4-amino-6-(4-(1-(2-(azetidin-1-yl)ethyl)-4-(4-fluoro-3-methylphenyl)-1H-imidazol-2-yl)piperidin-1-yl)pyrimidine-5-carbonitrile. LC-MS: (M+1=419, obsd.=419).

4-amino-6-(4-(1-(2-(azetidin-1-yl)ethyl)-4-(thiophen-3-yl)-1H-imidazol-2-yl)piperidin-1-yl)pyrimidine-5-carbonitrile ("130")

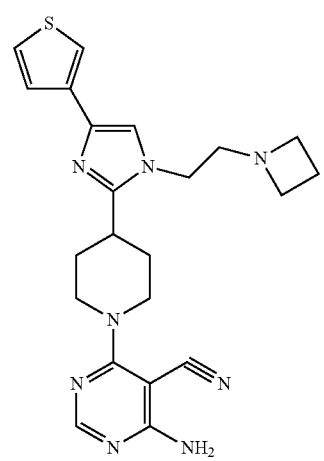 [SMILES: N#Cc1c(N)ncnc1N1CCC(c2nc(-c3ccsc3)cn2CCN2CCC2)CC1]

The title compound was prepared in an analogous manner as 4-amino-6-(4-(1-(2-(azetidin-1-yl)ethyl)-4-(4-fluoro-3-methylphenyl)-1H-imidazol-2-yl)piperidin-1-yl)pyrimidine-5-carbonitrile. LC-MS: (M+1=435, obsd.=435).

4-amino-6-(4-(1-(2-(azetidin-1-yl)ethyl)-4-phenyl-1H-imidazol-2-yl)piperidin-1-yl)pyrimidine-5-carbonitrile ("131")

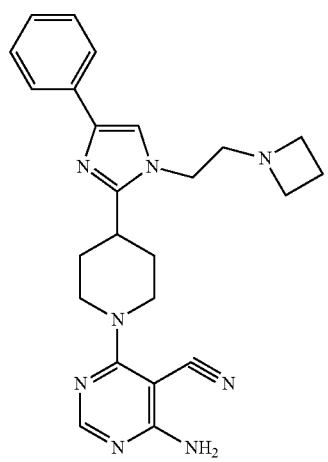 [SMILES: N#Cc1c(N)ncnc1N1CCC(c2nc(-c3ccccc3)cn2CCN2CCC2)CC1]

The title compound was prepared in an analogous manner as 4-amino-6-(4-(1-(2-(azetidin-1-yl)ethyl)-4-(4-fluoro-3- methylphenyl)-1H-imidazol-2-yl)piperidin-1-yl)pyrimidine-5-carbonitrile. LC-MS: (M+1=429, obsd.=429).

4-amino-6-(4-(1-(2-(azetidin-1-yl)ethyl)-4-(isoxazol-4-yl)-1H-imidazol-2-yl)piperidin-1-yl)pyrimidine-5-carbonitrile ("132")

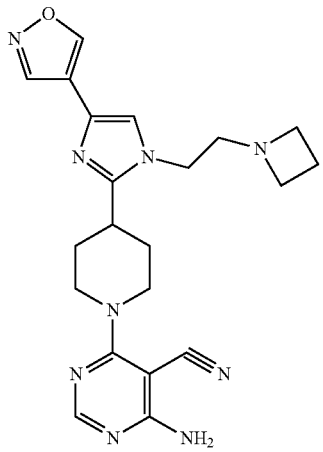 [SMILES: N#Cc1c(N)ncnc1N1CCC(c2nc(-c3cnoc3)cn2CCN2CCC2)CC1]

The title compound was prepared in an analogous manner as 4-amino-6-(4-(1-(2-(azetidin-1-yl)ethyl)-4-(4-fluoro-3-methylphenyl)-1H-imidazol-2-yl)piperidin-1-yl)pyrimidine-5-carbonitrile. LC-MS: (M+1=420, obsd.=420).

4-amino-6-(4-(1-(2-(azetidin-1-yl)ethyl)-4-(furan-3-yl)-1H-imidazol-2-yl)piperidin-1-yl)pyrimidine-5-carboxamide ("133")

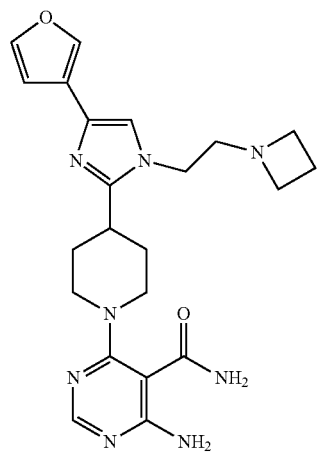 [SMILES: NC(=O)c1c(N)ncnc1N1CCC(c2nc(-c3ccsc3)cn2CCN2CCC2)CC1]

The title compound was prepared in an analogous manner as 4-amino-6-(4-(1-(2-(azetidin-1-yl)ethyl)-4-(4-fluoro-3- methoxyphenyl)-1H-imidazol-2-yl)piperidin-1-yl)pyrimidine-5-carboxamide. LC-MS: (M+1=437, obsd.=437).

4-amino-6-(4-(1-(2-(azetidin-1-yl)ethyl)-4-(thiophen-3-yl)-1H-imidazol-2-yl)piperidin-1-yl)pyrimidine-5-carboxamide ("134")

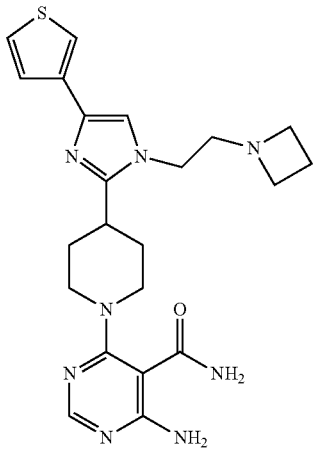

The title compound was prepared in an analogous manner as 4-amino-6-(4-(1-(2-(azetidin-1-yl)ethyl)-4-(4-fluoro-3-methoxyphenyl)-1H-imidazol-2-yl)piperidin-1-yl)pyrimidine-5-carboxamide. LC-MS: (M+1=453, obsd.=453).

4-amino-6-(4-(1-(2-(azetidin-1-yl)ethyl)-4-(isoxazol-4-yl)-1H-imidazol-2-yl)piperidin-1-yl)pyrimidine-5-carboxamide ("135")

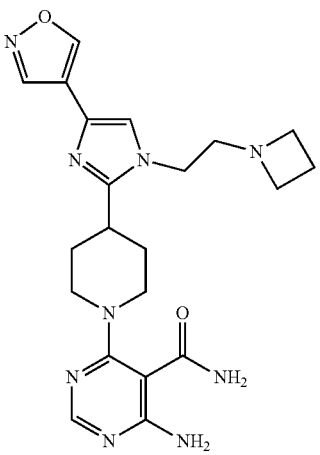 [SMILES: NC(=O)c1c(N)ncnc1N1CCC(c2nc(-c3cnoc3)cn2CCN2CCC2)CC1]

The title compound was prepared in an analogous manner as 4-amino-6-(4-(1-(2-(azetidin-1-yl)ethyl)-4-(4-fluoro-3- methoxyphenyl)-1H-imidazol-2-yl)piperidin-1-yl)pyrimidine-5-carboxamide. LC-MS: (M+1=437, obsd.=437).

4-amino-6-(4-(1-(2-(azetidin-1-yl)ethyl)-4-phenyl-1H-imidazol-2-yl)piperidin-1-yl)pyrimidine-5-carboxamide ("136")

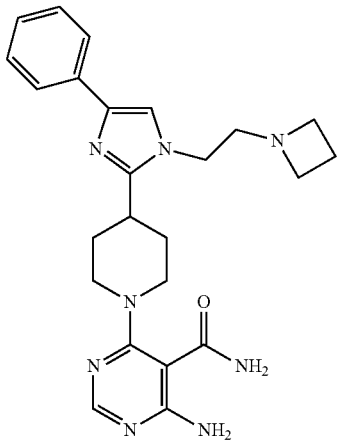 [SMILES: NC(=O)c1c(N)ncnc1N1CCC(c2nc(-c3ccccc3)cn2CCN2CCC2)CC1]

The title compound was prepared in an analogous manner as 4-amino-6-(4-(1-(2-(azetidin-1-yl)ethyl)-4-(4-fluoro-3-methoxyphenyl)-1H-imidazol-2-yl)piperidin-1-yl)pyrimidine-5-carboxamide. LC-MS: (M+1=447, obsd.=447).

4-amino-6-(4-(4-(4-fluoro-3-(trifluoromethyl)phenyl)-1-(pyrrolidin-3-yl)-1H-imidazol-2-yl)piperidin-1-yl)pyrimidine-5-carbonitrile ("137")

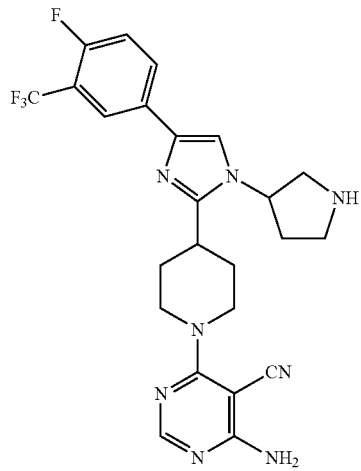 [SMILES: N#Cc1c(N)ncnc1N1CCC(c2nc(-c3ccc(F)c(C(F)(F)F)c3)cn2C2CCNC2)CC1]

Step 1:
3-Methanesulfonyloxy-pyrrolidine-1-carboxylic acid tert-butyl ester

To a solution of 3-hydroxy-pyrrolidine-1-carboxylic acid tert-butyl ester (2000.00 mg; 10.68 mmol; 1.00 eq.) in DCM 10 ml added ethyl-diisopropyl-amine (2.49 ml; 13.89 mmol; 1.30 eq.), then added dropwise methanesulfonyl chloride (0.89 ml; 11.22 mmol; 1.05 eq.) at 0° C., the reaction mixture was stirred for overnight at RT. TLC (EA/HEX=7:3) showed staring material converted to desired completed. Diluted the reaction solution with EA, washed with brine, organic layer was dried, filtered through silica gel 10 g, most color material was absorbed on silica gel, the filtrate was evaporated off solvent, got residue as title compound directly using for the next step reaction, TLC was clean.

Step 2: Benzyl 4-(1-(1-(tert-butoxycarbonyl)pyrrolidin-3-yl)-4-(4-fluoro-3-(trifluoromethyl)phenyl)-1H-imidazol-2-yl)piperidine-1-carboxylate To a solution of 4-[4-(4-Fluoro-3-trifluoromethyl-phenyl)-1H-imidazol-2-yl]-piperidine-1-carboxylic acid benzyl ester (1000.00 mg; 2.24 mmol; 1.00 eq.) in DMF 8 ml added NaH (107.27 mg; 2.68 mmol; 1.20 eq.), stirred at RT for 20 mins, added 3-methanesulfonyloxy-pyrrolidine-1-carboxylic acid tert-butyl ester (1186.02 mg; 4.47 mmol; 2.00 eq.), the reaction mixture was stirred 85° C. for 5 hr, lc-ms showed around 40% desired, continued stirring for over night, no big changed, purified the product by HPLC (basic) with 30-100% acetonitrile/water, collected title compound 220 mg, yield 16%.

Step 3: tert-butyl 3-(4-(4-fluoro-3-(trifluoromethyl)phenyl)-2-(piperidin-4-yl)-1H-imidazol-1-yl)pyrrolidine-1-carboxylate To a solution of 4-[1-(1-tert-butoxycarbonyl-pyrrolidin-2-ylmethyl)-4-(4-fluoro-3-trifluoromethyl-phenyl)-1H-imidazol-2-yl]-piperidine-1-carboxylic acid benzyl ester (200.00 mg; 0.32 mmol; 1.00 eq.) in methanol 5 ml added trifluoroacetic acid (54.24 mg; 0.48 mmol; 1.50 eq.), stirred at RT for 5 min, added ammonium formate (199.96 mg; 3.17 mmol; 10.00 eq.) and 200 mg wet 10% Pd/C, stirred at RT for 1 hr, lc-ms showed clean desired. Removed off solvent, added EA 50 ml, washed with Brine and 5% NaHCO3, dried, removed off solvent, got title compound 110 mg, yield 70%.

Step 4: tert-butyl 3-(2-(1-(6-amino-5-cyanopyrimidin-4-yl)piperidin-4-yl)-4-(4-fluoro-3-(trifluoromethyl)phenyl)-1H-imidazol-1-yl)pyrrolidine-1-carboxylate 3-[4-(4-fluoro-3-trifluoromethyl-phenyl)-2-piperidin-4-yl-imidazol-1-yl]-pyrrolidine-1-carboxylic acid tert-butyl ester (109.27 mg; 0.23 mmol; 1.00 eq.) in acetonitrile 2 ml was added ethyl-diisopropyl-amine (0.08 ml; 0.45 mmol; 2.00 eq.) and 4-amino-6-chloro-pyrimidine-5-carbonitrile (35.00 mg; 0.23 mmol; 1.00 eq.), the reaction mixture was stirred at RT for 1 hr, lc-ms showed desired as major product, removed off solvent, got residue, which as title compound directly using for the next step reaction.

Step 5: 4-amino-6-(4-(4-(4-fluoro-3-(trifluoromethyl)phenyl)-1-(pyrrolidin-3-yl)-1H-imidazol-2-yl)piperidin-1-yl)pyrimidine-5-carbonitrile Tert-butyl 3-(2-(1-(6-amino-5-cyanopyrimidin-4-yl)piperidin-4-yl)-4-(4-fluoro-3-(trifluoromethyl)phenyl)-1H-imidazol-1-yl)pyrrolidine-1-carboxylate 21.00 mg in 0.5 ml of methanol was added 0.5 ml of 4.0M HCl in dioxane, stirred at RT for 3 hrs, LC-MS showed desired. Purified by prep HPLC, collected title compound. LC-MS: (M+1=501, obsd.=501).

4-amino-6-(4-(4-(4-fluoro-3-(trifluoromethyl)phenyl)-1-(pyrrolidin-3-yl)-1H-imidazol-2-yl)piperidin-1-yl)pyrimidine-5-carboxamide ("138")

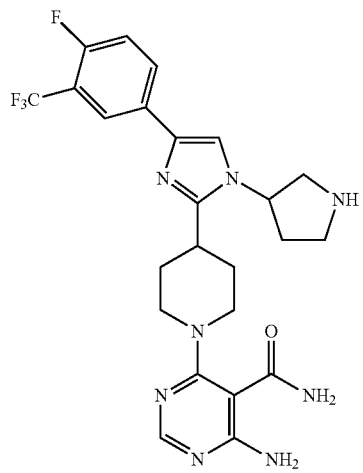 [SMILES: NC(=O)c1c(N)ncnc1N1CCC(c2nc(-c3ccc(F)c(C(F)(F)F)c3)cn2C2CCNC2)CC1]

Step 1: tert-butyl 3-(2-(1-(6-amino-5-carbamoylpyrimidin-4-yl)piperidin-4-yl)-4-(4-fluoro-3-(trifluoromethyl)phenyl)-1H-imidazol-1-yl)pyrrolidine-1-carboxylate A reaction mixture of 3-[2-[1-(6-amino-5-cyano-pyrimidin-4-yl)-piperidin-4-yl]-4-(4-fluoro-3-trifluoromethyl-phenyl)-imidazol-1-yl]-pyrrolidine-1-carboxylic acid tert-butyl ester (100.00 mg; 0.17 mmol; 1.00 eq.) and 2.0N NaOHaq (0.83 ml; 1.66 mmol; 10.00 eq.), in DMSO 8 ml was stirred at RT for 5 mins, added H₂O₂ (0.16 ml; 1.66 mmol; 10.00 eq.) stirred at RT for 2 hr. Purified the product by HPLC (basic), collected title compound 45 mg, yield 43%.

Step 2: 4-amino-6-(4-(4-(4-fluoro-3-(trifluoromethyl)phenyl)-1-(pyrrolidin-3-yl)-1H-imidazol-2-yl)piperidin-1-yl)pyrimidine-5-carboxamide 3-[2-[1-(6-amino-5-carbamoyl-pyrimidin-4-yl)-piperidin-4-yl]-4-(4-fluoro-3-trifluoromethyl-phenyl)-imidazol-1-yl]-pyrrolidine-1-carboxylic acid tert-butyl ester (60.00 mg; 0.10 mmol; 1.00 eq.) in 0.5 ml methanol was added 0.5 ml 4.0 MHCl in dioxane, stirred at RT for 3 hrs, showed desired by lc-ms, removed off solvent, got white solid 52.5 mg as title compound. LC-MS: (M+1=519, obsd.=519).

6-(4-(1-(2-aminoethyl)-4-(4-fluoro-3-(trifluoromethyl)phenyl)-1H-imidazol-2-yl)piperidin-1-yl)-5-ethylpyrimidin-4-amine ("139")

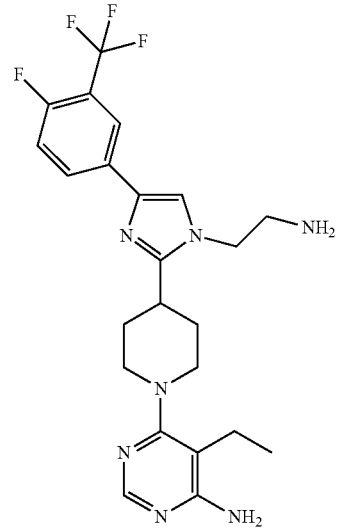 [SMILES: CCc1c(N)ncnc1N1CCC(c2nc(-c3ccc(F)c(C(F)(F)F)c3)cn2CCN)CC1]

The title compound was prepared in an analogous manner as 6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine. LC-MS: (M+1=478, obsd.=478).

4-amino-6-(4-(1-(azetidin-3-ylmethyl)-4-(4-fluoro-3-(trifluoromethyl)phenyl)-1H-imidazol-2-yl)piperidin-1-yl)pyrimidine-5-carboxamide ("140")

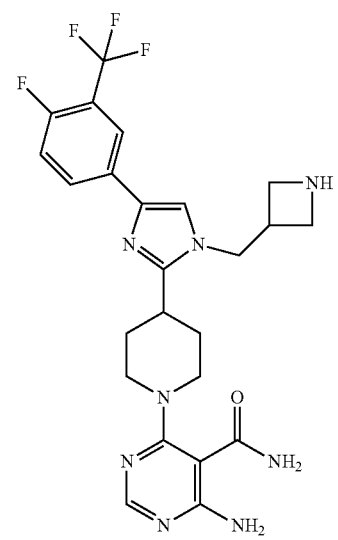 [SMILES: NC(=O)c1c(N)ncnc1N1CCC(c2nc(-c3ccc(F)c(C(F)(F)F)c3)cn2CC2CNC2)CC1]

The title compound was prepared in an analogous manner as 4-amino-6-(4-(4-(4-fluoro-3-(trifluoromethyl)phenyl)-1-

(pyrrolidin-3-yl)-1H-imidazol-2-yl)piperidin-1-yl)pyrimidine-5-carboxamide. LC-MS: (M+1=519, obsd.=519).

4-amino-6-(4-(1-(azetidin-3-ylmethyl)-4-(4-fluoro-3-(trifluoromethyl)phenyl)-1H-imidazol-2-yl)piperidin-1-yl)pyrimidine-5-carbonitrile ("141")

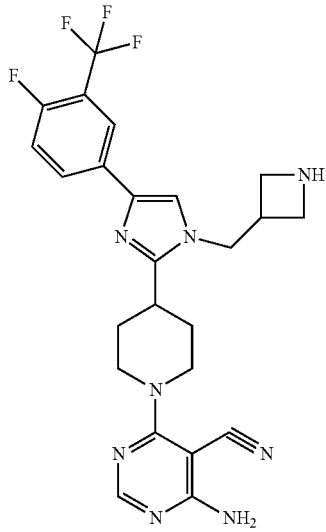 [SMILES: N#Cc1c(N)ncnc1N1CCC(c2nc(-c3ccc(F)c(C(F)(F)F)c3)cn2CC2CNC2)CC1]

The title compound was prepared in an analogous manner as 4-amino-6-(4-(4-(4-fluoro-3-(trifluoromethyl)phenyl)-1-(pyrrolidin-3-yl)-1H-imidazol-2-yl)piperidin-1-yl)pyrimidine-5-carboxamide. LC-MS: (M+1=501, obsd.=501).

4-amino-6-(4-(1-(azetidin-3-yl)-4-(4-fluoro-3-(trifluoromethyl)phenyl)-1H-imidazol-2-yl)piperidin-1-yl)pyrimidine-5-carbonitrile ("142")

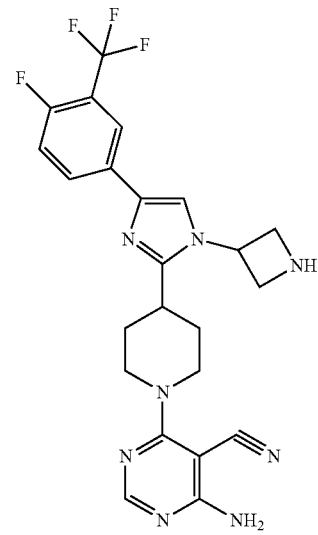 [SMILES: N#Cc1c(N)ncnc1N1CCC(c2nc(-c3ccc(F)c(C(F)(F)F)c3)cn2C2CNC2)CC1]

The title compound was prepared in an analogous manner as 4-amino-6-(4-(4-(4-fluoro-3-(trifluoromethyl)phenyl)-1-

(pyrrolidin-3-yl)-1H-imidazol-2-yl)piperidin-1-yl)pyrimidine-5-carboxamide. LC-MS: (M+1=487, obsd.=487).

4-amino-6-(4-(1-(azetidin-3-yl)-4-(4-fluoro-3-(trifluoromethyl)phenyl)-1H-imidazol-2-yl)piperidin-1-yl)pyrimidine-5-carboxamide ("143")

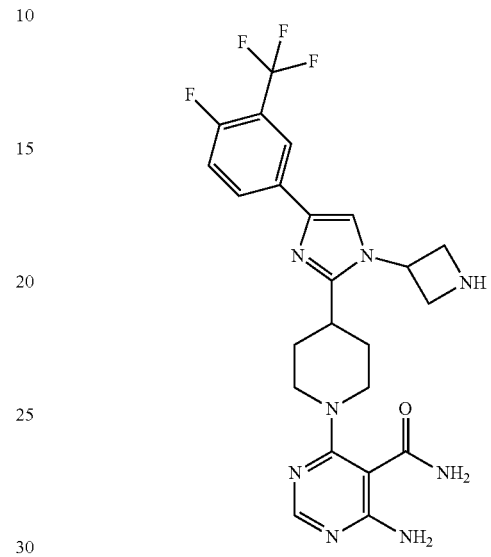

The title compound was prepared in an analogous manner as 4-amino-6-(4-(4-(4-fluoro-3-(trifluoromethyl)phenyl)-1-(pyrrolidin-3-yl)-1H-imidazol-2-yl)piperidin-1-yl)pyrimidine-5-carboxamide. LC-MS: (M+1=505, obsd.=505).

6-(4-(1-(2-(azetidin-1-yl)ethyl)-4-(2-(trifluoromethyl)pyridin-4-yl)-1H-imidazol-2-yl)piperidin-1-yl)-5-chloropyrimidin-4-amine ("144")

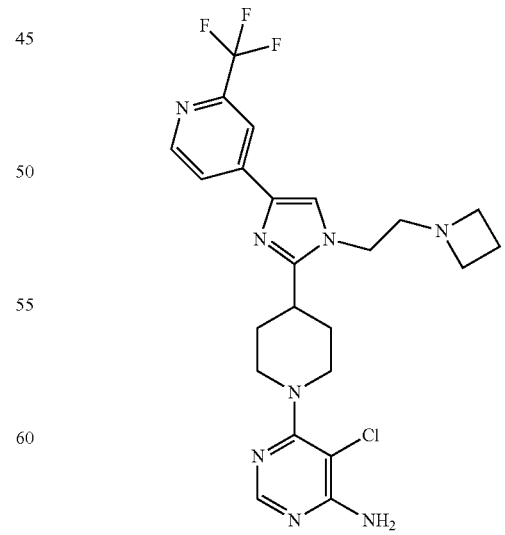

The title compound was prepared in an analogous manner as 6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine. LC-MS: (M+1=507, obsd.=507).

4-amino-6-(4-(1-(2-(azetidin-1-yl)ethyl)-4-(1H-pyrazol-4-yl)-1H-imidazol-2-yl)piperidin-1-yl)pyrimidine-5-carboxamide ("145")

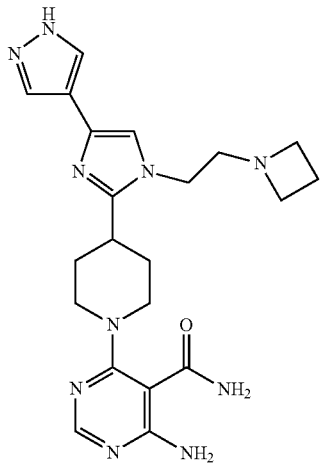 [SMILES: NC(=O)c1c(N)ncnc1N1CCC(c2nc(-c3cn[nH]c3)cn2CCN2CCC2)CC1]

The title compound was prepared in an analogous manner as 4-amino-6-(4-(1-(2-(azetidin-1-yl)ethyl)-4-(4-fluoro-3-methoxyphenyl)-1H-imidazol-2-yl)piperidin-1-yl)pyrimidine-5-carboxamide. LC-MS: (M+1=437, obsd.=437).

(S)-4-amino-6-(4-(1-(azetidin-2-ylmethyl)-4-(4-fluoro-3-(trifluoromethyl)phenyl)-1H-imidazol-2-yl)piperidin-1-yl)pyrimidine-5-carbonitrile ("146")

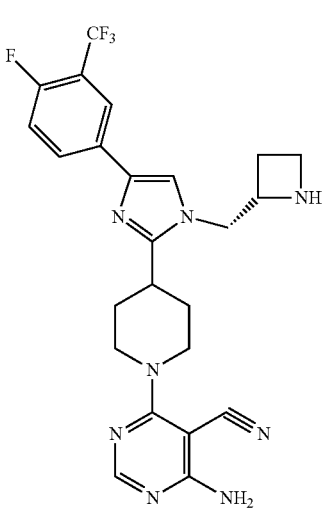

The title compound was prepared in an analogous manner as 4-amino-6-(4-(4-(4-fluoro-3-(trifluoromethyl)phenyl)-1-

(pyrrolidin-3-yl)-1H-imidazol-2-yl)piperidin-1-yl)pyrimidine-5-carboxamide. LC-MS: (M+1=501, obsd.=501).

4-amino-6-(4-(4-(4-fluoro-3-(trifluoromethyl)phenyl)-1-(pyrrolidin-2-ylmethyl)-1H-imidazol-2-yl)piperidin-1-yl)pyrimidine-5-carbonitrile ("147")

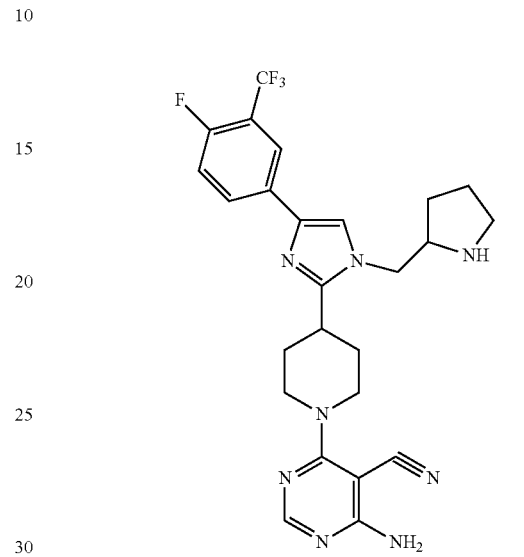

The title compound was prepared in an analogous manner as 4-amino-6-(4-(4-(4-fluoro-3-(trifluoromethyl)phenyl)-1-(pyrrolidin-3-yl)-1H-imidazol-2-yl)piperidin-1-yl)pyrimidine-5-carboxamide. LC-MS: (M+1=515, obsd.=515).

6-(4-(1-(azetidin-3-ylmethyl)-4-(4-fluoro-3-(trifluoromethyl)phenyl)-1H-imidazol-2-yl)piperidin-1-yl)-5-chloropyrimidin-4-amine ("148")

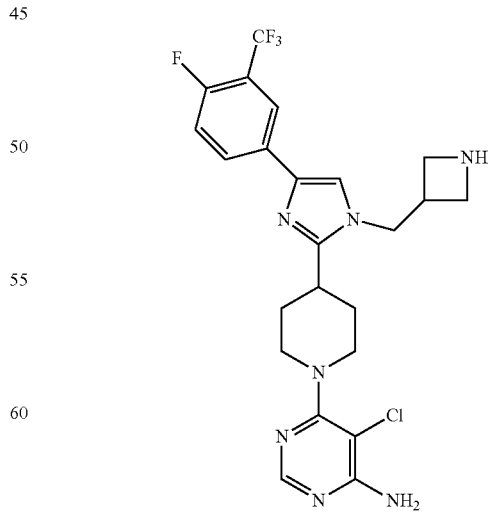

The title compound was prepared in an analogous manner as 6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine. LC-MS: (M+1=510, obsd.=510).

(S)-6-(4-(1-(azetidin-2-ylmethyl)-4-(4-fluoro-3-(trifluoromethyl)phenyl)-1H-imidazol-2-yl)piperidin-1-yl)-5-chloropyrimidin-4-amine ("149")

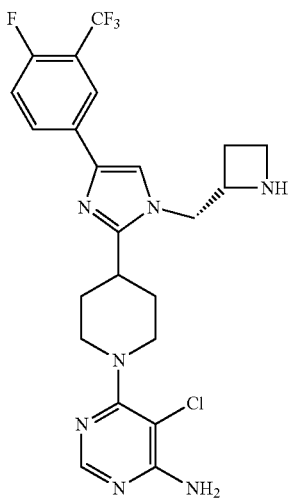

The title compound was prepared in an analogous manner as 6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine. LC-MS: (M+1=510, obsd.=510).

(S)-4-amino-6-(4-(1-(azetidin-2-ylmethyl)-4-(4-fluoro-3-(trifluoromethyl)phenyl)-1H-imidazol-2-yl)piperidin-1-yl)pyrimidine-5-carboxamide ("150")

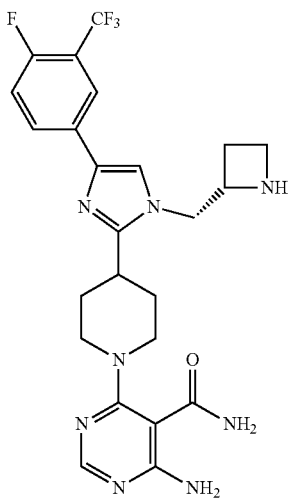

The title compound was prepared in an analogous manner as 4-amino-6-(4-(4-(4-fluoro-3-(trifluoromethyl)phenyl)-1-

(pyrrolidin-3-yl)-1H-imidazol-2-yl)piperidin-1-yl)pyrimidine-5-carboxamide. LC-MS: (M+1=519, obsd.=519).

6-(4-(1-(azetidin-3-ylmethyl)-4-(4-fluoro-3-(trifluoromethyl)phenyl)-1H-imidazol-2-yl)piperidin-1-yl)-5-ethylpyrimidin-4-amine ("151")

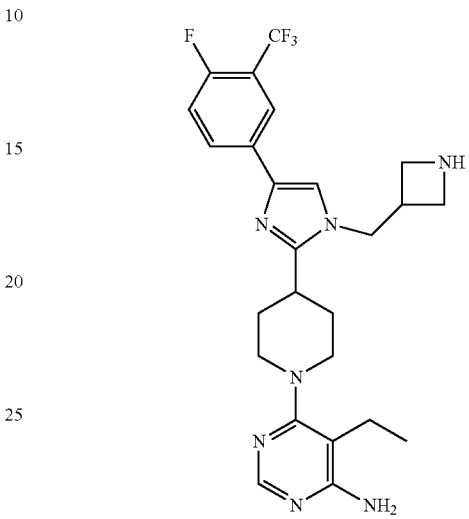

The title compound was prepared in an analogous manner as 6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine. LC-MS: (M+1=504, obsd.=504).

(S)-6-(4-(1-(azetidin-2-ylmethyl)-4-(4-fluoro-3-(trifluoromethyl)phenyl)-1H-imidazol-2-yl)piperidin-1-yl)-5-ethylpyrimidin-4-amine ("152")

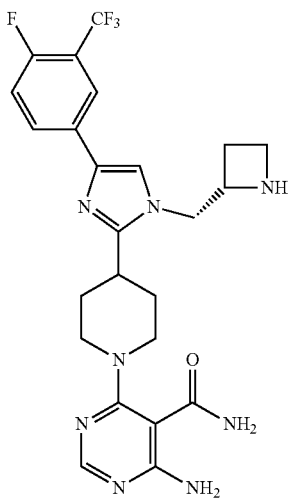

The title compound was prepared in an analogous manner as 6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine. LC-MS: (M+1=504, obsd.=504).

4-amino-6-(4-(4-(4-fluoro-3-(trifluoromethyl)phenyl)-1-(pyrrolidin-2-ylmethyl)-1H-imidazol-2-yl)piperidin-1-yl)pyrimidine-5-carboxamide ("153")

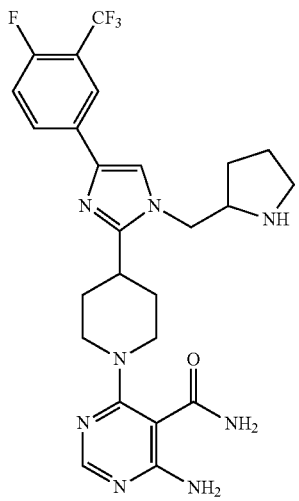 [SMILES: NC(=O)c1c(N)ncnc1N1CCC(c2nc(-c3ccc(F)c(C(F)(F)F)c3)cn2CC2CCCN2)CC1]

The title compound was prepared in an analogous manner as 4-amino-6-(4-(4-(4-fluoro-3-(trifluoromethyl)phenyl)-1-(pyrrolidin-3-yl)-1H-imidazol-2-yl)piperidin-1-yl)pyrimidine-5-carboxamide. LC-MS: (M+1=533, obsd.=533).

4-amino-6-(4-(4-(4-fluoro-3-(trifluoromethyl)phenyl)-1-(piperidin-4-yl)-1H-imidazol-2-yl)piperidin-1-yl)pyrimidine-5-carboxamide ("154")

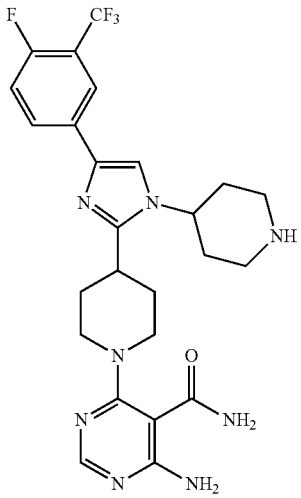 [SMILES: NC(=O)c1c(N)ncnc1N1CCC(c2nc(-c3ccc(F)c(C(F)(F)F)c3)cn2C2CCNCC2)CC1]

The title compound was prepared in an analogous manner as 4-amino-6-(4-(4-(4-fluoro-3-(trifluoromethyl)phenyl)-1-(pyrrolidin-3-yl)-1H-imidazol-2-yl)piperidin-1-yl)pyrimidine-5-carboxamide. LC-MS: (M+1=533, obsd.=533).

4-amino-6-(4-(4-(4-fluoro-3-(trifluoromethyl)phenyl)-1-(piperidin-4-yl)-1H-imidazol-2-yl)piperidin-1-yl)pyrimidine-5-carbonitrile ("155")

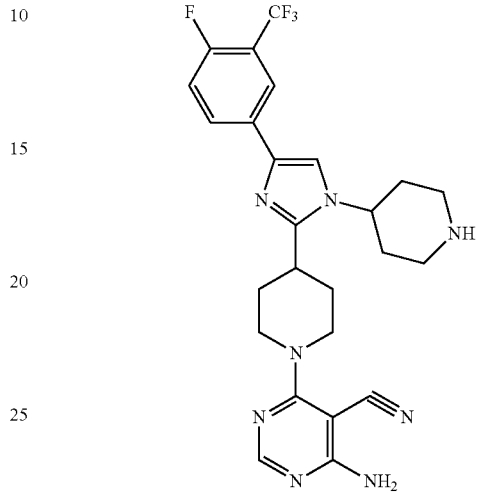

The title compound was prepared in an analogous manner as 4-amino-6-(4-(4-(4-fluoro-3-(trifluoromethyl)phenyl)-1-(pyrrolidin-3-yl)-1H-imidazol-2-yl)piperidin-1-yl)pyrimidine-5-carboxamide. LC-MS: (M+1=515, obsd.=515).

4-amino-6-(4-(4-(4-fluoro-3-(trifluoromethyl)phenyl)-1-((1-methylazetidin-3-yl)methyl)-1H-imidazol-2-yl)piperidin-1-yl)pyrimidine-5-carboxamide ("156")

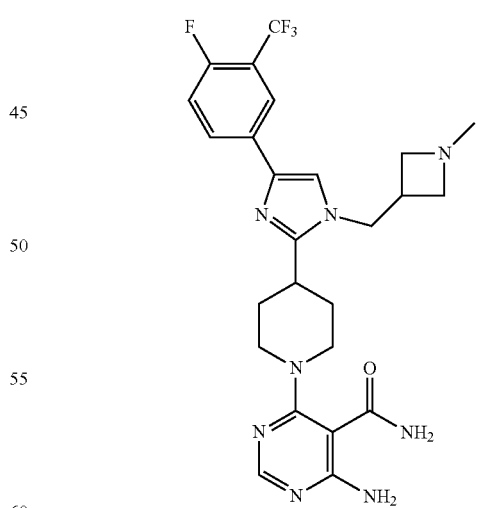

To a solution of 4-amino-6-{4-[1-azetidin-3-ylmethyl-4-(4-fluoro-3-trifluoromethyl-phenyl)-1H-imidazol-2-yl]-piperidin-1-yl}-pyrimidine-5-carboxylic acid amide trifluoroacetate (2) (25.00 mg; 0.03 mmol; 1.00 eq.) in ethanol 1 ml added formic acid (0.00 1 ml; 0.08 mmol; 2.50 eq.) and formaldehyde (0.001 ml; 0.04 mmol; 1.20 eq.), stirred at 65°

C. for 3 hr. lc-ms showed clean desired peak. Removed off solvent, purified by HPLC, collected title compound 14.8 mg. LC-MS (M+1=533, obsd.=533).

5-ethyl-6-(4-(4-(4-fluoro-3-(trifluoromethyl)phenyl)-1-(piperidin-4-yl)-1H-imidazol-2-yl)piperidin-1-yl)pyrimidin-4-amine ("157")

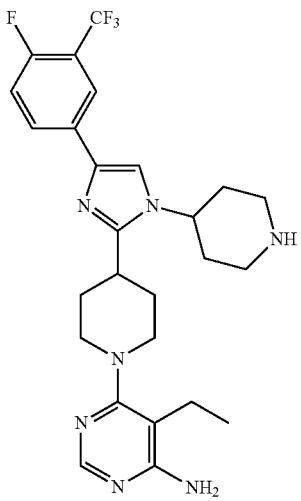 [SMILES: CCc1c(N)ncnc1N1CCC(c2nc(-c3ccc(F)c(C(F)(F)F)c3)cn2C2CCNCC2)CC1]

The title compound was prepared in an analogous manner as 6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine. LC-MS: (M+1=518, obsd.=518).

4-amino-6-(4-(1-(2-aminoethyl)-4-(4-fluoro-3-(trifluoromethyl)phenyl)-1H-imidazol-2-yl)piperidin-1-yl)pyrimidine-5-carbonitrile ("158")

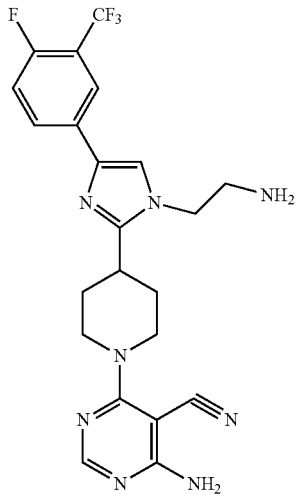 [SMILES: N#Cc1c(N)ncnc1N1CCC(c2nc(-c3ccc(F)c(C(F)(F)F)c3)cn2CCN)CC1]

The title compound was prepared in an analogous manner as 4-amino-6-(4-(4-(4-fluoro-3-(trifluoromethyl)phenyl)-1-(pyrrolidin-3-yl)-1H-imidazol-2-yl)piperidin-1-yl)pyrimidine-5-carboxamide. LC-MS: (M+1=475, obsd.=475).

4-amino-6-(4-(1-(2-aminoethyl)-4-(4-fluoro-3-(trifluoromethyl)phenyl)-1H-imidazol-2-yl)piperidin-1-yl)pyrimidine-5-carboxamide ("159")

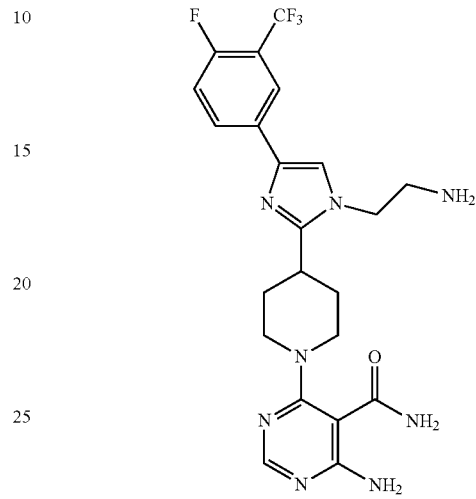

The title compound was prepared in an analogous manner as 4-amino-6-(4-(4-(4-fluoro-3-(trifluoromethyl)phenyl)-1-(pyrrolidin-3-yl)-1H-imidazol-2-yl)piperidin-1-yl)pyrimidine-5-carboxamide. LC-MS: (M+1=493, obsd.=493).

2-(2-(1-(6-amino-5-(1H-pyrazol-4-yl)pyrimidin-4-yl)piperidin-4-yl)-4-(4-fluoro-3-methylphenyl)-1H-imidazol-1-yl)ethanol ("160")

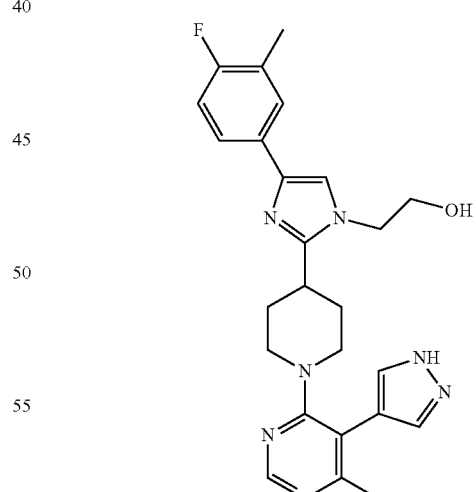

Step 1: 4-[4-(4-Fluoro-3-methyl-phenyl)-1-(2-hydroxy-ethyl)-1H-imidazol-2-yl]-piperidine-1-carboxylic acid tert-butyl ester A mixture of 4-[4-Bromo-1-(2-hydroxy-ethyl)-1H-imidazol-2-yl]-piperidine-1-carboxylic acid tert-butyl ester (2000.00 mg; 5.34 mmol; 1.00 eq.), 2-(4-fluoro-3-trifluoromethyl-phenyl)-4,4,5,5-tetramethyl-[1,3,2]dioxaborolane (1233.97 mg; 8.02 mmol; 1.50 eq.), mg; 0.53 mmol; 0.10 eq.) and Cs2CO3 (3483 mg, 10.69 mmol) in dioxane 15 ml and water 1.5 ml was purged with argon, added Pd(0)(tBu$_3$)$_2$ (273 mg, 0.53 mmol), stirred at 50° C. for overnight. LC-MS showed desired as major product. Diluted reaction solution with EA 70 ml, washed with brine 30mlX2, separated out organic layer, dried, removed off solvent, got crude product, which was subjected to biotage NASP column (100 g), elated with 40-100% EA in hexane and contained 0.5% TEA in EA, collected title compound 1650 mg, 76%

Step 2: 2-[4-(4-Fluoro-3-methyl-phenyl)-2-piperidin-4-yl-imidazol-1-yl]-ethanol hydrochloride To a solution of 4-[4-(4-Fluoro-3-methyl-phenyl)-1-(2-hydroxy-ethyl)-1H-imidazol-2-yl]-piperidine-1-carboxylic acid tert-butyl ester (1600.00 mg; 3.97 mmol; 1.00 eq.) in methanol 10 ml added 4.0M HCl in dioxane (9.91 ml; 39.65 mmol; 10.00 eq.), the reaction mixture was stirred at RT for 3 hrs, lc-ms showed clean desired, removed off solvent, got white solid as title compound.

Step 3: 2-(2-(1-(6-amino-5-bromopyrimidin-4-yl)piperidin-4-yl)-4-(4-fluoro-3-methylphenyl)-1H-imidazol-1-yl)ethanol A reaction mixture of 5-bromo-6-chloro-pyrimidin-4-ylamine (370.00 mg; 1.78 mmol; 1.00 eq.), 2-[4-(4-fluoro-3-methyl-phenyl)-2-piperidin-4-yl-imidazol-1-yl]-ethanol hydrochloride (3) (732.67 mg; 1.78 mmol; 1.00 eq.), and Cs2CO3 (2313.40 mg; 7.10 mmol; 4.00 eq.) in DMSO 10 ml, stirred at 100° C. for overnight, cooled, poured into water 60 ml, stirred for 15 mins, filtered, collected light yellow solid, which was washed with water, dried, got title compound, 750 mg, 88.9%.

Step 4: tert-butyl 4-(4-amino-6-(4-(4-(4-fluoro-3-methylphenyl)-1-(2-hydroxyethyl)-1H-imidazol-2-yl)piperidin-1-yl)pyrimidin-5-yl)-1H-pyrazole-1-carboxylate a mixture of 2-[2-[1-(6-amino-5-bromo-pyrimidin-4-yl)-piperidin-4-yl]-4-(4-fluoro-3-methyl-phenyl)-imidazol-1-yl]-ethanol (1333.00 mg; 2.80 mmol; 1.00 eq.), 4-(4,4,5,5-tetramethyl-[1,3,2]dioxaborolan-2-yl)-pyrazole-1-carboxylic acid tert-butyl ester (1237.31 mg; 4.21 mmol; 1.50 eq.), Cs2CO3 (548 mg, 1.68 mmol) in doxane 10 ml and water 1 ml, purged with argon, added Pd(0) (tBu$_3$)$_2$ (143 mg, 0.28 mmol) stirred at 50° C. for overnight. LC-MS showed desired as major product, removed off solvent, purified by prep HPLC (Basic), collected title compound 400 mg, 25.4%

Step 5: 2-(2-(1-(6-amino-5-(1H-pyrazol-4-yl)pyrimidin-4-yl)piperidin-4-yl)-4-(4-fluoro-3-methylphenyl)-1H-imidazol-1-yl)ethanol tert-butyl 4-(4-amino-6-(4-(4-(4-fluoro-3-methylphenyl)-1-(2-hydroxyethyl)-1H-imidazol-2-yl)piperidin-1-yl)pyrimidin-5-yl)-1H-pyrazole-1-carboxylate (10.00 mg; 0.02 mmol) in 0.5 ml methanol was added 0.5 ml 4.0M HCl in dioxane, stirred at RT for 3 hrs, showed clean desired by LC-MS. Removed off solvent, got white solid as title compound. LC-MS: (M+1=463, obsd.=463).

6-(4-(1-(2-(cyclooropylamino)ethyl)-4-(4-fluoro-3-methylphenyl)-1H-imidazol-2-yl)piperidin-1-yl)-5-(1H-pyrazol-4-yl)pyrimidin-4-amine ("161")

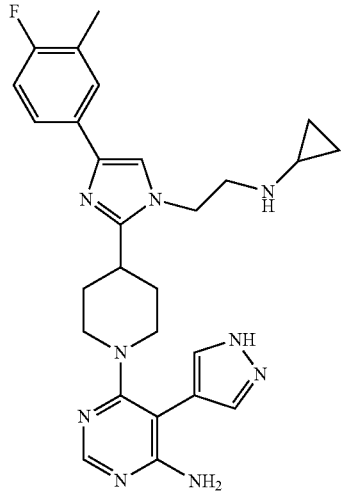 [SMILES: Cc1cc(-c2cn(CCNC3CC3)c(C3CCN(c4ncnc(N)c4-c4cn[nH]c4)CC3)n2)ccc1F]

Step 1: tert-butyl 4-(4-amino-6-(4-(4-(4-fluoro-3-methylphenyl)-1-(2-((methylsulfonyl)oxy)ethyl)-1H-imidazol-2-yl)piperidin-1-yl)pyrimidin-5-yl)-1H-pyrazole-1-carboxylate To a stirring solution of 4-(4-amino-6-{4-[4-(4-fluoro-3-methyl-phenyl)-1-(2-hydroxy-ethyl)-1H-imidazol-2-yl]-piperidin-1-yl}-pyrimidin-5-yl)-pyrazole-1-carboxylic acid tert-butyl ester (350.00 mg; 0.62 mmol; 1.00 eq.) in THF 5 ml added ethyl-diisopropyl-amine (0.28 ml; 1.56 mmol; 2.50 eq.), then added drop wised methanesulfonyl chloride (0.10 ml; 1.24 mmol; 2.00 eq.) at 0° C., the reaction mixture was stirred at RT for 1 hr, LC-MS showed desired as major, and starting material disappeared, removed off solvent, directly carried the crude product for next step reaction.

Step 2: 6-(4-(1-(2-(cyclopropylamino)ethyl)-4-(4-fluoro-3-methylphenyl)-1H-imidazol-2-yl)piperidin-1-yl)-5-(1H-pyrazol-4-yl)pyrimidin-4-amine 4-(4-Amino-6-{4-[4-(4-fluoro-3-methyl-phenyl)-1-(2-methanesulfonyloxy-ethyl)-1H-imidazol-2-yl]-piperidin-1-yl}-pyrimidin-5-yl)-pyrazole-1-carboxylic acid tert-butyl ester (100.00 mg; 0.16 mmol; 1.00 eq.) in seal tube was added THF 2 ml and cyclopropylamine (0.70 ml; 9.81 mmol; 62.84 eq.), stirred at 50° C. for overnight.

LC-MS showed desired as major, purified product by HPLC, collected title compound 35 mg. LC-MS: (M+1=502, obsd.=502).

IC$_{50}$ 12.9 nM (p70S6K enzyme), 150 nM (AKT enzyme).

135

6-(4-(4-(4-fluoro-3-methylphenyl)-1-(2-(methylamino)ethyl)-1H-imidazol-2-yl)piperidin-1-yl)-5-(1H-pyrazol-4-yl)pyrimidin-4-amine ("162")

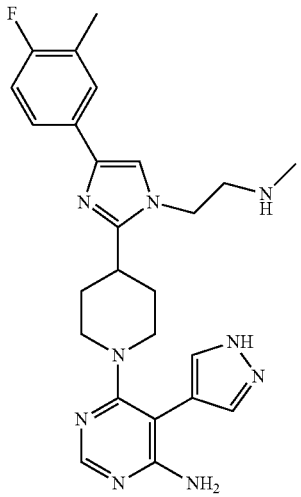

The title compound was prepared in an analogous manner as 6-(4-(1-(2-(cyclopropylamino)ethyl)-4-(4-fluoro-3-methylphenyl)-1H-imidazol-2-yl)piperidin-1-yl)-5-(1H-pyrazol-4-yl)pyrimidin-4-amine LC-MS: (M+1=476, obsd.=476).

6-(4-(1-(2-(dimethylamino)ethyl)-4-(4-fluoro-3-methylphenyl)-1H-imidazol-2-yl)piperidin-1-yl)-5-(1H-pyrazol-4-yl)pyrimidin-4-amine ("163")

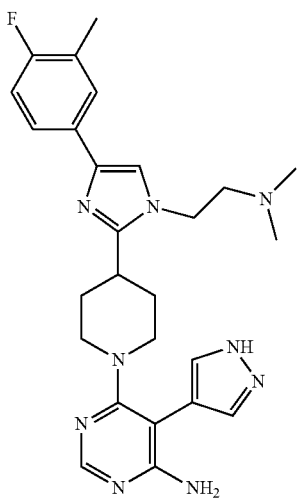 [SMILES: Cc1cc(-c2cn(CCN(C)C)c(C3CCN(c4ncnc(N)c4-c4cn[nH]c4)CC3)n2)ccc1F]

The title compound was prepared in an analogous manner as 6-(4-(1-(2-(cyclopropylamino)ethyl)-4-(4-fluoro-3-meth-

136 ylphenyl)-1H-imidazol-2-yl)piperidin-1-yl)-5-(1H-pyrazol-4-yl)pyrimidin-4-amine LC-MS: (M+1=490, obsd.=490).

6-(4-(1-(2-(azetidin-1-yl)ethyl)-4-(4-fluoro-3-methylphenyl)-1H-imidazol-2-yl)piperidin-1-yl)-5-(1H-pyrazol-4-yl)pyrimidin-4-amine ("164")

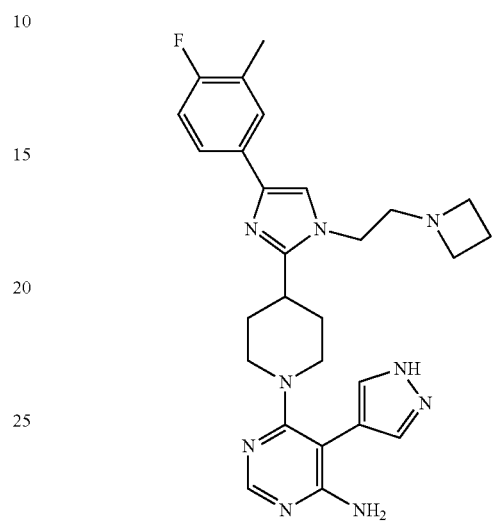

The title compound was prepared in an analogous manner as 6-(4-(1-(2-(cyclopropylamino)ethyl)-4-(4-fluoro-3-methylphenyl)-1H-imidazol-2-yl)piperidin-1-yl)-5-(1H-pyrazol-4-yl)pyrimidin-4-amine LC-MS: (M+1=502, obsd.=502).

6-(4-(1-(2-(tert-butylamino)ethyl)-4-(4-fluoro-3-methylphenyl)-1H-imidazol-2-yl)piperidin-1-yl)-5-(1H-pyrazol-4-yl)pyrimidin-4-amine ("165")

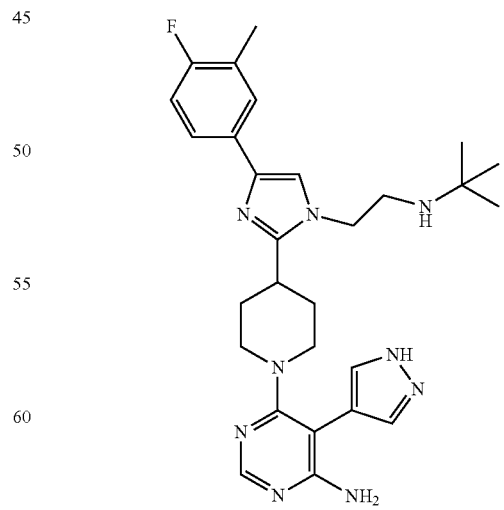

The title compound was prepared in an analogous manner as 6-(4-(1-(2-(cyclopropylamino)ethyl)-4-(4-fluoro-3-methylphenyl)-1H-imidazol-2-yl)piperidin-1-yl)-5-(1H-pyrazol-4-yl)pyrimidin-4-amine LC-MS: (M+1=518, obsd.=518).

5-bromo-6-(4-(1-(2-(methylamino)ethyl)-4-(2-(trifluoromethyl)pyridin-4-yl)-1H-imidazol-2-yl)piperidin-1-yl)pyrimidin-4-amine ("166")

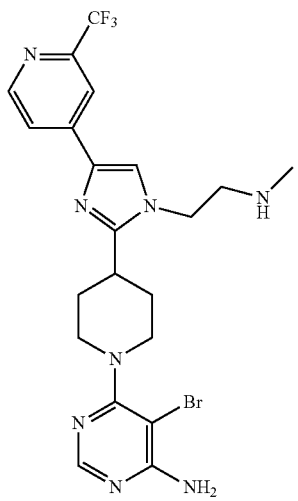 [SMILES: CNCCn1cc(-c2ccnc(C(F)(F)F)c2)nc1C1CCN(c2ncnc(N)c2Br)CC1]

The title compound was prepared in an analogous manner as 6-(4-(1-(2-(cyclopropylamino)ethyl)-4-(4-fluoro-3-methylphenyl)-1H-imidazol-2-yl)piperidin-1-yl)-5-(1H-pyrazol-4-yl)pyrimidin-4-amine. LC-MS: (M+1=525, obsd.=525/527).

6-(4-(1-(2-(methylamino)ethyl)-4-(2-(trifluoromethyl)pyridin-4-yl)-1H-imidazol-2-yl)piperidin-1-yl)pyrimidin-4-amine ("167")

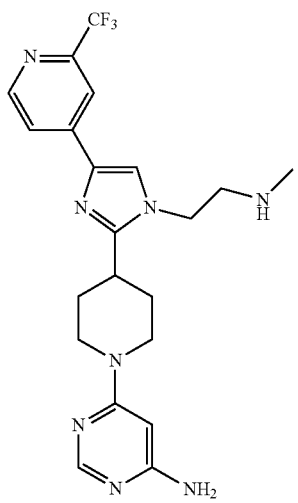 [SMILES: CNCCn1cc(-c2ccnc(C(F)(F)F)c2)nc1C1CCN(c2cc(N)ncn2)CC1]

The title compound was a side product by preparing 5-bromo-6-(4-(1-(2-(methylamino)ethyl)-4-(2-(trifluoromethyl)pyridin-4-yl)-1H-imidazol-2-yl)piperidin-1-yl)pyrimidin-4-amine. LC-MS: (M+1=447, obsd.=447).

6-(4-(1-(2-(azetidin-1-yl)ethyl)-4-(2-(trifluoromethyl)pyridin-4-yl)-1H-imidazol-2-yl)piperidin-1-yl)-5-(isoxazol-4-yl)pyrimidin-4-amine ("168")

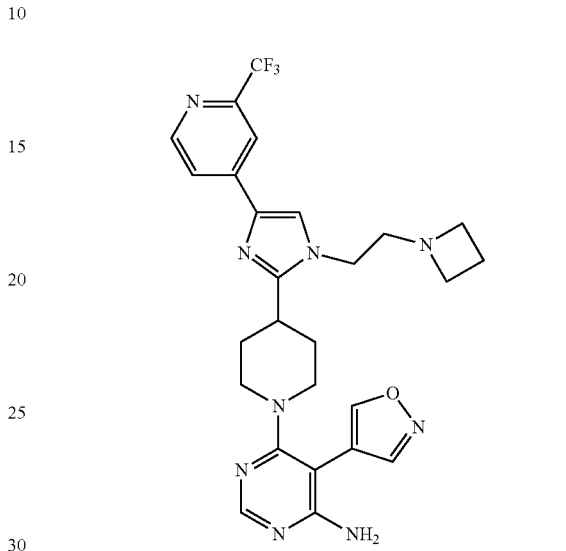

The title compound was prepared in an analogous manner as 6-(4-(1-(2-(cyclopropylamino)ethyl)-4-(4-fluoro-3-methylphenyl)-1H-imidazol-2-yl)piperidin-1-yl)-5-(1H-pyrazol-4-yl)pyrimidin-4-amine. LC-MS: (M+1=540, obsd.=540).

4-amino-6-(4-(1-(2-(methylamino)ethyl)-4-(2-(trifluoromethyl)pyridin-4-yl)-1H-imidazol-2-yl)piperidin-1-yl)pyrimidine-5-carbonitrile ("169")

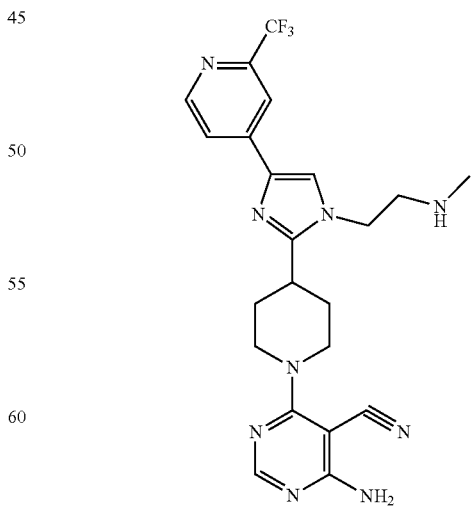

The title compound was prepared in an analogous manner as 6-(4-(1-(2-(cyclopropylamino)ethyl)-4-(4-fluoro-3-methylphenyl)-1H-imidazol-2-yl)piperidin-1-yl)-5-(1H-pyrazol-4-yl)pyrimidin-4-amine. LC-MS: (M+1=471, obsd.=471).

5-(4,5-dihydroisoxazol-4-yl)-6-(4-(1-(2-(methylamino)ethyl)-4-(2-(trifluoromethyl)pyridin-4-yl)-1H-imidazol-2-yl)piperidin-1-yl)pyrimidin-4-amine ("170")

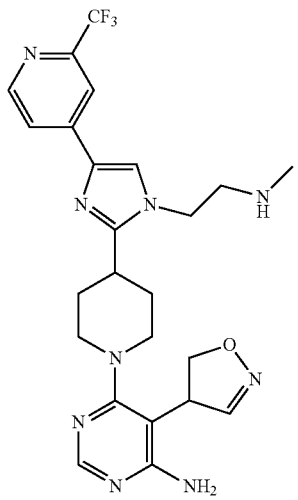 [SMILES: CNCCn1cc(-c2ccnc(C(F)(F)F)c2)nc1C1CCN(c2ncnc(N)c2C2C=NOC2)CC1]

The title compound was prepared in an analogous manner as 6-(4-(1-(2-(cyclopropylamino)ethyl)-4-(4-fluoro-3-methylphenyl)-1H-imidazol-2-yl)piperidin-1-yl)-5-(1H-pyrazol-4-yl)pyrimidin-4-amine. LC-MS: (M+1=516, obsd.=516).

5-ethyl-6-(4-(1-(2-(methylamino)ethyl)-4-(2-(trifluoromethyl)pyridin-4-yl)-1H-imidazol-2-yl)piperidin-1-yl)pyrimidin-4-amine ("171")

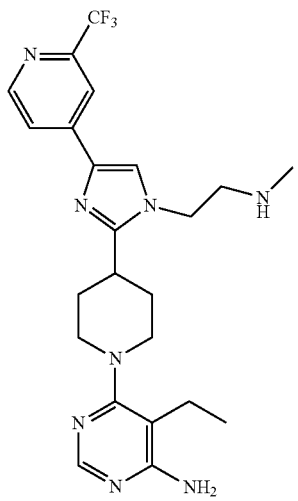 [SMILES: CCc1c(N)ncnc1N1CCC(c2nc(-c3ccnc(C(F)(F)F)c3)cn2CCNC)CC1]

The title compound was prepared in an analogous manner as 6-(4-(1-(2-(cyclopropylamino)ethyl)-4-(4-fluoro-3-methylphenyl)-1H-imidazol-2-yl)piperidin-1-yl)-5-(1H-pyrazol-4-yl)pyrimidin-4-amine. LC-MS: (M+1=475, obsd.=475).

5-chloro-6-(4-(1-(2-(methylamino)ethyl)-4-(2-(trifluoromethyl)pyridin-4-yl)-1H-imidazol-2-yl)piperidin-1-yl)pyrimidin-4-amine ("172")

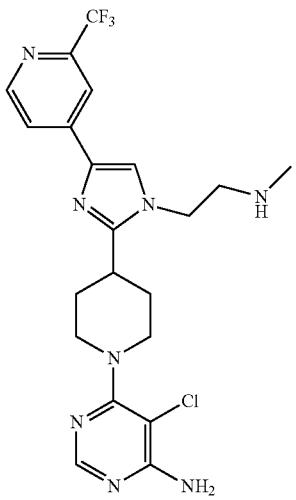 [SMILES: CNCCn1cc(-c2ccnc(C(F)(F)F)c2)nc1C1CCN(c2ncnc(N)c2Cl)CC1]

The title compound was prepared in an analogous manner as 6-(4-(1-(2-(cyclopropylamino)ethyl)-4-(4-fluoro-3-methylphenyl)-1H-imidazol-2-yl)piperidin-1-yl)-5-(1H-pyrazol-4-yl)pyrimidin-4-amine. LC-MS: (M+1=481, obsd.=481).

5-chloro-6-(4-(1-(2-(cyclopropylamino)ethyl)-4-(2-(trifluoromethyl)pyridin-4-yl)-1H-imidazol-2-yl)piperidin-1-yl)pyrimidin-4-amine ("173")

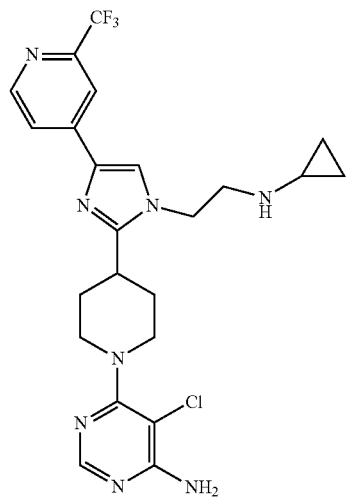 [SMILES: Nc1ncnc(N2CCC(c3nc(-c4ccnc(C(F)(F)F)c4)cn3CCNC3CC3)CC2)c1Cl]

The title compound was prepared in an analogous manner as 6-(4-(1-(2-(cyclopropylamino)ethyl)-4-(4-fluoro-3-methylphenyl)-1H-imidazol-2-yl)piperidin-1-yl)-5-(1H-pyrazol-4-yl)pyrimidin-4-amine. LC-MS: (M+1=507, obsd.=507).

6-(4-(1-(2-(ethylamino)ethyl)-4-(4-fluoro-3-(trifluoromethyl)phenyl)-1H-imidazol-2-yl)piperidin-1-yl)-5-isopropoxypyrimidin-4-amine ("174")

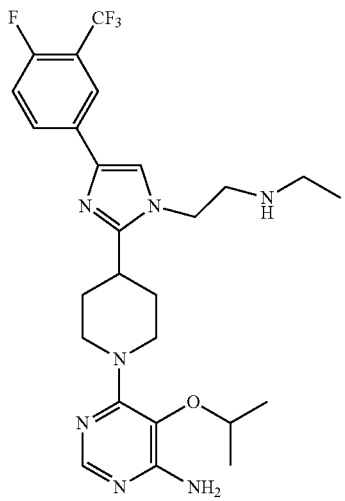 [SMILES: CCNCCn1cc(-c2ccc(F)c(C(F)(F)F)c2)nc1C1CCN(c2ncnc(N)c2OC(C)C)CC1]

The title compound was prepared in an analogous manner as 6-(4-(1-(2-(cyclopropylamino)ethyl)-4-(4-fluoro-3-methylphenyl)-1H-imidazol-2-yl)piperidin-1-yl)-5-(1H-pyrazol-4-yl)pyrimidin-4-amine. LC-MS: (M+1=536, obsd.=536).

6-(4-(1-(azetidin-3-ylmethyl)-4-(4-fluoro-3-(trifluoromethyl)phenyl)-1H-imidazol-2-yl)piperidin-1-yl)-5-isopropoxypyrimidin-4-amine ("175")

The title compound was prepared in an analogous manner as 4-amino-6-(4-(4-(4-fluoro-3-(trifluoromethyl)phenyl)-1-

(pyrrolidin-3-yl)-1H-imidazol-2-yl)piperidin-1-yl)pyrimidine-5-carboxamide. LC-MS: (M+1=534, obsd.=534).

6-(4-(1-(azetidin-3-ylmethyl)-4-(4-fluoro-3-(trifluoromethyl)phenyl)-1H-imidazol-2-yl)piperidin-1-yl)-5-ethoxypyrimidin-4-amine ("176")

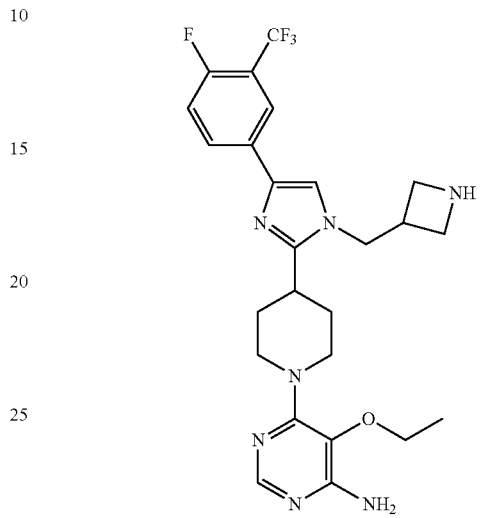

The title compound was prepared in an analogous manner as 4-amino-6-(4-(4-(4-fluoro-3-(trifluoromethyl)phenyl)-1-(pyrrolidin-3-yl)-1H-imidazol-2-yl)piperidin-1-yl)pyrimidine-5-carboxamide. LC-MS: (M+1=520, obsd.=520).

6-(4-(1-(2-(azetidin-1-yl)ethyl)-4-(4-fluoro-3-(trifluoromethyl)phenyl)-1H-imidazol-2-yl)piperidin-1-yl)-5-ethoxypyrimidin-4-amine ("177")

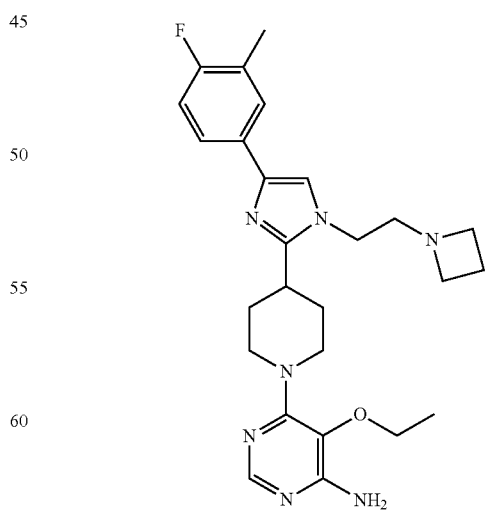

The title compound was prepared in an analogous manner as 6-(4-(1-(2-(azetidin-1-yl)ethyl)-4-(2-(trifluoromethyl)pyridin-4-yl)-1H-imidazol-2-yl)piperidin-1-yl)-5-methoxypyrimidin-4-amine. LC-MS: (M+1=480, obsd.=480).

6-(4-(1-(2-(azetidin-1-yl)ethyl)-4-(4-fluoro-3-methylphenyl)-1H-imidazol-2-yl)piperidin-1-yl)-5-isopropoxypyrimidin-4-amine ("178")

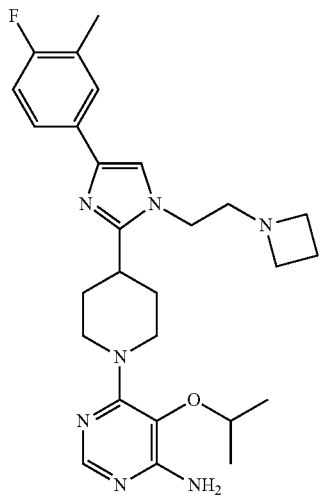 [SMILES: Cc1cc(-c2cn(CCN3CCC3)c(C3CCN(c4ncnc(N)c4OC(C)C)CC3)n2)ccc1F]

The title compound was prepared in an analogous manner as 6-(4-(1-(2-(azetidin-1-yl)ethyl)-4-(2-(trifluoromethyl)pyridin-4-yl)-1H-imidazol-2-yl)piperidin-1-yl)-5-methoxypyrimidin-4-amine. LC-MS: (M+1=494, obsd.=494).

6-(4-(1-(2-(azetidin-1-yl)ethyl)-4-(2-isopropylpyridin-4-yl)-1H-imidazol-2-yl)piperidin-1-yl)-5-ethylpyrimidin-4-amine ("179")

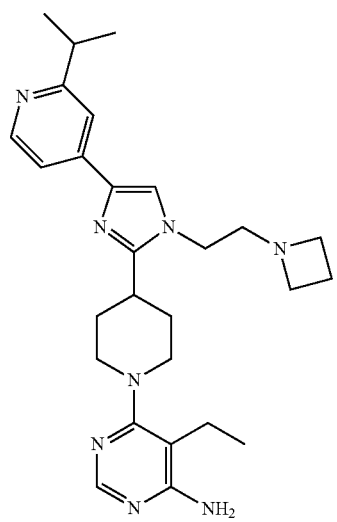 [SMILES: CCc1c(N)ncnc1N1CCC(c2nc(-c3ccnc(C(C)C)c3)cn2CCN2CCC2)CC1]

The title compound was prepared in an analogous manner as 6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine. LC-MS: (M+1=475, obsd.=475).

6-(4-(1-(2-(azetidin-1-yl)ethyl)-4-(2-isopropylpyridin-4-yl)-1H-imidazol-2-yl)piperidin-1-yl)-5-chloropyrimidin-4-amine ("180")

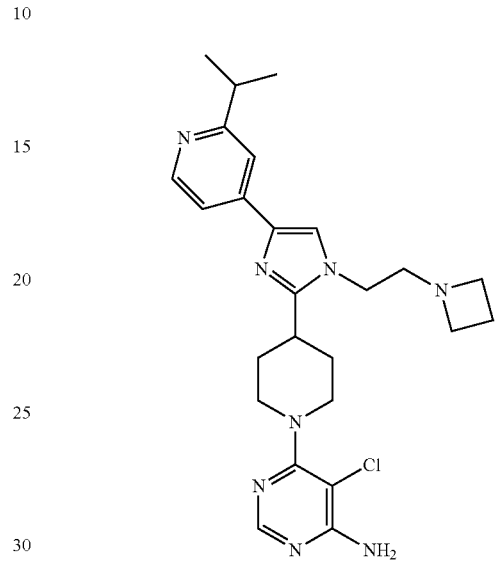

The title compound was prepared in an analogous manner as 6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine. LC-MS: (M+1=481, obsd.=481).

6-(4-(1-(2-(azetidin-1-yl)ethyl)-4-(2-isopropylpyridin-4-yl)-1H-imidazol-2-yl)piperidin-1-yl)-5-bromopyrimidin-4-amine ("181")

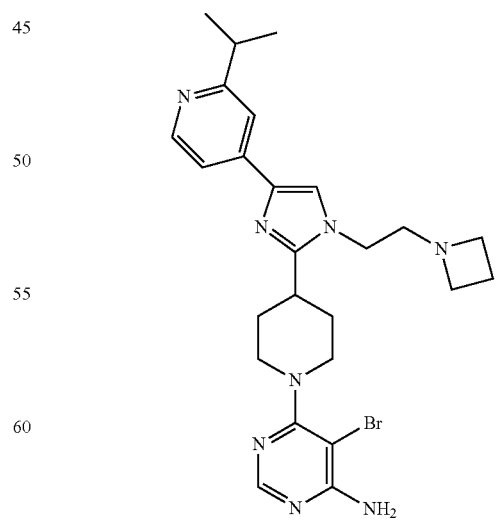

The title compound was prepared in an analogous manner as 6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine. LC-MS: (M+1=525, obsd.=525/527).

6-(4-(1-(2-(azetidin-1-yl)ethyl)-4-(2-isopropylpyridin-4-yl)-1H-imidazol-2-yl)piperidin-1-yl)-5-vinylpyrimidin-4-amine ("182")

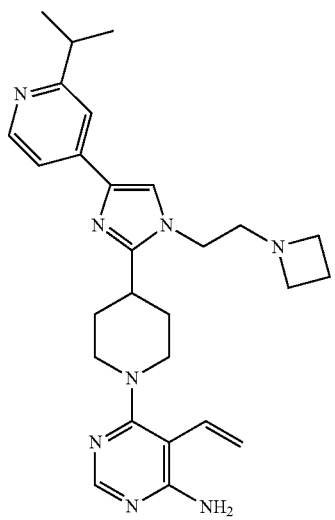 [SMILES: C=Cc1c(N)ncnc1N1CCC(c2nc(-c3ccnc(C(C)C)c3)cn2CCN2CCC2)CC1]

a mixture of 6-{4-[1-(2-Azetidin-1-yl-ethyl)-4-(2-isopropyl-pyridin-4-yl)-1H-imidazol-2-yl]-piperidin-1-yl}-5-bromo-pyrimidin-4-ylamine (70.00 mg; 0.13 mmol; 1.00 eq.), 4,4,5,5-Tetramethyl-2-vinyl-[1,3,2]dioxaborolane (0.03 ml; 0.16 mmol; 1.20 eq.), (4.77 mg; 0.01 mmol; 0.07 eq.) and in doxane 15 ml and water 1.5 ml, stirred at 50 C for overnight.

LC-MS showed desired as major product, purified by HPLC, collected title compound.

LC-MS: (M+1=473, obsd.=473).

6-(4-(1-(azetidin-3-ylmethyl)-4-(4-fluoro-3-(trifluoromethyl)phenyl)-1H-imidazol-2-yl)piperidin-1-yl)-5-vinylpyrimidin-4-amine ("183")

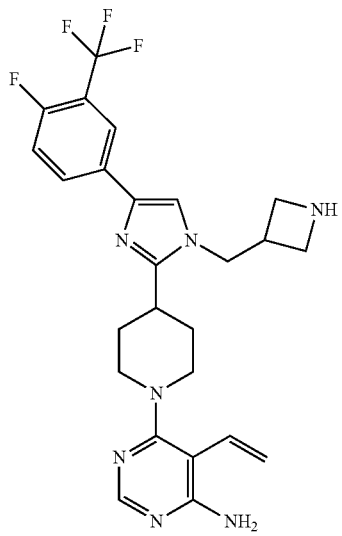 [SMILES: C=Cc1c(N)ncnc1N1CCC(c2nc(-c3ccc(F)c(C(F)(F)F)c3)cn2CC2CNC2)CC1]

The title compound was prepared in an analogous manner as 6-(4-(1-(2-(azetidin-1-yl)ethyl)-4-(2-isopropylpyridin-4-yl)-1H-imidazol-2-yl)piperidin-1-yl)-5-vinylpyrimidin-4-amine. LC-MS: (M+1=502, obsd.=502).

6-(4-(1-(azetidin-3-ylmethyl)-4-(4-fluoro-3-methylphenyl)-1H-imidazol-2-yl)piperidin-1-yl)-5-methoxypyrimidin-4-amine ("184")

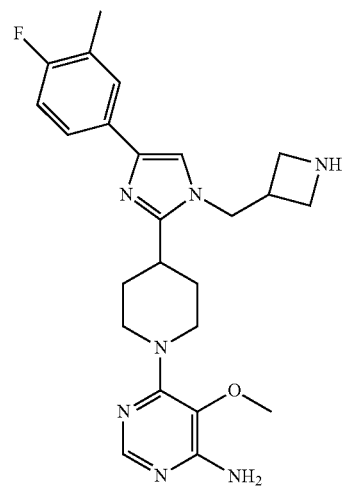 [SMILES: COc1c(N)ncnc1N1CCC(c2nc(-c3ccc(F)c(C)c3)cn2CC2CNC2)CC1]

The title compound was prepared in an analogous manner as 6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine. LC-MS: (M+1=451, obsd.=451).

6-(4-(1-(azetidin-3-ylmethyl)-4-(4-fluoro-3-methylphenyl)-1H-imidazol-2-yl)piperidin-1-yl)-5-ethoxypyrimidin-4-amine ("185")

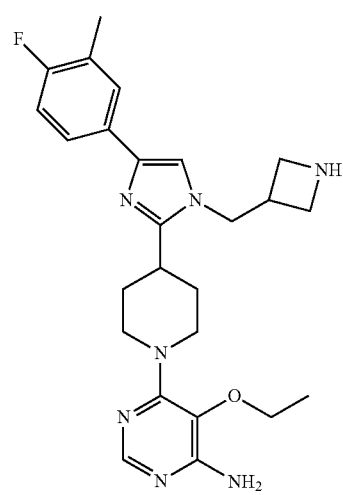

The title compound was prepared in an analogous manner as 6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine. LC-MS: (M+1=466, obsd.=466).

6-(4-(1-(azetidin-3-ylmethyl)-4-(4-fluoro-3-methylphenyl)-1H-imidazol-2-yl)piperidin-1-yl)-5-(2,2,2-trifluoroethoxy)pyrimidin-4-amine ("186")

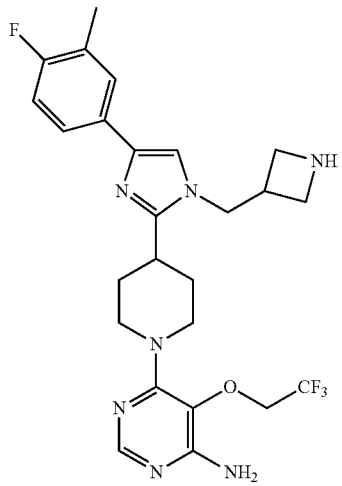 [SMILES: Cc1cc(-c2cn(CC3CNC3)c(C3CCN(c4ncnc(N)c4OCC(F)(F)F)CC3)n2)ccc1F]

The title compound was prepared in an analogous manner as 6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine. LC-MS: (M+1=520, obsd.=520).

6-(4-(1-(azetidin-3-ylmethyl)-4-(4-fluoro-3-methylphenyl)-1H-imidazol-2-yl)piperidin-1-yl)-5-isopropoxypyrimidin-4-amine ("187")

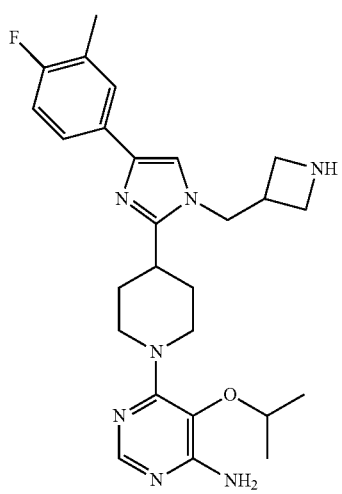 [SMILES: Cc1cc(-c2cn(CC3CNC3)c(C3CCN(c4ncnc(N)c4OC(C)C)CC3)n2)ccc1F]

The title compound was prepared in an analogous manner as 6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine. LC-MS: (M+1=480, obsd.=480).

6-(4-(1-(azetidin-3-ylmethyl)-4-(4-fluoro-3-methylphenyl)-1H-imidazol-2-yl)piperidin-1-yl)-5-ethylpyrimidin-4-amine ("188")

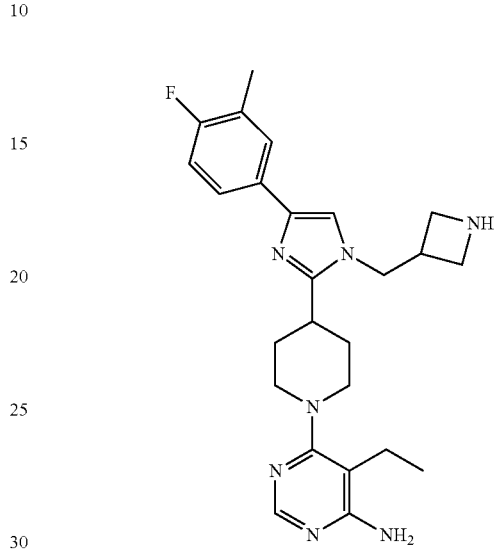

The title compound was prepared in an analogous manner as 6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine. LC-MS: (M+1=450, obsd.=450).

6-(4-(1-(azetidin-3-ylmethyl)-4-(4-fluoro-3-methylphenyl)-1H-imidazol-2-yl)piperidin-1-yl)-5-isopropylpyrimidin-4-amine ("189")

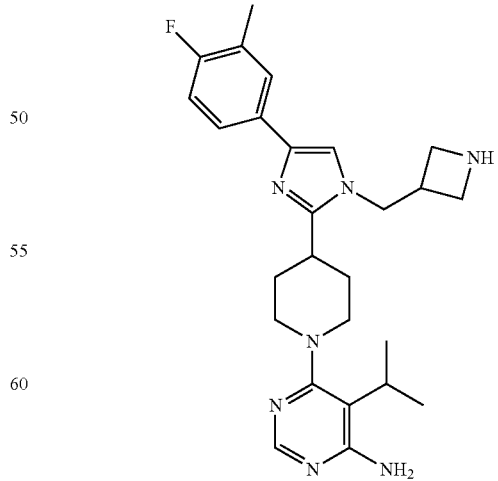

The title compound was prepared in an analogous manner as 6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine. LC-MS: (M+1=464, obsd.=464).

6-(4-(1-(2-(azetidin-1-yl)ethyl)-4-(4-fluoro-3-methylphenyl)-1H-imidazol-2-yl)piperidin-1-yl)-5-bromopyrimidin-4-amine ("190")

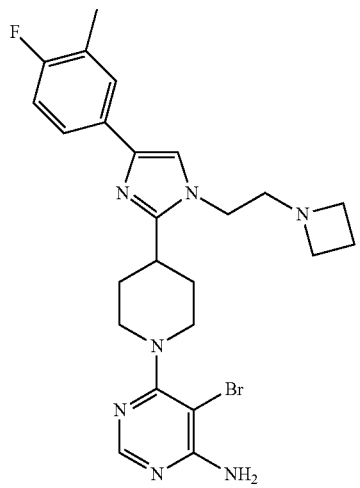 [SMILES: Cc1cc(-c2cn(CCN3CCC3)c(C3CCN(c4ncnc(N)c4Br)CC3)n2)ccc1F]

The title compound was prepared in an analogous manner as 6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine. LC-MS: (M+1=515, obsd.=515/517).

4-amino-6-(4-(1-(azetidin-3-ylmethyl)-4-(4-fluoro-3-methylphenyl)-1H-imidazol-2-yl)piperidin-1-yl)pyrimidine-5-carbonitrile ("191")

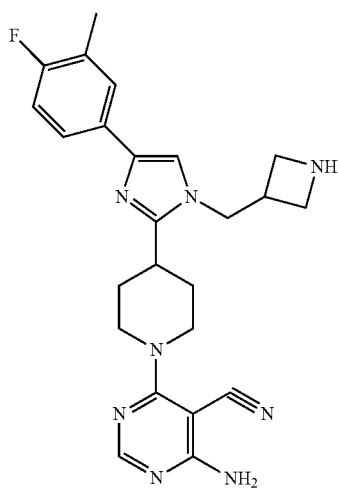 [SMILES: Cc1cc(-c2cn(CC3CNC3)c(C3CCN(c4ncnc(N)c4C#N)CC3)n2)ccc1F]

The title compound was prepared in an analogous manner as 6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine. LC-MS: (M+1=447, obsd.=447).

6-(4-(1-(2-(azetidin-1-yl)ethyl)-4-(2-(trifluoromethyl)pyridin-4-yl)-1H-imidazol-2-yl)piperidin-1-yl)-5-chloro-N-methylpyrimidin-4-amine ("192")

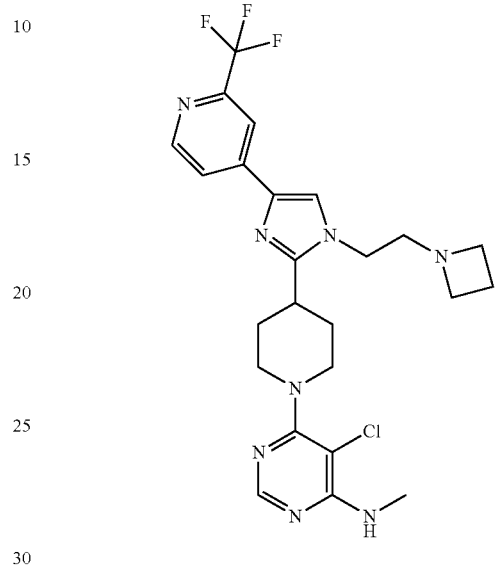

A reaction mixture of 5,6-Dichloro-pyrimidin-4-yl)-methyl-amine (30.00 mg; 0.17 mmol; 1.00 eq.), 4-[1-(2-azetidin-1-yl-ethyl)-2-piperidin-4-yl-1H-imidazol-4-yl]-2-trifluoromethyl-pyridine hydrochloride (4) (97.37 mg; 0.19 mmol; 1.10 eq.), and Ethyl-diisopropyl-amine (219.63 mg; 0.67 mmol; 4.00 eq.) in DMSO 1 ml was stirred at 100° C. for overnight. Purified by HPLC, collected title compound. LC-MS: (M+1=521, obsd.=521).

(6-{4-[1-Azetidin-3-ylmethyl-4-(4-fluoro-3-methylphenyl)-1H-imidazol-2-yl]-piperidin-1-yl}-5-chloropyrimidin-4-yl)-methyl-amine ("193")

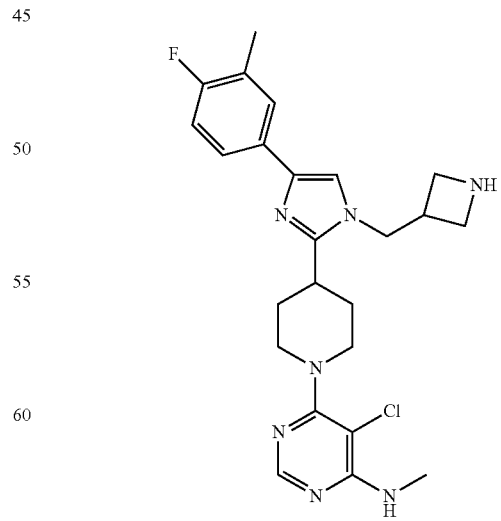

The title compound was prepared in an analogous manner as 6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine. LC-MS: (M+1=470, obsd.=470).

6-(4-(1-(azetidin-3-ylmethyl)-4-(4-fluoro-3-methylphenyl)-1H-imidazol-2-yl)cyclohexyl)-5-isopropylpyrimidin-4-amine ("194")

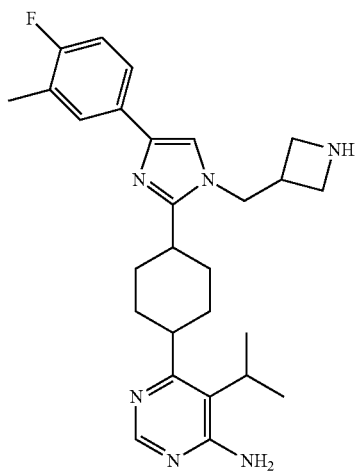 [SMILES: Cc1cc(-c2cn(CC3CNC3)c(C3CCC(c4ncnc(N)c4C(C)C)CC3)n2)ccc1F]

The title compound was prepared in an analogous manner as 6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine. LC-MS: (M+1=464, obsd.=464).

5-Ethyl-6-{4-[4-(4-fluoro-phenyl)-1-(2-morpholin-4-yl-ethyl)-1H-imidazol-2-yl]-piperidin-1-yl}-pyrimidin-4-ylamine ("195")

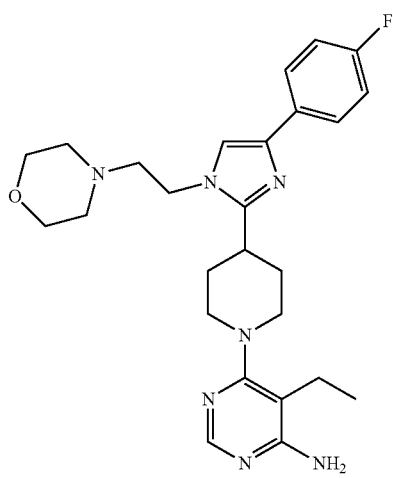 [SMILES: CCc1c(N)ncnc1N1CCC(c2nc(-c3ccc(F)cc3)cn2CCN2CCOCC2)CC1]

The title compound was prepared in an analogous manner as 5-ethyl-6-(4-(4-(4-fluoro-3-(trifluoromethyl)phenyl)-1-

(2-(3-fluoroazetidin-1-yl)ethyl)-1H-imidazol-2-yl)piperidin-1-yl)pyrimidin-4-amine. LC-MS: (M+1=480, obsd.=480).

6-{4-[4-(3,4-Difluoro-phenyl)-1-(2-morpholin-4-yl-ethyl)-1H-imidazol-2-yl]-piperidin-1-yl}-5-ethyl-pyrimidin-4-ylamine ("196")

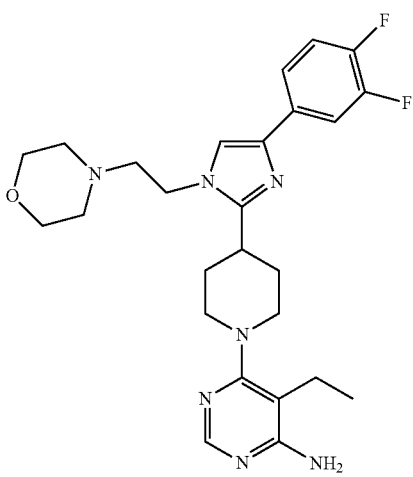 [SMILES: CCc1c(N)ncnc1N1CCC(c2nc(-c3ccc(F)c(F)c3)cn2CCN2CCOCC2)CC1]

The title compound was prepared in an analogous manner as 5-ethyl-6-(4-(4-(4-fluoro-3-(trifluoromethyl)phenyl)-1-(2-(3-fluoroazetidin-1-yl)ethyl)-1H-imidazol-2-yl)piperidin-1-yl)pyrimidin-4-amine. LC-MS: (M+1=498, obsd.=498).

5-Ethyl-6-(4-{4-(4-fluoro-phenyl)-1-[2-(2-oxa-6-aza-spiro[3.3]hept-6-yl)-ethyl]-1H-imidazol-2-yl}-piperidin-1-yl)-pyrimidin-4-ylamine ("197")

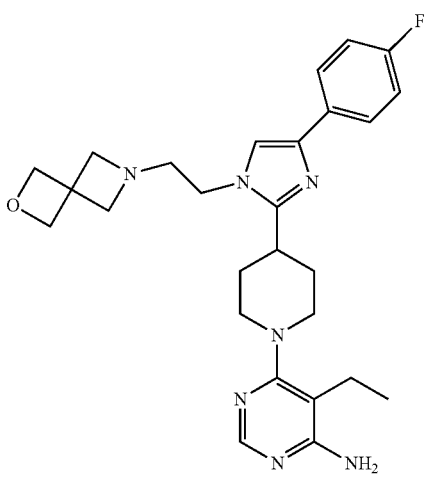 [SMILES: CCc1c(N)ncnc1N1CCC(c2nc(-c3ccc(F)cc3)cn2CCN2CC3(COC3)C2)CC1]

The title compound was prepared in an analogous manner as 5-ethyl-6-(4-(4-(4-fluoro-3-(trifluoromethyl)phenyl)-1-

(2-(3-fluoroazetidin-1-yl)ethyl)-1H-imidazol-2-yl)piperidin-1-yl)pyrimidin-4-amine. LC-MS: (M+1=492, obsd.=492).

6-(4-{4-(3,4-Difluoro-phenyl)-1-[2-(2-oxa-6-azaspiro[3.3]hept-6-yl)-ethyl]-1H-imidazol-2-yl}-piperidin-1-yl)-5-ethyl-pyrimidin-4-ylamine ("198")

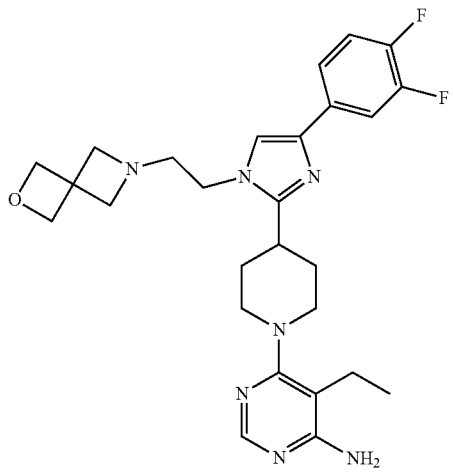 [SMILES: CCc1c(N)ncnc1N1CCC(c2nc(-c3ccc(F)c(F)c3)cn2CCN2CC3(COC3)C2)CC1]

The title compound was prepared in an analogous manner as 5-ethyl-6-(4-(4-(4-fluoro-3-(trifluoromethyl)phenyl)-1-(2-(3-fluoroazetidin-1-yl)ethyl)-1H-imidazol-2-yl)piperidin-1-yl)pyrimidin-4-amine. LC-MS: (M+1=510, obsd.=510).

6-(4-{4-(3,4-Difluoro-phenyl)-1-[2-(3-fluoro-azetidin-1-yl)-ethyl]-1H-imidazol-2-yl}-piperidin-1-yl)-5-ethyl-pyrimidin-4-ylamine ("199")

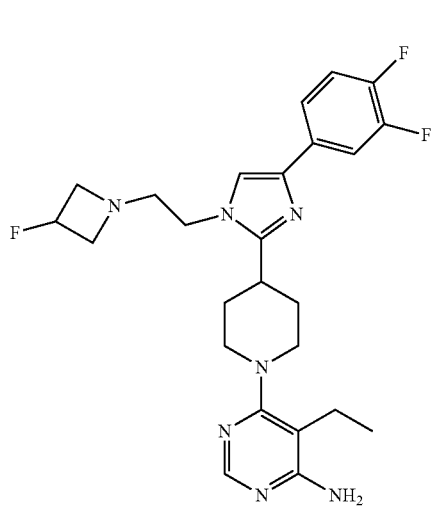 [SMILES: CCc1c(N)ncnc1N1CCC(c2nc(-c3ccc(F)c(F)c3)cn2CCN2CC(F)C2)CC1]

The title compound was prepared in an analogous manner as 5-ethyl-6-(4-(4-(4-fluoro-3-(trifluoromethyl)phenyl)-1-

(2-(3-fluoroazetidin-1-yl)ethyl)-1H-imidazol-2-yl)piperidin-1-yl)pyrimidin-4-amine. LC-MS: (M+1=486, obsd.=486).

5-Ethyl-6-{4-[1-[2-(3-fluoro-azetidin-1-yl)-ethyl]-4-(4-fluoro-phenyl)-1H-imidazol-2-yl]-piperidin-1-yl}-pyrimidin-4-ylamine ("200")

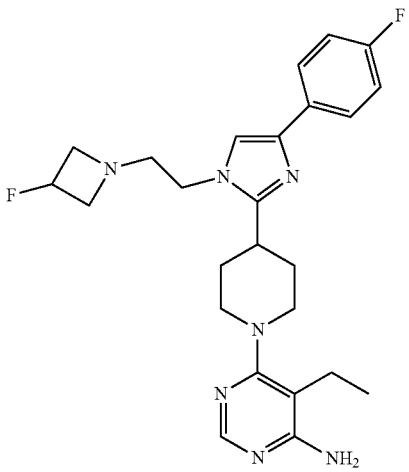 [SMILES: CCc1c(N)ncnc1N1CCC(c2nc(-c3ccc(F)cc3)cn2CCN2CC(F)C2)CC1]

The title compound was prepared in an analogous manner as 5-ethyl-6-(4-(4-(4-fluoro-3-(trifluoromethyl)phenyl)-1-(2-(3-fluoroazetidin-1-yl)ethyl)-1H-imidazol-2-yl)piperidin-1-yl)pyrimidin-4-amine. LC-MS: (M+1=468, obsd.=468).

5-Ethyl-6-(4-{4-(4-fluoro-phenyl)-1-[2-(2-oxa-6-aza-spiro[3.4]oct-6-yl)-ethyl]-1H-imidazol-2-yl}-piperidin-1-yl)-pyrimidin-4-ylamine ("201")

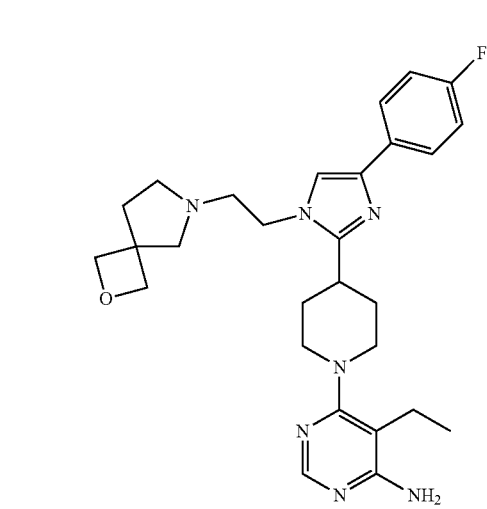 [SMILES: CCc1c(N)ncnc1N1CCC(c2nc(-c3ccc(F)cc3)cn2CCN2CCC3(COC3)C2)CC1]

The title compound was prepared in an analogous manner as 5-ethyl-6-(4-(4-(4-fluoro-3-(trifluoromethyl)phenyl)-1-

(2-(3-fluoroazetidin-1-yl)ethyl)-1H-imidazol-2-yl)piperidin-1-yl)pyrimidin-4-amine. LC-MS: (M+1=506, obsd.=506).

6-(4-{4-(3,4-Difluoro-phenyl)-1-[2-(2-oxa-6-aza-spiro[3.4]oct-6-yl)-ethyl]-1H-imidazol-2-yl}-piperidin-1-yl)-5-ethyl-pyrimidin-4-ylamine ("202")

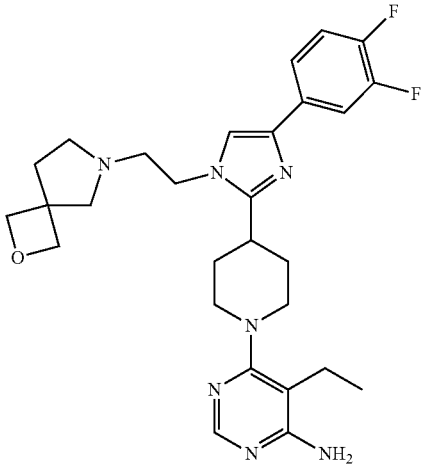 [SMILES: CCc1c(N)ncnc1N1CCC(c2nc(-c3ccc(F)c(F)c3)cn2CCN2CCC3(COC3)C2)CC1]

The title compound was prepared in an analogous manner as 5-ethyl-6-(4-(4-(4-fluoro-3-(trifluoromethyl)phenyl)-1-(2-(3-fluoroazetidin-1-yl)ethyl)-1H-imidazol-2-yl)piperidin-1-yl)pyrimidin-4-amine. LC-MS: (M+1=524, obsd.=524).

6-(4-{4-(3,4-Difluoro-phenyl)-1-[2-(6-oxa-1-aza-spiro[3.3]hept-1-yl)-ethyl]-1H-imidazol-2-yl}-piperidin-1-yl)-5-ethyl-pyrimidin-4-ylamine ("203")

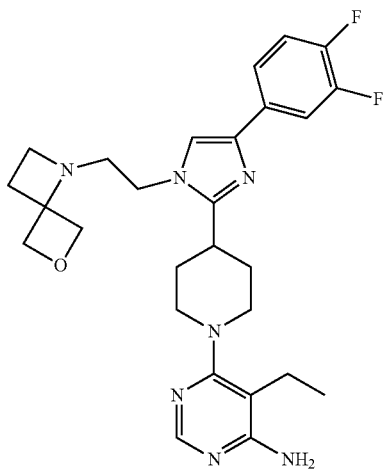 [SMILES: CCc1c(N)ncnc1N1CCC(c2nc(-c3ccc(F)c(F)c3)cn2CCN2CCC23COC3)CC1]

The title compound was prepared in an analogous manner as 5-ethyl-6-(4-(4-(4-fluoro-3-(trifluoromethyl)phenyl)-1-

(2-(3-fluoroazetidin-1-yl)ethyl)-1H-imidazol-2-yl)piperidin-1-yl)pyrimidin-4-amine. LC-MS: (M+1=510, obsd.=510).

5-Ethyl-6-(4-{4-(4-fluoro-phenyl)-1-[2-(6-oxa-1-aza-spiro[3.3]hept-1-yl)-ethyl]-1H-imidazol-2-yl}-piperidin-1-yl)-pyrimidin-4-ylamine ("204")

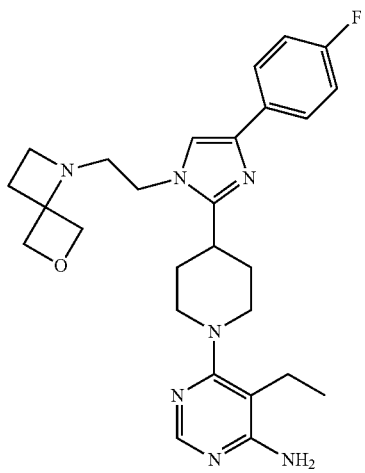 [SMILES: CCc1c(N)ncnc1N1CCC(c2nc(-c3ccc(F)cc3)cn2CCN2CCC23COC3)CC1]

The title compound was prepared in an analogous manner as 5-ethyl-6-(4-(4-(4-fluoro-3-(trifluoromethyl)phenyl)-1-(2-(3-fluoroazetidin-1-yl)ethyl)-1H-imidazol-2-yl)piperidin-1-yl)pyrimidin-4-amine. LC-MS: (M+1=492, obsd.=492).

4-Amino-6-{4-[1-(2-azetidin-1-yl-ethyl)-4-(5-chloro-6-fluoro-pyridin-3-yl)-1H-imidazol-2-yl]-piperidin-1-yl}-pyrimidine-5-carbonitrile ("205")

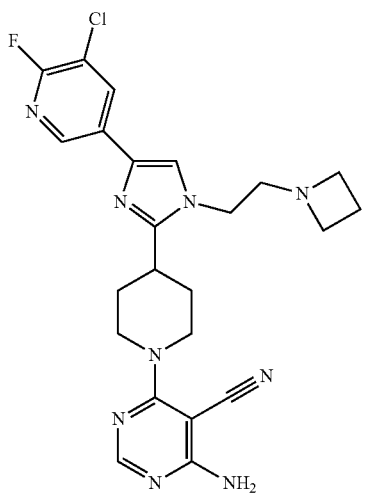

The title compound was prepared in an analogous manner as 4-amino-6-(4-(4-(4-fluoro-3-(trifluoromethyl)phenyl)-1-

(pyrrolidin-3-yl)-1H-imidazol-2-yl)piperidin-1-yl)pyrimidine-5-carboxamide. LC-MS: (M+1=482, obsd.=482).

4-Amino-6-{4-[1-(2-azetidin-1-yl-ethyl)-4-(2-fluoro-pyridin-4-yl)-1H-imidazol-2-yl]-piperidin-1-yl}-pyrimidine-5-carbonitrile ("206")

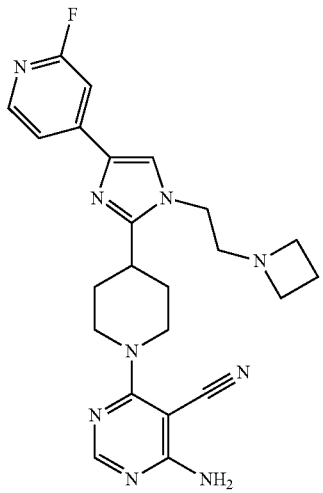 [SMILES: N#Cc1c(N)ncnc1N1CCC(c2nc(-c3ccnc(F)c3)cn2CCN2CCC2)CC1]

The title compound was prepared in an analogous manner as 4-amino-6-(4-(4-(4-fluoro-3-(trifluoromethyl)phenyl)-1-(pyrrolidin-3-yl)-1H-imidazol-2-yl)piperidin-1-yl)pyrimidine-5-carboxamide. LC-MS: (M+1=448, obsd.=448).

4-Amino-6-{4-[1-(2-azetidin-1-yl-ethyl)-4-(1H-indazol-5-yl)-1H-imidazol-2-yl]-piperidin-1-yl}-pyrimidine-5-carbonitrile ("207")

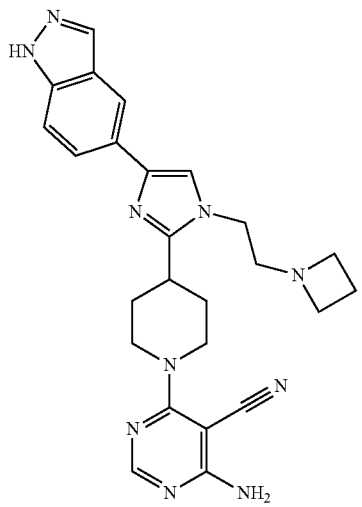 [SMILES: N#Cc1c(N)ncnc1N1CCC(c2nc(-c3ccc4[nH]ncc4c3)cn2CCN2CCC2)CC1]

The title compound was prepared in an analogous manner as 4-amino-6-(4-(4-(4-fluoro-3-(trifluoromethyl)phenyl)-1-(pyrrolidin-3-yl)-1H-imidazol-2-yl)piperidin-1-yl)pyrimidine-5-carboxamide. LC-MS: (M+1=469, obsd.=469).

6-{4-(4-fluoro-3-trifluoromethyl-phenyl)-1-2-pyrrolidin-1-yl-ethyl)-1H-imidazol-2-yl]-piperidin-1-yl}-5-ethyl-pyrimidin-4-ylamine ("208")

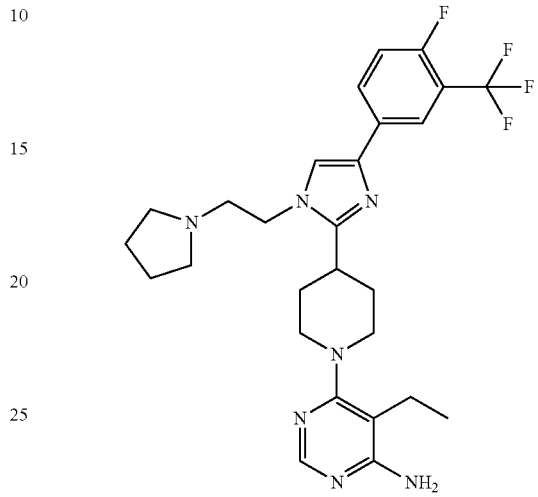

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-trifluoromethyl-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=532, obsd.=532).

5-Chloro-6{4-(4-fluoro-3-trifluoromethyl-phenyl)-1-2-pyrrolidin-1-yl-ethyl)-1H-imidazol-2-yl]-piperidin-1-yl}-pyrimidin-4-ylamine ("209")

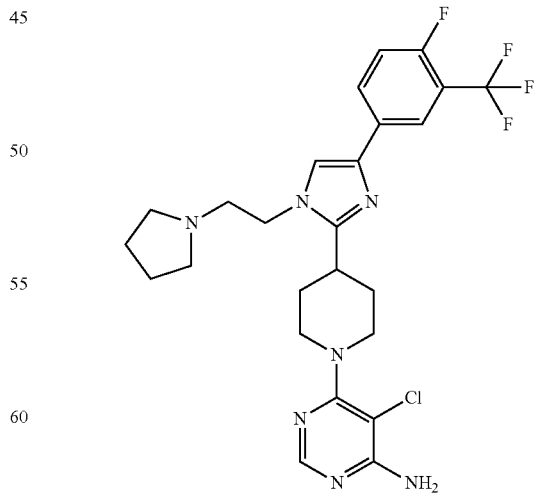

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4- ylamine using 4-[4-(4-fluoro-3-trifluoromethyl-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=538, obsd.=538).

5-Chloro-6{4-(4-hydroxy-3-trifluoromethyl-phenyl)-1-2-pyrrolidin-1-yl-ethyl)-1H-imidazol-2-yl]-piperidin-1-yl}-pyrimidin-4-ylamine ("210")

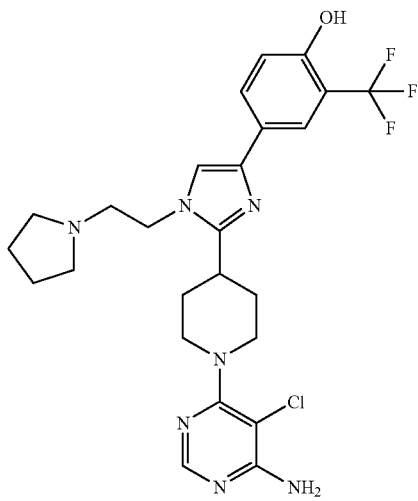 [SMILES: Nc1ncnc(N2CCC(c3nc(-c4ccc(O)c(C(F)(F)F)c4)cn3CCN3CCCC3)CC2)c1Cl]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-hydroxy-3-trifluoromethyl-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=536, obsd.=536).

5-Fluoro-6{4-(4-fluoro-3-trifluoromethyl-phenyl)-1-2-pyrrolidin-1-yl-ethyl)-1H-imidazol-2-yl]-piperidin-1-yl}-pyrimidin-4-ylamine ("211")

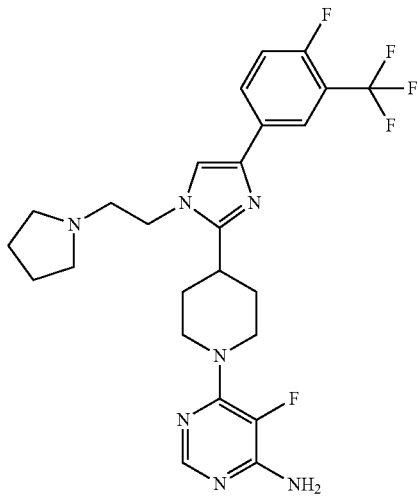 [SMILES: Nc1ncnc(N2CCC(c3nc(-c4ccc(F)c(C(F)(F)F)c4)cn3CCN3CCCC3)CC2)c1F]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-trifluoromethyl-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=522, obsd.=522).

6-{4-(4-fluoro-3-trifluoromethyl-phenyl)-1-2-piperidin-1-yl-ethyl)-1H-imidazol-2-yl]-piperidin-1-yl}-5-isopropylene-pyrimidin-4-ylamine ("212")

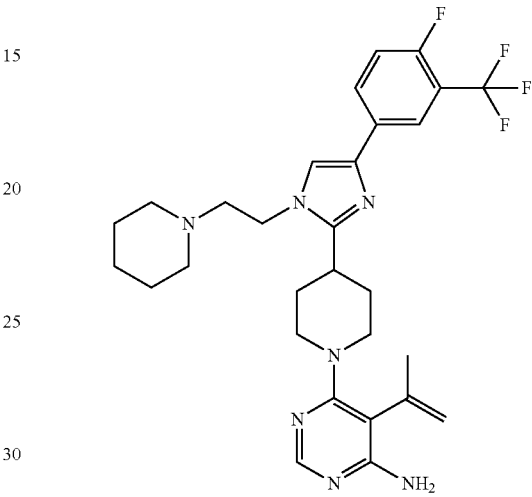

The title compound was prepared in an analogous manner 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-trifluoromethyl-phenyl)-1-(2-piperidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=558, obsd.=558).

6-{4-(4-fluoro-3-trifluoromethyl-phenyl)-1-2-pyrrolidin-1-yl-ethyl)-1H-imidazol-2-yl]-piperidin-1-yl}-5-isopropylene-pyrimidin-4-ylamine ("213")

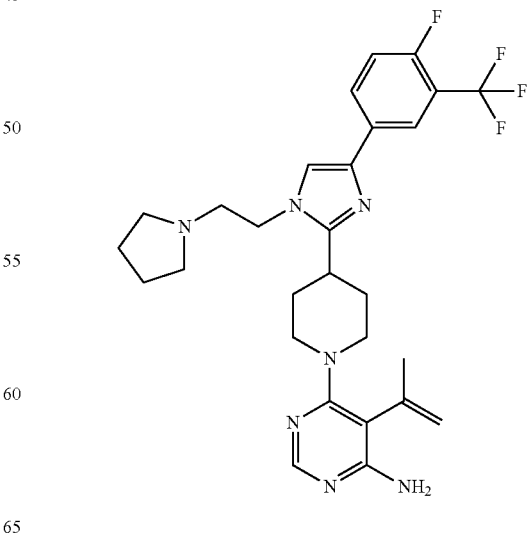

The title compound was prepared in an analogous manner 5-Bromo-6-{4-[4-(4-fluoro-3-trifluoromethyl-phenyl)-1- methyl-1H-imidazol-2-yl]-piperidin-1-yl}-pyrimidin-4-ylamine using 4-[4-(4-fluoro-3-trifluoromethyl-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=544, obsd.=544).

6-{4-(4-fluoro-3-trifluoromethyl-phenyl)-1-2-pyrrolidin-1-yl-ethyl)-1H-imidazol-2-yl]-piperidin-1-yl}-yrimidin-4-ylamine ("214")

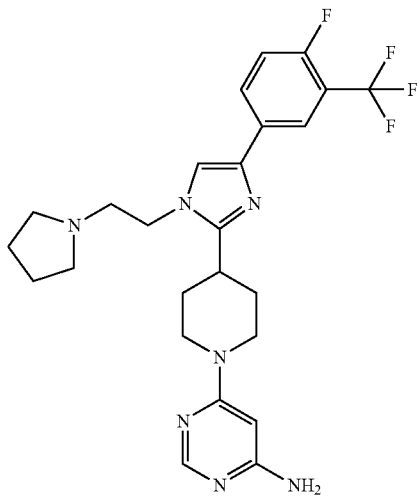 [SMILES: Nc1cc(N2CCC(c3nc(-c4ccc(F)c(C(F)(F)F)c4)cn3CCN3CCCC3)CC2)ncn1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-trifluoromethyl-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=504, obsd.=504).

6-{4-(4-fluoro-3-trifluoromethyl-phenyl)-1-2-pyrrolidin-1-yl-ethyl)-1H-imidazol-2-yl]-piperidin-1-yl}-5-methyl-pyrimidin-4-ylamine ("215")

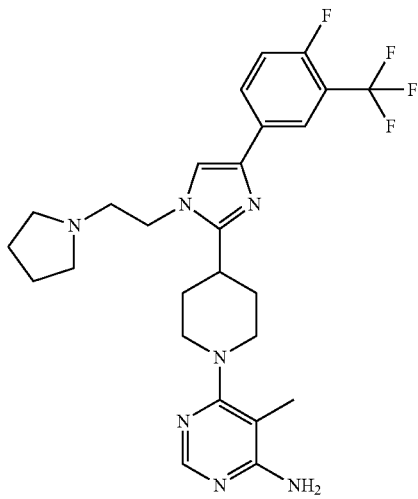 [SMILES: Cc1c(N)ncnc1N1CCC(c2nc(-c3ccc(F)c(C(F)(F)F)c3)cn2CCN2CCCC2)CC1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-trifluoromethyl-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=518, obsd.=518).

5-Chloro-6-{4-(4-fluoro-3-trifluoromethyl-phenyl)-1-2-piperidin-1-yl-ethyl)-1H-imidazol-2-yl]-piperidin-1-yl}-pyrimidin-4-ylamine ("216")

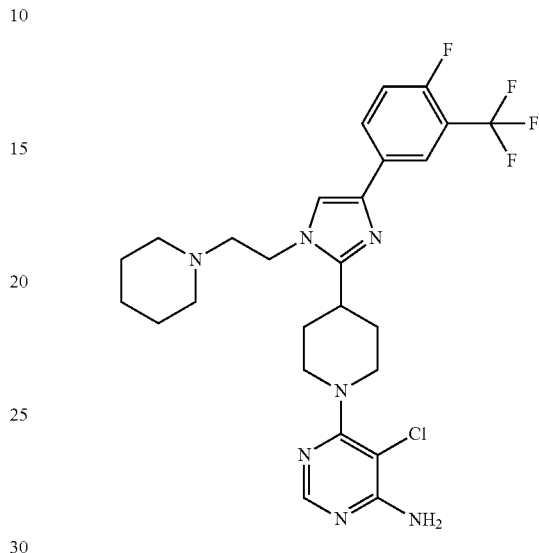

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-trifluoromethyl-phenyl)-1-(2-piperidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=552, obsd.=552).

5-Bromo-6{4-(4-fluoro-3-trifluoromethyl-phenyl)-1-2-pyrrolidin-1-yl-ethyl)-1H-imidazol-2-yl]-azetidin-1-yl}-pyrimidin-4-ylamine ("217")

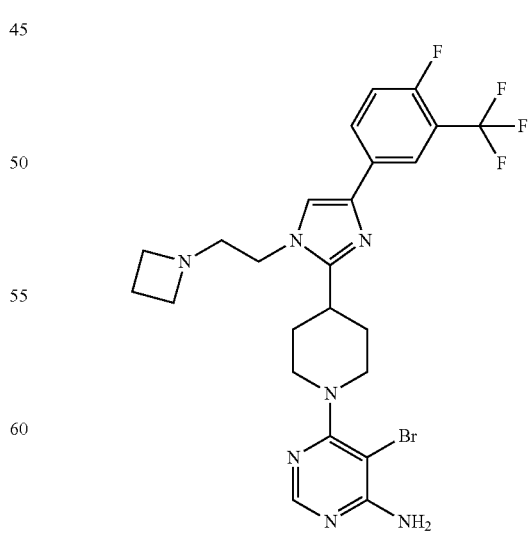

The title compound was prepared in an analogous manner as 5-Bromo-6-{4-[4-(4-fluoro-3-trifluoromethyl-phenyl)-1- methyl-1H-imidazol-2-yl]-piperidin-1-yl}-pyrimidin-4-ylamine using 4-[4-(4-fluoro-3-trifluoromethyl-phenyl)-1-(2-azetidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=568, obsd.=568).

5-Chloro-6{4-(4-fluoro-3-trifluoromethyl-phenyl)-1-2-pyrrolidin-1-yl-ethyl)-1H-imidazol-2-yl]-azetidin-1-yl}-pyrimidin-4-ylamine ("218")

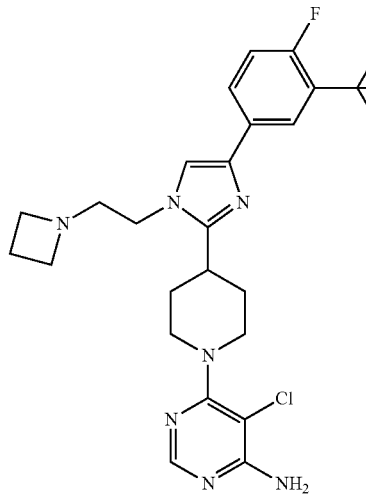

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-trifluoromethyl-phenyl)-1-(2-azetidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=524, obsd.=524).

5-(4-fluorophenyl)-6{4-(4-fluoro-3-trifluoromethyl-phenyl)-1-2-azetidin-1-yl-ethyl)-1H-imidazol-2-yl]-piperidin-1-yl}-pyrimidin-4-ylamine ("219")

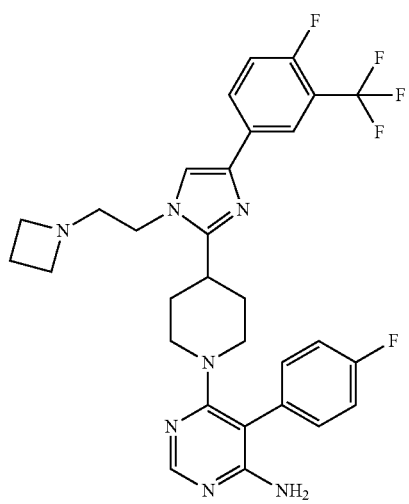 [SMILES: Nc1ncnc(N2CCC(c3nc(-c4ccc(F)c(C(F)(F)F)c4)cn3CCN3CCC3)CC2)c1-c1ccc(F)cc1]

The title compound was prepared in an analogous manner as 5-Bromo-6-{4-[4-(4-fluoro-3-trifluoromethyl-phenyl)-1- methyl-1H-imidazol-2-yl]-piperidin-1-yl}-pyrimidin-4-ylamine using 4-[4-(4-fluoro-3-trifluoromethyl-phenyl)-1-(2-azetidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=584, obsd.=584).

5-vinyl-6{4-(4-fluoro-3-trifluoromethyl-phenyl)-1-2-azetidin-1-yl-ethyl)-1H-imidazol-2-yl]-piperidin-1-yl}-pyrimidin-4-ylamine ("220")

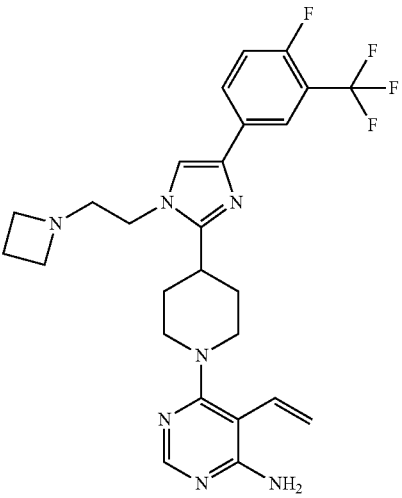 [SMILES: C=Cc1c(N)ncnc1N1CCC(c2nc(-c3ccc(F)c(C(F)(F)F)c3)cn2CCN2CCC2)CC1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-trifluoromethyl-phenyl)-1-(2-azetidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=516, obsd.=516).

6{4-(4-fluoro-3-trifluoromethyl-phenyl)-1-2-azetidin-1-yl-ethyl)-1H-imidazol-2-yl]-piperidin-1-yl}-pyrimidin-4-ylamine ("221")

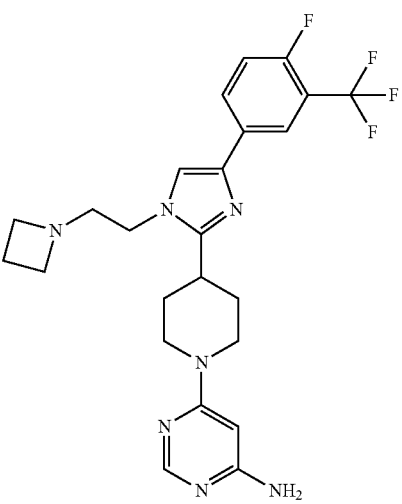 [SMILES: Nc1cc(N2CCC(c3nc(-c4ccc(F)c(C(F)(F)F)c4)cn3CCN3CCC3)CC2)ncn1]

The title compound was prepared in an analogous manner as 5-Bromo-6-{4-[4-(4-fluoro-3-trifluoromethyl-phenyl)-1- methyl-1H-imidazol-2-yl]-piperidin-1-yl}-pyrimidin-4-ylamine using 4-[4-(4-fluoro-3-trifluoromethyl-phenyl)-1-(2-azetidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=490, obsd.=490).

5-(4-methyl carboxyesterphenyl)-6{4-(4-fluoro-3-trifluoromethyl-phenyl)-1-2-azetidin-1-yl-ethyl)-1H-imidazol-2-yl]-piperidin-1-yl}-pyrimidin-4-ylamine ("222")

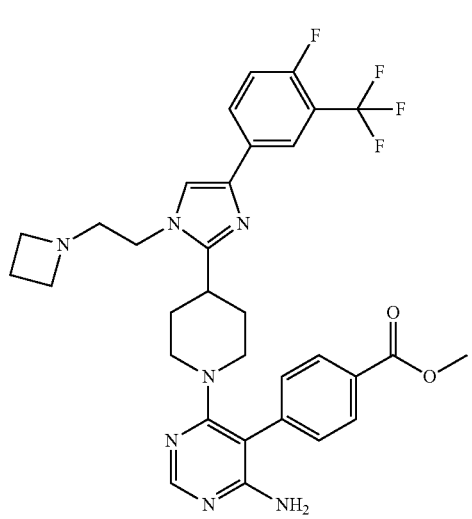 [SMILES: COC(=O)c1ccc(-c2c(N)ncnc2N2CCC(c3nc(-c4ccc(F)c(C(F)(F)F)c4)cn3CCN3CCC3)CC2)cc1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-trifluoromethyl-phenyl)-1-(2-azetidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=624, obsd.=624).

5-(4-methyl carboxyesterphenyl)-6{4-(4-fluoro-3-trifluoromethyl-phenyl)-1-2-pyrrolidin-1-yl-ethyl)-1H-imidazol-2-yl]-piperidin-1-yl}-pyrimidin-4-ylamine ("223")

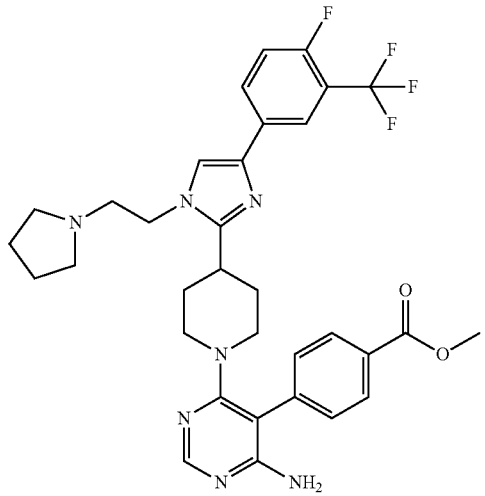 [SMILES: COC(=O)c1ccc(-c2c(N)ncnc2N2CCC(c3nc(-c4ccc(F)c(C(F)(F)F)c4)cn3CCN3CCCC3)CC2)cc1]

The title compound was prepared in an analogous manner as 5-Bromo-6-{4-[4-(4-fluoro-3-trifluoromethyl-phenyl)-1- methyl-1H-imidazol-2-yl]-piperidin-1-yl}-pyrimidin-4-ylamine using 4-[4-(4-fluoro-3-trifluoromethyl-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=638, obsd.=638).

5-(4-carboxy acid phenyl)-6{4-(4-fluoro-3-trifluoromethyl-phenyl)-1-2-azetidin-1-yl-ethyl)-1H-imidazol-2-yl]-piperidin-1-yl}-pyrimidin-4-ylamine ("224")

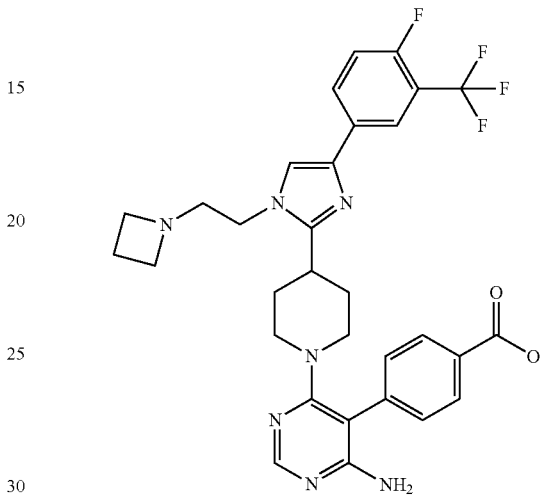

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-trifluoromethyl-phenyl)-1-(2-azetidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=610, obsd.=610).

5-(4-carboxy acid phenyl)-6{4-(4-fluoro-3-trifluoromethyl-phenyl)-1-2-pyrrolidin-1-yl-ethyl)-1H-imidazol-2-yl]-piperidin-1-yl}-pyrimidin-4-ylamine ("225")

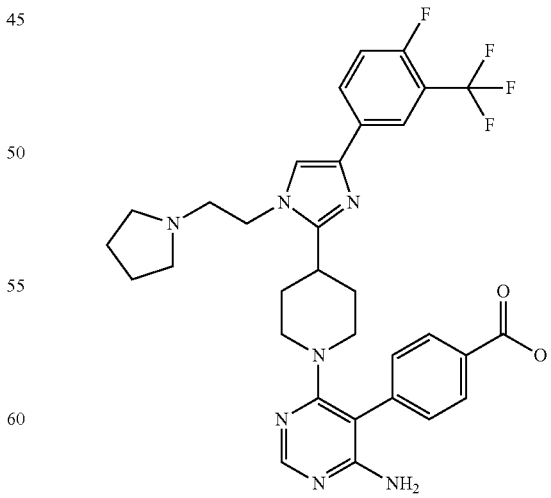

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4- ylamine using 4-[4-(4-fluoro-3-trifluoromethyl-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=624, obsd.=624).

5-Bromo-6{4-(3,4-difluorophenyl)-1-2-pyrrolidin-1-yl-ethyl)-1H-imidazol-2-yl]-piperidin-1-yl}-pyrimidin-4-ylamine ("226")

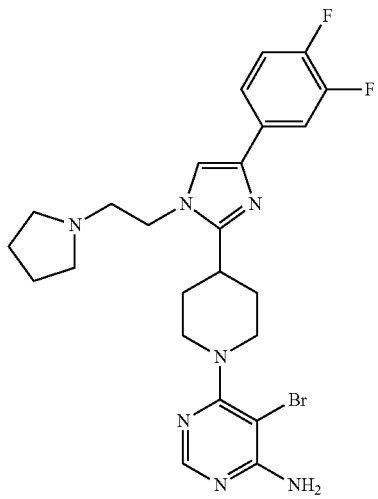 [SMILES: Nc1ncnc(N2CCC(c3nc(-c4ccc(F)c(F)c4)cn3CCN3CCCC3)CC2)c1Br]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(3,4-difluoro-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=532, obsd.=532).

5-Bromo-6{4-(4-fluorophenyl)-1-2-pyrrolidin-1-yl-ethyl)-1H-imidazol-2-yl]-piperidin-1-yl}-pyrimidin-4-ylamine ("227")

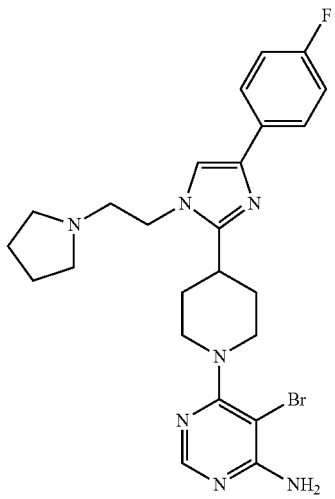

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=514, obsd.=514).

5-Bromo-6{4-(3-fluorophenyl)-1-2-pyrrolidin-1-yl-ethyl)-1H-imidazol-2-yl]-piperidin-1-yl}-pyrimidin-4-ylamine ("228")

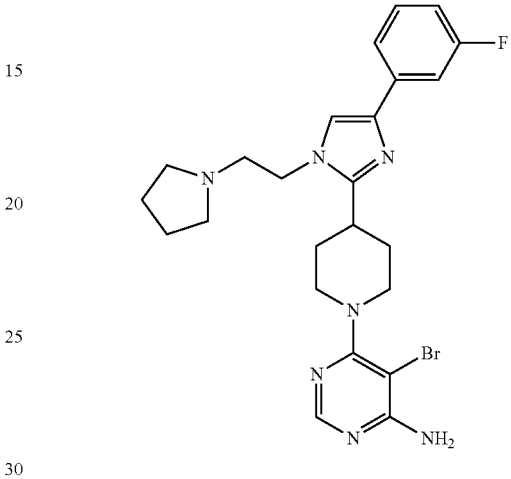

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(3-fluorophenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=514, obsd.=514).

5-Bromo-6{4-(3-fluoro-4-trifluoromethyl-phenyl)-1-2-pyrrolidin-1-yl-ethyl)-1H-imidazol-2-yl]-piperidin-1-yl}-pyrimidin-4-ylamine ("229")

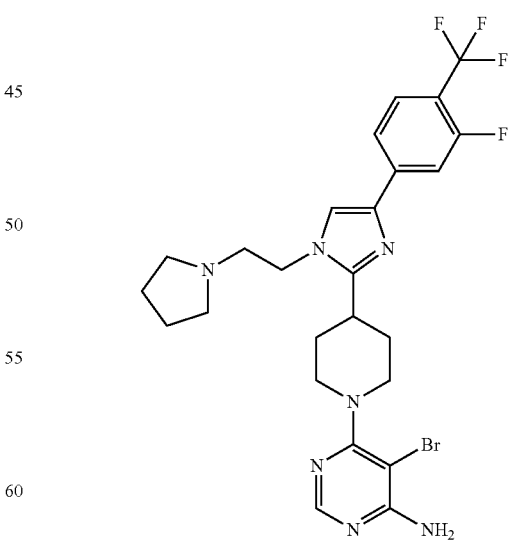

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(3-fluoro-4-trifluoromethyl-phenyl)-1-

(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=582, obsd.=582).

5-Ethyl-6{4-(4-fluoro-3-trifluoromethyl-phenyl)-1-2-azetidin-1-yl-ethyl)-1H-imidazol-2-yl]-piperidin-1-yl}-pyrimidin-4-ylamine ("230")

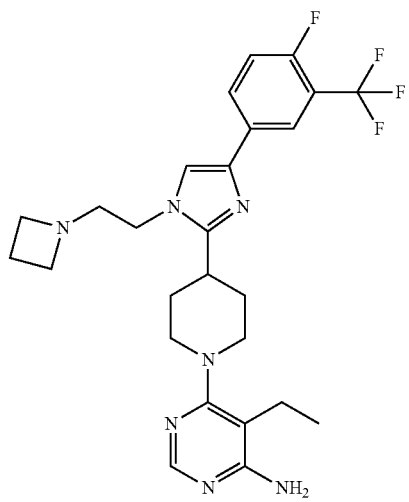 [SMILES: CCc1c(N)ncnc1N1CCC(c2nc(-c3ccc(F)c(C(F)(F)F)c3)cn2CCN2CCC2)CC1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-trifluoromethyl-phenyl)-1-(2-azetidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=518, obsd.=518).

5-Ethyl-6{4-(3-fluorophenyl)-1-2-pyrrolidin-1-yl-ethyl)-1H-imidazol-2-yl]-piperidin-1-yl}-pyrimidin-4-ylamine ("231")

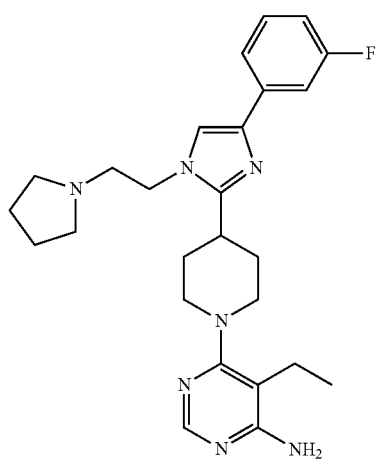 [SMILES: CCc1c(N)ncnc1N1CCC(c2nc(-c3cccc(F)c3)cn2CCN2CCCC2)CC1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(3-fluorophenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=464, obsd.=464).

5-Ethyl-6{4-(4-fluorophenyl)-1-2-pyrrolidin-1-yl-ethyl)-1H-imidazol-2-yl]-piperidin-1-yl}-pyrimidin-4-ylamine ("232")

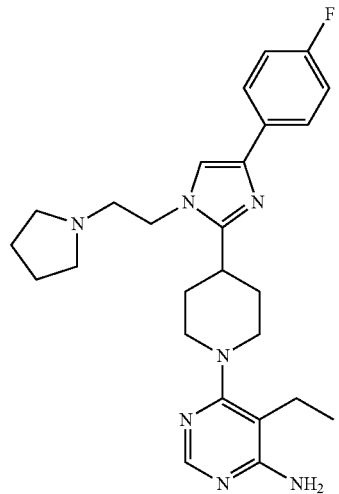

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=464, obsd.=464).

5-Ethyl-6{4-(3,4-difluorophenyl)-1-2-pyrrolidin-1-yl-ethyl)-1H-imidazol-2-yl]-piperidin-1-yl}-pyrimidin-4-ylamine ("233")

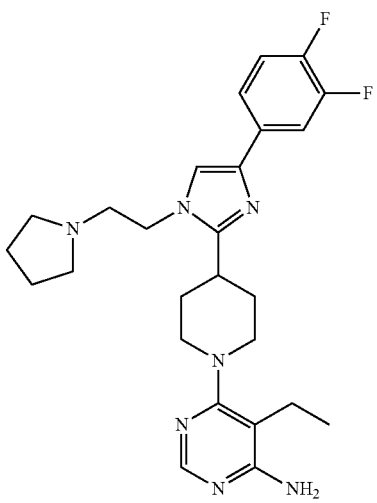 [SMILES: CCc1c(N)ncnc1N1CCC(c2nc(-c3ccc(F)c(F)c3)cn2CCN2CCCC2)CC1]

The title compound was prepared in an analogous manner as 5-Bromo-6-{4-[4-(4-fluoro-3-trifluoromethyl-phenyl)-1- methyl-1H-imidazol-2-yl]-piperidin-1-yl}-pyrimidin-4-ylamine using 4-[4-(3,4-difluorophenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=482, obsd.=482).

5-Ethyl-6{4-(3-fluoro-4-trifluoromethyl phenyl)-1-2-pyrrolidin-1-yl-ethyl)-1H-imidazol-2-yl]-piperidin-1-yl}-pyrimidin-4-ylamine ("234")

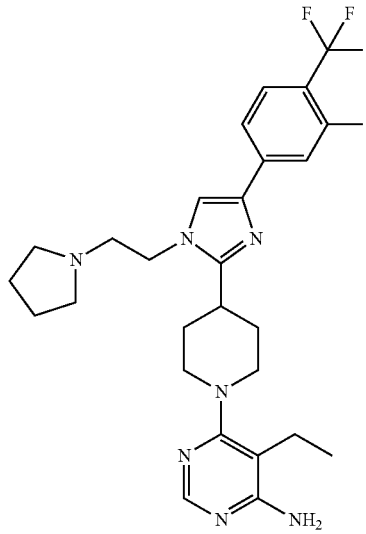

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(3-fluoro-4-trifluoromethyl-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=532, obsd.=532).

5-Chloro-6{4-(3-fluoro-4-trifluoromethylphenyl)-1-2-pyrrolidin-1-yl-ethyl)-1H-imidazol-2-yl]-piperidin-1-yl}-pyrimidin-4-ylamine ("235")

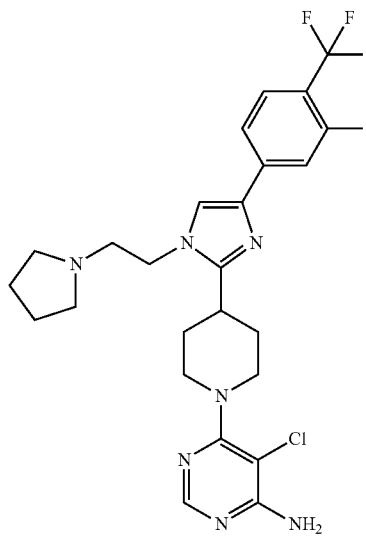

The title compound was prepared in an analogous manner as 5-Bromo-6-{4-[4-(4-fluoro-3-trifluoromethyl-phenyl)-1- methyl-1H-imidazol-2-yl]-piperidin-1-yl}-pyrimidin-4-ylamine using 4-[4-(3-fluoro-4-trifluoromethyl-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=538, obsd.=538).

5-Chloro-6{4-(3-fluoromethylphenyl)-1-2-pyrrolidin-1-yl-ethyl)-1H-imidazol-2-yl]-piperidin-1-yl}-pyrimidin-4-ylamine ("236")

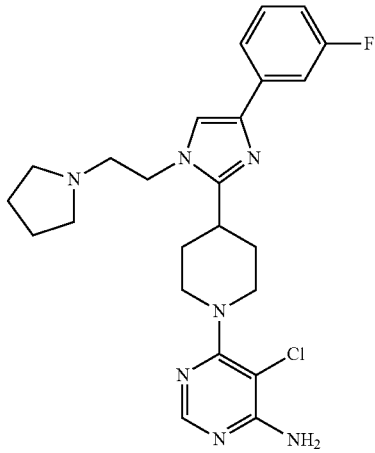 [SMILES: Nc1ncnc(N2CCC(c3nc(-c4cccc(F)c4)cn3CCN3CCCC3)CC2)c1Cl]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(3-fluorophenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=470, obsd.=470).

5-Chloro-6{4-(4-fluoromethylphenyl)-1-2-pyrrolidin-1-yl-ethyl)-1H-imidazol-2-yl]-piperidin-1-yl}-pyrimidin-4-ylamine ("237")

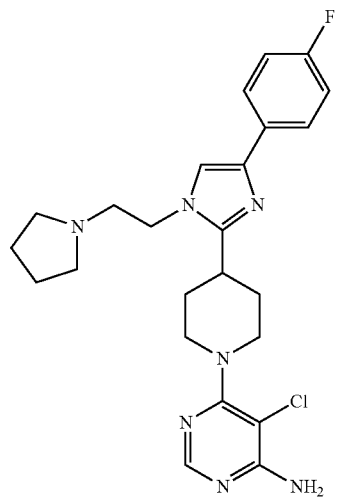 [SMILES: Nc1ncnc(N2CCC(c3nc(-c4ccc(F)cc4)cn3CCN3CCCC3)CC2)c1Cl]

The title compound was prepared in an analogous manner as 5-Bromo-6-{4-[4-(4-fluoro-3-trifluoromethyl-phenyl)-1- methyl-1H-imidazol-2-yl]-piperidin-1-yl}-pyrimidin-4-ylamine using 4-[4-(4-fluorophenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=470, obsd.=470).

5-Chloro-6{4-(3,4-difluoromethylphenyl)-1-2-pyrrolidin-1-yl-ethyl)-1H-imidazol-2-yl]-piperidin-1-yl}-pyrimidin-4-ylamine ("238")

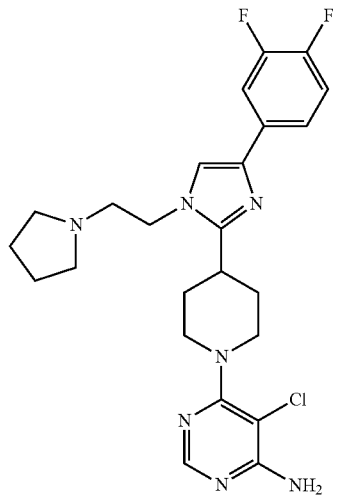 [SMILES: Nc1ncnc(N2CCC(c3nc(-c4ccc(F)c(F)c4)cn3CCN3CCCC3)CC2)c1Cl]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(3,4-difluorophenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=488, obsd.=488).

5-Vinyl-6{4-(3-fluoro-4-trifluoromethylphenyl)-1-2-pyrrolidin-1-yl-ethyl)-1H-imidazol-2-yl]-piperidin-1-yl}-pyrimidin-4-ylamine ("239")

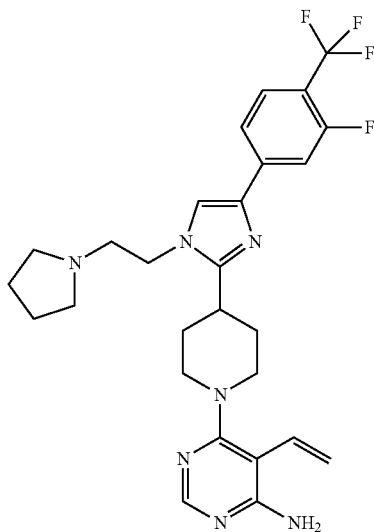 [SMILES: C=Cc1c(N)ncnc1N1CCC(c2nc(-c3ccc(C(F)(F)F)c(F)c3)cn2CCN2CCCC2)CC1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(3-fluoro-4-trifluoromethyl-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=530, obsd.=530).

5-Vinyl-6{4-(3-fluorophenyl)-1-2-pyrrolidin-1-yl-ethyl)-1H-imidazol-2-yl]-piperidin-1-yl}-pyrimidin-4-ylamine ("240")

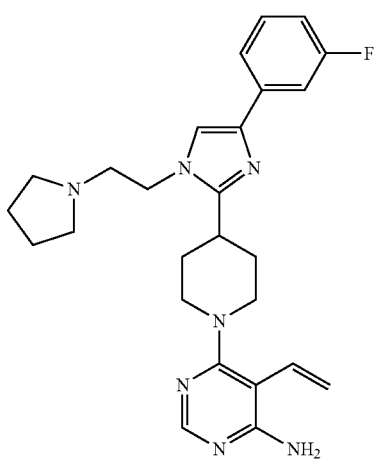 [SMILES: C=Cc1c(N)ncnc1N1CCC(c2nc(-c3cccc(F)c3)cn2CCN2CCCC2)CC1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(3-fluorophenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=462, obsd.=462).

5-Vinyl-6{4-(4-fluorophenyl)-1-2-pyrrolidin-1-yl-ethyl)-1H-imidazol-2-yl]-piperidin-1-yl}-pyrimidin-4-ylamine ("241")

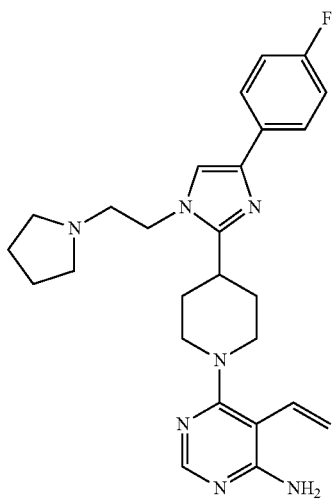 [SMILES: C=Cc1c(N)ncnc1N1CCC(c2nc(-c3ccc(F)cc3)cn2CCN2CCCC2)CC1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4- ylamine using 4-[4-(4-fluorophenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=462, obsd.=462).

5-Vinyl-6{4-(3,4-difluorophenyl)-1-2-pyrrolidin-1-yl-ethyl)-1H-imidazol-2-yl]-piperidin-1-yl}-pyrimidin-4-ylamine ("242")

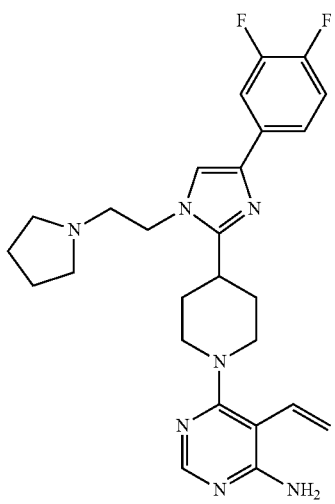 [SMILES: C=Cc1c(N)ncnc1N1CCC(c2nc(-c3ccc(F)c(F)c3)cn2CCN2CCCC2)CC1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(3,4-difluorophenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=480, obsd.=480).

6{4-(3,4-difluorophenyl)-1-2-pyrrolidin-1-yl-ethyl)-1H-imidazol-2-yl]-piperidin-1-yl}-pyrimidin-4-ylamine ("243")

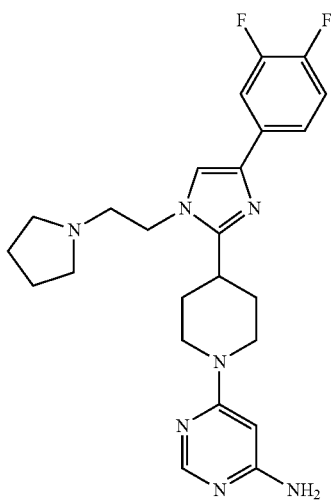 [SMILES: Nc1cc(N2CCC(c3nc(-c4ccc(F)c(F)c4)cn3CCN3CCCC3)CC2)ncn1]

The title compound was prepared in an analogous manner as 5-Bromo-6-{4-[4-(4-fluoro-3-trifluoromethyl-phenyl)-1- methyl-1H-imidazol-2-yl]-piperidin-1-yl}-pyrimidin-4-ylamine using 4-[4-(3,4-difluorophenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=454, obsd.=454).

6{4-(3-fluorophenyl)-1-2-pyrrolidin-1-yl-ethyl)-1H-imidazol-2-yl]-piperidin-1-yl}-pyrimidin-4-ylamine ("244")

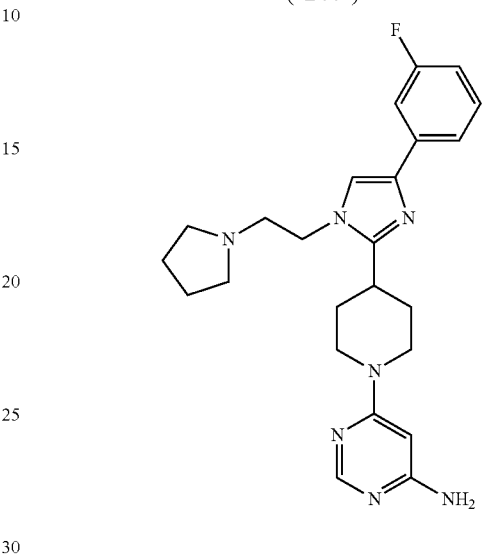

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(3-fluorophenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=436, obsd.=436).

5-Ethyl-6{4-(3-fluoro-4-trifluoromethylphenyl)-1-2-((S)-3-fluoro-pyrrolidin-1-yl)-ethyl)-1H-imidazol-2-yl]-piperidin-1-yl}-pyrimidin-4-ylamine ("245")

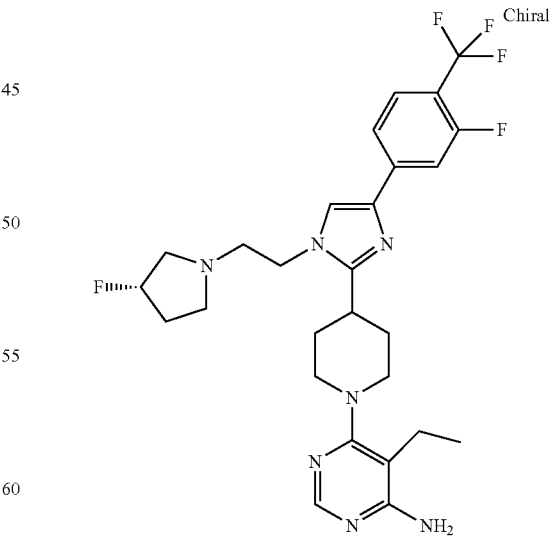

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-trifluoromethyl-phenyl)-1-

(2-((S)-3-fluoro-pyrrolidin-1-yl)-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=550, obsd.=550).

5-Ethyl-6{4-(3-fluoro-4-trifluoromethyl phenyl)-1-2-((R)-3-fluoro-pyrrolidin-1-yl)-ethyl)-1H-imidazol-2-yl]-piperidin-1-yl}-pyrimidin-4-ylamine ("246")

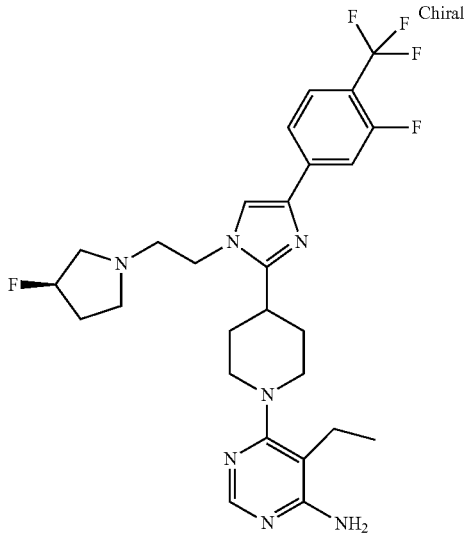 [SMILES: CCc1c(N)ncnc1N1CCC(c2nc(-c3ccc(C(F)(F)F)c(F)c3)cn2CCN2CC[C@@H](F)C2)CC1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-trifluoromethyl-phenyl)-1-(2-((S)-3-fluoropyrrolidin-1-yl)-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=550, obsd.=550).

5-Ethyl-6{4-(3-fluoro-4-trifluoromethylphenyl)-1-2-(4,4-difluoro-piperidin-1-yl)-ethyl)-1H-imidazol-2-yl]-piperidin-1-yl}-pyrimidin-4-ylamine ("247")

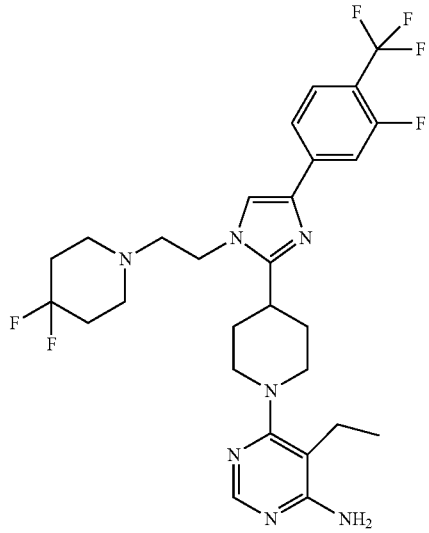 [SMILES: CCc1c(N)ncnc1N1CCC(c2nc(-c3ccc(C(F)(F)F)c(F)c3)cn2CCN2CCC(F)(F)CC2)CC1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-trifluoromethyl-phenyl)-1-(2-(4,4-difluoropiperidin-1-yl)-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=582, obsd.=582).

5-Ethyl-6{4-(3-fluoro-4-trifluoromethylphenyl)-1-2-(3,3-difluoro-piperidin-1-yl)-ethyl)-1H-imidazol-2-yl]-piperidin-1-yl}-pyrimidin-4-ylamine ("248")

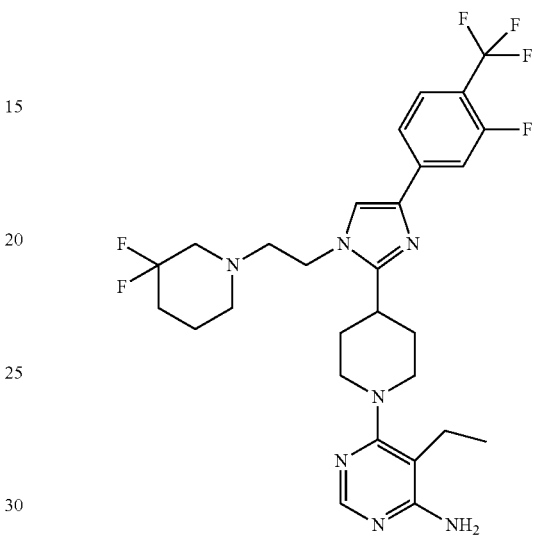

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-trifluoromethyl-phenyl)-1-(2-(3,3-difluoro-piperidin-1-yl)-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=582, obsd.=582).

5-Ethyl-6{4-(3-fluoro-4-trifluoromethylphenyl)-1-2-(4-fluoro-piperidin-1-yl)-ethyl)-1H-imidazol-2-yl]-piperidin-1-yl}-pyrimidin-4-ylamine ("249")

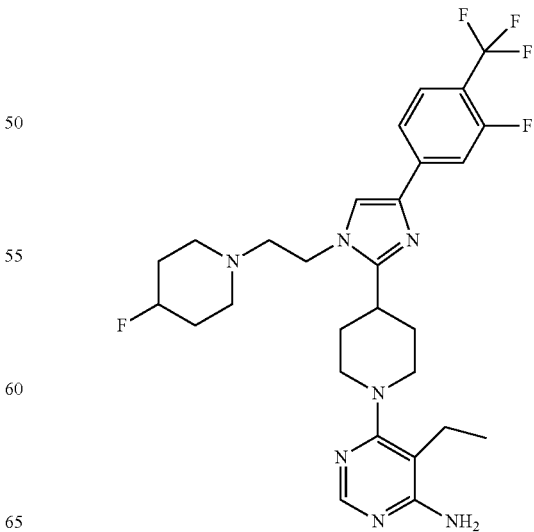

The title compound was prepared in an analogous manner 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-trifluoromethyl-phenyl)-1-(2-(4-fluoro-piperidin-1-yl)-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=564, obsd.=564).

5-Ethyl-6{4-(3-fluoro-4-trifluoromethylphenyl)-1-2-(3-fluoro-piperidin-1-yl)-ethyl]-1H-imidazol-2-yl]-piperidin-1-yl}-pyrimidin-4-ylamine ("250")

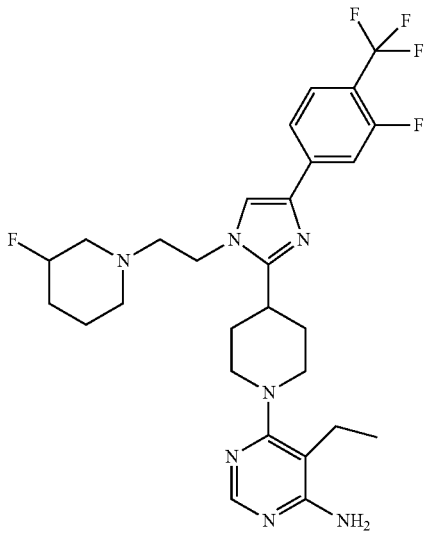 [SMILES: CCc1c(N)ncnc1N1CCC(c2nc(-c3ccc(C(F)(F)F)c(F)c3)cn2CCN2CCCC(F)C2)CC1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(3-fluoro-3-trifluoromethyl-phenyl)-1-(2-(3-fluoro-piperidin-1-yl)-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=564, obsd.=564).

5-Ethyl-6{4-(3-fluoro-4-chlorophenyl)-1-2-(pyrrolidin-1-yl-ethyl)-1H-imidazol-2-yl]-piperidin-1-yl}-pyrimidin-4-ylamine ("251")

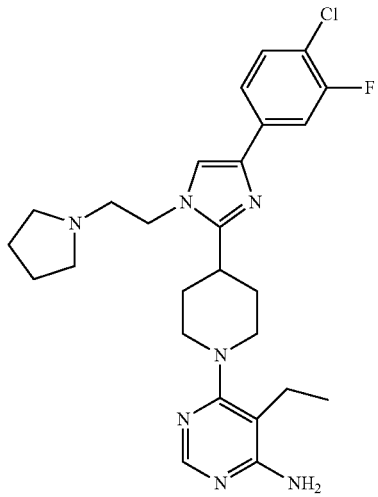 [SMILES: CCc1c(N)ncnc1N1CCC(c2nc(-c3ccc(Cl)c(F)c3)cn2CCN2CCCC2)CC1]

The title compound was prepared in an analogous manner 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-chloro-3-fluoro-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=498, obsd.=498).

5-Ethyl-6{4-(4-fluoro-3-chlorophenyl)-1-2-(pyrrolidin-1-yl-ethyl)-1H-imidazol-2-yl]-piperidin-1-yl}-pyrimidin-4-ylamine ("252")

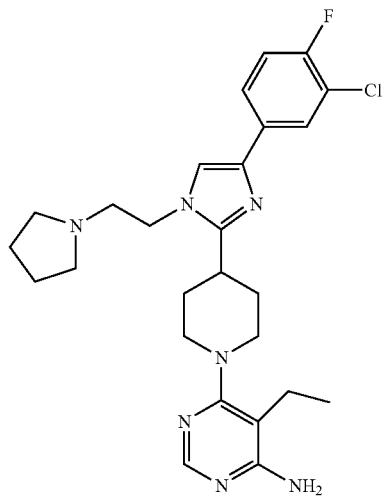 [SMILES: CCc1c(N)ncnc1N1CCC(c2nc(-c3ccc(F)c(Cl)c3)cn2CCN2CCCC2)CC1]

The title compound was prepared in an analogous manner 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(3-chloro-4-fluoro-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=498, obsd.=498).

5-cyclobutyl-6{4-(3-fluoro-4-trifluoromethylphenyl)-1-2-(piperidin-1-yl-ethyl)-1H-imidazol-2-yl]-piperidin-1-yl}-pyrimidin-4-ylamine ("253")

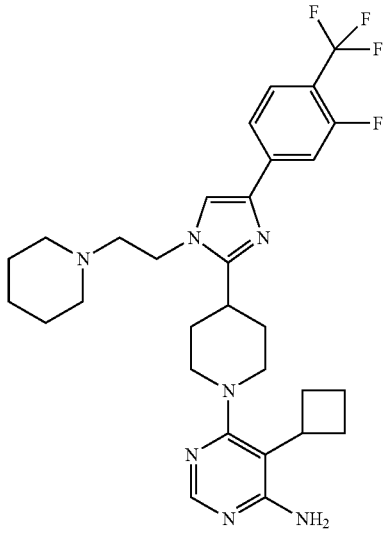 [SMILES: Nc1ncnc(N2CCC(c3nc(-c4ccc(C(F)(F)F)c(F)c4)cn3CCN3CCCCC3)CC2)c1C1CCC1]

The title compound was prepared in an analogous manner as 5-Bromo-6-{4-[4-(4-fluoro-3-trifluoromethyl-phenyl)-1- methyl-1H-imidazol-2-yl]-piperidin-1-yl}-pyrimidin-4-ylamine using 4-[4-(3-fluoro-3-trifluoromethyl-phenyl)-1-(2-(piperidin-1-yl)-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=572, obsd.=572).

5-cyclobutyl-6{4-(3-fluoro-4-trifluoromethylphenyl)-1-2-(pyrrolidin-1-yl-ethyl)-1H-imidazol-2-yl]-piperidin-1-yl}-pyrimidin-4-ylamine ("254")

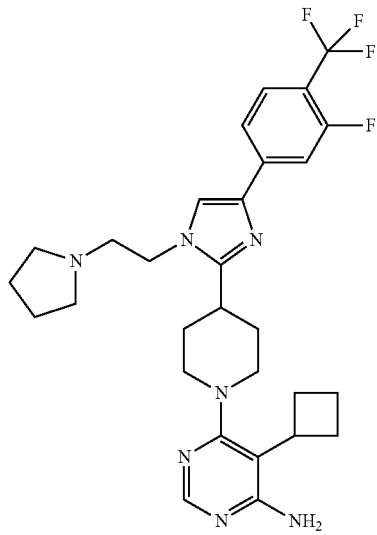

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-trifluoromethyl-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=558, obsd.=558).

5-cyclobutyl-6{4-(3,4-difluorophenyl)-1-2-(pyrrolidin-1-yl-ethyl)-1H-imidazol-2-yl]-piperidin-1-yl}-pyrimidin-4-ylamine ("255")

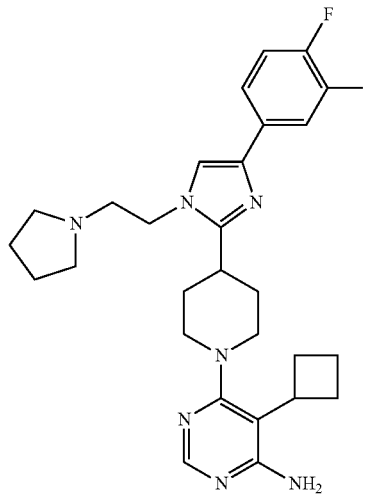

The title compound was prepared in an analogous manner as 5-Bromo-6-{4-[4-(4-fluoro-3-trifluoromethyl-phenyl)-1- methyl-1H-imidazol-2-yl]-piperidin-1-yl}-pyrimidin-4-ylamine using 4-[4-(3,4-difluoro-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=508, obsd.=508).

5-cyclobutyl-6{4-(4-fluorophenyl)-1-2-(pyrrolidin-1-yl-ethyl)-1H-imidazol-2-yl]-piperidin-1-yl}-pyrimidin-4-ylamine ("256")

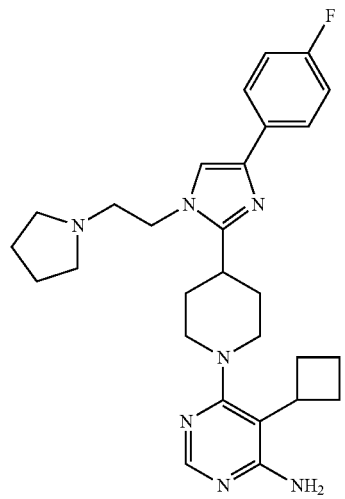

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=490, obsd.=490).

5-cyclobutyl-6{4-(3-fluorophenyl)-1-2-(pyrrolidin-1-yl-ethyl)-1H-imidazol-2-yl]-piperidin-1-yl}-pyrimidin-4-ylamine ("257")

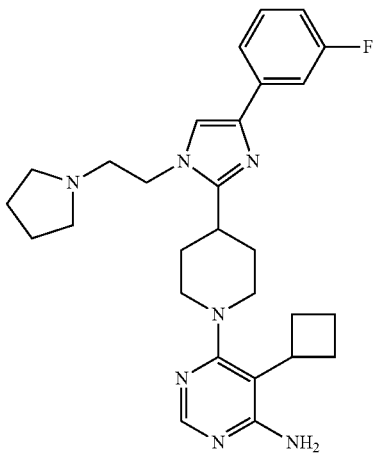 [SMILES: Nc1ncnc(N2CCC(c3nc(-c4cccc(F)c4)cn3CCN3CCCC3)CC2)c1C1CCC1]

The title compound was prepared in an analogous manner 5-Bromo-6-{4-[4-(4-fluoro-3-trifluoromethyl-phenyl)-1- methyl-1H-imidazol-2-yl]-piperidin-1-yl}-pyrimidin-4-ylamine using 4-[4-(3-fluoro-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=490, obsd.=490).

5-cyclobutyl-6{4-(3-fluoro-4-trifluoromethyl-phenyl)-1-2-(pyrrolidin-1-yl-ethyl)-1H-imidazol-2-yl]-piperidin-1-yl}-pyrimidin-4-ylamine ("258")

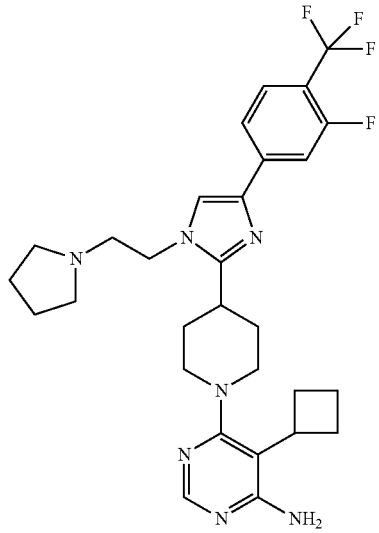 [SMILES: Nc1ncnc(N2CCC(c3nc(-c4ccc(C(F)(F)F)c(F)c4)cn3CCN3CCCC3)CC2)c1C1CCC1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(3-fluoro-4-trifluoromethyl-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=558, obsd.=558).

5-cyclobutyl-6{4-(4-trifluoromethyl-phenyl)-1-2-(pyrrolidin-1-yl-ethyl)-1H-imidazol-2-yl]-piperidin-1-yl}-pyrimidin-4-ylamine ("259")

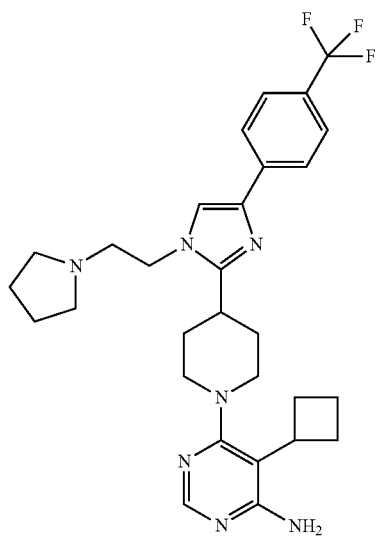 [SMILES: Nc1ncnc(N2CCC(c3nc(-c4ccc(C(F)(F)F)cc4)cn3CCN3CCCC3)CC2)c1C1CCC1]

The title compound was prepared in an analogous manner as 5-Bromo-6-{4-[4-(4-fluoro-3-trifluoromethyl-phenyl)-1- methyl-1H-imidazol-2-yl]-piperidin-1-yl}-pyrimidin-4-ylamine using 4-[4-(4-trifluoromethyl-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=540, obsd.=540).

5-cyclobutyl-6{4-(4-chloro-3-fluoro-phenyl)-1-2-(pyrrolidin-1-yl-ethyl)-1H-imidazol-2-yl]-piperidin-1-yl}-pyrimidin-4-ylamine ("260")

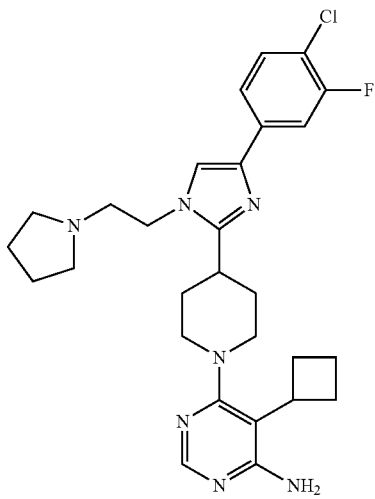 [SMILES: Nc1ncnc(N2CCC(c3nc(-c4ccc(Cl)c(F)c4)cn3CCN3CCCC3)CC2)c1C1CCC1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-chloro-3-fluoro-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=525, obsd.=525).

5-cyclobutyl-6{4-(3-trifluoromethyl-phenyl)-1-2-(pyrrolidin-1-yl-ethyl)-1H-imidazol-2-yl]-piperidin-1-yl}-pyrimidin-4-ylamine ("261")

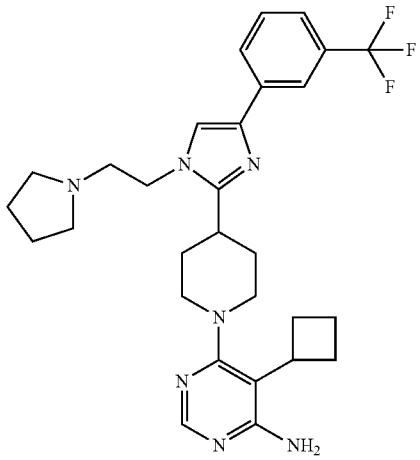 [SMILES: Nc1ncnc(N2CCC(c3nc(-c4cccc(C(F)(F)F)c4)cn3CCN3CCCC3)CC2)c1C1CCC1]

The title compound was prepared in an analogous manner as 5-Bromo-6-{4-[4-(4-fluoro-3-trifluoromethyl-phenyl)-1- methyl-1H-imidazol-2-yl]-piperidin-1-yl}-pyrimidin-4-ylamine using 4-[4-(3-trifluoromethyl-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=540, obsd.=540).

5-cyclobutyl-6{4-(3-chloro-4-fluoro-phenyl)-1-2-(pyrrolidin-1-yl-ethyl)-1H-imidazol-2-yl]-piperidin-1-yl}-pyrimidin-4-ylamine ("262")

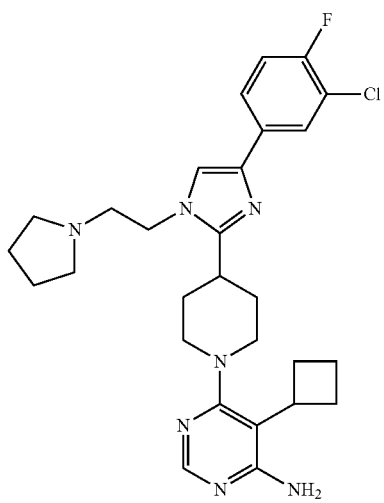 [SMILES: Nc1ncnc(N2CCC(c3nc(-c4ccc(F)c(Cl)c4)cn3CCN3CCCC3)CC2)c1C1CCC1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(3-chloro-4-fluoro-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=525, obsd.=525).

5-cyclobutyl-6{4-(4-chloro-phenyl)-1-2-(pyrrolidin-1-yl-ethyl)-1H-imidazol-2-yl]-piperidin-1-yl}-pyrimidin-4-ylamine ("263")

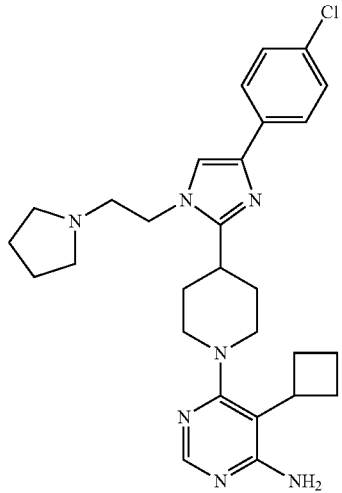 [SMILES: Nc1ncnc(N2CCC(c3nc(-c4ccc(Cl)cc4)cn3CCN3CCCC3)CC2)c1C1CCC1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-chloro-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=507, obsd.=507).

5-cyclobutyl-6{4-(3-chloro-phenyl)-1-2-(pyrrolidin-1-yl-ethyl)-1H-imidazol-2-yl]-piperidin-1-yl}-pyrimidin-4-ylamine ("264")

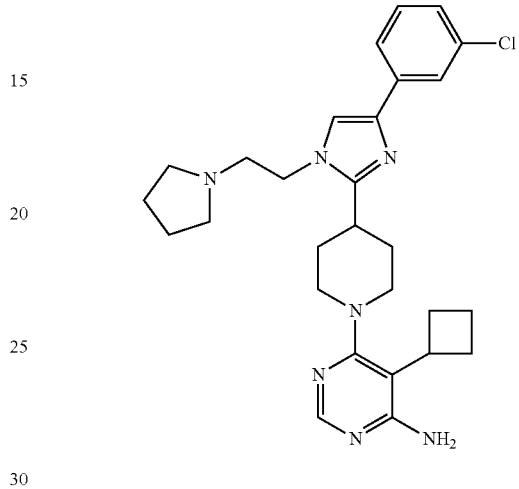

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(3-chloro-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=507, obsd.=507).

5-Bromo-6{4-(4-trifluoromethyl-phenyl)-1-2-pyrrolidin-1-yl-ethyl)-1H-imidazol-2-yl]-piperidin-1-yl}-pyrimidin-4-ylamine ("265")

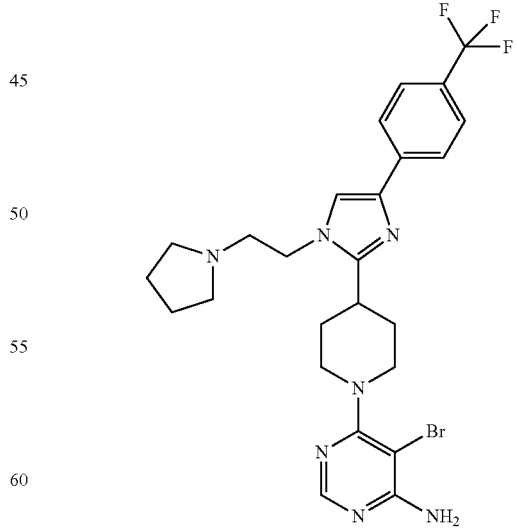

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-trifluoromethyl-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=565, obsd.=565).

5-Bromo-6{4-(4-chloro-3-fluorophenyl)-1-2-pyrrolidin-1-yl-ethyl)-1H-imidazol-2-yl]-piperidin-1-yl}-pyrimidin-4-ylamine ("266")

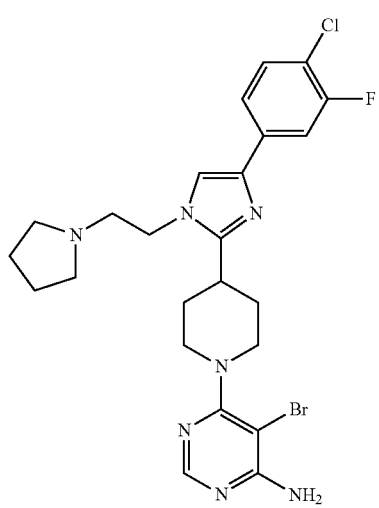

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-chloro-3-fluoro-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=549, obsd.=549).

5-Bromo-6{4-(3-trifluoromethyl-phenyl)-1-2-pyrrolidin-1-yl-ethyl)-1H-imidazol-2-yl]-piperidin-1-yl}-pyrimidin-4-ylamine ("267")

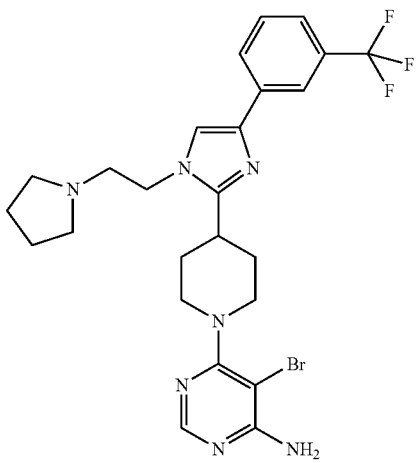 [SMILES: Nc1ncnc(N2CCC(c3nc(-c4cccc(C(F)(F)F)c4)cn3CCN3CCCC3)CC2)c1Br]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(3-trifluoromethyl-phenyl)-1-(2-pyrrolidindin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=565, obsd.=565).

5-Bromo-6{4-(3-chloro-4-fluorophenyl)-1-2-pyrrolidin-1-yl-ethyl)-1H-imidazol-2-yl]-piperidin-1-yl}-pyrimidin-4-ylamine ("268")

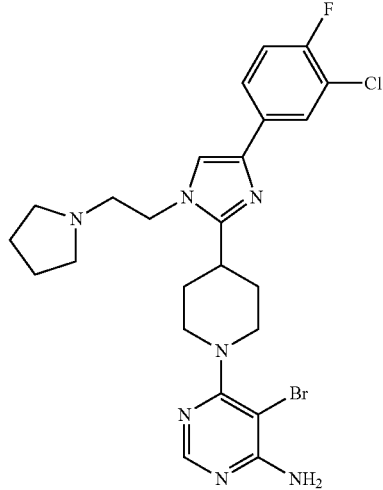 [SMILES: Nc1ncnc(N2CCC(c3nc(-c4ccc(F)c(Cl)c4)cn3CCN3CCCC3)CC2)c1Br]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(3-chloro-4-fluoro-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=549, obsd.=549).

5-vinyl-6{4-(4-trifluoromethyl-phenyl)-1-2-(pyrrolidin-1-yl-ethyl)-1H-imidazol-2-yl]-piperidin-1-yl}-pyrimidin-4-ylamine ("269")

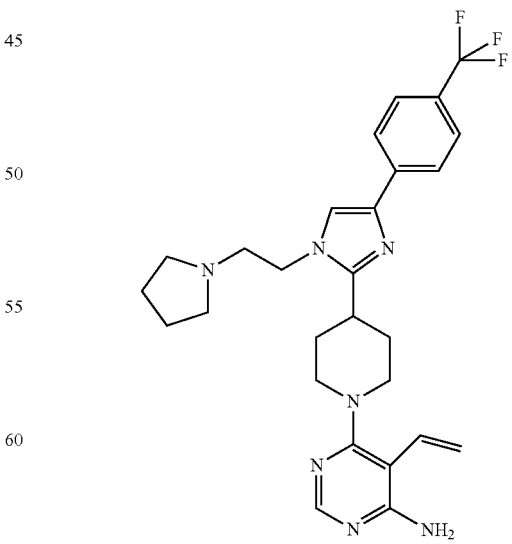

The title compound was prepared in an analogous manner as 5-Bromo-6-{4-[4-(4-fluoro-3-trifluoromethyl-phenyl)-1- methyl-1H-imidazol-2-yl]-piperidin-1-yl}-pyrimidin-4-ylamine using 4-[4-(4-trifluoromethyl-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=512, obsd.=512).

6{4-(4-trifluoromethyl-phenyl)-1-2-(pyrrolidin-1-yl-ethyl)-1H-imidazol-2-yl]-piperidin-1-yl}-pyrimidin-4-ylamine ("270")

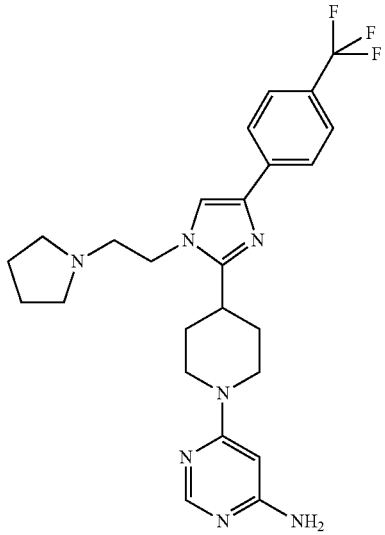 [SMILES: Nc1cc(N2CCC(c3nc(-c4ccc(C(F)(F)F)cc4)cn3CCN3CCCC3)CC2)ncn1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-trifluoromethyl-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=486, obsd.=486).

5-Ethyl-6{4-(4-trifluoromethyl-phenyl)-1-2-(pyrrolidin-1-yl-ethyl)-1H-imidazol-2-yl]-piperidin-1-yl}-pyrimidin-4-ylamine ("271")

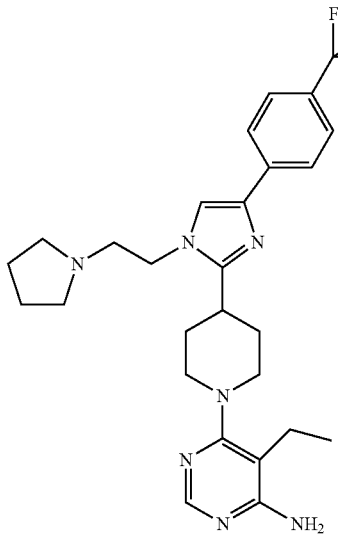

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-trifluoromethyl-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=514, obsd.=514).

5-Ethyl-6{4-(3-trifluoromethyl-phenyl)-1-2-(pyrrolidin-1-yl-ethyl)-1H-imidazol-2-yl]-piperidin-1-yl}-pyrimidin-4-ylamine ("272")

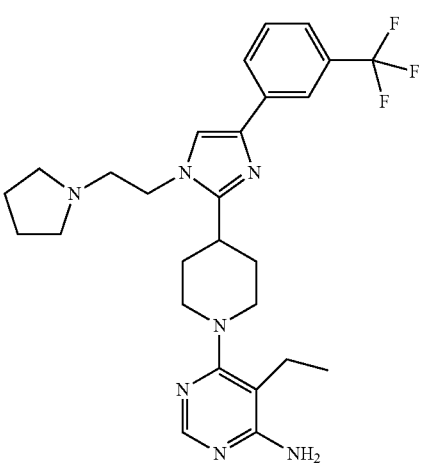 [SMILES: CCc1c(N)ncnc1N1CCC(c2nc(-c3cccc(C(F)(F)F)c3)cn2CCN2CCCC2)CC1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(3-trifluoromethyl-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=514, obsd.=514).

5-Ethyl-6{4-(4-chloro-phenyl)-1-2-(pyrrolidin-1-yl-ethyl)-1H-imidazol-2-yl]-piperidin-1-yl}-pyrimidin-4-ylamine ("273")

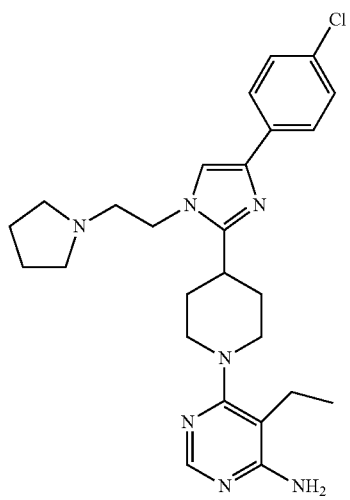 [SMILES: CCc1c(N)ncnc1N1CCC(c2nc(-c3ccc(Cl)cc3)cn2CCN2CCCC2)CC1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4- ylamine using 4-[4-(4-chloro-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=481, obsd.=481).

5-Ethyl-6{4-(3-chloro-phenyl)-1-2-(pyrrolidin-1-yl-ethyl)-1H-imidazol-2-yl]-piperidin-1-yl}-pyrimidin-4-ylamine ("274")

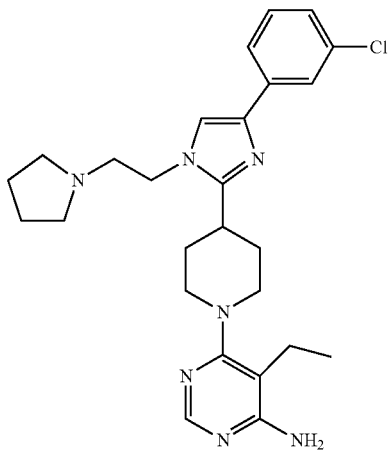 [SMILES: CCc1c(N)ncnc1N1CCC(c2nc(-c3cccc(Cl)c3)cn2CCN2CCCC2)CC1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(3-chloro-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=481, obsd.=481).

5-Ethyl-6{4-(4-fluoro-3-trifluoromethyl-phenyl)-1-2-((3,3-difluoro-pyrrolidin-1-yl)-ethyl)-1H-imidazol-2-yl]-piperidin-1-yl}-pyrimidin-4-ylamine ("275")

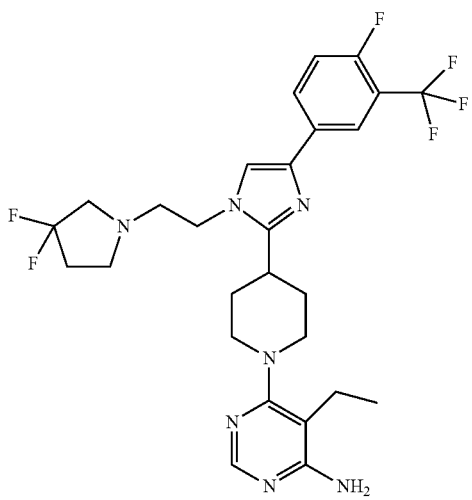 [SMILES: CCc1c(N)ncnc1N1CCC(c2nc(-c3ccc(F)c(C(F)(F)F)c3)cn2CCN2CCC(F)(F)C2)CC1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-trifluoromethyl-phenyl)-1-(2-(3,3-difluoro-pyrrolidin-1-yl)-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=568, obsd.=568).

5-Ethyl-6{4-(4-fluoro-3-trifluoromethyl-phenyl)-1-2-((piperidin-1-yl)-ethyl)-1H-imidazol-2-yl]-piperidin-1-yl}-pyrimidin-4-ylamine ("276")

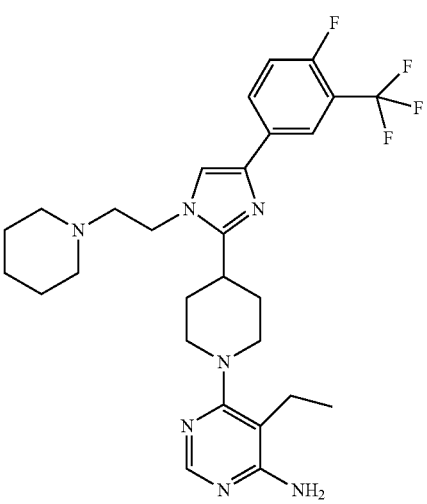 [SMILES: CCc1c(N)ncnc1N1CCC(c2nc(-c3ccc(F)c(C(F)(F)F)c3)cn2CCN2CCCCC2)CC1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-trifluoromethyl-phenyl)-1-(2-(piperidin-1-yl)-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=546, obsd.=546).

5-Ethyl-6{4-(3-trifluoromethyl-phenyl)-1-2-(azetidin-1-yl-ethyl)-1H-imidazol-2-yl]-piperidin-1-yl}-pyrimidin-4-ylamine ("277")

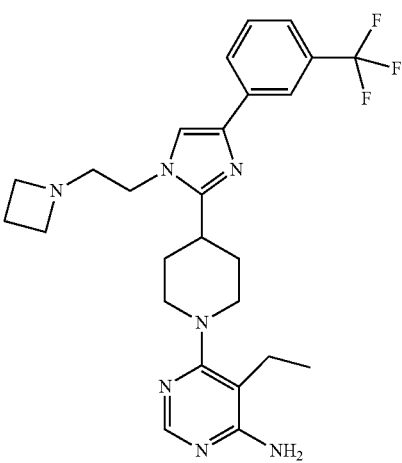 [SMILES: CCc1c(N)ncnc1N1CCC(c2nc(-c3cccc(C(F)(F)F)c3)cn2CCN2CCC2)CC1]

The title compound was prepared in an analogous manner as 5-Bromo-6-{4-[4-(4-fluoro-3-trifluoromethyl-phenyl)-1- methyl-1H-imidazol-2-yl]-piperidin-1-yl}-pyrimidin-4-ylamine using 4-[4-(3-trifluoromethyl-phenyl)-1-(2-azetidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=500, obsd.=500).

5-Ethyl-6{4-(3-fluoro-phenyl)-1-2-(azetidin-1-yl-ethyl)-1H-imidazol-2-yl]-piperidin-1-yl}-pyrimidin-4-ylamine ("278")

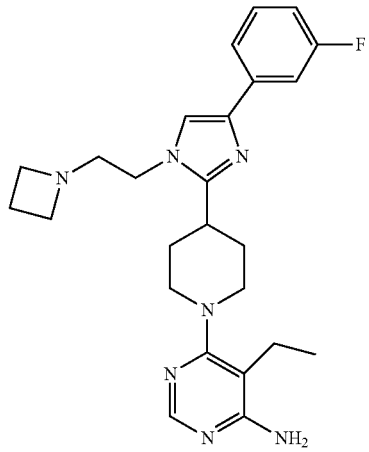 [SMILES: CCc1c(N)ncnc1N1CCC(c2nc(-c3cccc(F)c3)cn2CCN2CCC2)CC1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(3-fluoro-phenyl)-1-(2-azetidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=450, obsd.=450).

5-Ethyl-6{4-(3-chloro-phenyl)-1-2-(azetidin-1-yl-ethyl)-1H-imidazol-2-yl]-piperidin-1-yl}-pyrimidin-4-ylamine ("279")

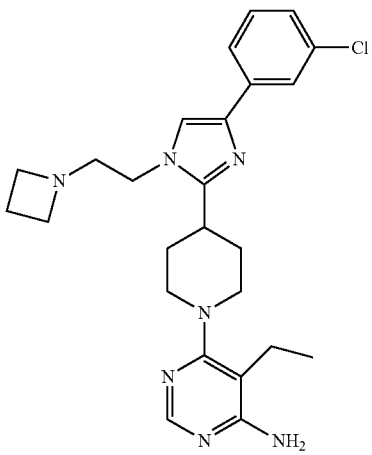 [SMILES: CCc1c(N)ncnc1N1CCC(c2nc(-c3cccc(Cl)c3)cn2CCN2CCC2)CC1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(3-chloro-phenyl)-1-(2-azetidin-1-ylethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=467, obsd.=467).

5-cyclobutyl-6{4-(3-fluoro-4-trifluoromethylphenyl)-1-2-(azetidin-1-yl-ethyl)-1H-imidazol-2-yl]-piperidin-1-yl}-pyrimidin-4-ylamine ("280")

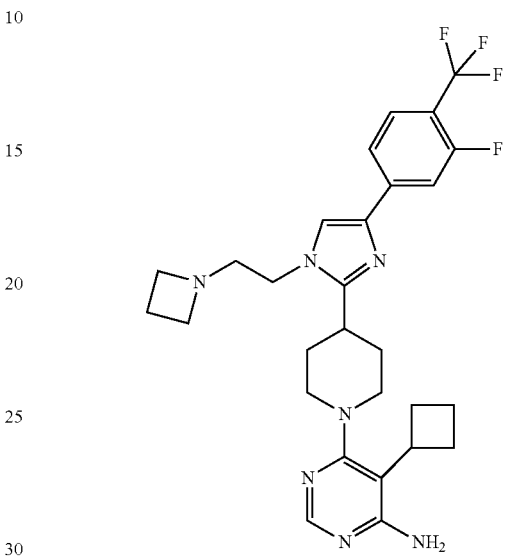

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-trifluoromethyl-phenyl)-1-(2-azetidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=544, obsd.=544).

5-Ethyl-6{4-(4-fluoro-3-chlorophenyl)-1-2-(azetidin-1-yl-ethyl)-1H-imidazol-2-yl]-piperidin-1-yl}-pyrimidin-4-ylamine ("281")

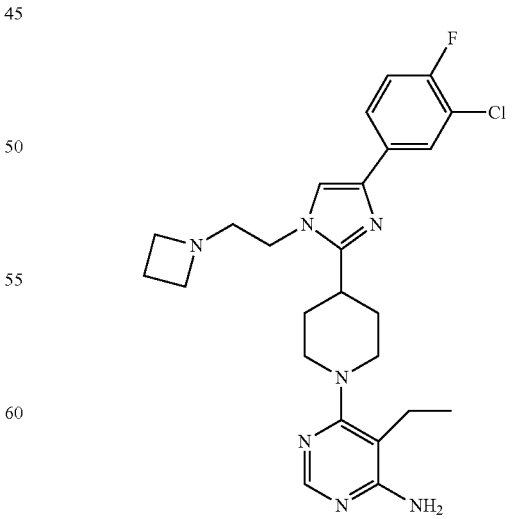

The title compound was prepared in an analogous manner as 5-Bromo-6-{4-[4-(4-fluoro-3-trifluoromethyl-phenyl)-1- methyl-1H-imidazol-2-yl]-piperidin-1-yl}-pyrimidin-4-ylamine using 4-[4-(4-fluoro-3-chloro-phenyl)-1-(2-azetidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=584, obsd.=584).

5-Ethyl-6{4-(3,4-difluorophenyl)-1-2-(azetidin-1-yl-ethyl)-1H-imidazol-2-yl]-piperidin-1-yl}-pyrimidin-4-ylamine ("282")

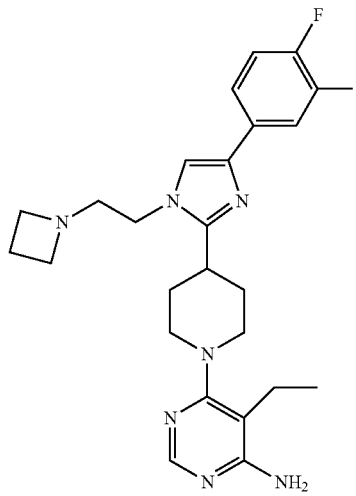

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(3,4-difluoro-phenyl)-1-(2-azetidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=568, obsd.=568).

5-Nitro-6{4-(4-fluoro-3-trifluomethyl-phenyl)-1-2-(azetidin-1-yl-ethyl)-1H-imidazol-2-yl]-piperidin-1-yl}-pyrimidin-4-ylamine ("283")

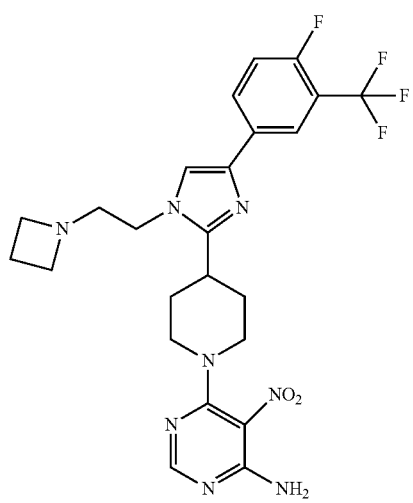 [SMILES: Nc1ncnc(N2CCC(c3nc(-c4ccc(F)c(C(F)(F)F)c4)cn3CCN3CCC3)CC2)c1[N+](=O)[O-]]

The title compound was prepared in an analogous manner as 5-Bromo-6-{4-[4-(4-fluoro-3-trifluoromethyl-phenyl)-1- methyl-1H-imidazol-2-yl]-piperidin-1-yl}-pyrimidin-4-ylamine using 4-[4-(4-fluoro-3-trifluoromethyl-phenyl)-1-(2-azetidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=535, obsd.=535).

5-Amino-6{4-(4-fluoro-3-trifluomethyl-phenyl)-1-2-(azetidin-1-yl-ethyl)-1H-imidazol-2-yl]-piperidin-1-yl}-pyrimidin-4-ylamine ("284")

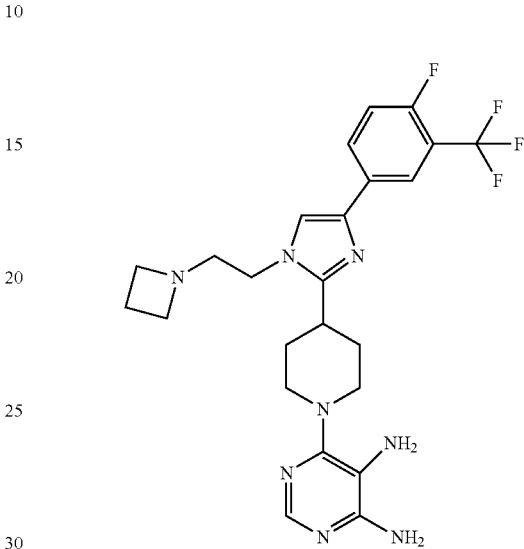

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-trifluoromethyl-phenyl)-1-(2-azetidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=505, obsd.=505).

5-Formyl-6{4-(4-fluoro-3-trifluomethyl-phenyl)-1-2-(azetidin-1-yl-ethyl)-1H-imidazol-2-yl]-piperidin-1-yl}-pyrimidin-4-ylamine ("285")

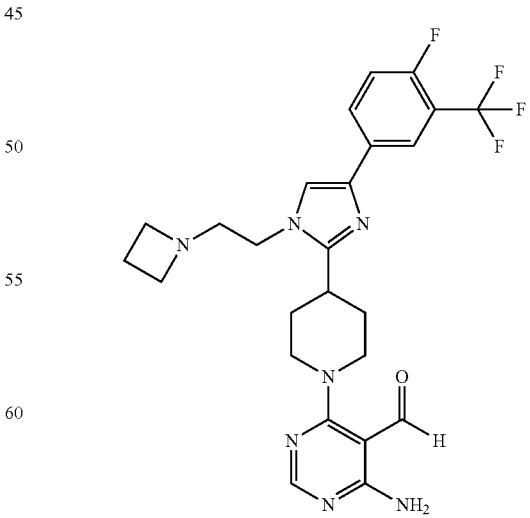

The title compound was prepared in an analogous manner as 5-Bromo-6-{4-[4-(4-fluoro-3-trifluoromethyl-phenyl)-1- methyl-1H-imidazol-2-yl]-piperidin-1-yl}-pyrimidin-4-ylamine using 4-[4-(4-fluoro-3-trifluoromethyl-phenyl)-1-(2-azetidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=518, obsd.=518).

6{4-(4-fluoro-3-trifluomethyl-phenyl)-1-2-(pyrrolidin-1-yl-ethyl)-1H-imidazol-2-yl]-piperidin-1-yl}-pyrimidin-4-ylamine-5-carboxy acid ("286")

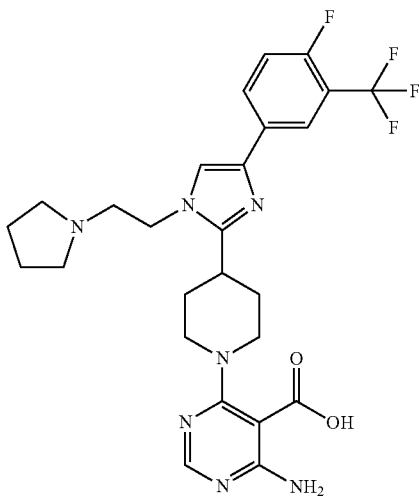 [SMILES: Nc1ncnc(N2CCC(c3nc(-c4ccc(F)c(C(F)(F)F)c4)cn3CCN3CCCC3)CC2)c1C(=O)O]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-trifluoromethyl-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=548, obsd.=548).

5-Formyl-6{4-(4-fluoro-3-trifluomethyl-phenyl)-1-2-(pyrrolidin-1-yl-ethyl)-1H-imidazol-2-yl]-piperidin-1-yl}-pyrimidin-4-ylamine ("287")

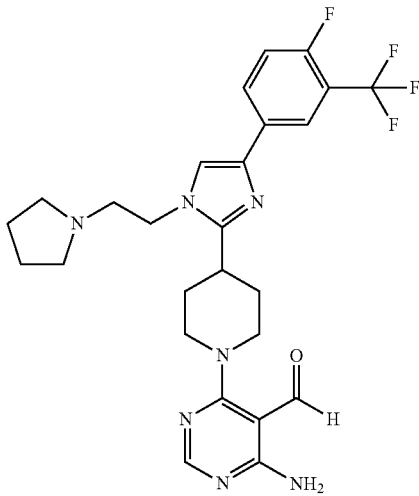 [SMILES: Nc1ncnc(N2CCC(c3nc(-c4ccc(F)c(C(F)(F)F)c4)cn3CCN3CCCC3)CC2)c1C=O]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-trifluoromethyl-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=532, obsd.=532).

5-Ethylamide-6{4-(4-fluoro-3-trifluomethyl-phenyl)-1-2-(azetidin-1-yl-ethyl)-1H-imidazol-2-yl]-piperidin-1-yl}-pyrimidin-4-ylamine ("288")

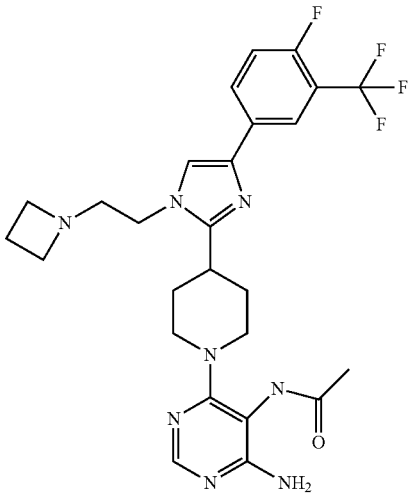 [SMILES: CC(=O)Nc1c(N)ncnc1N1CCC(c2nc(-c3ccc(F)c(C(F)(F)F)c3)cn2CCN2CCC2)CC1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-trifluoromethyl-phenyl)-1-(2-azetidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=547, obsd.=547).

5-Ethoxy-6{4-(3-chloro-4-fluorophenyl)-1-2-(pyrrolidin-1-yl-ethyl)-1H-imidazol-2-yl]-piperidin-1-yl}-pyrimidin-4-ylamine ("289")

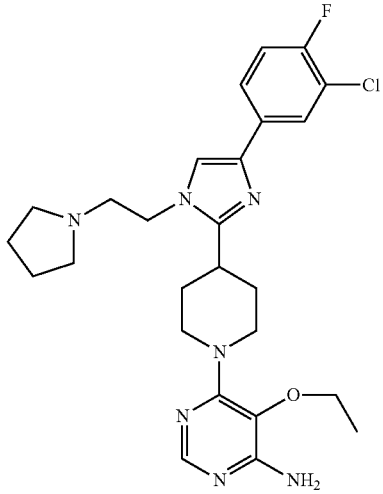 [SMILES: CCOc1c(N)ncnc1N1CCC(c2nc(-c3ccc(F)c(Cl)c3)cn2CCN2CCCC2)CC1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4- ylamine using 4-[4-(3-chloro-4-fluoro-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=515, obsd.=515).

5-isopropoxy-6{4-(3-chloro-4-fluorophenyl)-1-2-(pyrrolidin-1-yl-ethyl)-1H-imidazol-2-yl]-piperidin-1-yl}-pyrimidin-4-ylamine ("290")

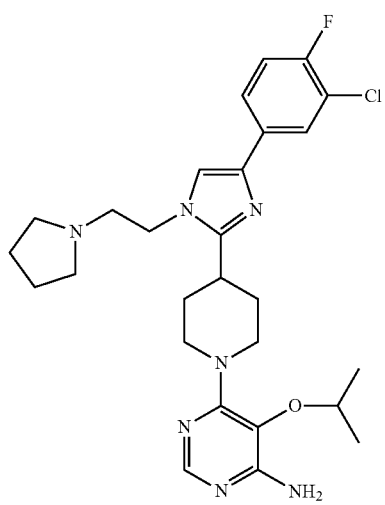 [SMILES: CC(C)Oc1c(N)ncnc1N1CCC(c2nc(-c3ccc(F)c(Cl)c3)cn2CCN2CCCC2)CC1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(3-chloro-4-fluoro-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=529, obsd.=529).

5-Ethoxy-6{4-(4-fluoro-3-trifluomethyl-phenyl)-1-2-(N,N-dimethylamino-1-yl-ethyl)-1H-imidazol-2-yl]-piperidin-1-yl}-pyrimidin-4-ylamine ("291")

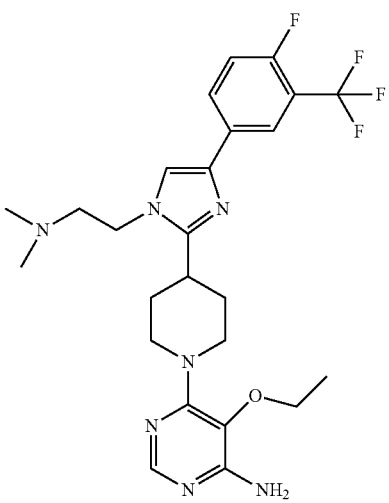 [SMILES: CCOc1c(N)ncnc1N1CCC(c2nc(-c3ccc(F)c(C(F)(F)F)c3)cn2CCN(C)C)CC1]

The title compound was prepared in an analogous manner as 5-Bromo-6-{4-[4-(4-fluoro-3-trifluoromethyl-phenyl)-1- methyl-1H-imidazol-2-yl]-piperidin-1-yl}-pyrimidin-4-ylamine using 4-[4-(4-fluoro-3-trifluoromethyl-phenyl)-1-(2-(N,N-dimethylamino)-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=522, obsd.=522).

5-isopropoxy-6{4-(4-fluoro-3-trifluomethyl-phenyl)-1-2-(N,N-dimethylamino-1-yl-ethyl)-1H-imidazol-2-yl]-piperidin-1-yl}-pyrimidin-4-ylamine ("292")

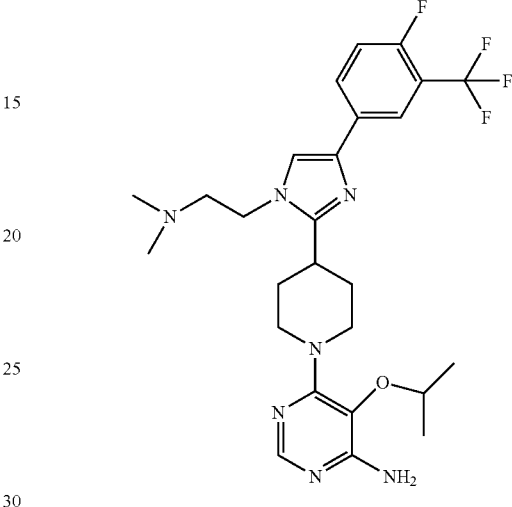

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-trifluoromethyl-phenyl)-1-(2-(N,N-dimethylamino)-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=536, obsd.=536).

5-Ethoxy-6{4-(4-fluoro-3-methyl-phenyl)-1-2-(N,N-dimethylamino-1-yl-ethyl)-1H-imidazol-2-yl]-piperidin-1-yl}-pyrimidin-4-ylamine ("293")

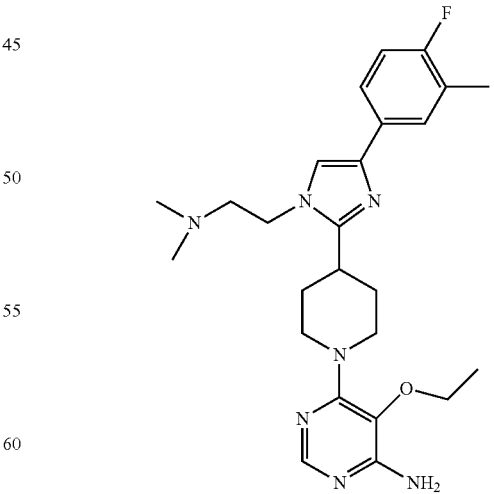

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-methyl-phenyl)-1-(2-(N,N- dimethylamino)-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=468, obsd.=468).

5-isopropoxy-6{4-(4-fluoro-3-methyl-phenyl)-1-2-(N,N-dimethylamino-1-yl-ethyl)-1H-imidazol-2-yl]-piperidin-1-yl}-pyrimidin-4-ylamine ("294")

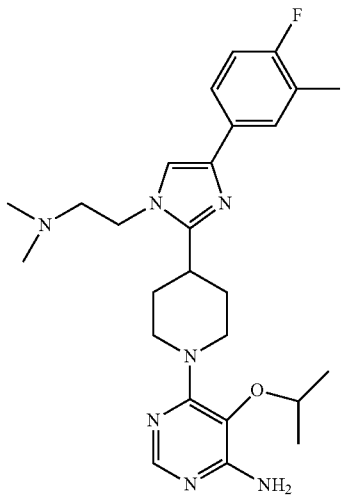

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-methyl-phenyl)-1-(2-(N,N-dimethylamino)-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=482, obsd.=482).

5-Ethyl-6{4-(4-fluoro-3-methyl-phenyl)-1-2-(N,N-dimethylamino-1-yl-ethyl)-1H-imidazol-2-yl]-piperidin-1-yl}-pyrimidin-4-ylamine ("295")

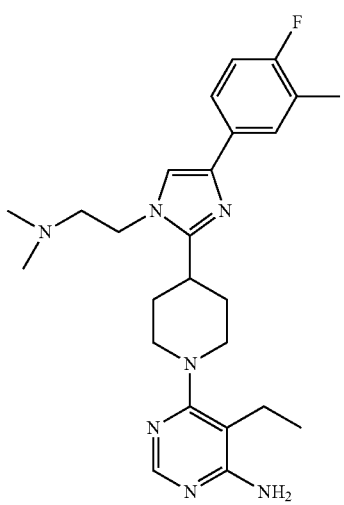

The title compound was prepared in an analogous manner as 5-Bromo-6-{4-[4-(4-fluoro-3-trifluoromethyl-phenyl)-1- methyl-1H-imidazol-2-yl]-piperidin-1-yl}-pyrimidin-4-ylamine using 4-[4-(4-fluoro-3-methyl-phenyl)-1-(2-(N,N-dimethylamino)-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=452, obsd.=452).

5-Ethyl-6{4-(4-fluoro-3-methyl-phenyl)-1-2-(N,N-diethylamino-1-yl-ethyl)-1H-imidazol-2-yl]-piperidin-1-yl}-pyrimidin-4-ylamine ("296")

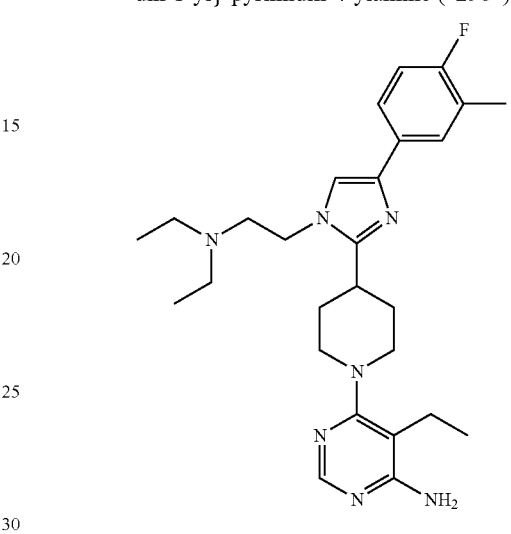

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-methyl-phenyl)-1-(2-(N,N-diethylamino)-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=480, obsd.=480).

5-Ethyl-6{4-(4-fluoro-3-methyl-phenyl)-1-2-(pyrrolidin-1-yl-ethyl)-1H-imidazol-2-yl]-piperidin-1-yl}-pyrimidin-4-ylamine ("297")

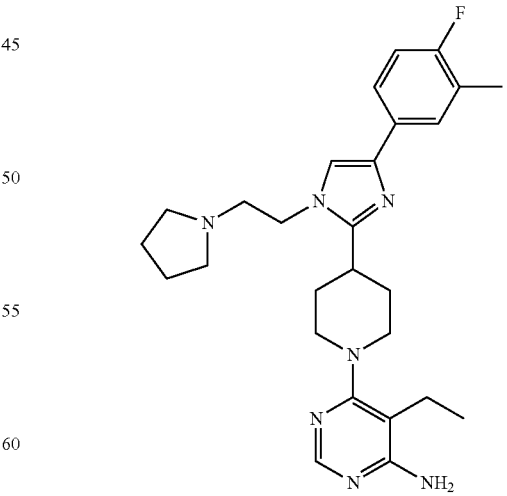

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-methyl-phenyl)-1-(2-(pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=478, obsd.=478).

5-Ethoxy-6{4-(4-fluoro-3-methyl-phenyl)-1-2-(pyrrolidin-1-yl-ethyl)-1H-imidazol-2-yl]-piperidin-1-yl}-pyrimidin-4-ylamine ("298")

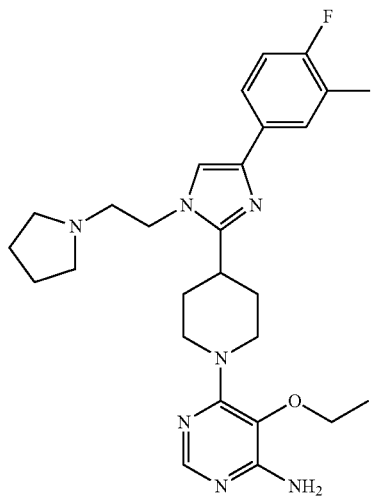 [SMILES: CCOc1c(N)ncnc1N1CCC(c2nc(-c3ccc(F)c(C)c3)cn2CCN2CCCC2)CC1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-methyl-phenyl)-1-(2-(pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=494, obsd.=494).

5-Isopropoxy-6{4-(4-fluoro-3-methyl-phenyl)-1-2-(pyrrolidin-1-yl-ethyl)-1H-imidazol-2-yl]-piperidin-1-yl}-pyrimidin-4-ylamine ("299")

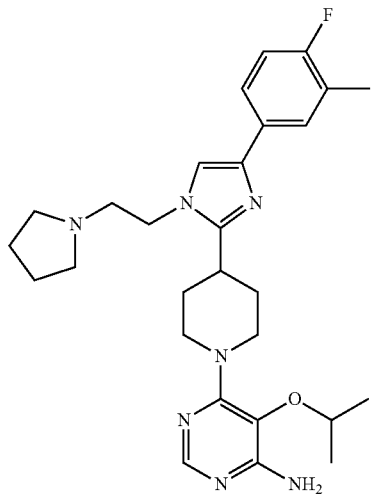 [SMILES: Cc1cc(-c2cn(CCN3CCCC3)c(C3CCN(c4ncnc(N)c4OC(C)C)CC3)n2)ccc1F]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4- ylamine using 4-[4-(4-fluoro-3-methyl-phenyl)-1-(2-(pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=508, obsd.=508).

5-Ethyl-6-{4-(4-fluoro-3-methyl-phenyl)-1-2-(N,N-isopropylethylamino-1-yl-ethyl)-1H-imidazol-2-yl]-piperidin-1-yl}-pyrimidin-4-ylamine ("300")

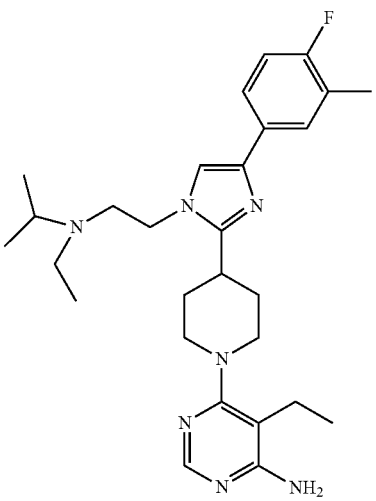 [SMILES: CCc1c(N)ncnc1N1CCC(c2nc(-c3ccc(F)c(C)c3)cn2CCN(CC)C(C)C)CC1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-methyl-phenyl)-1-(2-(N,N-isopropylethylamino)-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=494, obsd.=494).

5-Ethoxy-6{4-(4-fluoro-3-methyl-phenyl)-1-2-(N,N-isopropylethylamino-1-yl-ethyl)-1H-imidazol-2-yl]-piperidin-1-yl}-pyrimidin-4-ylamine ("301")

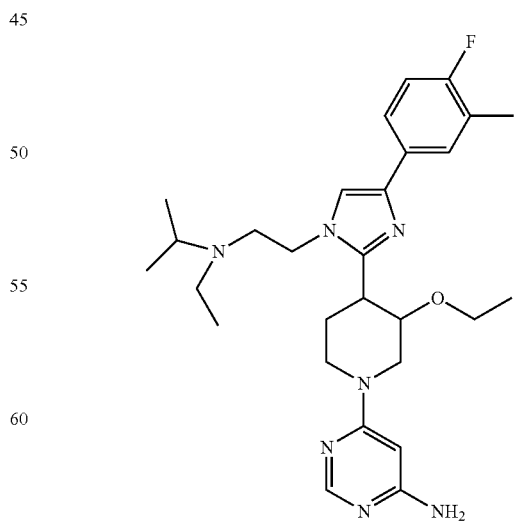

The title compound was prepared in an analogous manner as 5-Bromo-6-{4-[4-(4-fluoro-3-trifluoromethyl-phenyl)-1- methyl-1H-imidazol-2-yl]-piperidin-1-yl}-pyrimidin-4-ylamine using 4-[4-(4-fluoro-3-methyl-phenyl)-1-(2-(N,N-isopropylethylamino)-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=510, obsd.=510).

5-Isopropoxy-6{4-(4-fluoro-3-methyl-phenyl)-1-2-(N,N-isopropylethylamino-1-yl-ethyl)-1H-imidazol-2-yl]-piperidin-1-yl}-pyrimidin-4-ylamine ("302")

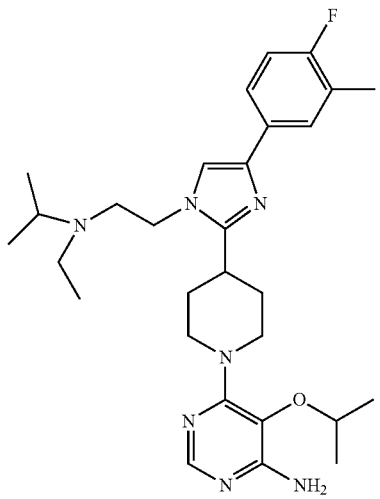 [SMILES: CCN(CCn1cc(-c2ccc(F)c(C)c2)nc1C1CCN(c2ncnc(N)c2OC(C)C)CC1)C(C)C]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-methyl-phenyl)-1-(2-(N,N-isopropylethylamino)-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=524, obsd.=524).

5-Ethoxy-6{4-(4-fluoro-3-methyl-phenyl)-1-2-(N,N-diethylamino-1-yl-ethyl)-1H-imidazol-2-yl]-piperidin-1-yl}-pyrimidin-4-ylamine ("303")

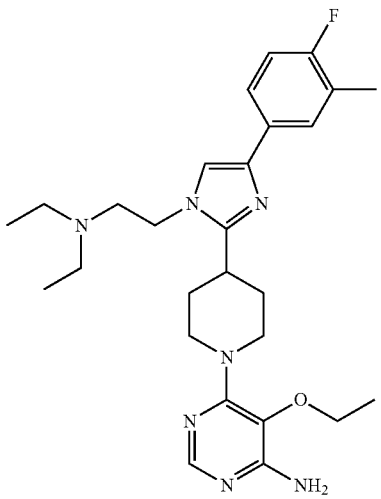 [SMILES: CCOc1c(N)ncnc1N1CCC(c2nc(-c3ccc(F)c(C)c3)cn2CCN(CC)CC)CC1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-methyl-phenyl)-1-(2-(N,N- diethylamino)-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=496, obsd.=496).

5-Isopropoxy-6{4-(4-fluoro-3-methyl-phenyl)-1-2-(N,N-diethylamino-1-yl-ethyl)-1H-imidazol-2-yl]-piperidin-1-yl}-pyrimidin-4-ylamine ("304")

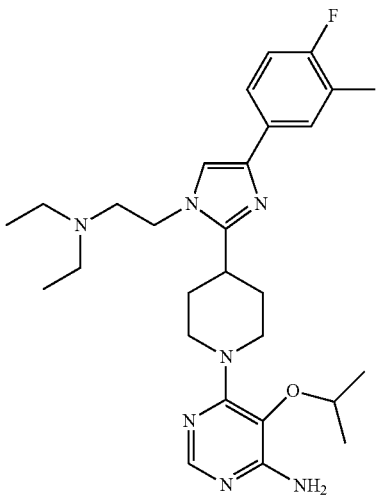 [SMILES: CCN(CC)CCn1cc(-c2ccc(F)c(C)c2)nc1C1CCN(c2ncnc(N)c2OC(C)C)CC1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[4-(4-fluoro-3-methyl-phenyl)-1-(2-(N,N-diethylamino)-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=510, obsd.=510).

4-amino-6{4-(4-fluoro-3-trifluoromethyl-phenyl)-1-2-(pyrrolidin-1-yl-ethyl)-1H-imidazol-2-yl]-piperidin-1-yl}-pyrimidin-5-carbonitrile ("305")

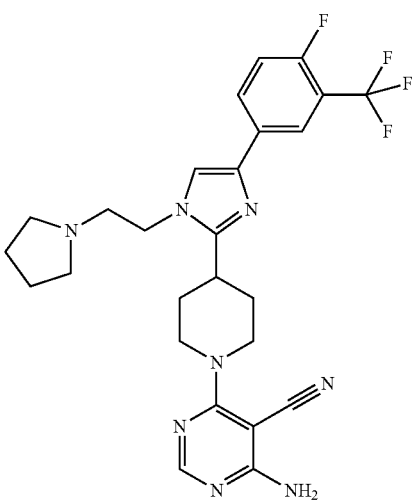 [SMILES: N#Cc1c(N)ncnc1N1CCC(c2nc(-c3ccc(F)c(C(F)(F)F)c3)cn2CCN2CCCC2)CC1]

The title compound was prepared in an analogous manner as 4-Amino-6-{4-[4-(4-fluoro-3-trifluoromethyl-phenyl)-1- methyl-1H-imidazol-2-yl]-piperidin-1-yl}-pyrimidine-5-carbonitrile using 4-[4-(4-fluoro-3-trifluoromethyl-phenyl)-1-(2-pyrrolidin-1-yl-ethyl)-1H-imidazol-2-yl]-piperidine instead of 4-[4-(3,4-difluoro-phenyl)-1-methyl-1h-imidazol-2-yl]-piperidine. LC-MS: (M+1=529, obsd.=529).

4-amino-6{4-(3,4-difluorophenyl)-1-2-(pyrrolidin-1-yl-ethyl)-1H-imidazol-2-yl]-piperidin-1-yl}-pyrimidin-5-carbonitrile ("306")

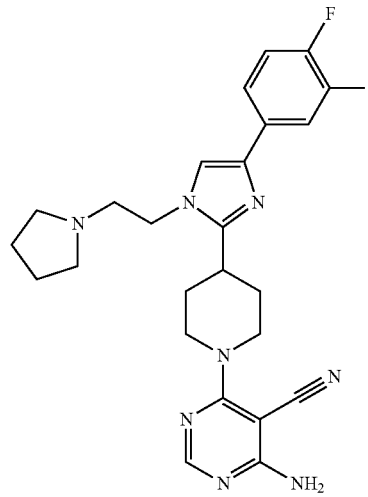

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carbonitrile using 4-[4-(3,4-difluoro-phenyl)-1-(2-pyrrolidin-1-yl-ethyl)-1H-imidazol-2-yl]-piperidine instead of 4-[4-(3,4-difluoro-phenyl)-1-methyl-1h-imidazol-2-yl]-piperidine. LC-MS: (M+1=479, obsd.=479).

4-amino-6{4-(3-chloro-4-fluorophenyl)-1-2-(pyrrolidin-1-yl-ethyl)-1H-imidazol-2-yl]-piperidin-1-yl}-pyrimidin-5-carbonitrile ("307")

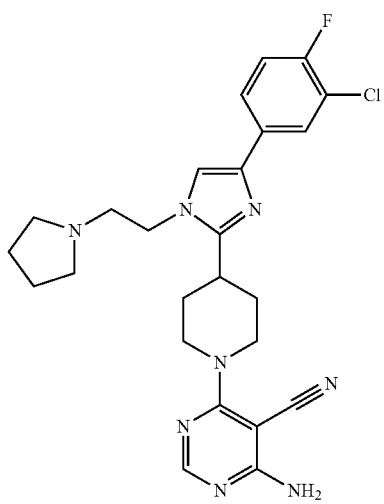 [SMILES: N#Cc1c(N)ncnc1N1CCC(c2nc(-c3ccc(F)c(Cl)c3)cn2CCN2CCCC2)CC1]

The title compound was prepared in an analogous manner as 4-Amino-6-{4-[4-(4-fluoro-3-trifluoromethyl-phenyl)-1- methyl-1H-imidazol-2-yl]-piperidin-1-yl}-pyrimidine-5-carbonitrile using 4-[4-(4-fluoro-3-chloro-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=496, obsd.=496).

4-amino-6{4-(4-fluorophenyl)-1-2-(pyrrolidin-1-yl-ethyl)-1H-imidazol-2-yl]-piperidin-1-yl}-pyrimidin-5-carbonitrile ("308")

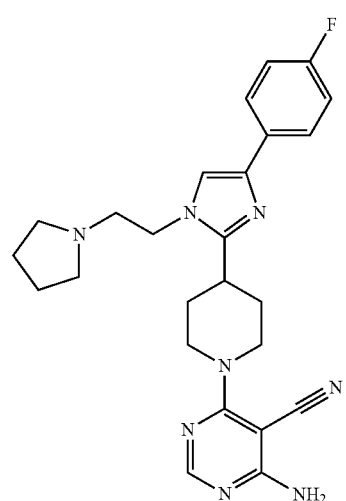 [SMILES: N#Cc1c(N)ncnc1N1CCC(c2nc(-c3ccc(F)cc3)cn2CCN2CCCC2)CC1]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carbonitrile using 4-[4-(4-fluoro-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=461, obsd.=461).

4-amino-6{4-(3-fluorophenyl)-1-2-(pyrrolidin-1-yl-ethyl)-1H-imidazol-2-yl]-piperidin-1-yl}-pyrimidin-5-carbonitrile ("309")

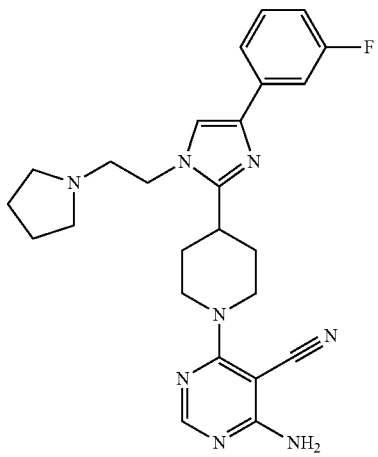 [SMILES: N#Cc1c(N)ncnc1N1CCC(c2nc(-c3cccc(F)c3)cn2CCN2CCCC2)CC1]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5- carbonitrile using 4-[4-(3-fluoro-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=461, obsd.=461).

4-amino-6{4-(3-trifluoromethyl-phenyl)-1-2-(pyrrolidin-1-yl-ethyl)-1H-imidazol-2-yl]-piperidin-1-yl}-pyrimidin-5-carbonitrile ("310")

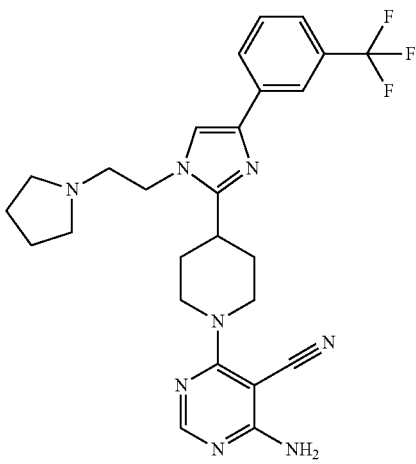 [SMILES: N#Cc1c(N)ncnc1N1CCC(c2nc(-c3cccc(C(F)(F)F)c3)cn2CCN2CCCC2)CC1]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carbonitrile using 4-[4-(3-trifluoromethyl-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=511, obsd.=511).

4-amino-6{4-(3-chloro-phenyl)-1-2-(pyrrolidin-1-yl-ethyl)-1H-imidazol-2-yl]-piperidin-1-yl}-pyrimidin-5-carbonitrile ("311")

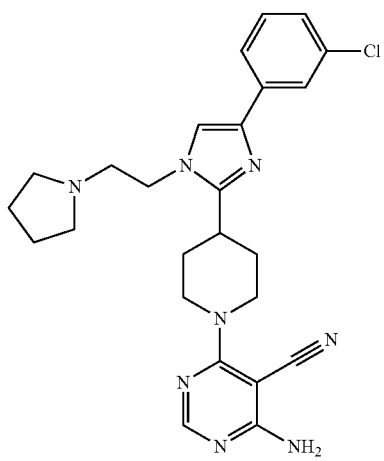 [SMILES: N#Cc1c(N)ncnc1N1CCC(c2nc(-c3cccc(Cl)c3)cn2CCN2CCCC2)CC1]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carbonitrile using 4-[4-(3-chloro-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=478, obsd.=478).

4-amino-6{4-(4-fluoro-3-trifluoromethyl-phenyl)-1-2-(piperidin-1-yl-ethyl)-1H-imidazol-2-yl]-piperidin-1-yl}-pyrimidin-5-carbonitrile ("312")

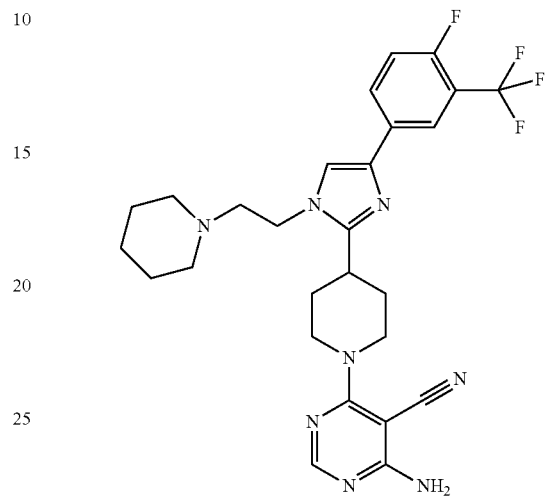

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carbonitrile using 4-[4-(4-fluoro-3-trifluoromethyl-phenyl)-1-(2-piperidin-1-yl-ethyl)-1H-imidazol-2-yl]-piperidine instead of 4-[4-(3,4-difluoro-phenyl)-1-methyl-1h-imidazol-2-yl]-piperidine. LC-MS: (M+1=543, obsd.=543).

4-amino-6{4-(3,4-difluorophenyl)-1-2-(azetidin-1-yl-ethyl)-1H-imidazol-2-yl]-piperidin-1-yl}-pyrimidin-5-carbonitrile ("313")

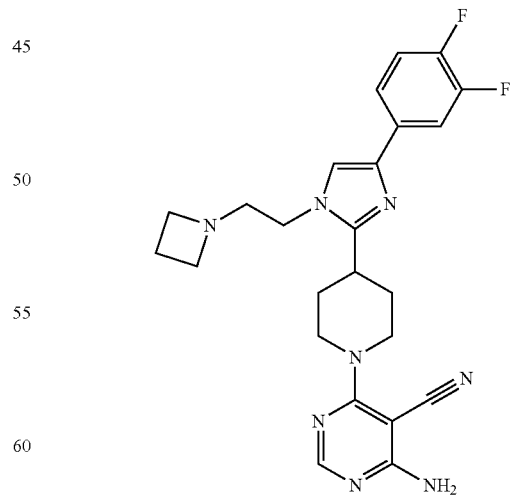

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carbonitrile using 4-[4-(3,4-fluoro-3-difluoro-phenyl)-1-(2- azetidin-1-yl-ethyl)-1H-imidazol-2-yl]-piperidine instead of 4-[4-(3,4-difluoro-phenyl)-1-methyl-1h-imidazol-2-yl]-piperidine. LC-MS: (M+1=465, obsd.=465).

4-amino-6{4-(4-fluoro-3-difluoromethoxy-phenyl)-1-2-(azetidin-1-yl-ethyl)-1H-imidazol-2-yl]-piperidin-1-yl}-pyrimidin-5-carbonitrile ("314")

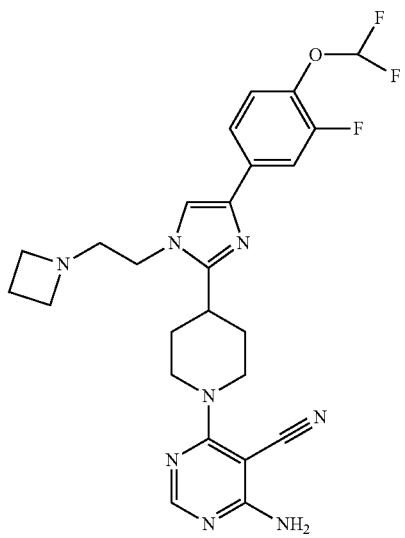 [SMILES: N#Cc1c(N)ncnc1N1CCC(c2nc(-c3ccc(OC(F)F)c(F)c3)cn2CCN2CCC2)CC1]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carbonitrile using 4-[4-(4-fluoro-3-difluoromethoxy-phenyl)-1-(2-azetidin-1-yl-ethyl)-1H-imidazol-2-yl]-piperidine instead of 4-[4-(3,4-difluoro-phenyl)-1-methyl-1h-imidazol-2-yl]-piperidine. LC-MS: (M+1=513, obsd.=513).

4-amino-6{4-(2-oxo-1,2-dihydro-pyridin-4-yl)-1-2-(azetidin-1-yl-ethyl)-1H-imidazol-2-yl]-piperidin-1-yl}-pyrimidin-5-carbonitrile ("315")

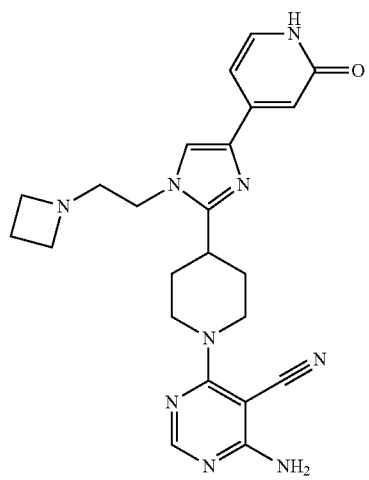 [SMILES: N#Cc1c(N)ncnc1N1CCC(c2nc(-c3cc[nH]c(=O)c3)cn2CCN2CCC2)CC1]

The title compound was prepared in an analogous manner as 4-Amino-6-{4-[4-(4-fluoro-3-trifluoromethyl-phenyl)-1- methyl-1H-imidazol-2-yl]-piperidin-1-yl}-pyrimidine-5-carbonitrile using 4-[4-(2-oxo-1,2-dihydro-pyridin-4-yl)-1-(2-azetidin-1-yl-ethyl)-1H-imidazol-2-yl]-piperidine instead of 4-[4-(3,4-difluoro-phenyl)-1-methyl-1h-imidazol-2-yl]-piperidine. LC-MS: (M+1=446, obsd.=446).

4-amino-6-{4-(4-methyl-3-trifluoromethyl-phenyl)-1-2-(azetidin-1-yl-ethyl)-1H-imidazol-2-yl]-piperidin-1-yl}-pyrimidin-5-carbonitrile ("316")

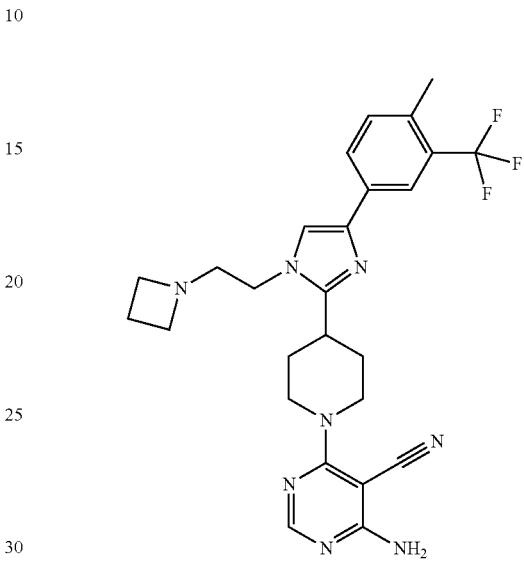

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carbonitrile using 4-[4-(4-methyl-3-trifluoromethyl)-1-(2-azetidin-1-yl-ethyl)-1H-imidazol-2-yl]-piperidine instead of 4-[4-(3,4-difluoro-phenyl)-1-methyl-1h-imidazol-2-yl]-piperidine. LC-MS: (M+1=511, obsd.=511).

4-amino-6{4(2-isopropyl-pyridin-4-yl)-1-2-(azetidin-1-yl-ethyl)-1H-imidazol-2-yl]-piperidin-1-yl}-pyrimidin-5-carbonitrile ("317")

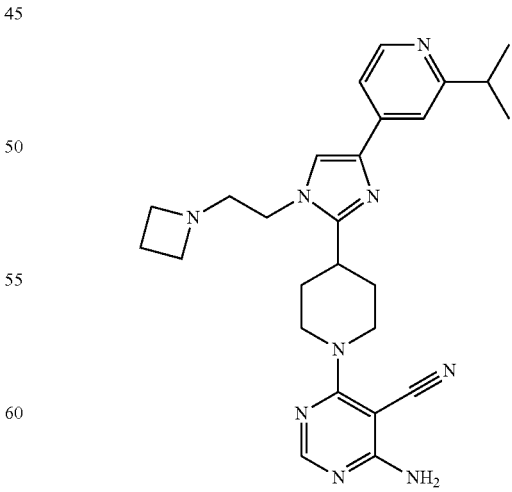

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5- carbonitrile using 4-[4-(2-isopropyl-pyridin-4-yl)-1-(2-azetidin-1-yl-ethyl)-1H-imidazol-2-yl]-piperidine instead of 4-[4-(3,4-difluoro-phenyl)-1-methyl-1h-imidazol-2-yl]-piperidine. LC-MS: (M+1=472, obsd.=472).

4-amino-6{4(2-ethyl-pyridin-4-yl)-1-2-(azetidin-1-yl-ethyl)-1H-imidazol-2-yl]-piperidin-1-yl}-pyrimidin-5-carbonitrile ("318")

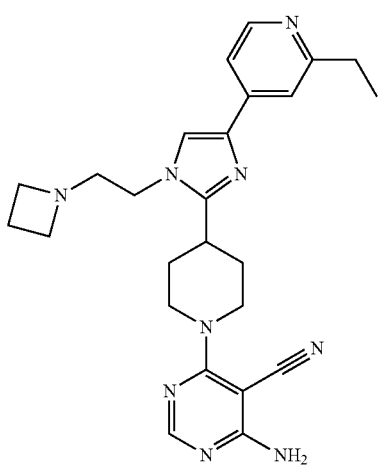 [SMILES: CCc1cc(-c2cn(CCN3CCC3)c(C3CCN(c4ncnc(N)c4C#N)CC3)n2)ccn1]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carbonitrile using 4-[4-(2-ethyl-pyridin-4-yl)-1-(2-azetidin-1-yl-ethyl)-1H-imidazol-2-yl]-piperidine instead of 4-[4-(3,4-difluoro-phenyl)-1-methyl-1h-imidazol-2-yl]-piperidine. LC-MS: (M+1=458, obsd.=458).

4-amino-6{4(2-cyclopropyl-pyridin-4-yl)-1-2-(azetidin-1-yl-ethyl)-1H-imidazol-2-yl]-piperidin-1-yl}-pyrimidin-5-carbonitrile ("319")

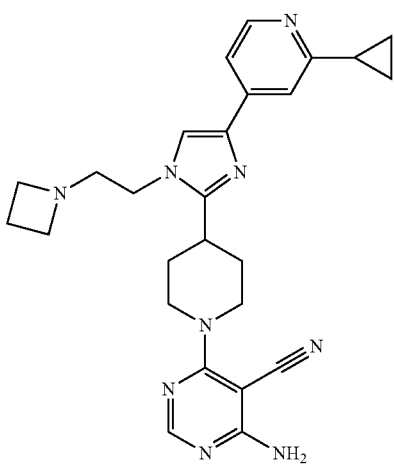 [SMILES: N#Cc1c(N)ncnc1N1CCC(c2nc(-c3ccnc(C4CC4)c3)cn2CCN2CCC2)CC1]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carbonitrile using 4-[4-(2-cyclopropyl-pyridin-4-yl)-1-(2-azetidin-1-yl-ethyl)-1H-imidazol-2-yl]-piperidine instead of 4-[4-(3,4-difluoro-phenyl)-1-methyl-1h-imidazol-2-yl]-piperidine. LC-MS: (M+1=470, obsd.=470).

4-amino-6{4-(4-methyl-3-fluoro-phenyl)-1-2-(azetidin-1-yl-ethyl)-1H-imidazol-2-yl]-piperidin-1-yl}-pyrimidin-5-carbonitrile ("320")

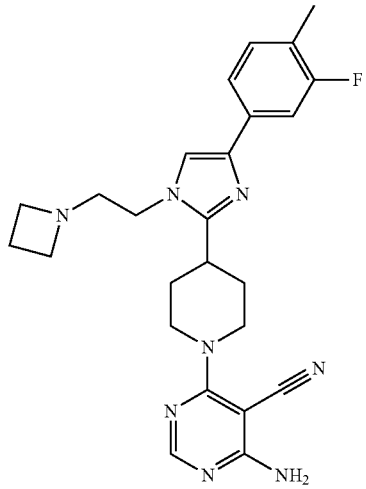 [SMILES: Cc1ccc(-c2cn(CCN3CCC3)c(C3CCN(c4ncnc(N)c4C#N)CC3)n2)cc1F]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carbonitrile using 4-[4-(4-methyl-3-fluoro-phenyl)-1-(2-azetidin-1-yl-ethyl)-1H-imidazol-2-yl]-piperidine instead of 4-[4-(3,4-difluoro-phenyl)-1-methyl-1h-imidazol-2-yl]-piperidine. LC-MS: (M+1=461, obsd.=461).

4-amino-6{4-(4-methoxy-3-fluoro-phenyl)-1-2-(azetidin-1-yl-ethyl)-1H-imidazol-2-yl]-piperidin-1-yl}-pyrimidin-5-carbonitrile ("321")

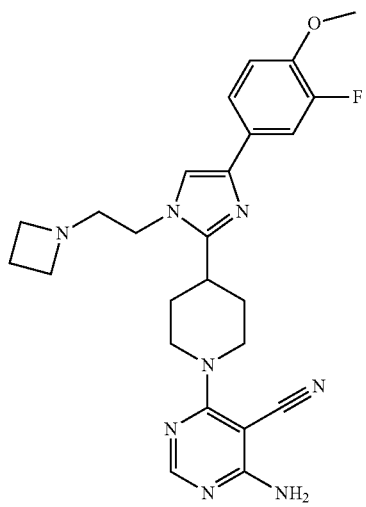 [SMILES: COc1ccc(-c2cn(CCN3CCC3)c(C3CCN(c4ncnc(N)c4C#N)CC3)n2)cc1F]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carbonitrile using 4-[4-(4-methoxy-3-fluoro-phenyl)-1-(2- azetidin-1-yl-ethyl)-1H-imidazol-2-yl]-piperidine instead of 4-[4-(3,4-difluoro-phenyl)-1-methyl-1h-imidazol-2-yl]-piperidine. LC-MS: (M+1=477, obsd.=477).

4-amino-6{4-(4-methyl-3-chloro-phenyl)-1-2-(azetidin-1-yl-ethyl)-1H-imidazol-2-yl]-piperidin-1-yl}-pyrimidin-5-carbonitrile ("322")

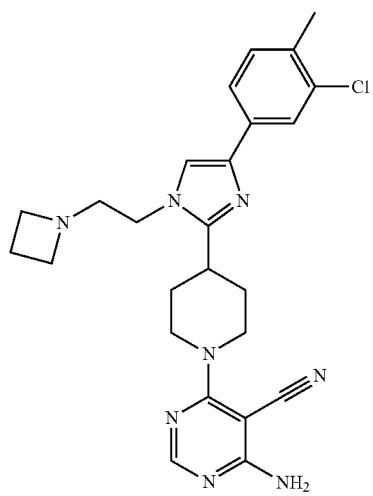 [SMILES: Cc1ccc(-c2cn(CCN3CCC3)c(C3CCN(c4ncnc(N)c4C#N)CC3)n2)cc1Cl]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carbonitrile using 4-[4-(4-methyl-3-chloro-phenyl)-1-(2-azetidin-1-yl-ethyl)-1H-imidazol-2-yl]-piperidine instead of 4-[4-(3,4-difluoro-phenyl)-1-methyl-1h-imidazol-2-yl]-piperidine. LC-MS: (M+1=478, obsd.=478).

4-amino-6{4-(4-methoxy-3-chloro-phenyl)-1-2-(azetidin-1-yl-ethyl)-1H-imidazol-2-yl]-piperidin-1-yl}-pyrimidin-5-carbonitrile ("323")

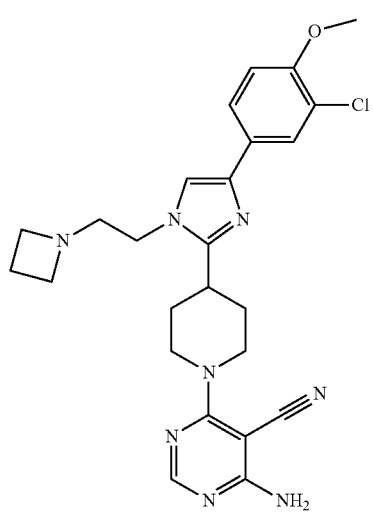 [SMILES: COc1ccc(-c2cn(CCN3CCC3)c(C3CCN(c4ncnc(N)c4C#N)CC3)n2)cc1Cl]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carbonitrile using 4-[4-(4-methoxy-3-chloro-phenyl)-1-(2-azetidin-1-yl-ethyl)-1H-imidazol-2-yl]-piperidine instead of 4-[4-(3,4-difluoro-phenyl)-1-methyl-1h-imidazol-2-yl]-piperidine. LC-MS: (M+1=494, obsd.=494).

4-amino-6-{4-(3-methyl-4-fluoro-phenyl)-1-2-(pyrrolidin-1-yl-ethyl)-1H-imidazol-2-yl]-piperidin-1-yl}-pyrimidin-5-carbonitrile ("324")

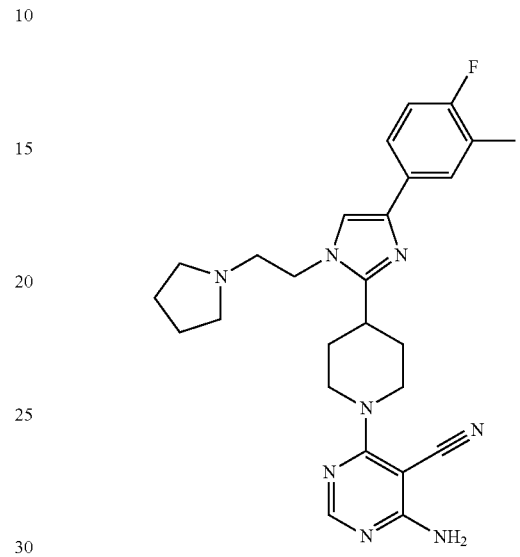

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carbonitrile using 4-[4-(4-methyl-4-fluoro-phenyl)-1-(2-pyrrolidin-1-yl-ethyl)-1H-imidazol-2-yl]-piperidine instead of 4-[4-(3,4-difluoro-phenyl)-1-methyl-1h-imidazol-2-yl]-piperidine. LC-MS: (M+1=475, obsd.=475).

4-amino-6{4-(3-methyl-4-fluoro-phenyl)-1-2-(N,N-dimethylamino)-1-yl-ethyl)-1H-imidazol-2-yl]-piperidin-1-yl}-pyrimidin-5-carbonitrile ("325")

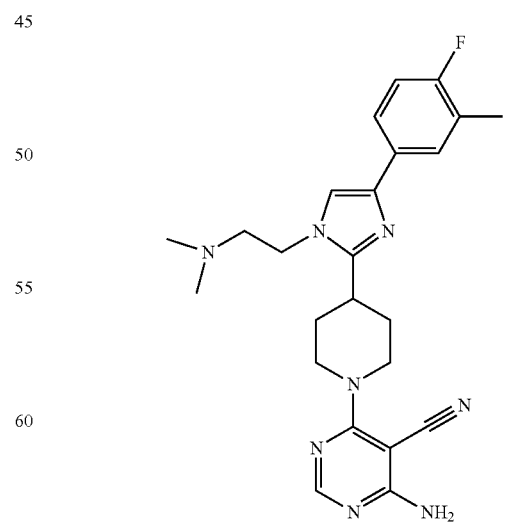

The title compound was prepared in an analogous manner as 4-Amino-6-{4-[4-(4-fluoro-3-trifluoromethyl-phenyl)-1- methyl-1H-imidazol-2-yl]-piperidin-1-yl}-pyrimidine-5-carbonitrile using 4-[4-(4-methyl-4-fluoro-phenyl)-1-(2-(N,N-dimethylamino)-1-yl-ethyl)-1H-imidazol-2-yl]-piperidine instead of 4-[4-(3,4-difluoro-phenyl)-1-methyl-1h-imidazol-2-yl]-piperidine. LC-MS: (M+1=449, obsd.=449).

4-amino-6{4-(3-methyl-4-fluoro-phenyl)-1-2-(N,N-diethylamino)-1-yl-ethyl)-1H-imidazol-2-yl]-piperidin-1-yl}-pyrimidin-5-carbonitrile ("326")

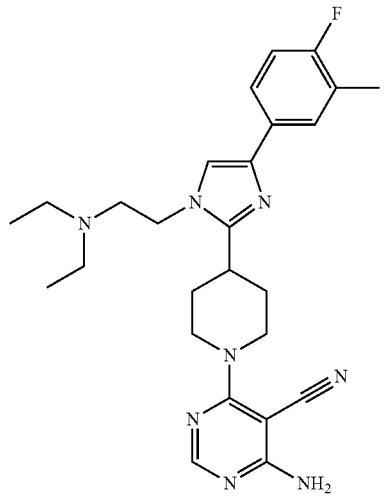 [SMILES: CCN(CC)CCn1cc(-c2ccc(F)c(C)c2)nc1C1CCN(c2ncnc(N)c2C#N)CC1]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carbonitrile using 4-[4-(4-methyl-4-fluoro-phenyl)-1-(2-(N,N-diethylamino)-1-yl-ethyl)-1H-imidazol-2-yl]-piperidine instead of 4-[4-(3,4-difluoro-phenyl)-1-methyl-1h-imidazol-2-yl]-piperidine. LC-MS: (M+1=477, obsd.=477).

4-amino-6{4-(3-methyl-4-fluoro-phenyl)-1-2-(N,N-isopropylethylamino)-1-yl-ethyl)-1H-imidazol-2-yl]-piperidin-1-yl}-pyrimidin-5-carbonitrile ("327")

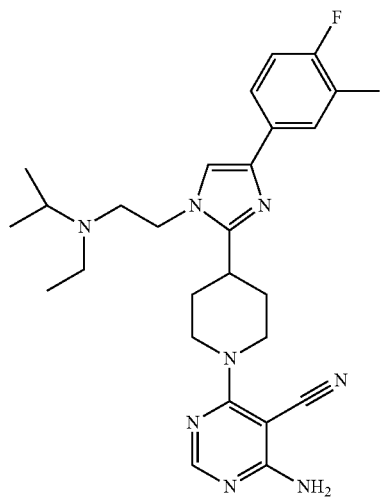 [SMILES: CCN(CCn1cc(-c2ccc(F)c(C)c2)nc1C1CCN(c2ncnc(N)c2C#N)CC1)C(C)C]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carbonitrile using 4-[4-(4-methyl-4-fluoro-phenyl)-1-(2-(N,N-isopropylethylamino)-1-yl-ethyl)-1H-imidazol-2-yl]-piperidine instead of 4-[4-(3,4-difluoro-phenyl)-1-methyl-1h-imidazol-2-yl]-piperidine. LC-MS: (M+1=491, obsd.=491).

4-amino-6{4-(3,4-difluorophenyl)-1-2-(azetidin-1-yl-ethyl)-1H-imidazol-2-yl]-piperidin-1-yl}-pyrimidin-5-carboxylic acid amide ("328")

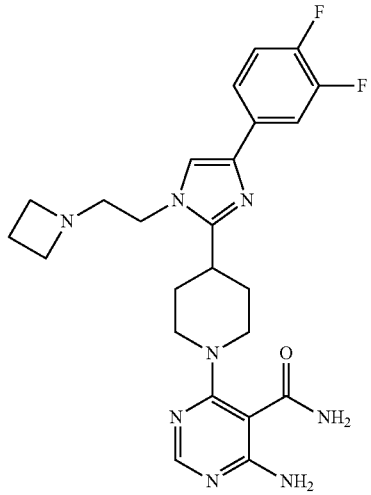 [SMILES: NC(=O)c1c(N)ncnc1N1CCC(c2nc(-c3ccc(F)c(F)c3)cn2CCN2CCC2)CC1]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-{4-[1-(2-azetidin-ethyl)-4-(3,4-difluoro-phenyl)-1H-imidazol-2-yl]-piperidin-1-yl}-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=483, obsd.=483).

4-amino-6{4-(3,4-difluorophenyl)-1-2-(pyrrolidin-1-yl-ethyl)-1H-imidazol-2-yl]-piperidin-1-yl}-pyrimidin-5-carboxylic acid amide ("329")

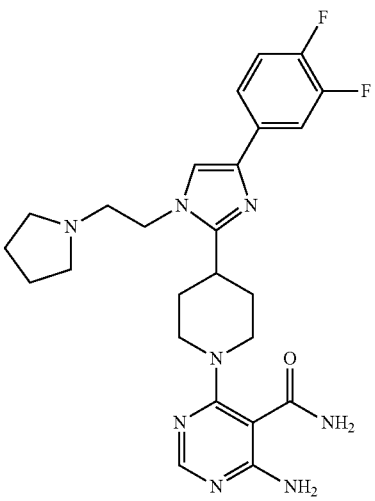 [SMILES: NC(=O)c1c(N)ncnc1N1CCC(c2nc(-c3ccc(F)c(F)c3)cn2CCN2CCCC2)CC1]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-[4-(3,4-difluoro-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=498, obsd.=498).

4-amino-6{4-(3-chloro-4-fluorophenyl)-1-2-(pyrrolidin-1-yl-ethyl)-1H-imidazol-2-yl]-piperidin-1-yl}-pyrimidin-5-carboxylic acid amide ("330")

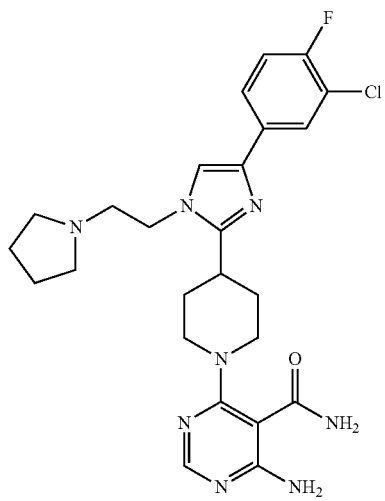 [SMILES: NC(=O)c1c(N)ncnc1N1CCC(c2nc(-c3ccc(F)c(Cl)c3)cn2CCN2CCCC2)CC1]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-[4-(3-chloro-4-fluoro-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=515, obsd.=515).

4-amino-6{4-(4-fluoro-3-trifluoromethylphenyl)-1-2-(pyrrolidin-1-yl-ethyl)-1H-imidazol-2-yl]-piperidin-1-yl}-pyrimidin-5-carboxylic acid amide ("331")

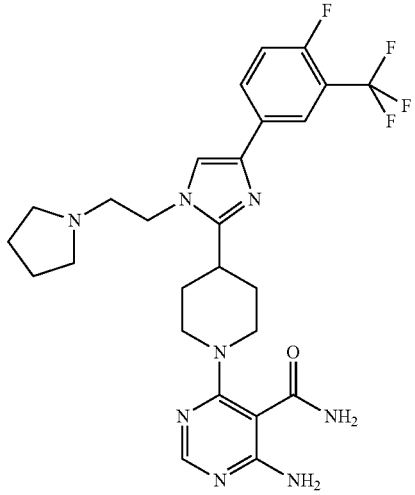 [SMILES: NC(=O)c1c(N)ncnc1N1CCC(c2nc(-c3ccc(F)c(C(F)(F)F)c3)cn2CCN2CCCC2)CC1]

The title compound was prepared in an analogous manner as 4-Amino-6-{4-[4-(4-fluoro-3-trifluoromethyl-phenyl)-1- methyl-1H-imidazol-2-yl]-piperidin-1-yl}-pyrimidine-5-carboxamide using 4-[4-(3-fluoro-4-trifluoromethyl-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=548, obsd.=548).

4-amino-6{4(2-isopropyl-pyridin-4-yl)-1-2-(azetidin-1-yl-ethyl)-1H-imidazol-2-yl]-piperidin-1-yl}-pyrimidin-5-carboxylic acid amide ("332")

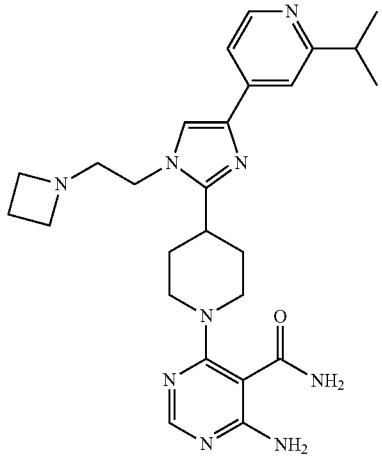 [SMILES: CC(C)c1cc(-c2cn(CCN3CCC3)c(C3CCN(c4ncnc(N)c4C(N)=O)CC3)n2)ccn1]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-[4-(2-isopropyl-pyridin-4-yl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=490, obsd.=490).

4-amino-6{4-(4-fluorophenyl)-1-2-(pyrrolidin-1-yl-ethyl)-1H-imidazol-2-yl]-piperidin-1-yl}-pyrimidin-5-carboxylic acid amide ("333")

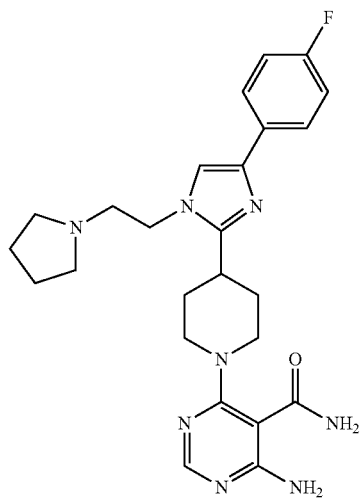 [SMILES: NC(=O)c1c(N)ncnc1N1CCC(c2nc(-c3ccc(F)cc3)cn2CCN2CCCC2)CC1]

The title compound was prepared in an analogous manner as 4-Amino-6-{4-[4-(4-fluoro-3-trifluoromethyl-phenyl)-1- methyl-1H-imidazol-2-yl]-piperidin-1-yl}-pyrimidine-5-carboxamide using 4-[4-(4-fluoro-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=479, obsd.=479).

4-amino-6{4-(3-fluorophenyl)-1-2-(pyrrolidin-1-yl-ethyl)-1H-imidazol-2-yl]-piperidin-1-yl}-pyrimidin-5-carboxylic acid amide ("334")

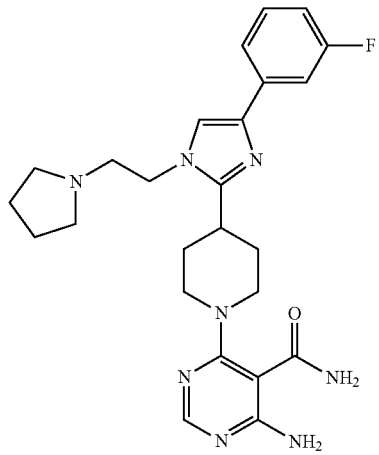 [SMILES: NC(=O)c1c(N)ncnc1N1CCC(c2nc(-c3cccc(F)c3)cn2CCN2CCCC2)CC1]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-[4-(3-fluoro-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=479, obsd.=479).

4-amino-6{4-(3-trifluoromethyl-phenyl)-1-2-(pyrrolidin-1-yl-ethyl)-1H-imidazol-2-yl]-piperidin-1-yl}-pyrimidin-5-carboxylic acid amide ("335")

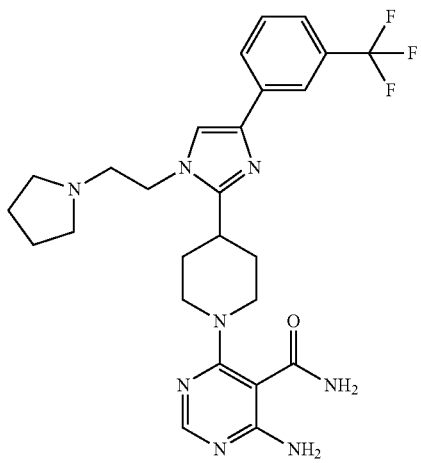 [SMILES: NC(=O)c1c(N)ncnc1N1CCC(c2nc(-c3cccc(C(F)(F)F)c3)cn2CCN2CCCC2)CC1]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-[4-(3-trifluoromethyl-phenyl)-1-(2- pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=529, obsd.=529).

4-amino-6{4-(3-chloro-phenyl)-1-2-(pyrrolidin-1-yl-ethyl)-1H-imidazol-2-yl]-piperidin-1-yl}-pyrimidin-5-carboxylic acid amide ("336")

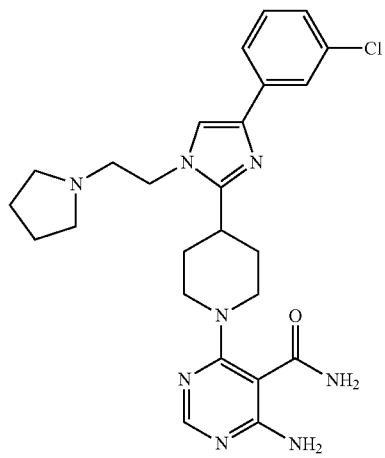 [SMILES: NC(=O)c1c(N)ncnc1N1CCC(c2nc(-c3cccc(Cl)c3)cn2CCN2CCCC2)CC1]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-[4-(3-chloro-phenyl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=496, obsd.=496).

4-amino-6{4-(4-fluoro-3-trifluoromethyl-phenyl)-1-2-(piperidin-1-yl-ethyl)-1H-imidazol-2-yl]-piperidin-1-yl}-pyrimidin-5-carboxylic acid amide ("337")

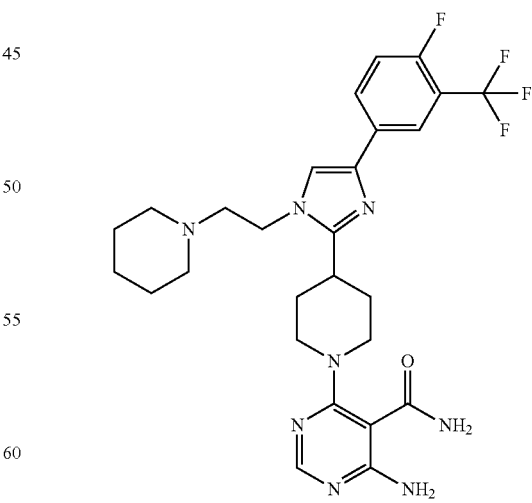

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-[4-(4-fluoro-3-trifluomethyl-phenyl)-

1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=561, obsd.=561).

4-amino-6{4-(4-fluoro-3-difluoromethoxy-phenyl)-1-2-(azetidin-1-yl-ethyl)-1H-imidazol-2-yl]-piperidin-1-yl}-pyrimidin-5-carboxylic acid amide ("338")

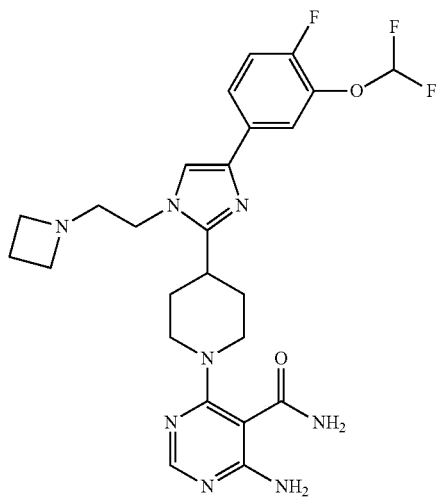 [SMILES: NC(=O)c1c(N)ncnc1N1CCC(c2nc(-c3ccc(F)c(OC(F)F)c3)cn2CCN2CCC2)CC1]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-[4-(4-fluoro-3-difluoromethoxy-phenyl)-1-(2-azetidine-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=531, obsd.=531).

4-amino-6{4-(2-oxo-pyridin-4-yl)-1-2-(azetidin-1-yl-ethyl)-1H-imidazol-2-yl]-piperidin-1-yl}-pyrimidin-5-carboxylic acid amide ("339")

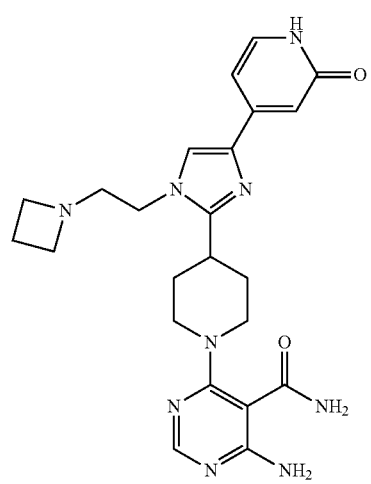 [SMILES: NC(=O)c1c(N)ncnc1N1CCC(c2nc(-c3cc[nH]c(=O)c3)cn2CCN2CCC2)CC1]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-[4-(2-oxo-pyridin-4-yl)-1-(2-azetidin-1-yl-ethyl)-1H-imidazol-2-yl]-piperidine instead of 4-[4-(4-fluoro-3-difluoromethoxy-phenyl)-1-methyl-1h-imidazol-2-yl]-piperidine. LC-MS: (M+1=464, obsd.=464).

4-amino-6{4-(4-methyl-3-trifluomethyl-phenyl)-1-2-(azetidin-1-yl-ethyl)-1H-imidazol-2-yl]-piperidin-1-yl}-pyrimidin-5-carboxylic acid amide ("340")

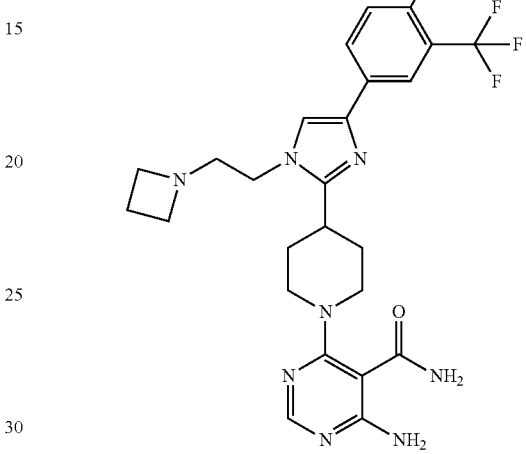

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-{4-[1-(2-azetidin-ethyl)-4-(4-methyl-3-trifluomethyl-phenyl)-1H-imidazol-2-yl]-piperidin-1-yl}-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=529, obsd.=529).

4-amino-6{4(2-ethyl-pyridin-4-yl)-1-2-(azetidin-1-yl-ethyl)-1H-imidazol-2-yl]-piperidin-1-yl}-pyrimidin-5-carboxylic acid amide ("341")

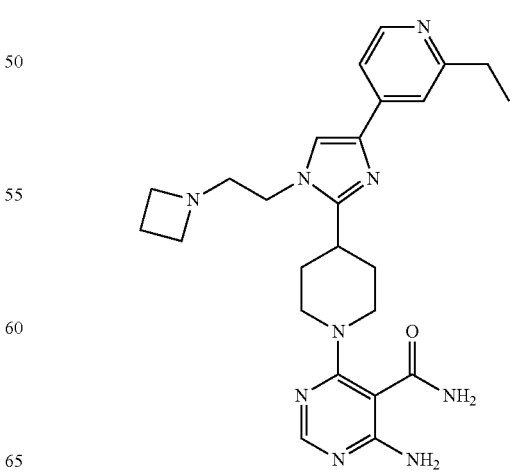

The title compound was prepared in an analogous manner as 4-Amino-6-{4-[4-(4-fluoro-3-trifluoromethyl-phenyl)-1-

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-[4-(2-ethyl-pyridin-4-yl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=476, obsd.=476).

4-amino-6{4(2-cylopropyl-pyridin-4-yl)-1-2-(azetidin-1-yl-ethyl)-1H-imidazol-2-yl]-piperidin-1-yl}-pyrimidin-5-carboxylic acid amide ("342")

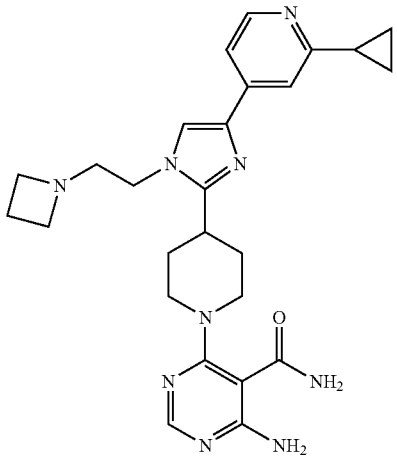 [SMILES: NC(=O)c1c(N)ncnc1N1CCC(c2nc(-c3ccnc(C4CC4)c3)cn2CCN2CCC2)CC1]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-[4-(2-cyclopropyl-pyridin-4-yl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=488, obsd.=488).

4-amino-6{4(2-tert-butyl-pyridin-4-yl)-1-2-(azetidin-1-yl-ethyl)-1H-imidazol-2-yl]-piperidin-1-yl}-pyrimidin-5-carboxylic acid amide ("343")

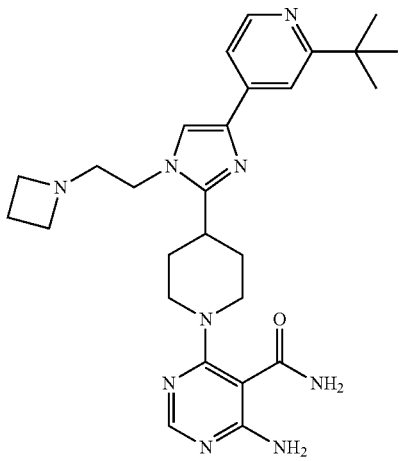 [SMILES: CC(C)(C)c1cc(-c2cn(CCN3CCC3)c(C3CCN(c4ncnc(N)c4C(N)=O)CC3)n2)ccn1]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-[4-(2-tert-butyl-pyridin-4-yl)-1-(2-pyrrolidin-1-yl-ethyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=504, obsd.=504).

4-amino-6{4-(4-methyl-3-fluoro-phenyl)-1-2-(azetidin-1-yl-ethyl)-1H-imidazol-2-yl]-piperidin-1-yl}-pyrimidin-5-carboxylic acid amide ("344")

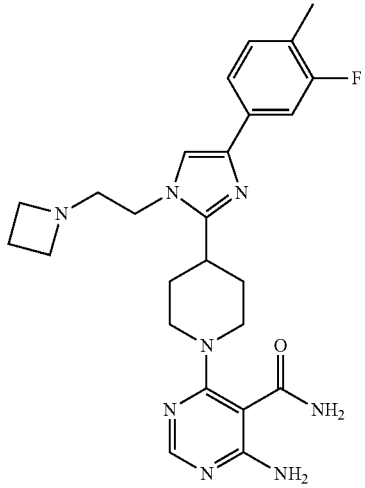 [SMILES: Cc1ccc(-c2cn(CCN3CCC3)c(C3CCN(c4ncnc(N)c4C(N)=O)CC3)n2)cc1F]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-{4-[1-(2-azetidin-ethyl)-4-(4-methyl-3-fluoro-phenyl)-1H-imidazol-2-yl]-piperidin-1-yl}-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=479, obsd.=479).

4-amino-6{4-(4-methoxy-3-fluoro-phenyl)-1-2-(azetidin-1-yl-ethyl)-1H-imidazol-2-yl]-piperidin-1-yl}-pyrimidin-5-carboxylic acid amide ("345")

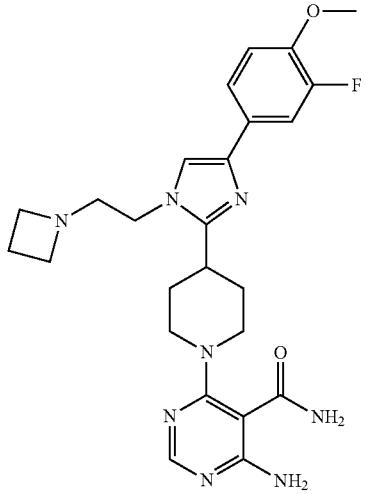 [SMILES: COc1ccc(-c2cn(CCN3CCC3)c(C3CCN(c4ncnc(N)c4C(N)=O)CC3)n2)cc1F]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-{4-[1-(2-azetidin-ethyl)-4-

(4-methoxy-3-fluoro-phenyl)-1H-imidazol-2-yl]-piperidin-1-yl}-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=495, obsd.=495).

4-amino-6{4-(3-chloro-4-methyl-phenyl)-1-2-(azetidin-1-yl-ethyl)-1H-imidazol-2-yl]-piperidin-1-yl}-pyrimidin-5-carboxylic acid amide ("346")

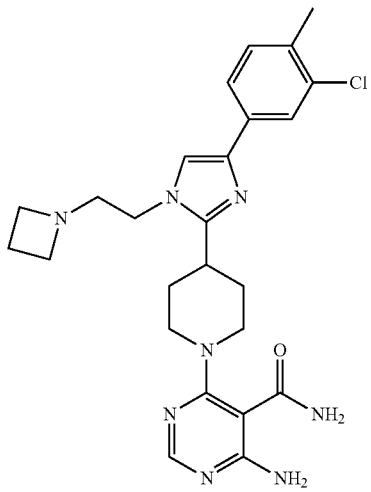 [SMILES: Cc1ccc(-c2cn(CCN3CCC3)c(C3CCN(c4ncnc(N)c4C(N)=O)CC3)n2)cc1Cl]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-{4-[1-(2-azetidin-ethyl)-4-(3-chloro-4-methyl-phenyl)-1H-imidazol-2-yl]-piperidin-1-yl}-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=496, obsd.=496).

4-amino-6{4-(3-chloro-4-methoxy]phenyl)-1-2-(azetidin-1-yl-ethyl)-1H-imidazol-2-yl]-piperidin-1-yl}-pyrimidin-5-carboxylic acid amide ("347")

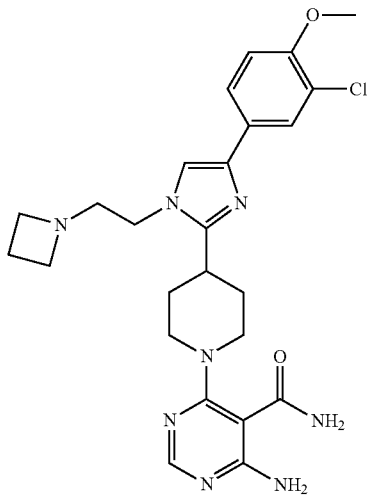 [SMILES: COc1ccc(-c2cn(CCN3CCC3)c(C3CCN(c4ncnc(N)c4C(N)=O)CC3)n2)cc1Cl]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-{4-[1-(2-azetidin-ethyl)-4-

(3-chloro-4-methoxy-phenyl)-1H-imidazol-2-yl]-piperidin-1-yl}-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=512, obsd.=512).

4-amino-6{4-(4-fluoro-3-methyl-phenyl)-1-2-(N,N-dimethylamino-ethyl)-1H-imidazol-2-yl]-piperidin-1-yl}-pyrimidin-5-carboxylic acid amide ("348")

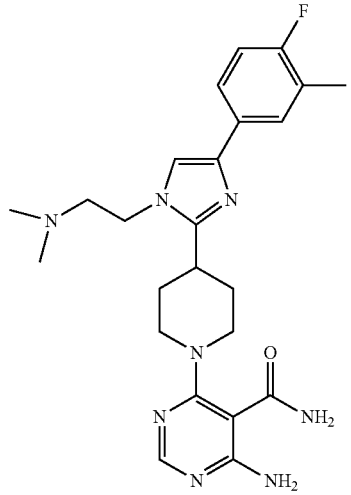

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-{4-[1-(2-(N,N-dimethylamino-ethyl)-4-(4-fluoro-3-methyl-phenyl)-1H-imidazol-2-yl]-piperidin-1-yl}-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=467, obsd.=467).

4-amino-6{4-(4-fluoro-3-methyl-phenyl)-1-2-(N,N-diethylamino-ethyl)-1H-imidazol-2-yl]-piperidin-1-yl}-pyrimidin-5-carboxylic acid amide ("349")

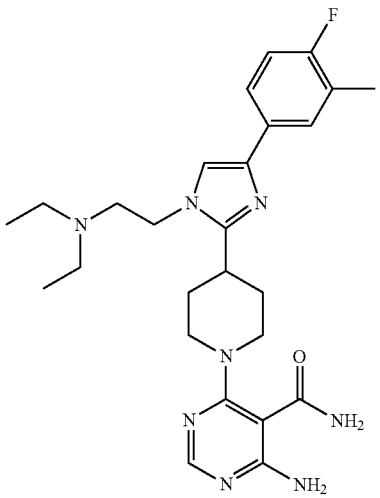 [SMILES: CCN(CC)CCn1cc(-c2ccc(F)c(C)c2)nc1C1CCN(c2ncnc(N)c2C(N)=O)CC1]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-{4-[1-(2-(N,N-diethylamino-ethyl)-4-(4-fluoro-3-methyl-phenyl)-1H-imidazol-2-yl]-piperidin-1-yl}-pyrimidine-5-carbonitrile instead of 4-amino-6-(4-{4-(4-fluoro-3-(trifluoromethyl)phenyl]-1-methyl-1H-imidazol-2-yl}piperidin-1-yl)pyrimidine-5-carbonitrile. LC-MS: (M+1=495, obsd.=495).

4-amino-6{4-(4-fluoro-3-methyl-phenyl)-1-2-(pyrrolidin-1-yl-ethyl)-1H-imidazol-2-yl]-piperidin-1-yl}-pyrimidin-5-carboxylic acid amide ("350")

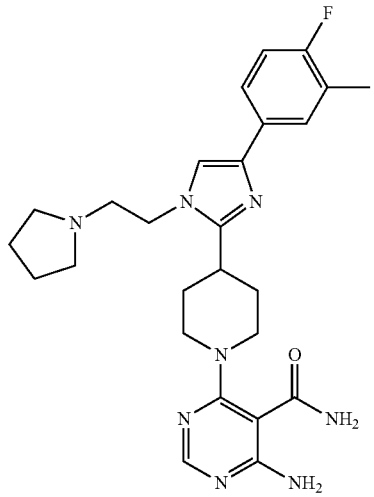 [SMILES: Cc1cc(-c2cn(CCN3CCCC3)c(C3CCN(c4ncnc(N)c4C(N)=O)CC3)n2)ccc1F]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-{4-[1-(2-(pyrrolidin-1-yl-ethyl)-4-(4-fluoro-3-methyl-phenyl)-1H-imidazol-2-yl]-piperidin-1-yl}-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=493, obsd.=493).

4-amino-6{4-(4-fluoro-3-methyl-phenyl)-1-2-(N,N-ethylisopropylamino-ethyl)-1H-imidazol-2-yl]-piperidin-1-yl}-pyrimidin-5-carboxylic acid amide ("351")

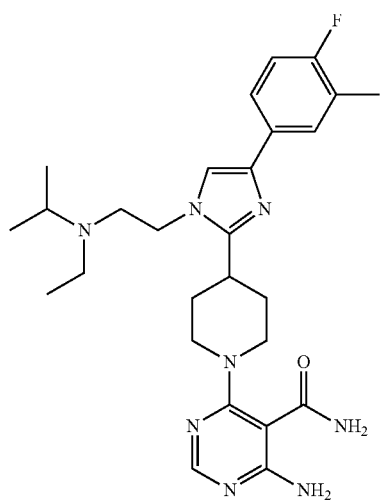 [SMILES: CCN(CCn1cc(-c2ccc(F)c(C)c2)nc1C1CCN(c2ncnc(N)c2C(N)=O)CC1)C(C)C]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-{4-[1-(2-(N,N-ethylisopropylamino-ethyl)-4-(4-fluoro-3-methyl-phenyl)-1H-imidazol-2-yl]-piperidin-1-yl}-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=509, obsd.=509).

6-{4-[1-(2-Azetidin-1-yl-ethyl)-4-(2-dimethylamino-pyrimidin-5-yl)-1H-imidazol-2-yl]-piperidin-1-yl}-5-ethyl-pyrimidin-4-ylamine ("352")

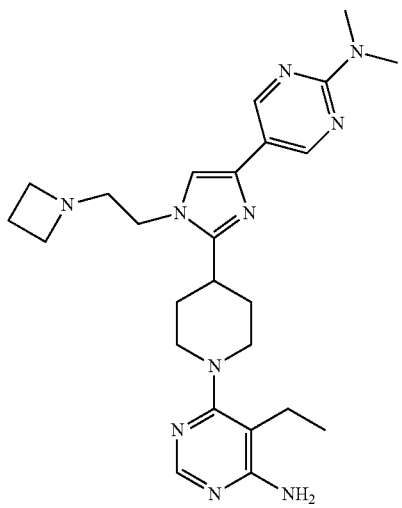 [SMILES: CCc1c(N)ncnc1N1CCC(c2nc(-c3cnc(N(C)C)nc3)cn2CCN2CCC2)CC1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using {5-[1-(2-Azetidin-1-yl-ethyl)-2-piperidin-4-yl-1H-imidazol-4-yl]-pyrimidin-2-yl}-dimethyl-amine instead of 4-[4-(4-fluoro-3-trifluoromethyl-phenyl)-1-methyl-1h-imidazol-2-yl]-piperidine. LC-MS: (M+1=477, obsd.=477).

4-Amino-6-{4-[1-(2-azetidin-1-yl-ethyl)-4-(2-fluoro-phenyl)-1H-imidazol-2-yl]-piperidin-1-yl}-pyrimidine-5-carbonitrile ("353")

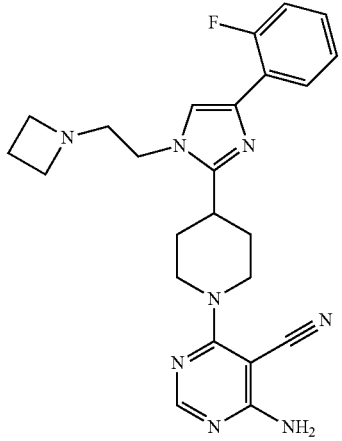 [SMILES: N#Cc1c(N)ncnc1N1CCC(c2nc(-c3ccccc3F)cn2CCN2CCC2)CC1]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 4-[1-(2-Azetidin-1-yl-ethyl)-4-(2-fluoro-phenyl)-1H-imidazol-2-yl]-piperidine instead of 4-[4-(4-fluoro-3-trifluoromethyl-phenyl)-1-methyl-1h-imidazol-2-yl]-piperidine. LC-MS: (M+1=447, obsd.=447).

3-[2-[1-(6-Amino-5-cyano-pyrimidin-4-yl)-piperidin-4-yl]-1-(2-azetidin-1-yl-ethyl)-1H-imidazol-4-yl]-benzenesulfonamide ("354")

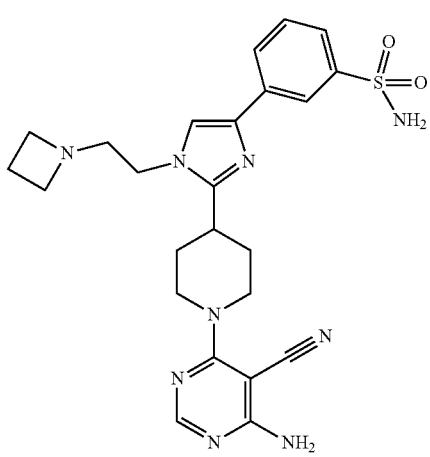 [SMILES: N#Cc1c(N)ncnc1N1CCC(c2nc(-c3cccc(S(N)(=O)=O)c3)cn2CCN2CCC2)CC1]

The title compound was prepared in an analogous manner as 5-bromo-6-{4-[4-(4-fluoro-3-trifluoromethyl-phenyl)-1-methyl-1H-imidazol-2-yl]-piperidin-1-yl}-pyrimidin-4-ylamine using 3-[1-(2-Azetidin-1-yl-ethyl)-2-piperidin-4-yl-1H-imidazol-4-yl]-benzenesulfonamide trifluoroacetate instead of 4-[4-(4-fluoro-3-trifluoromethyl-phenyl)-1-methyl-1h-imidazol-2-yl]-piperidine. LC-MS: (M+1=508, obsd.=508).

4-Amino-6-{4-[1-(2-azetidin-1-yl-ethyl)-4-(3-methanesulfonyl-phenyl)-1H-imidazol-2-yl]-piperidin-1-yl}-pyrimidine-5-carbonitrile ("355")

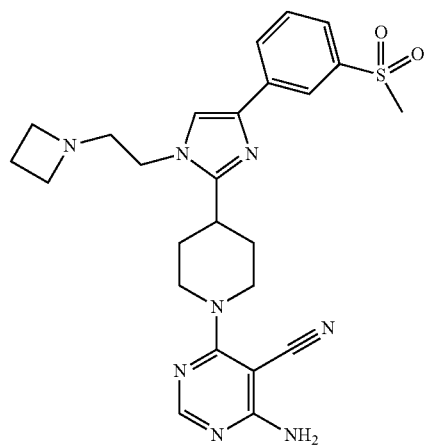 [SMILES: CS(=O)(=O)c1cccc(-c2cn(CCN3CCC3)c(C3CCN(c4ncnc(N)c4C#N)CC3)n2)c1]

The title compound was prepared in an analogous manner as 5-bromo-6-{4-[4-(4-fluoro-3-trifluoromethyl-phenyl)-1-methyl-1H-imidazol-2-yl]-piperidin-1-yl}-pyrimidin-4-ylamine using 4-[1-(2-Azetidin-1-yl-ethyl)-4-(3-methanesulfonyl-phenyl)-1H-imidazol-2-yl]-piperidine trifluoroacetate instead of 4-[4-(4-fluoro-3-trifluoromethyl-phenyl)-1-methyl-1h-imidazol-2-yl]-piperidine. LC-MS: (M+1=507, obsd.=507).

4-Amino-6-{4-[1-(2-azetidin-1-yl-ethyl)-4-(3-methanesulfonyl-phenyl)-1H-imidazol-2-yl]-piperidin-1-yl}-pyrimidine-5-carboxylic acid amide ("356")

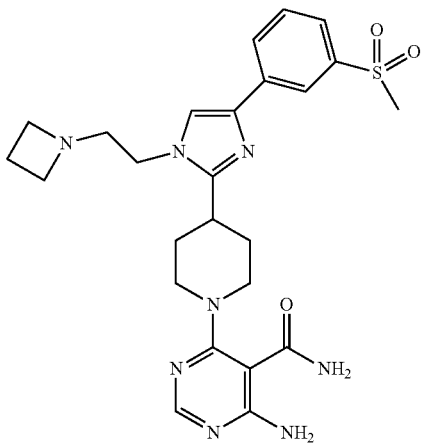 [SMILES: CS(=O)(=O)c1cccc(-c2cn(CCN3CCC3)c(C3CCN(c4ncnc(N)c4C(N)=O)CC3)n2)c1]

The title compound was prepared in an analogous manner as 4-amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-{4-[1-(2-azetidin-1-yl-ethyl)-4-(3-methanesulfonyl-phenyl)-1H-imidazol-2-yl]-piperidin-1-yl}-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=525, obsd.=525).

4-Amino-6-{4-[4-(4-fluoro-3-trifluoromethyl-phenyl)-1-(2-hydroxy-ethyl)-1H-imidazol-2-yl]-piperidin-1-yl}-pyrimidine-5-carbonitrile ("357")

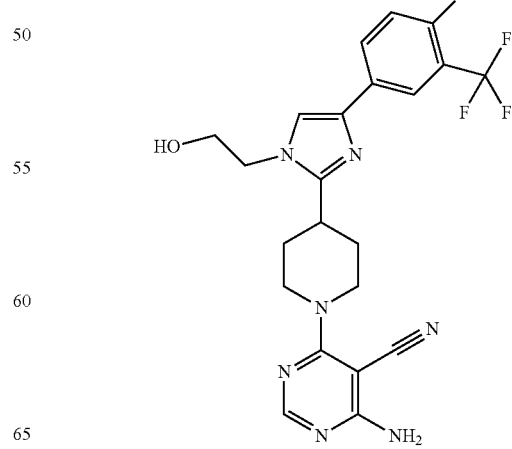

The title compound was prepared in an analogous manner as 5-bromo-6-{4-[4-(4-fluoro-3-trifluoromethyl-phenyl)-1-methyl-1H-imidazol-2-yl]-piperidin-1-yl}-pyrimidin-4-ylamine using 2-[4-(4-Fluoro-3-trifluoromethyl-phenyl)-2-piperidin-4-yl-imidazol-1-yl]-ethanol trifluoroacetate instead of 4-[4-(4-fluoro-3-trifluoromethyl-phenyl)-1-methyl-1h-imidazol-2-yl]-piperidine. LC-MS: (M+1=476, obsd.=476).

4-Amino-6-{4-[1-[2-(cyclopropylmethyl-amino)-ethyl]-4-(4-fluoro-3-trifluoromethyl-phenyl)-1H-imidazol-2-yl]-piperidin-1-yl}-pyrimidine-5-carbonitrile ("358")

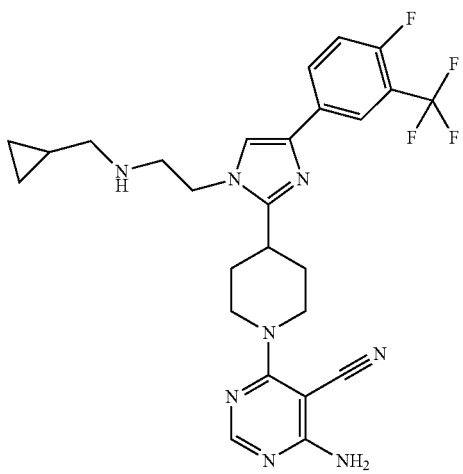 [SMILES: N#Cc1c(N)ncnc1N1CCC(c2nc(-c3ccc(F)c(C(F)(F)F)c3)cn2CCNCC2CC2)CC1]

4-Amino-6-{4-[4-(4-fluoro-3-trifluoromethyl-phenyl)-1-(2-hydroxy-ethyl)-1H-imidazol-2-yl]-piperidin-1-yl}-pyrimidine-5-carbonitrile (22.8 mg; 0.47 mmol; 1.00 eq) was dissolved in dichloromethane (10.00 mL) and chilled to −78° C. The solution was charged with triethylamine (0.20 mL; 1.41 mmol; 3.00 eq) and methanesulfonyl chloride (0.05 mL; 0.70 mmol; 1.50 eq). The reaction was stirred, cold, for 1 hour, then allowed to warm to ambient temperature. The reaction mixture was quenched by dropwise addition of sodium bicarbonate (saturated aq; 10 mL). The organic layer was separated, dried over sodium sulphate, filtered and concentrated to yield methanesulfonic acid 2-[2-[1-(6-amino-5-cyano-pyrimidin-4-yl)-piperidin-4-yl]-4-(4-fluoro-3-trifluoromethyl-phenyl)-imidazol-1-yl]-ethyl ester (259 mg; 0.47 mmol; 99.8%). LC-MS: (M+1=554, obsd.=554).

The title compound was prepared by stirring methanesulfonic acid 2-[2-[1-(6-amino-5-cyano-pyrimidin-4-yl)-piperidin-4-yl]-4-(4-fluoro-3-trifluoromethyl-phenyl)-imidazol-1-yl]-ethyl ester (85.0 mg; 0.15 mmol; 1.00 eq) in cyclopropylmethylamine (54.6 mg, 0.77 mmol; 5.0 eq) at ambient temperature. The reaction mixture was purified via flash chromatography using a gradient of 0-10% methanol in dichloromethane to give 4-Amino-6-{4-[1-[2-(cyclopropyl-methyl-amino)-ethyl]-4-(4-fluoro-3-trifluoromethyl-phenyl)-1H-imidazol-2-yl]-piperidin-1-yl}-pyrimidine-5-carbonitrile (32.7 mg; 0.06 mmol; 40.3%). LC-MS: (M+1=529, obsd.=529).

4-Amino-6-{4-[1-[2-(cyclopropylmethyl-amino)-ethyl]-4-(4-fluoro-3-trifluoromethyl-phenyl)-1H-imidazol-2-yl]-piperidin-1-yl}-pyrimidine-5-carboxylic acid amide ("359")

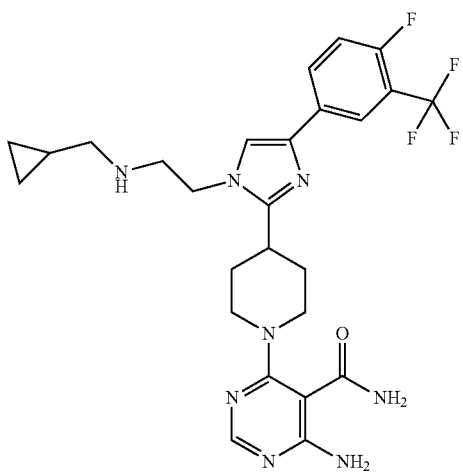 [SMILES: NC(=O)c1c(N)ncnc1N1CCC(c2nc(-c3ccc(F)c(C(F)(F)F)c3)cn2CCNCC2CC2)CC1]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-{4-[1-[2-(cyclopropylmethyl-amino)-ethyl]-4-(4-fluoro-3-trifluoromethyl-phenyl)-1H-imidazol-2-yl]-piperidin-1-yl}-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=547, obsd.=547).

4-Amino-6-(4-{4-(4-fluoro-3-trifluoromethyl-phenyl)-1-[2-(isopropyl-methyl-amino)-ethyl]-1H-imidazol-2-yl}-piperidin-1-yl)-pyrimidine-5-carbonitrile ("360")

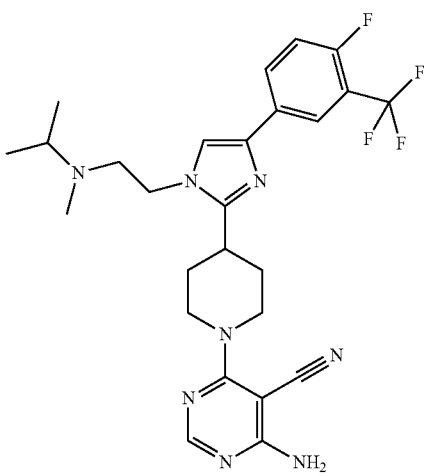 [SMILES: CC(C)N(C)CCn1cc(-c2ccc(F)c(C(F)(F)F)c2)nc1C1CCN(c2ncnc(N)c2C#N)CC1]

The title compound was prepared in an analogous manner as 4-Amino-6-{4-[1-[2-(cyclopropylmethyl-amino)-ethyl]-4-(4-fluoro-3-trifluoromethyl-phenyl)-1H-imidazol-2-yl]-piperidin-1-yl}-pyrimidine-5-carbonitrile using N-isopropyl-N-methylamine instead of cyclopropylmethylamine. LC-MS: (M+1=531, obsd.=531).

4-Amino-6-(4-{4-(4-fluoro-3-trifluoromethyl-phenyl)-1-[2-(isopropyl-methyl-amino)-ethyl]-1H-imidazol-2-yl}-piperidin-1-yl)-pyrimidine-5-carboxylic acid amide ("361")

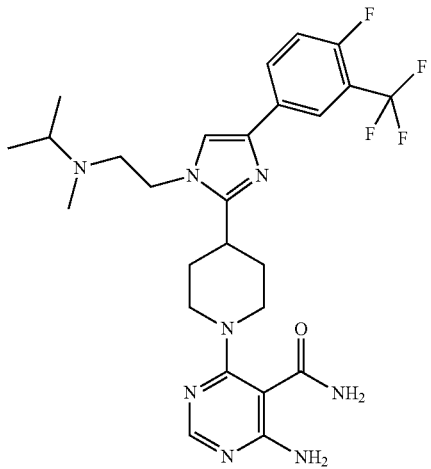 [SMILES: CC(C)N(C)CCn1cc(-c2ccc(F)c(C(F)(F)F)c2)nc1C1CCN(c2ncnc(N)c2C(N)=O)CC1]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-(4-{4-(4-fluoro-3-trifluoromethyl-phenyl)-1-[2-(isopropyl-methyl-amino)-ethyl]-1H-imidazol-2-yl}-piperidin-1-yl)-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=549, obsd.=549).

4-Amino-6-{4-[1-{2-[(2-dimethylamino-ethyl)-methyl-amino]-ethyl}-4-(4-fluoro-3-trifluoromethyl-phenyl)-1H-imidazol-2-yl]-piperidin-1-yl}-pyrimidine-5-carbonitrile ("362")

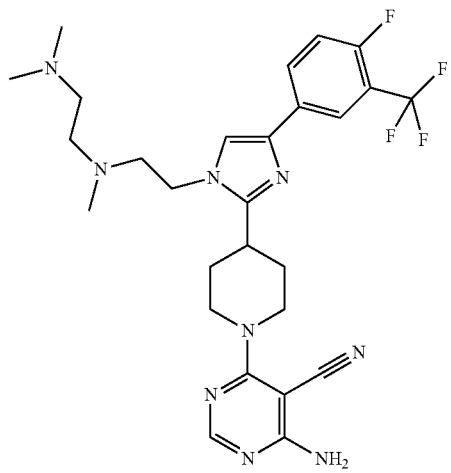 [SMILES: CN(C)CCN(C)CCn1cc(-c2ccc(F)c(C(F)(F)F)c2)nc1C1CCN(c2ncnc(N)c2C#N)CC1]

The title compound was prepared in an analogous manner as 4-Amino-6-{4-[1-[2-(cyclopropylmethyl-amino)-ethyl]-4-(4-fluoro-3-trifluoromethyl-phenyl)-1H-imidazol-2-yl]-piperidin-1-yl}-pyrimidine-5-carbonitrile using N,N,N'-trimethylethylenediamine instead of cyclopropylmethylamine. LC-MS: (M+1=560, obsd.=560).

4-Amino-6-[4-(4-(4-fluoro-3-trifluoromethyl-phenyl)-1-{2-[(2-methoxy-ethyl)-methyl-amino]-ethyl}-1H-imidazol-2-yl)-piperidin-1-yl]-pyrimidine-5-carbonitrile ("363")

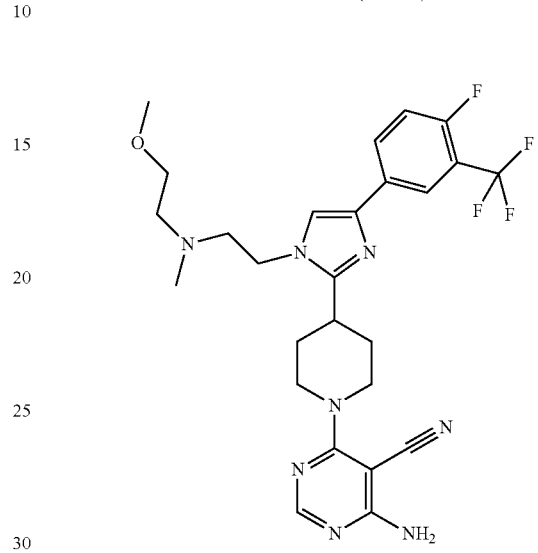

The title compound was prepared in an analogous manner as 4-Amino-6-{4-[1-[2-(cyclopropylmethyl-amino)-ethyl]-4-(4-fluoro-3-trifluoromethyl-phenyl)-1H-imidazol-2-yl]-piperidin-1-yl}-pyrimidine-5-carbonitrile using N-(2-methoxyethyl)methylamine instead of cyclopropylmethylamine. LC-MS: (M+1=547, obsd.=547).

4-Amino-6-(4-{4-(4-fluoro-3-trifluoromethyl-phenyl)-1-[2-(2-methoxy-ethylamino)-ethyl]-1H-imidazol-2-yl}-piperidin-1-yl)-pyrimidine-5-carbonitrile ("364")

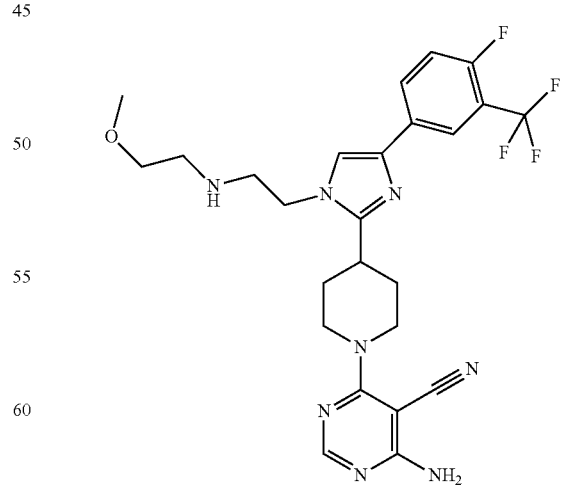

The title compound was prepared in an analogous manner as 4-Amino-6-{4-[1-[2-(cyclopropylmethyl-amino)-ethyl]-4-(4-fluoro-3-trifluoromethyl-phenyl)-1H-imidazol-2-yl]- piperidin-1-yl}-pyrimidine-5-carbonitrile using 2-methoxy-ethylamine instead of cyclopropylmethylamine. LC-MS: (M+1=533, obsd.=533).

4-Amino-6-{4-[1-{2-[(2-dimethylamino-ethyl)-methyl-amino]-ethyl}-4-(4-fluoro-3-trifluoromethyl-phenyl)-1H-imidazol-2-yl]-piperidin-1-yl}-pyrimidine-5-carboxylic acid amide ("365")

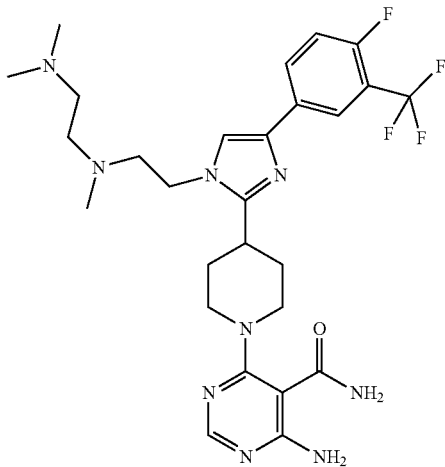 [SMILES: CN(C)CCN(C)CCn1cc(-c2ccc(F)c(C(F)(F)F)c2)nc1C1CCN(c2ncnc(N)c2C(N)=O)CC1]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-(4-{4-(4-fluoro-3-trifluoromethyl-phenyl)-1-[2-(isopropyl-methyl-amino)-ethyl]-1H-imidazol-2-yl}-piperidin-1-yl)-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=549, obsd.=549).

4-Amino-6-[4-(4-(4-fluoro-3-trifluoromethyl-phenyl)-1-{2-[(2-methoxy-ethyl)-methyl-amino]-ethyl}-1H-imidazol-2-yl)-piperidin-1-yl]-pyrimidine-5-carboxylic acid amide ("366")

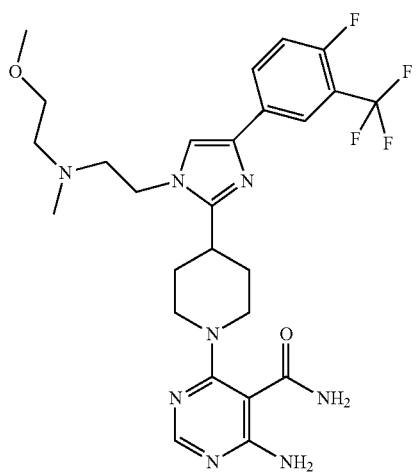 [SMILES: COCCN(C)CCn1cc(-c2ccc(F)c(C(F)(F)F)c2)nc1C1CCN(c2ncnc(N)c2C(N)=O)CC1]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-[4-(4-(4-fluoro-3-trifluoromethyl-phenyl)-1-{2-[(2-methoxy-ethyl)-methyl-amino]-ethyl}-1H-imidazol-2-yl)-piperidin-1-yl]-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=565, obsd.=565).

4-Amino-6-(4-{4-(4-fluoro-3-trifluoromethyl-phenyl)-1-[2-(2-methoxy-ethylamino)-ethyl]-1H-imidazol-2-yl}-piperidin-1-yl)-pyrimidine-5-carboxylic acid amide ("367")

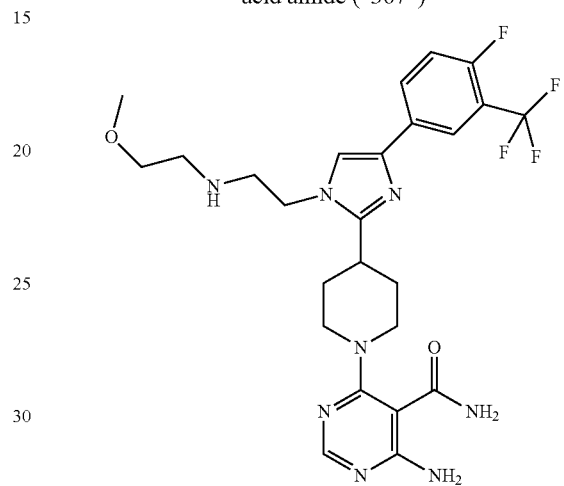

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-(4-{4-(4-fluoro-3-trifluoromethyl-phenyl)-1-[2-(2-methoxy-ethylamino)-ethyl]-1H-imidazol-2-yl}-piperidin-1-yl)-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=551, obsd.=551).

4-Amino-6-{4[1-[2-(benzyl-methyl-amino)-ethyl]-4-(4-fluoro-3-trifluoromethyl-phenyl)-1H-imidazol-2-yl]-piperidin-1-yl}-pyrimidine-5-carboxylic acid amide ("368")

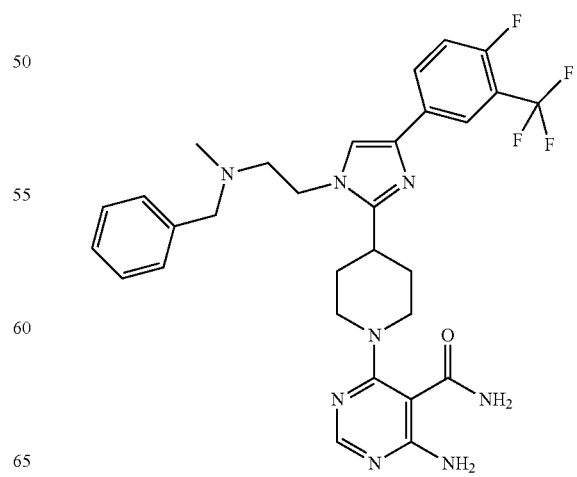

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-{4-[1-[2-(benzyl-methyl-amino)-ethyl]-4-(4-fluoro-3-trifluoromethyl-phenyl)-1H-imidazol-2-yl]-piperidin-1-yl}-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=597, obsd.=597).

4-Amino-6-{4-[4-(4-fluoro-3-trifluoromethyl-phenyl)-1-(2-isopropylamino-ethyl)-1H-imidazol-2-yl]-piperidin-1-yl}-pyrimidine-5-carbonitrile ("369")

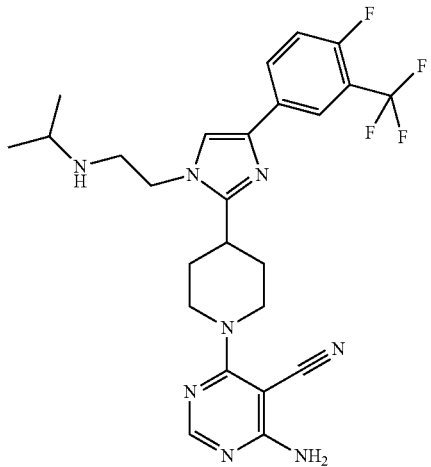 [SMILES: CC(C)NCCn1cc(-c2ccc(F)c(C(F)(F)F)c2)nc1C1CCN(c2ncnc(N)c2C#N)CC1]

The title compound was prepared in an analogous manner as 4-Amino-6-{4-[1-[2-(cyclopropylmethyl-amino)-ethyl]-4-(4-fluoro-3-trifluoromethyl-phenyl)-1H-imidazol-2-yl]-piperidin-1-yl}-pyrimidine-5-carbonitrile using isopropylamine instead of cyclopropylmethylamine. LC-MS: (M+1=517, obsd.=517).

4-Amino-6-{4-[4-(4-fluoro-3-trifluoromethyl-phenyl)-1-(2-isopropylamino-ethyl)-1H-imidazol-2-yl]-piperidin-1-yl}-pyrimidine-5-carboxylic acid amide ("370")

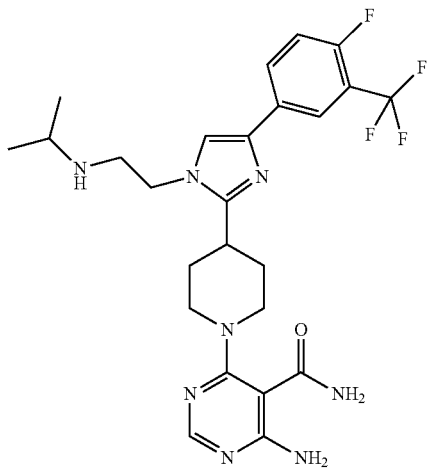 [SMILES: CC(C)NCCn1cc(-c2ccc(F)c(C(F)(F)F)c2)nc1C1CCN(c2ncnc(N)c2C(N)=O)CC1]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-{4-[4-(4-fluoro-3-trifluoromethyl-phenyl)-1-(2-isopropylamino-ethyl)-1H-imidazol-2-yl]-piperidin-1-yl}-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=535, obsd.=535).

4-Amino-6-(4-{4-(4-fluoro-3-trifluoromethyl-phenyl)-1-[2-(2-methoxy-1-methyl-ethylamino)-ethyl]-1H-imidazol-2-yl}-piperidin-1-yl)-pyrimidine-5-carboxylic acid amide ("371")

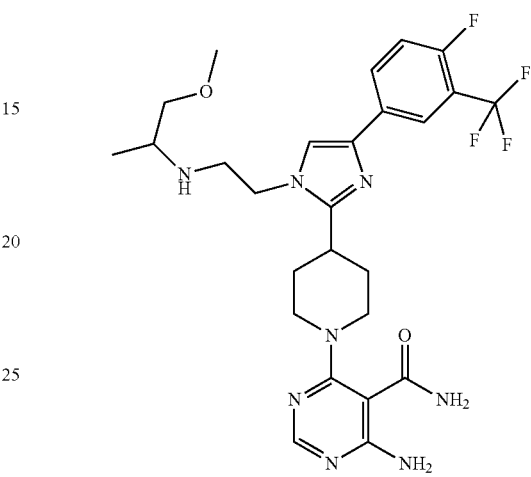

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-(4-{4-(4-fluoro-3-trifluoromethyl-phenyl)-1-[2-(2-methoxy-1-methyl-ethylamino)-ethyl]-1H-imidazol-2-yl}-piperidin-1-yl)-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=565, obsd.=565).

4-Amino-6-{4-[4-(4-fluoro-3-trifluoromethyl-phenyl)-1-(2-isobutylamino-ethyl)-1H-imidazol-2-yl]-piperidin-1-yl}-pyrimidine-5-carbonitrile ("372")

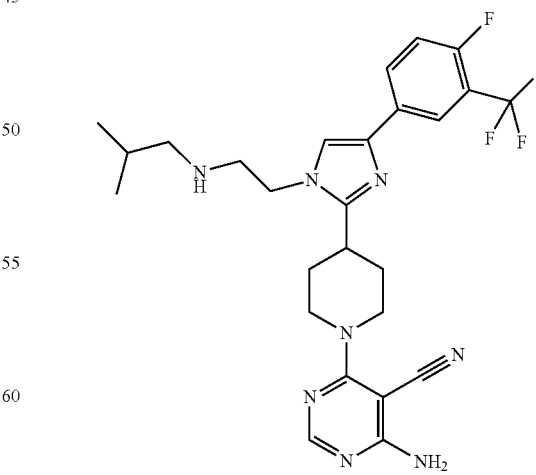

The title compound was prepared in an analogous manner as 4-Amino-6-{4-[1-[2-(cyclopropylmethyl-amino)-ethyl]-4-(4-fluoro-3-trifluoromethyl-phenyl)-1H-imidazol-2-yl]- piperidin-1-yl}-pyrimidine-5-carbonitrile using isobutylamine instead of cyclopropylmethylamine. LC-MS: (M+1=531, obsd.=531).

4-Amino-6-{4-[4-(4-fluoro-3-trifluoromethyl-phenyl)-1-(2-isobutylamino-ethyl)-1H-imidazol-2-yl]-piperidin-1-yl}-pyrimidine-5-carboxylic acid amide ("373")

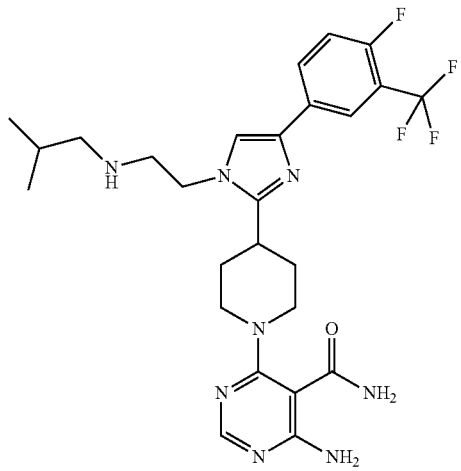 [SMILES: CC(C)CNCCn1cc(-c2ccc(F)c(C(F)(F)F)c2)nc1C1CCN(c2ncnc(N)c2C(N)=O)CC1]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-{4-[4-(4-fluoro-3-trifluoromethyl-phenyl)-1-(2-isobutylamino-ethyl)-1H-imidazol-2-yl]-piperidin-1-yl}-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=549, obsd.=549).

4-Amino-6-{4-[4-(4-fluoro-3-trifluoromethyl-phenyl)-1-(2-methylamino-ethyl)-1H-imidazol-2-yl]-piperidin-1-yl}-pyrimidine-5-carbonitrile ("374")

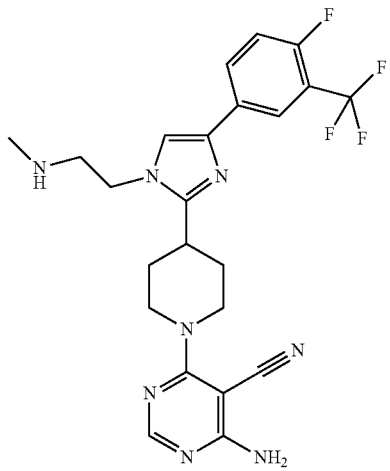 [SMILES: CNCCn1cc(-c2ccc(F)c(C(F)(F)F)c2)nc1C1CCN(c2ncnc(N)c2C#N)CC1]

The title compound was prepared in an analogous manner as 4-Amino-6-{4-[1-[2-(cyclopropylmethyl-amino)-ethyl]-4-(4-fluoro-3-trifluoromethyl-phenyl)-1H-imidazol-2-yl]-piperidin-1-yl}-pyrimidine-5-carbonitrile using methylamine instead of cyclopropylmethylamine. LC-MS: (M+1=489, obsd.=489).

4-Amino-6-{4-[1-(2-tert-butylamino-ethyl)-4-(4-fluoro-3-trifluoromethyl-phenyl)-1H-imidazol-2-yl]-piperidin-1-yl}-pyrimidine-5-carbonitrile ("375")

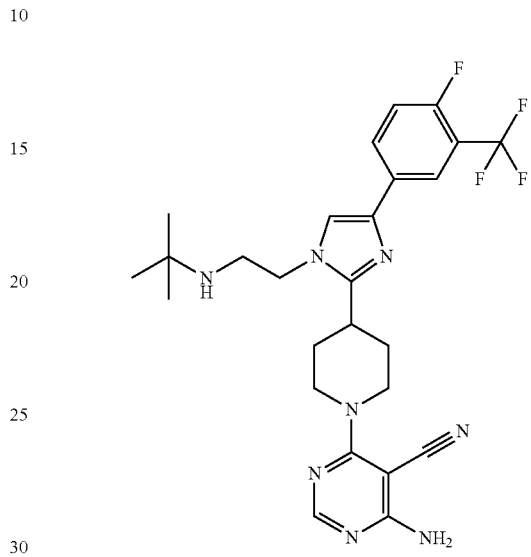

The title compound was prepared in an analogous manner as 4-Amino-6-{4-[1-[2-(cyclopropylmethyl-amino)-ethyl]-4-(4-fluoro-3-trifluoromethyl-phenyl)-1H-imidazol-2-yl]-piperidin-1-yl}-pyrimidine-5-carbonitrile using tert-butylamine instead of cyclopropylmethylamine. LC-MS: (M+1=531, obsd.=531).

4-Amino-6-{4-[4-(4-fluoro-3-trifluoromethyl-phenyl)-1-(2-methylamino-ethyl)-1H-imidazol-2-yl]-piperidin-1-yl}-pyrimidine-5-carboxylic acid amide ("376")

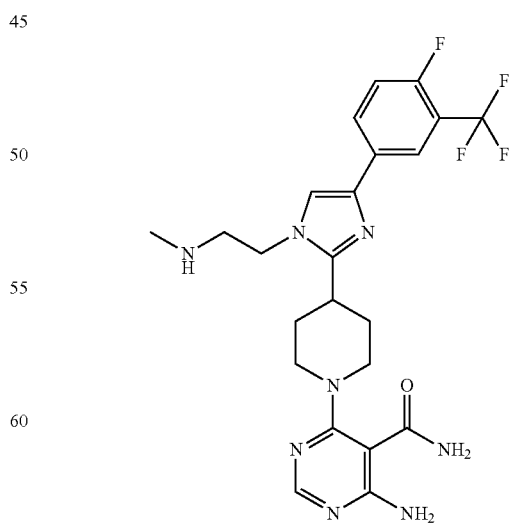

The title compound was prepared in an analogous manner as 4-Amino-6-{4-[4-(4-fluoro-3-trifluoromethyl-phenyl)-1- methyl-1H-imidazol-2-yl]-piperidin-1-yl}-pyrimidine-5-carboxamide using 4-Amino-6-{4-[4-(4-fluoro-3-trifluoromethyl-phenyl)-1-(2-methylamino-ethyl)-1H-imidazol-2-yl]-piperidin-1-yl}-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=507, obsd.=507).

4-Amino-6-{4-[1-(2-tert-butylamino-ethyl)-4-(4-fluoro-3-trifluoromethyl-phenyl)-1H-imidazol-2-yl]-piperidin-1-yl}-pyrimidine-5-carboxylic acid amide ("377")

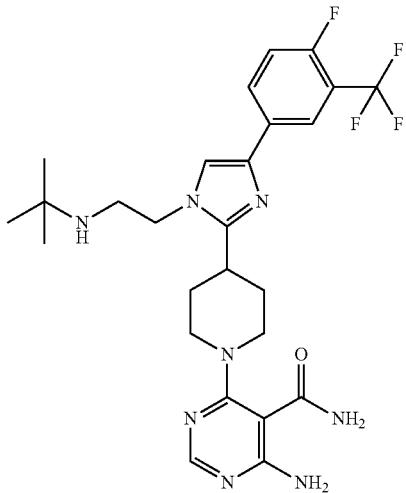 [SMILES: CC(C)(C)NCCn1cc(-c2ccc(F)c(C(F)(F)F)c2)nc1C1CCN(c2ncnc(N)c2C(N)=O)CC1]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-{4-[1-(2-tert-butylamino-ethyl)-4-(4-fluoro-3-trifluoromethyl-phenyl)-1H-imidazol-2-yl]-piperidin-1-yl}-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=549, obsd.=549).

4-Amino-6-{4-[1-[2-(cyclopropylmethyl-amino)-ethyl]-4-(4-fluoro-3-methyl-phenyl)-1H-imidazol-2-yl]-piperidin-1-yl}-pyrimidine-5-carbonitrile ("378")

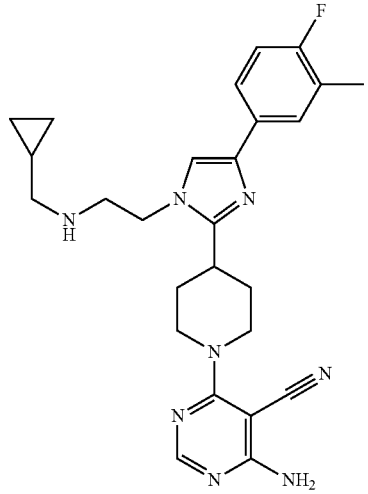 [SMILES: Cc1cc(-c2cn(CCNCC3CC3)c(C3CCN(c4ncnc(N)c4C#N)CC3)n2)ccc1F]

The title compound was prepared in an analogous manner as 4-Amino-6-{4-[1-[2-(cyclopropylmethyl-amino)-ethyl]-4-(4-fluoro-3-trifluoromethyl-phenyl)-1H-imidazol-2-yl]-piperidin-1-yl}-pyrimidine-5-carbonitrile using methanesulfonic acid 2-[2-[1-(6-amino-5-cyano-pyrimidin-4-yl)-piperidin-4-yl]-4-(4-fluoro-3-methyl-phenyl)-imidazol-1-yl]-ethyl ester instead of methanesulfonic acid 2-[2-[1-(6-amino-5-cyano-pyrimidin-4-yl)-piperidin-4-yl]-4-(4-fluoro-3-trifluoromethyl-phenyl)-imidazol-1-yl]-ethyl ester. LC-MS: (M+1=475, obsd.=475).

4-Amino-6-(4-{4-(4-fluoro-3-methyl-phenyl)-1-[2-(isopropyl-methyl-amino)-ethyl]-1H-imidazol-2-yl}-piperidin-1-yl)-pyrimidine-5-carbonitrile ("379")

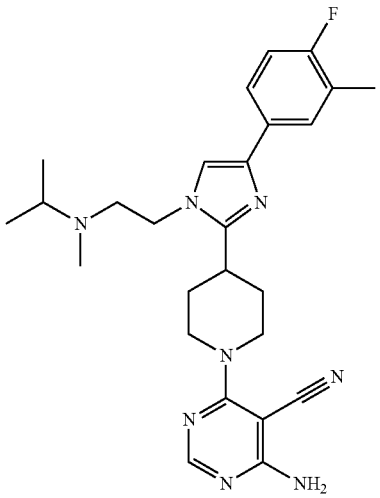 [SMILES: Cc1cc(-c2cn(CCN(C)C(C)C)c(C3CCN(c4ncnc(N)c4C#N)CC3)n2)ccc1F]

The title compound was prepared in an analogous manner as 4-Amino-6-{4-[1-[2-(cyclopropylmethyl-amino)-ethyl]-4-(4-fluoro-3-methyl-phenyl)-1H-imidazol-2-yl]-piperidin-1-yl}-pyrimidine-5-carbonitrile using N-isobutyl-Nmethylamine instead of cyclopropylmethylamine. LC-MS: (M+1=477, obsd.=477).

4-Amino-6-{4-[4-(4-fluoro-3-methyl-phenyl)-1-(2-isopropylamino-ethyl)-1H-imidazol-2-yl]-piperidin-1-yl}-pyrimidine-5-carbonitrile ("380")

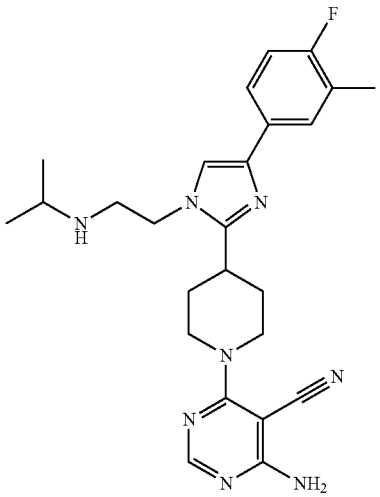 [SMILES: Cc1cc(-c2cn(CCNC(C)C)c(C3CCN(c4ncnc(N)c4C#N)CC3)n2)ccc1F]

The title compound was prepared in an analogous manner as 4-Amino-6-{4-[1-[2-(cyclopropylmethyl-amino)-ethyl]-

4-(4-fluoro-3-methyl-phenyl)-1H-imidazol-2-yl]-piperidin-1-yl}-pyrimidine-5-carbonitrile using isopropylamine instead of cyclopropylmethylamine. LC-MS: (M+1=463, obsd.=463).

4-Amino-6-{4-[1-(2-cyclopentylamino-ethyl)-4-(4-fluoro-3-trifluoromethyl-phenyl)-1H-imidazol-2-yl]-piperidin-1-yl}-pyrimidine-5-carbonitrile ("381")

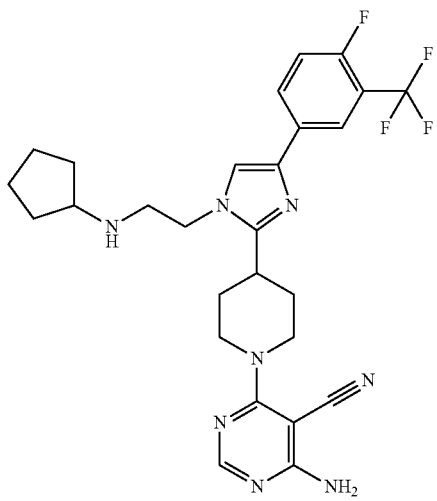 [SMILES: N#Cc1c(N)ncnc1N1CCC(c2nc(-c3ccc(F)c(C(F)(F)F)c3)cn2CCNC2CCCC2)CC1]

The title compound was prepared in an analogous manner as 4-Amino-6-{4-[1-[2-(cyclopropylmethyl-amino)-ethyl]-4-(4-fluoro-3-trifluoromethyl-phenyl)-1H-imidazol-2-yl]-piperidin-1-yl}-pyrimidine-5-carbonitrile using cyclopentylamine instead of cyclopropylmethylamine. LC-MS: (M+1=543, obsd.=543).

4-Amino-6-{4-[1-[2-(1,1-dimethyl-propylamino)-ethyl]-4-(4-fluoro-3-trifluoromethyl-phenyl)-1H-imidazol-2-yl]-piperidin-1-yl}-pyrimidine-5-carbonitrile ("382")

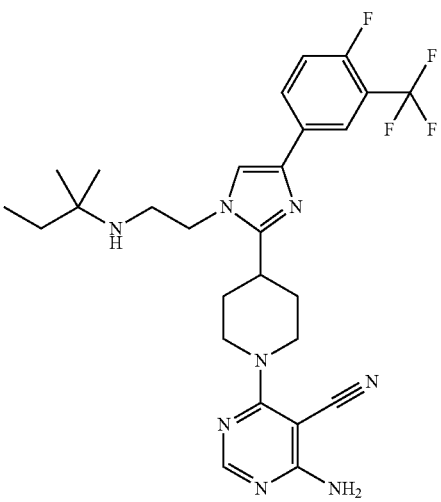 [SMILES: CCC(C)(C)NCCn1cc(-c2ccc(F)c(C(F)(F)F)c2)nc1C1CCN(c2ncnc(N)c2C#N)CC1]

The title compound was prepared in an analogous manner as 4-Amino-6-{4-[1-[2-(cyclopropylmethyl-amino)-ethyl]-

4-(4-fluoro-3-trifluoromethyl-phenyl)-1H-imidazol-2-yl]-piperidin-1-yl}-pyrimidine-5-carbonitrile using tert-amylamine instead of cyclopropylmethylamine. LC-MS: (M+1=545, obsd.=545).

4-Amino-6-{4-[1-[2-(cyclopropylmethyl-amino)-ethyl]-4-(4-fluoro-3-methyl-phenyl)-1H-imidazol-2-yl]-piperidin-1-yl}-pyrimidine-5-carboxylic acid amide ("383")

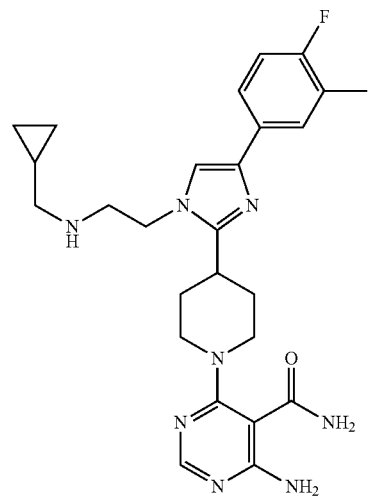 [SMILES: Cc1cc(-c2cn(CCNCC3CC3)c(C3CCN(c4ncnc(N)c4C(N)=O)CC3)n2)ccc1F]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-{4-[1-[2-(cyclopropylmethyl-amino)-ethyl]-4-(4-fluoro-3-methyl-phenyl)-1H-imidazol-2-yl]-piperidin-1-yl}-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=493, obsd.=493).

4-Amino-6-{4-[4-(4-fluoro-3-methyl-phenyl)-1-(2-hydroxy-ethyl)-1H-imidazol-2-yl]-piperidin-1-yl}-pyrimidine-5-carbonitrile ("384")

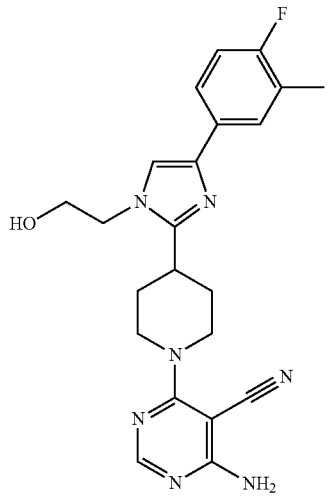 [SMILES: Cc1cc(-c2cn(CCO)c(C3CCN(c4ncnc(N)c4C#N)CC3)n2)ccc1F]

The title compound was prepared in an analogous manner as 5-Bromo-6-{4-[4-(4-fluoro-3-trifluoromethyl-phenyl)-1-methyl-1H-imidazol-2-yl]-piperidin-1-yl}-pyrimidin-4-ylamine using 2-[4-(4-Fluoro-3-methyl-phenyl)-2-piperidin- 4-yl-imidazol-1-yl]-ethanol trifluoroacetate instead of 4-[4-(4-fluoro-3-trifluoromethyl-phenyl)-1-methyl-1h-imidazol-2-yl]-piperidine. LC-MS: (M+1=422, obsd.=422).

4-Amino-6-(4-{4-(4-fluoro-3-methyl-phenyl)-1-[2-(isopropyl-methyl-amino)-ethyl]-1H-imidazol-2-yl}-piperidin-1-yl)-pyrimidine-5-carboxylic acid amide ("385")

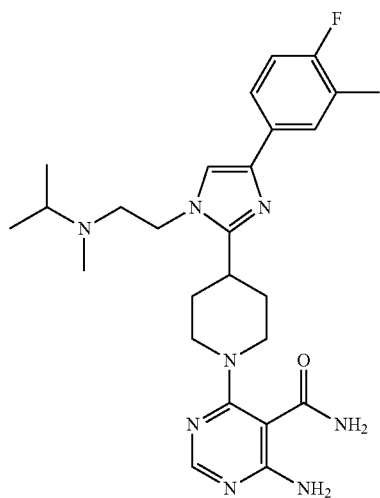 [SMILES: Cc1cc(-c2cn(CCN(C)C(C)C)c(C3CCN(c4ncnc(N)c4C(N)=O)CC3)n2)ccc1F]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-(4-{4-(4-fluoro-3-methyl-phenyl)-1-[2-(isopropyl-methyl-amino)-ethyl]-1H-imidazol-2-yl}-piperidin-1-yl)-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=495, obsd.=495).

4-Amino-6-{4-[4-(4-fluoro-3-methyl-phenyl)-1-(2-isopropylamino-ethyl)-1H-imidazol-2-yl]-piperidin-1-yl}-pyrimidine-5-carboxylic acid amide ("386")

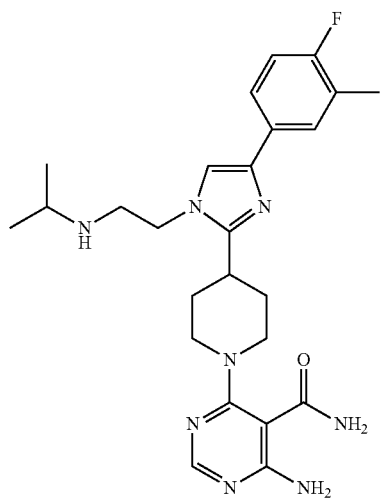 [SMILES: Cc1cc(-c2cn(CCNC(C)C)c(C3CCN(c4ncnc(N)c4C(N)=O)CC3)n2)ccc1F]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-{4-[4-(4-fluoro-3-methyl-phenyl)-1-(2-isopropylamino-ethyl)-1H-imidazol-2-yl]-piperidin-1-yl}-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=481, obsd.=481).

4-Amino-6-{4-[1-(2-cyclopentylamino-ethyl)-4-(4-fluoro-3-trifluoromethyl-phenyl)-1H-imidazol-2-yl]-piperidin-1-yl}-pyrimidine-5-carboxylic acid amide ("387")

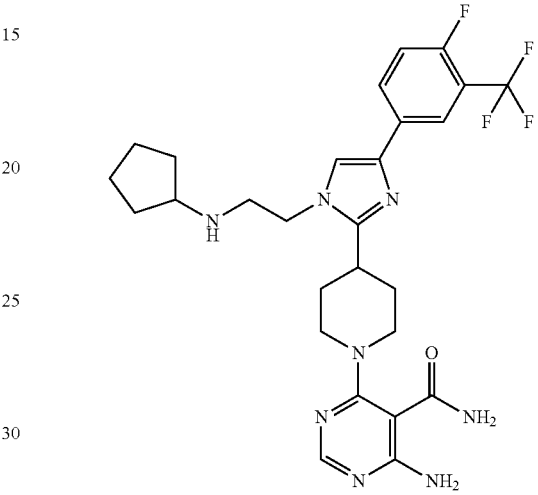

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-{4-[1-(2-cyclopentylamino-ethyl)-4-(4-fluoro-3-trifluoromethyl-phenyl)-1H-imidazol-2-yl]-piperidin-1-yl}-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=561, obsd.=561).

4-Amino-6-{4-[1-[2-(1,1-dimethyl-propylamino)-ethyl]-4-(4-fluoro-3-trifluoromethyl-phenyl)-1H-imidazol-2-yl]-piperidin-1-yl}-pyrimidine-5-carboxylic acid amide ("388")

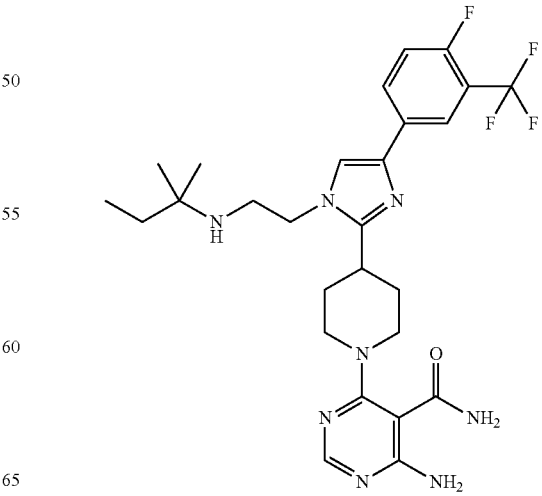

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-{4-[1-[2-(1,1-dimethyl-propylamino)-ethyl]-4-(4-fluoro-3-trifluoromethyl-phenyl)-1H-imidazol-2-yl]-piperidin-1-yl}-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=563, obsd.=563).

4-Amino-6-{4-[1-(2-cyclopentylamino-ethyl)-4-(4-fluoro-3-methyl-phenyl)-1H-imidazol-2-yl]-piperidin-1-yl}-pyrimidine-5-carbonitrile ("389")

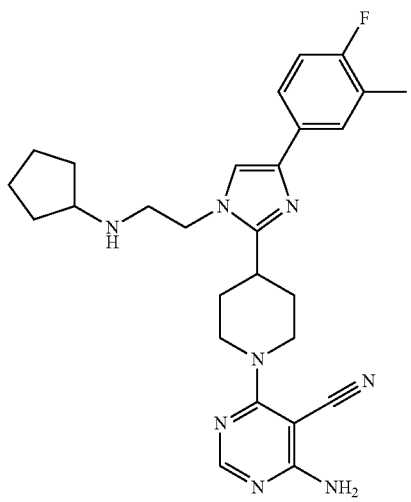 [SMILES: Cc1cc(-c2cn(CCNC3CCCC3)c(C3CCN(c4ncnc(N)c4C#N)CC3)n2)ccc1F]

The title compound was prepared in an analogous manner as 4-Amino-6-{4-[1-[2-(cyclopropylmethyl-amino)-ethyl]-4-(4-fluoro-3-methyl-phenyl)-1H-imidazol-2-yl]-piperidin-1-yl}-pyrimidine-5-carbonitrile using cyclopentylamine instead of cyclopropylmethylamine. LC-MS: (M+1=489, obsd.=489).

4-Amino-6-{4-[4-(4-fluoro-3-methyl-phenyl)-1-(2-isobutylamino-ethyl)-1H-imidazol-2-yl]-piperidin-1-yl}-pyrimidine-5-carbonitrile ("390")

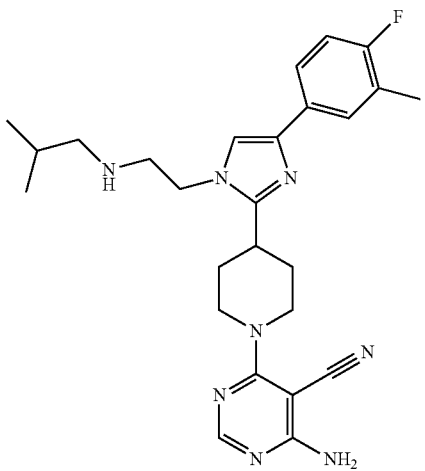 [SMILES: Cc1cc(-c2cn(CCNCC(C)C)c(C3CCN(c4ncnc(N)c4C#N)CC3)n2)ccc1F]

The title compound was prepared in an analogous manner as 4-Amino-6-{4-[1-[2-(cyclopropylmethyl-amino)-ethyl]-4-(4-fluoro-3-methyl-phenyl)-1H-imidazol-2-yl]-piperidin-1-yl}-pyrimidine-5-carbonitrile using isobutylamine instead of cyclopropylmethylamine. LC-MS: (M+1=477, obsd.=477).

4-Amino-6-{4-[1-(2-cyclopentylamino-ethyl)-4-(4-fluoro-3-methyl-phenyl)-1H-imidazol-2-yl]-piperidin-1-yl}-pyrimidine-5-carboxylic acid amide ("391")

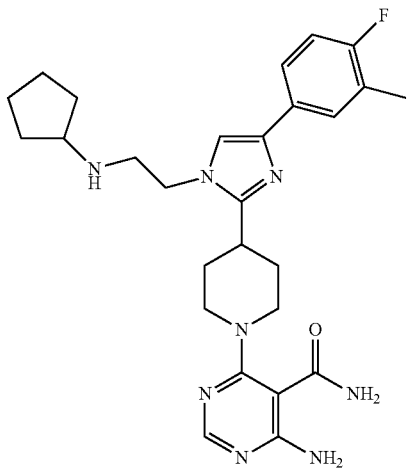 [SMILES: Cc1cc(-c2cn(CCNC3CCCC3)c(C3CCN(c4ncnc(N)c4C(N)=O)CC3)n2)ccc1F]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-{4-[1-(2-cyclopentylamino-ethyl)-4-(4-fluoro-3-methyl-phenyl)-1H-imidazol-2-yl]-piperidin-1-yl}-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=507, obsd.=507).

4-Amino-6-{4-[4-(4-fluoro-3-methyl-phenyl)-1-(2-isobutylamino-ethyl)-1H-imidazol-2-yl]-piperidin-1-yl}-pyrimidine-5-carboxylic acid amide ("392")

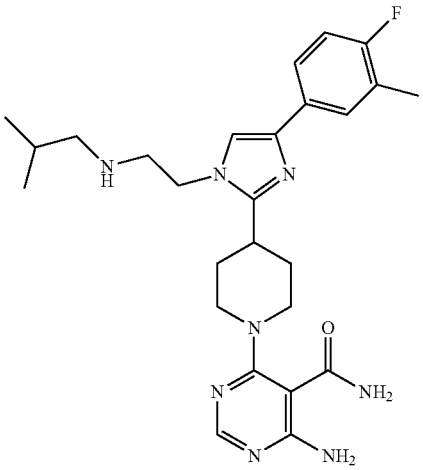 [SMILES: Cc1cc(-c2cn(CCNCC(C)C)c(C3CCN(c4ncnc(N)c4C(N)=O)CC3)n2)ccc1F]

The title compound was prepared in an analogous manner as 4-Amino-6-{4-[4-(4-fluoro-3-trifluoromethyl-phenyl)-1- methyl-1H-imidazol-2-yl]-piperidin-1-yl}-pyrimidine-5-carboxamide using 4-Amino-6-{4-[4-(4-fluoro-3-methyl-phenyl)-1-(2-isobutylamino-ethyl)-1H-imidazol-2-yl]-piperidin-1-yl}-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=495, obsd.=495).

4-Amino-6-{4-[4-(4-fluoro-3-methyl-phenyl)-1-(2-hydroxy-ethyl)-1H-imidazol-2-yl]-piperidin-1-yl}-pyrimidine-5-carboxylic acid amide ("393")

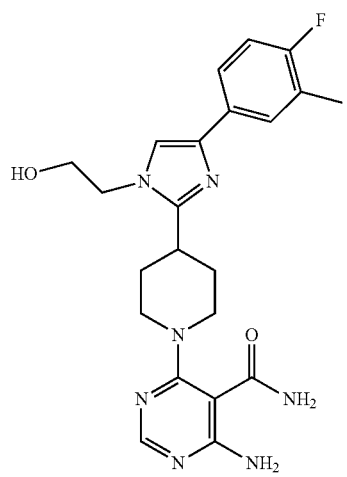 [SMILES: Cc1cc(-c2cn(CCO)c(C3CCN(c4ncnc(N)c4C(N)=O)CC3)n2)ccc1F]

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-{4-[4-(4-fluoro-3-methyl-phenyl)-1-(2-hydroxy-ethyl)-1H-imidazol-2-yl]-piperidin-1-yl}-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=440, obsd.=440).

4-Amino-6-{4-[4-(4-fluoro-3-methyl-phenyl)-1-(2-methylamino-ethyl)-1H-imidazol-2-yl]-piperidin-1-yl}-pyrimidine-5-carbonitrile ("394")

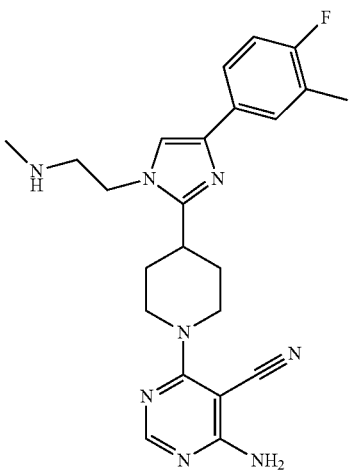

The title compound was prepared in an analogous manner as 4-Amino-6-{4-[1-[2-(cyclopropylmethyl-amino)-ethyl]-4-(4-fluoro-3-methyl-phenyl)-1H-imidazol-2-yl]-piperidin- 1-yl}-pyrimidine-5-carbonitrile using methylamine instead of cyclopropylmethylamine. LC-MS: (M+1=435, obsd.=435).

4-Amino-6-{4-[4-(4-fluoro-3-trifluoromethyl-phenyl)-1-(2-hydroxy-ethyl)-1H-imidazol-2-yl]-piperidin-1-yl}-pyrimidine-5-carboxylic acid amide ("395")

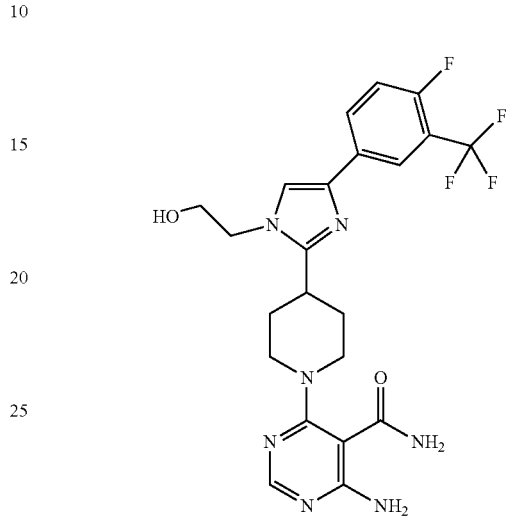

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-{4-[4-(4-fluoro-3-trifluoromethyl-phenyl)-1-(2-hydroxy-ethyl)-1H-imidazol-2-yl]-piperidin-1-yl}-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=494, obsd.=494).

2-[2-[1-(6-Amino-5-ethoxy-pyrimidin-4-yl)-piperidin-4-yl]-4-(4-fluoro-3-methyl-phenyl)-imidazol-1-yl]-ethanol ("396")

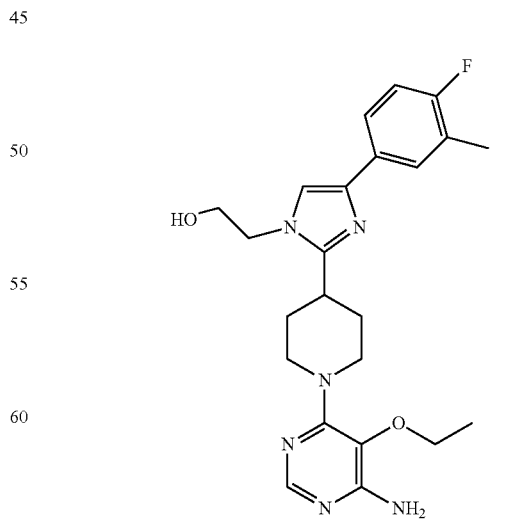

The title compound was prepared in an analogous manner as 5-Bromo-6-{4-[4-(4-fluoro-3-trifluoromethyl-phenyl)-1- methyl-1H-imidazol-2-yl]-piperidin-1-yl}-pyrimidin-4-ylamine using 6-chloro-5-ethoxy-pyrimidin-4-ylamine instead of 6-chloro-5-bromo-pyrimidin-4-ylamine. LC-MS: (M+1=441, obsd.=441).

4-Amino-6-{4-[4-(4-fluoro-3-methyl-phenyl)-1-(2-methylamino-ethyl)-1H-imidazol-2-yl]-piperidin-1-yl}-pyrimidine-5-carboxylic acid amide ("397")

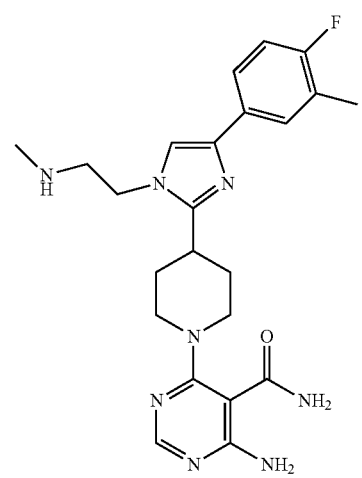

The title compound was prepared in an analogous manner as 4-Amino-6-{4-[4-(4-fluoro-3-trifluoromethyl-phenyl)-1-methyl-1H-imidazol-2-yl]-piperidin-1-yl}-pyrimidine-5-carboxamide using 4-Amino-6-{4-[4-(4-fluoro-3-methyl-phenyl)-1-(2-methylamino-ethyl)-1H-imidazol-2-yl]-piperidin-1-yl}-pyrimidine-5-carbonitrile instead of 4-amino-6-(4-{4-[4-fluoro-3-(trifluoromethyl)phenyl]-1-methyl-1H-imidazol-2-yl}piperidin-1-yl)pyrimidine-5-carbonitrile. LC-MS: (M+1=453, obsd.=453).

5-Ethoxy-6-{4-[4-(4-fluoro-3-trifluoromethyl-phenyl)-1-(2-isopropylamino-ethyl)-1H-imidazol-2-yl]-piperidin-1-yl}-pyrimidin-4-ylamine ("398")

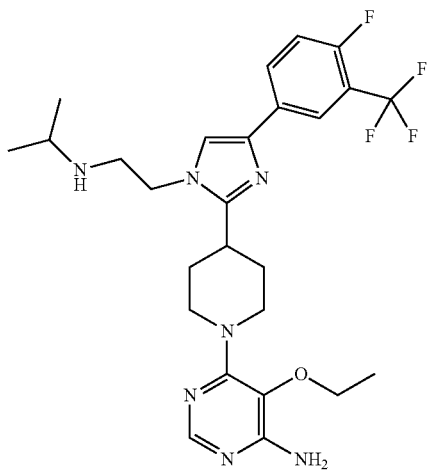 [SMILES: CCOc1c(N)ncnc1N1CCC(c2nc(-c3ccc(F)c(C(F)(F)F)c3)cn2CCNC(C)C)CC1]

The title compound was prepared in an analogous manner as 4-Amino-6-{4-[1-[2-(cyclopropylmethyl-amino)-ethyl]-4-(4-fluoro-3-methyl-phenyl)-1H-imidazol-2-yl]-piperidin-1-yl}-pyrimidine-5-carbonitrile using isopropylamine and methanesulfonic acid 2-[2-[1-(6-amino-5-ethoxy-pyrimidin-4-yl)-piperidin-4-yl]-4-(4-fluoro-3-trifluoromethyl-phenyl)-imidazol-1-yl]-ethyl ester instead of cyclopropylmethylamine and methanesulfonic acid 2-[2-[1-(6-amino-5-cyano-pyrimidin-4-yl)-piperidin-4-yl]-4-(4-fluoro-3-trifluoromethyl-phenyl)-imidazol-1-yl]ethyl ester. LC-MS: (M+1=536, obsd.=536).

{3-[2-[1-(6-Amino-5-isopropyl-pyrimidin-4-yl)-piperidin-4-yl]-4-(4-fluoro-3-methyl-phenyl)-imidazol-1-ylmethyl]-azetidin-1-yl}-methanol ("399")

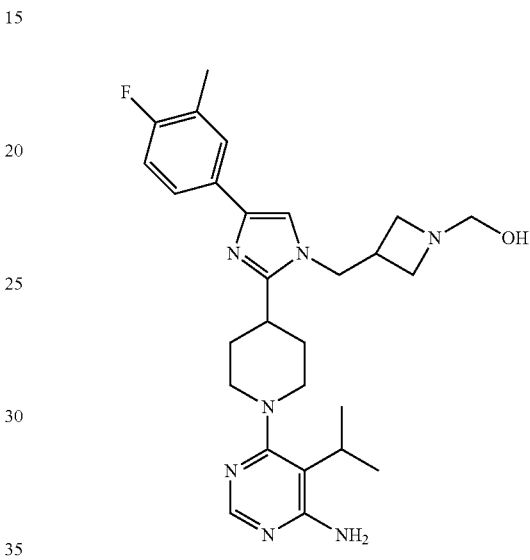

The title compound was prepared in an analogous manner as 6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine. LC-MS: (M+1=494, obsd.=494).

5-Ethyl-6-{4-[4-(4-fluoro-3-methyl-phenyl)-1-(1-methyl-azetidin-3-ylmethyl)-1H-imidazol-2-yl]-piperidin-1-yl}-pyrimidin-4-ylamine ("400")

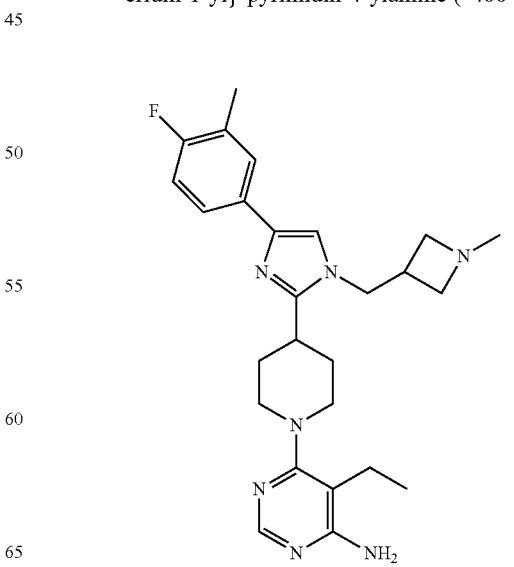

The title compound was prepared in an analogous manner as 6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine. LC-MS: (M+1=464, obsd.=464).

Biological Activity

P70S6K Enzyme Assay

P70S6K inhibitor compounds are diluted and plated in 96 well plates. A reaction mixture including the following components is then added to the compound plate to initiate the enzyme reaction; P70S6K (3 nM, T412E mutant, Millipore) is mixed with 24 μM ATP in an assay buffer containing 100 mM Hepes (pH 7.5), 5 mM MgCl2, 1 mM DTT, 0.015% Brij and 1 μM of the substrate peptide FITC-AHA-AKRRRLSS-LRA-OH (derived from the S6 ribosomal protein sequence, FITC=fluorescein isothiocyanate, AHA=6-aminohexanoic acid). The reaction is incubated for 90 min at 25° C., before the addition of 10 mM EDTA to stop the reaction. The proportion of substrate and product (phosphorylated) peptide is analysed on a Caliper Life Sciences Lab Chip 3000, using a pressure of −1.4 psi, and upstream and downstream voltages of −3000 and −700 respectively. Product peaks are resolved before substrate peaks on the resulting chromatograms.

AKT Enzyme Assay

A TTP Mosquito liquid handling instrument is used to place 125n1 of the appropriate concentration of inhibitor in 100% DMSO (for a dose response curve calculation) into each well of a 384-well plate. To this reaction components are added to a final volume of 12.5 μl:

0.1 ng/μl His-AKT (Full Length), (Invitrogen, Part # P2999, Lot #641228C).
160 uM ATP (Fluka, 02055)
1 mM DTT (Sigma, D0632)
1 mM MgCl2 (Sigma, M1028)
1 μM substrate peptide (sequence FITC-AHA-GRPRTSS-FAEG-NH2), synthesized by
Tufts Peptide Synthesis service.
100 mM HEPES pH 7.5 (Calbiochem, 391338)
0.015% Brij-35 (Sigma, B4184)

The reaction is incubated for 90 min at 25 C, and then stopped by the addition of 70 μl of Stop buffer (100 mM HEPES pH 7.5, 0.015% Brij-35, 10 mM EDTA (Sigma, E7889)).

The plate is read on a Caliper LC 3000 in an Off-Chip mobility shift assay format, using the following parameters for a 12-sipper chip: screening pressure −2.3 psi, upstream voltage −500, and downstream voltage −3000. These conditions cause unphosphorylated substrate and phosphorylated product peptide to resolve as separate peaks allowing direct measurement of percentage of conversion of substrate to product. The percent conversion can be plotted against concentration of inhibitor to produce a sigmoidal dose response curve, from which an IC50 can be calculated.

The values for the p70S6K and AKT enzyme inhibition assay for the compounds set out in the Experimental section are presented in Table 4.

TABLE 4 p70S6K and AKT Enzyme Inhibition by Compound Described by Formula (I) and Formula (II)

| Compound No. | IC$_{50}$ p70S6K (nM) | IC$_{50}$ AKT (nM) |
|---|---|---|
| 1 | 2.1 | 66 |
| 2 | 57.0 | — |
| 3 | 6.2 | 1700 |
| 4 | 31.9 | 6100 |
| 5 | 315 | — |
| 6 | 0.6 | 160 |
| 7 | 1.5 | 110 |
| 8 | 1.8 | 9.1 |
| 9 | 2.1 | 440 |
| 10 | 3.4 | 2200 |
| 11 | 4.7 | 520 |
| 12 | 87 | — |
| 13 | 7.3 | 8300 |
| 14 | 1.9 | 250 |
| 15 | 11 | 150 |
| 16 | 21 | — |
| 17 | 2.7 | 2.7 |
| 18 | 250 | — |
| 19 | 2.2 | 1700 |
| 20 | 7.1 | 2700 |
| 21 | 3.7 | — |
| 22 | 1.6 | — |
| 23 | 3.0 | — |
| 24 | 5.3 | — |
| 25 | 190 | — |
| 26 | 1000 | — |
| 27 | 3.0 | — |
| 28 | 4.4 | — |
| 29 | 9.8 | — |
| 30 | 6.3 | — |
| 31 | 7.5 | — |
| 32 | 4.2 | — |
| 33 | 2.7 | — |
| 34 | 12 | — |
| 35 | 9 | — |
| 36 | 2.2 | 1100 |
| 37 | 2.6 | 1600 |
| 38 | 3.5 | 84 |
| 39 | 1.4 | 860 |
| 40 | 2.3 | 2700 |
| 41 | 3 | 1400 |
| 42 | 5.4 | — |
| 43 | 1.7 | 600 |
| 44 | 2.4 | 9500 |
| 45 | 3.5 | — |
| 46 | 14 | — |
| 47 | 4.3 | — |
| 48 | 2.7 | 440 |
| 49 | 18.0 | — |
| 50 | 4.5 | — |
| 51 | 22.0 | — |
| 52 | 5.0 | — |
| 53 | 2.3 | 880 |
| 54 | 2.5 | 740 |
| 55 | 2.1 | 850 |
| 56 | 3.5 | 14 |
| 57 | 8.2 | 140 |
| 58 | 3.7 | 75 |
| 59 | 9.6 | 110 |
| 60 | 2.5 | 6.8 |
| 61 | 2.8 | 9 |
| 62 | 18.0 | 350 |
| 63 | 5.1 | 130 |
| 64 | 8.7 | 85 |
| 65 | 5.5 | 12 |
| 66 | 110 | 410 |
| 67 | 2.2 | 9.3 |
| 68 | 7.3 | 230 |
| 69 | 3.0 | 43 |
| 70 | 3.5 | 180 |
| 71 | 5.6 | 450 |
| 72 | 5.0 | 15 |
| 73 | 2.7 | 7.9 |
| 74 | 1.2 | 2.6 |
| 75 | 1.0 | 1.9 |
| 76 | 2.1 | 479 |
| 77 | 6.0 | 76 |
| 78 | 2.0 | 14 |

TABLE 4-continued p70S6K and AKT Enzyme Inhibition by Compound Described by Formula (I) and Formula (II)

| Compound No. | IC$_{50}$ p70S6K (nM) | IC$_{50}$ AKT (nM) |
| --- | --- | --- |
| 79 | 0.9 | 7.5 |
| 80 | 95 | 1400 |
| 81 | 98 | 15000 |
| 82 | 3.7 | 12 |
| 83 | 20 | 190 |
| 84 | 5.2 | 340 |
| 85 | 12 | 43 |
| 86 | 1.9 | 4 |
| 87 | 9.3 | 190 |
| 88 | 8.1 | 95 |
| 89 | 7.3 | 33 |
| 90 | 3.1 | 31 |
| 91 | 3.2 | 4.8 |
| 92 | 4.2 | 71 |
| 93 | 3.0 | 7.7 |
| 94 | 13 | 1600 |
| 95 | 47 | 520 |
| 96 | 5.3 | 7.9 |
| 97 | 2.2 | 6.1 |
| 98 | 3 | 6.9 |
| 99 | 4.5 | 18 |
| 100 | 2.3 | 16 |
| 101 | 7.6 | 31 |
| 102 | 2.4 | 4.1 |
| 103 | 4.2 | 6.6 |
| 104 | 3.1 | 16.5 |
| 105 | 2.7 | 13 |
| 106 | 21 | 49 |
| 107 | 98 | 160 |
| 108 | 2.2 | 4.8 |
| 109 | 0.9 | 1.6 |
| 110 | 0.7 | 1.9 |
| 111 | 8.7 | 106 |
| 112 | 64.5 | 940 |
| 113 | 84 | 465 |
| 114 | 3.6 | 6.6 |
| 115 | 2.8 | 21 |
| 116 | 2.4 | 8.2 |
| 117 | 4.9 | 9.1 |
| 118 | 9.7 | 21 |
| 119 | 25 | 420 |
| 120 | 1.0 | 2.4 |
| 121 | 1.0 | 2.4 |
| 122 | 0.7 | 2.0 |
| 123 | 58 | 780 |
| 124 | 2 | 14 |
| 125 | 1.5 | 9.7 |
| 126 | 0.5 | 2.2 |
| 127 | 1 | 2.8 |
| 128 | 5.5 | 90 |
| 129 | 11 | 250 |
| 130 | 2.6 | 91 |
| 131 | 5.7 | 165 |
| 132 | 23 | 220 |
| 133 | 46 | 3600 |
| 134 | 6 | 1900 |
| 135 | 860 | 760 |
| 136 | 8.4 | 1900 |
| 137 | 2.7 | 11 |
| 138 | 1.7 | 100 |
| 139 | 1.1 | 6.6 |
| 140 | 2.2 | 27 |
| 141 | 13 | 64.5 |
| 142 | 6.4 | 240 |
| 143 | 16 | 670 |
| 144 | 1.1 | 2.5 |
| 145 | 53 | 2200 |
| 146 | 3.8 | 31 |
| 147 | 1.8 | 2.9 |
| 148 | 4.8 | 16.5 |
| 149 | 4.8 | 38 |
| 150 | 10 | 220 |
| 151 | 2.2 | 19 |
| 152 | 5.2 | 280 |
| 153 | 10 | 220 |
| 154 | 3 | 480 |
| 155 | 0.9 | 160 |
| 156 | 4.9 | 81 |
| 157 | 2 | 190 |
| 158 | 1.5 | 3.6 |
| 159 | 1.5 | 15 |
| 160 | 6.7 | 670 |
| 161 | 12.9 | 150 |
| 162 | 5.9 | 21 |
| 163 | .73 | 4.8 |
| 164 | 4.4 | 5.5 |
| 165 | 2.8 | 5.5 |
| 166 | 1.3 | 1.5 |
| 167 | 130 | >1000 |
| 168 | 2.9 | 2.7 |
| 169 | 1.3 | 1.7 |
| 170 | 170 | 120 |
| 171 | 0.6 | 2.1 |
| 172 | 2.0 | 1.4 |
| 173 | 2.8 | 3.6 |
| 174 | 0.44 | 0.52 |
| 175 | 5.9 | 4.5 |
| 176 | 5.5 | 5 |
| 177 | 1.2 | 2.1 |
| 178 | 3.9 | 2.7 |
| 179 | 1.9 | 4.2 |
| 180 | 1.1 | 2.4 |
| 181 | 0.11 | 0.15 |
| 182 | 0.7 | 2.2 |
| 183 | 12 | 74 |
| 184 | 0.26 | 2.3 |
| 185 | 2.2 | 6.6 |
| 186 | 2.0 | 7.1 |
| 187 | 3.4 | 6.4 |
| 188 | 2.1 | 2.3 |
| 189 | 1.1 | 4.5 |
| 190 | 0.1 | 0.1 |
| 191 | 7.4 | 15 |
| 192 | 2700 | 7200 |
| 193 | 1300 | 5700 |
| 194 | 3.4 | 16 |
| 195 | 16 | >1000 |
| 196 | 5.5 | 370 |
| 197 | 6.3 | 130 |
| 198 | 11 | 255 |
| 199 | 12 | 385 |
| 200 | 21 | 640 |
| 201 | 16 | >1000 |
| 202 | 9 | 89 |
| 203 | 30 | 2500 |
| 204 | 37 | 3600 |
| 205 | 0.8 | 1.3 |
| 206 | 2.4 | 13 |
| 207 | 22 | 105 |
| 208 | 3.2 | 7.6 |
| 209 | 3.1 | 2.2 |
| 210 | 3.7 | 3.0 |
| 211 | 23 | 23 |
| 212 | 6.7 | 16 |
| 213 | 7.9 | 20 |
| 214 | 50 | 180 |
| 215 | 6.1 | 10 |
| 216 | 3.8 | 9 |
| 217 | 1.5 | 2.3 |
| 218 | 0.6 | 1 |
| 219 | 2.4 | 2.3 |
| 220 | 2.6 | 4.2 |
| 221 | 21 | 71 |
| 222 | 11 | 43 |
| 223 | 21 | 78 |
| 224 | 5.7 | 12 |
| 225 | 5.8 | 12 |
| 226 | 1.3 | 1.7 |

TABLE 4-continued p70S6K and AKT Enzyme Inhibition by Compound Described by Formula (I) and Formula (II)

| Compound No. | IC$_{50}$ p70S6K (nM) | IC$_{50}$ AKT (nM) |
|---|---|---|
| 227 | 1.4 | 2.9 |
| 228 | 1.4 | 5.9 |
| 229 | 6.3 | 71 |
| 230 | 2.1 | 4.1 |
| 231 | 3.6 | 46 |
| 232 | 2.3 | 20 |
| 233 | 1.1 | 8.2 |
| 234 | 13 | 470 |
| 235 | 10 | 1000 |
| 236 | 0.5 | 8.1 |
| 237 | 0.8 | 3.3 |
| 238 | 0.9 | 3.2 |
| 239 | 4.4 | 210 |
| 240 | 0.9 | 21 |
| 241 | 2.9 | 16 |
| 242 | 1.4 | 9.7 |
| 243 | 18 | 63 |
| 244 | 25 | 210 |
| 245 | 5.3 | 64 |
| 246 | 1.7 | 25 |
| 247 | 5.5 | 520 |
| 248 | 16 | 1000 |
| 249 | 10 | 86 |
| 250 | 5.7 | 210 |
| 251 | 2.6 | 76 |
| 252 | 0.2 | 0.4 |
| 253 | 19 | 28 |
| 254 | 8.1 | 9.1 |
| 255 | 6.9 | 9.4 |
| 256 | 6.5 | 11 |
| 257 | 4 | 20 |
| 258 | 36 | 380 |
| 259 | 37 | 430 |
| 260 | 21 | 67 |
| 261 | 6.3 | 8.1 |
| 262 | 4 | 4.9 |
| 263 | 25 | 79 |
| 264 | 4.1 | 6.2 |
| 265 | 6.2 | 110 |
| 266 | 3.3 | 16 |
| 267 | 2.2 | 4.2 |
| 268 | 1.4 | 1.8 |
| 269 | 10 | 190 |
| 270 | 360 | 1000 |
| 271 | 12 | 180 |
| 272 | 3.5 | 9.6 |
| 273 | 7.4 | 190 |
| 274 | 1.5 | 12 |
| 275 | 2.8 | 430 |
| 276 | 2.8 | 9.3 |
| 277 | 3.2 | 18 |
| 278 | 4.6 | 79.5 |
| 279 | 2.4 | 16 |
| 280 | 6 | 7.3 |
| 281 | 3.9 | 9.2 |
| 282 | 3.8 | 24 |
| 283 | 1.4 | 2.7 |
| 284 | 10.6 | 51.5 |
| 285 | 1 | 1.4 |
| 286 | 135 | 730 |
| 287 | 0.6 | 1 |
| 288 | 21 | 190 |
| 289 | 0.8 | 2.1 |
| 290 | 1.3 | 2 |
| 291 | 2.6 | 8 |
| 292 | 3.4 | 7.6 |
| 293 | 1 | 1.7 |
| 294 | 1.3 | 1.9 |
| 295 | 4.1 | 23 |
| 296 | 1.6 | 2.6 |
| 297 | 3.9 | 6.6 |
| 298 | 6.8 | 6.6 |
| 299 | 10 | 8.9 |
| 300 | 3.1 | 8.9 |
| 301 | 8.6 | 7.3 |
| 302 | 12 | 6.3 |
| 303 | 2.4 | 0.8 |
| 304 | 4.6 | 2.6 |
| 305 | 1.9 | 3.2 |
| 306 | 2 | 7.6 |
| 307 | 0.8 | 1.5 |
| 308 | 2.6 | 13 |
| 309 | 2.6 | 21 |
| 310 | 2.3 | 7.6 |
| 311 | 2.3 | 8.4 |
| 312 | 1.9 | 2.3 |
| 313 | 1.6 | 9.3 |
| 314 | 1.8 | 4.1 |
| 315 | 99 | 500 |
| 316 | 0.8 | 24 |
| 317 | 1.7 | 11 |
| 318 | 1.4 | 15 |
| 319 | 1.7 | 23 |
| 320 | 1.6 | 48 |
| 321 | 2.6 | 59 |
| 322 | 1.3 | 13 |
| 323 | 8.3 | 31 |
| 324 | 2.8 | 3.5 |
| 325 | 0.5 | 0.9 |
| 326 | 2.7 | 2.5 |
| 327 | 5.2 | 2.8 |
| 328 | 8.1 | 140 |
| 329 | 14 | 120 |
| 330 | 3.6 | 14 |
| 331 | 4.6 | 15 |
| 332 | 3.8 | 37 |
| 333 | 21 | 380 |
| 334 | 26 | 620 |
| 335 | 13 | 92 |
| 336 | 7.6 | 76 |
| 337 | 3.5 | 11 |
| 338 | 2 | 29 |
| 339 | 2700 | 5800 |
| 340 | 4 | 420 |
| 341 | 11 | 450 |
| 342 | 3.7 | 61 |
| 343 | 5.5 | 170 |
| 344 | 25 | 2400 |
| 345 | 100 | 13000 |
| 346 | 3.9 | 220 |
| 347 | 87 | 990 |
| 348 | 4 | 32 |
| 349 | 25 | 55 |
| 350 | 2.3 | 10 |
| 351 | 27 | 48 |
| 352 | 310 | 5700 |
| 353 | 14 | 140 |
| 354 | >10000 | >10000 |
| 355 | 17 | 80 |
| 356 | 80 | 560 |
| 357 | 0.8 | 130 |
| 358 | 1.1 | 1.6 |
| 359 | 2.7 | 12 |
| 360 | 2.2 | 2.7 |
| 361 | 6.4 | 11 |
| 362 | 4.1 | 76 |
| 363 | 3.4 | 26 |
| 364 | 1.4 | 2.5 |
| 365 | 6.3 | 730 |

TABLE 4-continued p70S6K and AKT Enzyme Inhibition by Compound Described by Formula (I) and Formula (II)

| Compound No. | IC$_{50}$ p70S6K (nM) | IC$_{50}$ AKT (nM) |
|---|---|---|
| 366 | 9.2 | 440 |
| 367 | 4 | 67 |
| 368 | 21 | 760 |
| 369 | 3.6 | 5.4 |
| 370 | 0.9 | 2.5 |
| 371 | 18 | 85 |
| 372 | 0.2 | 0.7 |
| 373 | 2.9 | 12 |
| 374 | 0.4 | 1.5 |
| 375 | 1.3 | 1.9 |
| 376 | 3.4 | 33 |
| 377 | 2 | 9.7 |
| 378 | 0.8 | 2.3 |
| 379 | 0.8 | 2.7 |
| 380 | 1.3 | 2.9 |
| 381 | 1.1 | 0.8 |
| 382 | 1.7 | 4.3 |
| 383 | 3.3 | 8.4 |
| 384 | 1.8 | 440 |
| 385 | 6.2 | 42 |
| 386 | 2.4 | 15 |
| 387 | 1.4 | 8.4 |
| 388 | 2 | 13 |
| 389 | 0.9 | 0.7 |
| 390 | 1.9 | 1.4 |
| 391 | 4 | 5.6 |
| 392 | 5.5 | 13 |
| 393 | 2.8 | 47 |
| 394 | 0.9 | 1.7 |
| 395 | 1.6 | 180 |
| 396 | 3.5 | 340 |
| 397 | 2.5 | 16 |
| 398 | 2.1 | 1.5 |
| 399 | 2.5 | 56 |
| 400 | 0.06 | --0.3 |

We claim:

1. A compound of Formula (I):

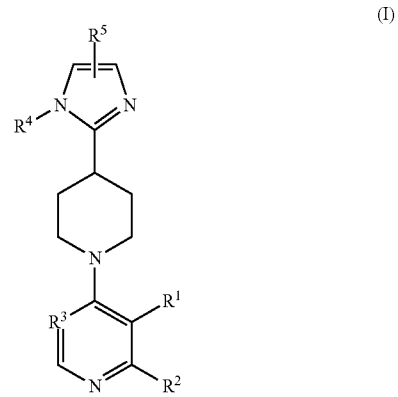

and pharmaceutically acceptable salts, solvates, or solvates of salts, wherein:

$R^1$ is Hal, LA, OH, O(LA), NH$_2$ and/or NH(LA), N(LA)$_2$, NO$_2$, CN, OCN, SCN, COOH, COO(LA), CONH$_2$, CONH(LA), CON(LA)$_2$, NHCO(LA), NHCONH(LA), NHCONH$_2$, NHSO$_2$(LA), CHO, CO(LA), SO$_2$NH$_2$, SO$_2$ (LA), or a mono- or bicyclic, aliphatic or aromatic homo- or heterocycle having 0, 1, 2, 3 or 4 N, S and/or O atoms and 4, 5 or 6, 7, 8, 9, or 10 skeleton atoms which may be unsubstituted or, independently of one another, mono-, di- or trisubstituted by Hal, LA, OH, O(LA), NH$_2$ and/or NH(LA), N(LA)$_2$, NO$_2$, CN, OCN, SCN, COOH, COO(LA), CONH$_2$, CONH(LA), CON(LA)$_2$, NHCO(LA), NHCONH(LA), NHCONH$_2$, NHSO$_2$ (LA), CHO, CO(LA), SO$_2$NH$_2$, SO$_2$ (LA) and/or SO$_2$Hal or an unbranched or branched linear or cyclic

SEQUENCE LISTING

<160> NUMBER OF SEQ ID NOS: 2

<210> SEQ ID NO 1
<211> LENGTH: 11
<212> TYPE: PRT
<213> ORGANISM: Artificial Sequence
<220> FEATURE:
<223> OTHER INFORMATION: substrate

<400> SEQUENCE: 1

Ala Lys Arg Arg Arg Leu Ser Ser Leu Arg Ala
1               5                   10

<210> SEQ ID NO 2
<211> LENGTH: 11
<212> TYPE: PRT
<213> ORGANISM: Artificial Sequence
<220> FEATURE:
<223> OTHER INFORMATION: substrate

<400> SEQUENCE: 2

Gly Arg Pro Arg Thr Ser Ser Phe Ala Glu Gly
1               5                   10 alkyl having 1, 2, 3, 4, 5, 6, 7 or 8 C atoms, in which one or two CH₂ groups may be replaced by an O atom and/or by an —NH—, NH(LA), —CO—, —NHCO— or —CH═CH— group, and/or in which a CH group may be replaced by —N—;

$R^2$ is H, NH₂, NH(LA), N(LA)₂ or NHCO(LA);

$R^3$ is N or CH;

$R^4$ is H, an unbranched or branched linear or mono- or bicyclic alkyl group having 1, 2, 3, 4, 5, 6, 7, 8 or 9 C atoms, in which one or two CH₂ groups may be replaced by an —O—,—NH—, group, and/or in which one or two CH groups may be replaced by —N—, and/or in which 1, 2 or 3 H atoms may be replaced by Hal or OH, $R^5$ is a monocyclic aromatic or aliphatic homo- or heterocycle having 0, 1 or 2 N, S and/or O atoms and 5 or 6 skeleton atoms which may be unsubstituted or, independently of one another, mono-, di- or trisubstituted by Hal, LA, OH, O(LA), NH₂ and/or NH(LA), N(LA)₂, NO₂, CN, OCN, SCN, COOH, COO(LA), CONH₂, CONH(LA), CON(LA)₂, NHCO(LA), NHCONH(LA), NHCONH₂, NHSO₂(LA), CHO, CO(LA), SO₂NH₂, SO₂(LA);

Hal is F, Cl, Br or I, and

LA is an unbranched or branched, saturated or partially unstaturated, linear hydrocarbon chain having 1, 2, 3 or 4 C atoms, wherein 1, 2 or 3 H atoms may be replaced by Hal.

2. The compound according to claim 1, of Formula (II):

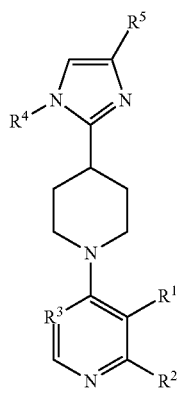

(II)

and pharmaceutically acceptable salts, solvates, or solvates of salts thereof.

3. The compound according to claim 1, wherein
$R^1$ is Hal, LA, O(LA), CN, CONH₂, or a monocyclic aliphatic or aromatic homo- or heterocycle having 0,1 or 2 N or O atoms and 5 or 6 skeleton atoms,
and pharmaceutically acceptable salts, solvates, or solvates of salts thereof.

4. Compounds according to claim 1, selected from:

5-Bromo-6-{4-[4-(4-fluoro-3-trifluoromethyl-phenyl)-1-methyl-1H-imidazol-2-yl]-piperidin-1-yl}-pyrimidin-4-ylamine ("1")

5-Bromo-6-{4-[5-(4-fluoro-3-trifluoromethyl-phenyl)-1-methyl-1H-imidazol-2-yl]-piperidin-1-yl}-pyrimidin-4-ylamine ("2")

5-Bromo-6-{4-[4-(3-trifluoromethyl-phenyl)-1H-imidazol-2-yl]-piperidin-1-yl}-pyrimidin-4-ylamine ("3")

5-Bromo-4-{4-[4-(3-trifluoromethyl-phenyl)-1H-imidazol-2-yl]-piperidin-1-yl}-pyrimidine ("4")

3-bromo-4-(4-{4-[3-(trifluoromethyl)phenyl]-1H-imidazol-2-yl}piperidin-1-yl)pyridine ("5")

4-Amino-6-{4-[4-(4-fluoro-3-trifluoromethyl-phenyl)-1-methyl-1H-imidazol-2-yl]-piperidin-1-yl}-pyrimidine-5-carbaldehyde ("6")

4-Amino-6-{4-[4-(4-fluoro-3-trifluoromethyl-phenyl)-1-methyl-1H-imidazol-2-yl]-piperidin-1-yl}-pyrimidine-5-carbonitrile ("7")

4-Amino-6-{4-[1-(2-dimethylamino-ethyl)-4-(4-fluoro-3-trifluoromethyl-phenyl)-1H-imidazol-2-yl]-piperidin-1-yl}-pyrimidine-5- carbonitrile ("8")

6-{4-[4-(4-Fluoro-3-trifluoromethyl-phenyl)-1-methyl-1H-imidazol-2-yl]-piperidin-1-yl}-5-methoxy-pyrimidin-4-ylamine ("9")

5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine ("10")

6-{4-[4-(4-Fluoro-3-trifluoromethyl-phenyl)-1-methyl-1H-imidazol-2-yl]-piperidin-1-yl}-5-(4-methoxy-phenyl)-pyrimidin-4-ylamine ("11")

6-{4-[4-(4-Fluoro-3-trifluoromethyl-phenyl)-1-methyl-1H-imidazol-2-yl]-piperidin-1-yl}-pyrimidin-4-ylamine ("12")

6-{4-[4-(4-Fluoro-3-trifluoromethyl-phenyl)-1-methyl-1H-imidazol-2-yl]-piperidin-1-yl}-5-p-tolyl-pyrimidin-4-ylamine ("13")

[4-(4-Amino-6-{4-[4-(4-fluoro-3-trifluoromethyl-phenyl)-1-methyl-1H-imidazol-2-yl]-piperidin-1-yl}-pyrimidin-5-yl)-phenyl]-methanol ("14")

3-(4-Amino-6-{4-[4-(4-fluoro-3-trifluoromethyl-phenyl)-1-methyl-1H-imidazol-2-yl]-piperidin-1-yl}-pyrimidin-5-yl)-benzonitrile ("15")

6-{4-[4-(Fluoro-3-trifluoromethyl-phenyl)-1-methyl-1H-imidazol-2-yl]-piperidin-1-yl}-5-(4-trifluoromethyl-phenyl)-pyrimidin-4-ylamine ("16")

4-(4-Amino-6-{4-[4-(4-fluoro-3-trifluoromethyl-phenyl)-1-methyl-1H-imidazol-2-yl]-piperidin-1-yl}-pyrimidin-5-yl)-benzonitrile ("17")

2-(4-Amino-6-{4-[4-(4-fluoro-3-trifluoromethyl-phenyl)-1-methyl-1H-imidazol-2-yl]-piperidin-1-yl}-pyrimidin-5-yl)-benzonitrile ("18")

6-{4-[4-(4-Fluoro-3-trifluoromethyl-phenyl)-1-methyl-1H-imidazol-2-yl]-piperidin-1-yl}-5-(6-methyl-pyridin-3-yl)-pyrimidin-4- ylamine ("19")

6-{4-[4-(4-Fluoro-3-trifluoromethyl-phenyl)-1-methyl-1H-imidazol-2-yl]-piperidin-1-yl}-5-(5-methyl-thiophen-2-yl)-pyrimidin-4- ylamine ("20")

6-{4-[4-(4-Fluoro-3-trifluoromethyl-phenyl)-1-methyl-1H-imidazol-2-yl]-piperidin-1-yl}-5-phenyl-pyrimidin-4-ylamine ("21")

5-(3-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine ("22")

5-(2-Fluorophenyl)-6-{4-[4-(4-fluoro-3-trifluoromethyl-phenyl)-1-methyl-1H-imidazol-2-yl]-piperidin-1-yl}-pyrimidin-4-ylamine (37 23")

5-(2-Chlorophenyl)-6-{4-[4-(4-fluoro-3-trifluoromethyl-phenyl)-1-methyl-1H-imidazol-2-yl]-piperidin-1-yl}-pyrimidin-4-ylamine ("24")

6-{4-[4-(4-Fluoro-3-trifluoromethyl-phenyl)-1-methyl-1H-imidazol-2-yl]-piperidin-1-yl}-5-(6-morpholin-4-yl-pyridin-3-yl)- pyrimidin-4-ylamine ("25")

6-{4-[4-(4-Fluoro-3-trifluoromethyl-phenyl)-1-methyl-1H-imidazol-2-yl]-piperidin-1-yl}-5-(6-piperazin-1-yl-pyridin-3-yl)- pyrimidin-4-ylamine ("26")

5-(6-Fluoro-pyridin-3-yl)-6-{4-[4-(4-fluoro-3-trifluoromethyl-phenyl)-1-methyl-1H-imidazol-2-yl]-piperidin-1-yl}-pyrimidin-4- ylamine ("27")

6'-{4-[4-(4-Fluoro-3-trifluoromethyl-phenyl)-1-methyl-1H-imidazol-2-yl]-piperidin-1-yl}-[5,5']bipyrimidinyl-2,4'-diamine ("28")

6-{4-[4-(4-Fluoro-3-trifluoromethyl-phenyl)-1-methyl-1H-imidazol-2-yl]-piperidin-1-yl}-5-(3-methoxyphenyl)-pyrimidin-4-ylamine ("29")

5-(3,4-Difluoro-phenyl)-6-{4-[4-(4-fluoro-3-trifluoromethyl-phenyl)-1-methyl-1H-imidazol-2-yl]-piperidin-1-yl}-pyrimidin-4-ylamine ("30")

6'-{4-[4-(4-Fluoro-3-trifluoromethyl-phenyl)-1-methyl-1H-imidazol-2-yl]-piperidin-1-yl}-N2,N2-dimethyl-[5,5']bipyrimidinyl-2,4'-diamine ("31")

5-(4-Aminomethyl-phenyl)-6-{4-[4-(4-fluoro-3-trifluoromethyl-phenyl)-1-methyl-1H-imidazol-2-yl]-piperidin-1-yl}-pyrimidin-4-ylamine ("32")

5-(4-Methoxy-phenyl)-6-{4-[4-(3-trifluoromethyl-phenyl)-1H-imidazol-2-yl]-piperidin-1-yl}-pyrimidin-4-ylamine ("33")

5-(4-Methoxy-phenyl)-4-{4-[4-(3-trifluoromethyl-phenyl)-1H-imidazol-2-yl]-piperidin-1-yl}-pyrimidine ("34")

3-(4-methoxyphenyl)-4-(4-{4-[3-(trifluoromethyl)phenyl]-1H-imidazol-2-yl}piperidin-1-yl)pyridine ("35")

(4-Amino-6-{4-[4-(4-fluoro-3-trifluoromethyl-phenyl)-1-methyl-1H-imidazol-2-yl]-piperidin-1-yl}-pyrimidin-5-yl)-methanol ("36")

4-Amino-6-{4-[4-(4-fluoro-3-trifluoromethyl-phenyl)-1-methyl-1H-imidazol-2-yl]-piperidin-1-yl}-pyrimidine-5-carboxamide ("37")

4-Amino-6-{4-[1-(2-dimethylamino-ethyl)-4-(4-fluoro-3-trifluoromethyl-phenyl)-1H-imidazol-2-yl]-piperidin-1-yl}-pyrimidine-5-carboxylic acid amide ("38")

6-{4-[4-(4-Fluoro-3-trifluoromethyl-phenyl)-1-methyl-1H-imidazol-2-yl]-piperidin-1-yl}-5-pyridin-4-yl-pyrimidin-4-ylamine ("39")

5-(6-Amino-pyridin-3-yl)-6-{4-[4-(4-fluoro-3-trifluoromethyl-phenyl)-1-methyl-1H-imidazol-2-yl]-piperidin-1-yl}-pyrimidin-4- ylamine ("40")

5-Bromo-4-{4-[4-(4-fluoro-3-trifluoromethyl-phenyl)-1-methyl-1H-imidazol-2-yl]-piperidin-1-yl}-pyrimidine ("41")

5-(4-Fluoro-phenyl)-4-{4-[4-(4-fluoro-3-trifluoromethyl-phenyl)-1-methyl-1H-imidazol-2-yl]-piperidin-1-yl}-pyrimidine ("42")

5-Bromo-6-{4-[4-(4-fluoro-3-trifluoromethyl-phenyl)-1H-imidazol-2-yl]-piperidin-1-yl}-pyrimidin-4-ylamine ("43")

5-(4-Fluoro-phenyl)-6-{4-[4-(4-fluoro-3-trifluoromethyl-phenyl)-1H-imidazol-2-yl]-piperidin-1-yl}-pyrimidin-4-ylamine ("44")

(E)-3-(4-Amino-6-{4-[4-(4-fluoro-3-trifluoromethyl-phenyl)-1-methyl-1H-imidazol-2-yl]-piperidin-1-yl}-pyrimidin-5-yl)-acrylic acid methyl ester ("45")

(E)-3-(4-Amino-6-{4-[4-(4-fluoro-3-trifluoromethyl-phenyl)-1-methyl-1H-imidazol-2-yl]-piperidin-1-yl}-pyrimidin-5-yl)-acrylamide ("46")

6-{4-[4-(4-Fluoro-3-trifluoromethyl-phenyl)-1-methyl-1H-imidazol-2-yl]-piperidin-1-yl}-5-(5-methoxy-pyridin-3-yl)-pyrimidin-4- ylamine ("47")

6-{4-[4-(4-Fluoro-3-trifluoromethyl-phenyl)-1-methyl-1H-imidazol-2-yl]-piperidin-1-yl}-[5,5']bipyrimidinyl-4-ylamine ("48")

6-{4-[4-(4-Fluoro-3-trifluoromethyl-phenyl)-1-methyl-1H-imidazol-2-yl]-piperidin-1-yl}-5-(1H-indol-5-yl)-pyrimidin-4-ylamine ("49")

5-(6-Chloro-pyridin-3-yl)-6-{4-[4-(4-fluoro-3-trifluoromethyl-phenyl)-1-methyl-1H-imidazol-2-yl]-piperidin-1-yl}-pyrimidin-4- ylamine ("50")

5-(3-Chloro-phenyl)-6-{4-[4-(4-fluoro-3-trifluoromethyl-phenyl)-1-methyl-1H-imidazol-2-yl]-piperidin-1-yl}-pyrimidin-4-ylamine ("51")

4-(4-Amino-6-{4-[4-(4-fluoro-3-trifluoromethyl-phenyl)-1-methyl-1H-imidazol-2-yl]-piperidin-1-yl}-pyrimidin-5-yl)-2-fluoro-benzonitrile ("52")

6-{4-[4-(4-Fluoro-3-trifluoromethyl-phenyl)-1-methyl-1H-imidazol-2-yl]-piperidin-1-yl}-5-pyridin-3-yl-pyrimidin-4-ylamine ("53")

6-{4-[4-(4-Fluoro-3-trifluoromethyl-phenyl)-1-methyl-1H-imidazol-2-yl]-piperidin-1-yl}-5-((E)-3-methoxy-propenyl)-pyrimidin-4-ylamine ("54")

6-{4-[4-(4-Fluoro-3-trifluoromethyl-phenyl)-1-methyl-1H-imidazol-2-yl]-piperidin-1-yl}-5-(2-methyl-thiazol-5-yl)-pyrimidin-4- ylamine ("55")

5-Bromo-6{4-(4-fluoro-3-trifluoromethyl-phenyl)-1-2-pyrrolidin-1-yl-ethyl)-1H-imidazol-2-yl]-piperidin-1-yl}-pyrimidin-4-ylamine ("56")

5-(4-Fluorophenyl)-6{4-(4-fluoro-3-trifluoromethyl-phenyl)-1-2-pyrrolidin-1-yl-ethyl)-1H-imidazol-2-yl]-piperidin-1-yl}-pyrimidin-4-ylamine ("57")

5-(2-Fluorophenyl)-6{4-(4-fluoro-3-trifluoromethyl-phenyl)-1-2-pyrrolidin-1-yl-ethyl)-1H-imidazol-2-yl]-piperidin-1-yl}-pyrimidin-4-ylamine ("58")

5-(3,4-Difluorophenyl)-6{4-(4-fluoro-3-trifluoromethyl-phenyl)-1-2-pyrrolidin-1-yl-ethyl)-1H-imidazol-2-yl]-piperidin-1-yl}-pyrimidin-4-ylamine ("59")

6-{4-(4-fluoro-3-trifluoromethyl-phenyl)-1-2-pyrrolidin-1-yl-ethyl)-1H-imidazol-2-yl]-piperidin-1-yl}-5-vinyl-pyrimidin-4-ylamine ("60")

5-Bromo-6-{4-[4-(4-fluoro-3-trifluoromethyl-phenyl)-1-(2-piperidin-1-yl-ethyl)-1H-imidazol-2-yl]-piperidin-1-yl}-pyrimidin-4- ylamine ("61")

5-(4-Fluorophenyl)-6{4-(4-fluoro-3-trifluoromethyl-phenyl)-1-2-piperidin-1-yl-ethyl)-1H-imidazol-2-yl]-piperidin-1-yl}-pyrimidin-4-ylamine ("62")

5-(2-Fluorophenyl)-6{4-(4-fluoro-3-trifluoromethyl-phenyl)-1-2-piperidin-1-yl-ethyl)-1H-imidazol-2-yl]-piperidin-1-yl}-pyrimidin-4-ylamine ("63")

5-(3-Fluorophenyl)-6{4-(4-fluoro-3-trifluoromethyl-phenyl)-1-2-piperidin-1-yl-ethyl)-1H-imidazol-2-yl]-piperidin-1-yl}-pyrimidin-4-ylamine ("64")

6-{4-[4-(4-Fluoro-3-trifluoromethyl-phenyl)-1-(2-piperidin-1-yl-ethyl)-1H-imidazol-2-yl]-piperidin-1-yl}-5-vinyl-pyrimidin-4- ylamine ("65")

6{4-(4-fluoro-3-trifluoromethyl-phenyl)-1-2-piperidin-1-yl-ethyl)-1H-imidazol-2-yl]-piperidin-1-yl}-pyrimidin-4-ylamine ("66")

5-Bromo-6-{4-[1-(2-dimethylamino-ethyl)-4-(4-fluoro-3-trifluoromethyl-phenyl)-1H-imidazol-2-yl]-piperidin-1-yl}-pyrimidin-4-ylamine ("67")

6-{4-[1-(2-Dimethylamino-ethyl)-4-(4-fluoro-3-trifluoromethly-phenyl)-1H-imidazol-2-yl]-piperidin-1-yl}-5-(4-fluoro-phenyl)-1-pyrimidin-4-ylamine ("68")

6-{4-[1-(2-Dimethylamino-ethyl)-4-(4-fluoro-3-trifluoromethyl-phenyl)-1H-imidazol-2-yl]-piperidin-1-yl}-5-pyridin-3-yl-pyrimidin-4-ylamine ("69")

6-{4-[1-(2-Dimethylamino-ethyl)-4-(4-fluoro-3-trifluoromethyl-phenyl)-1H-imidazol-2-yl]-piperidin-1-yl}-5-pyridin-4-yl-pyrimidin-4-ylamine ("70")

6'-{4-[1-(2-Dimethylamino-ethyl)-4-(4-fluoro-3-trifluoromethyl-phenyl)-1H-imidazol-2-yl]-piperidin-1-yl}-[5,5']bipyrimidinyl-2,4'-diamine ("71")

6-{4-[1-(2-Dimethylamino-ethyl)-4-(4-fluoro-3-trifluoromethyl-phenyl)-1H-imidazol-2-yl]-piperidin-1-yl}-5-isopropenyl-pyrimidin-4- ylamine ("72")

6-{4-[1-(2-Dimethylamino-ethyl)-4-(4-fluoro-3-trifluoromethyl-phenyl)-1H-imidazol-2-yl]-piperidin-1-yl}-5-vinyl-pyrimidin-4-ylamine ("73")

4-Amino-6-{4-[1-(2-azetidin-1-yl-ethly)-4-(4-fluoro-3-trifluoromethly-phenyl)-1H-imidazol-2-yl]-piperidin-1-yl}-pyrimidine-5-carbonitrile ("74")

4-Amino-6-{4-[1-(2-azetidin-1-yl-ethyl)-4-(3-chloro-4-fluoro-phenyl)-1H-imidazol-2-yl]-piperidin-1-yl}-pyrimidine-5-carbonitrile ("75")

4-Amino-6-{4-[1-(2-azetidin-1-yl-ethyl)-4-(4-difluoromethoxy-phenyl)-1H-imidazol-2-yl]-piperidin-1-yl}-pyrimidine-5-carbonitrile ("76")

4-Amino-6-{4-[1-(2-azetidin-1-yl-ethyl)-4-cyclohexyl-1H-imidazol-2-yl]-piperidin-1-yl}-pyrimidine-5-carbonitrile ("77")

4-Amino-6-{4-[1-(2-azetidin-1-yl-ethyl)-4-(4-fluoro-3-trifluoromethyl-phenyl)-1H-imidazol-2-yl]-piperidin-1-yl}-pyrimidine-5-carboxylic acid amide ("78")

4-Amino-6-{4-[1-(2-azetidin-1-yl-ethyl)-4-(3-chloro-4-fluoro-phenyl)-1H-imidazol-2-yl]-piperidin-1-yl}-pyrimidine-5-carboxylic acid amide ("79")

4-Amino-6-{4-[1-(2-azetidin-1-yl-ethyl)-4-cyclohexyl-1H-imidazol-2-yl]-piperidin-1-yl}-pyrimidine-5-carboxylic acid amide ("80")

4-Amino-6-{4-[1-(2-azetidin-1-yl-ethyl)-4-(4-difluoromethoxy-phenyl)-1H-imidazol-2-yl]-piperidin-1-yl}-pyrimidine-5-carboxylic acid amide ("81")

6-(4-(1-(2-(Dimethylamino)ethyl)-4-(4-fluoro-3-(trifluoromethyl)phenyl)-1H-imidazol-2-yl)piperidin-1-yl)-5-ethylpyrimidin-4-amine ("82")

5-(2-Cyclopropylethyl)-6-(4-(1-(2-(dimethylamino)ethyl)-4-(4-fluoro-3-(trifluoromethyl)phenyl)-1H-imidazol-2-yl)piperidin-1-yl)pyrimidin-1- amine ("83")

6-(4-(1-(2-(Dimethylamino)ethyl)-4-(4-fluoro-3-(trifluoromethyl)phenyl)-1H-imidazol-2-yl)piperidin-1-yl)-5-(2-ethoxyethyl)pyrimidin-4-amine ("84")

(E)-5-(2-Cyclopropylvinyl)-6-(4-(1-(2-(dimethylamino)ethyl)-4-(4-fluoro-3-(trifluoromethyl)phenyl-1H-imidazol-2-yl)piperidin-1-yl)pyrimidin-4-amine ("85")

(E)-6-(4-(1-(2-(Dimethylamino)ethyl)-4-(4-fluoro-3-(trifluoromethyl)phenyl)-1H-imidazol-2-yl)piperidin-1-yl)-5-(2-ethoxyvinyl)pyrimidin-4- amine ("86")

2-(4-(4-Amino-6-(4-(1-(2-(dimethylamino)ethyl)-4-(4-fluoro-3-(trifluoromethyl)phenyl)-1H-imidazol-2-yl)piperidin-1-yl)pyrimidin-5-yl)phenyl)propan-2-ol ("87")

Methyl 4-(4-amino-6-(4-(1-(2-(dimethylamino)ethyl)-4-(4-fluoro-3-(trifluoromethyl)phenyl)-1H-imidazol-2-yl)piperidin-1-yl)pyrimidin-5-yl)benzoate ("88")

4-(4-Amino-6-(4-(1-(2-(dimethylamino)ethyl)-4-(4-fluoro-3-(trifluoromethyl)phenyl)-1H-imidazol-2-yl)piperidin-1-yl)pyrimidin-5-yl)benzoic acid ("89")

5-(Cyclopent-1-en-1-yl)-6-(4-(1-(2-(dimethylamino)ethyl)-4-(4-fluoro-3-(trifluoromethyl)phenyl)-1H-imidazol-2-yl)piperidin-1-yl)pyrimidin- 4-amine ("90")

5-Cyclopropyl-6-(4-(1-(2-(dimethylamino)ethyl)-4-(4-fluoro-3-(trifluoromethyl)phenyl)-1H-imidazol-2-yl)piperidin-1-yl)pyrimidin-4-amine ("91")

5-ethyl-6-(4-(4-(4-fluoro-3-(trifluoromethyl)phenyl)-1-(2-(3-fluoroazetidin-1-yl)ethyl)-1H-imidazol-2-yl)piperidin-1-yl)pyrimidin-4- amine ("92")

5-ethyl-6-(4-(4-(4-fluoro-3-(trifluoromethyl)phenyl)-1-(2-(3-methylazetidin-1-yl)ethyl)-1H-imidazol-2-yl)piperidin-1-yl)pyrimidin-4- amine ("93")

6-(4-(1-(2-(3,3-difluoroazetidin-1-yl)ethyl)-4-(4-fluoro-3-(trifluoromethyl)phenyl)-1H-imidazol-2-yl)piperidin-1-yl)-5-ethylpyrimidin-4-amine ("94")

6-(4-(1-(2-(dimethylamino)ethyl)-4-(4-fluoro-3-(trifluoromethyl)phenyl)-1H-imidazol-2-yl)piperidin-1-yl)-5-((ethyl(methyl)amino)methyl)pyrimidin-4-amine ("95")

6-(4-(1-(2-(azetidin-1-yl)ethyl)-4-(4-fluoro-3-(trifluoromethyl)phenyl)-1H-imidazol-2-yl)piperidin-1-yl)-5-isopropoxypyrimidin-4-amine ("96")

6-(4-(1-(2-(azetidin-1-yl)ethyl)-4-(4-fluoro-3-(trifluoromethyl)phenyl)-1H-imidazol-2-yl)piperidin-1-yl)-5-methoxyprimidin-4-amine ("97")

6-(4-(1-(2-(azetidin-1-yl)ethyl)-4-(4-fluoro-3-(trifluoromethyl)phenyl)-1H-imidazol-2-yl)piperidin-1-yl)-5-(1H-pyrazol-4- yl)pyrimidin-4-amine ("98")

6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine ("99")

6-(4-(1-(2-(azetidin-1-yl)ethyl)-4-(3-(trifluoromethoxy)phenyl)-1H-imidazol-2-yl)piperidin-1-yl)-5-ethylpyrimidin-4-amine ("100")

6-(4-(1-(2-(azetidin-1-yl)ethyl)-4-(5-chloropyridin-3-yl)-1H-imidazol-2-yl)piperidin-1-yl)-5-ethylpyrimidin-4-amine ("101")

6-(4-(1-(2-(azetidin-1-yl)ethyl)-4-(4-fluoro-3-(trifluoromethyl)phenyl)-1H-imidazol-2-yl)piperidin-1-yl)-5-ethoxypyrimidin-4-amine ("102")

6-(4-(1-(2-(azetidin-1-yl)ethyl)-4-(4-fluoro-3-(trifluoromethyl)phenyl)-1H-imidazol-2-yl)piperidin-1-yl)-5-(2,2,2- trifluoroethoxy)pyrimidin-4-amine ("103")

6-(4-(1-(2-(azetidin-1-yl)ethyl)-4-(2-chloropyridin-4-yl)-1H-imidazol-2-yl)piperidin-1-yl)-5-ethylpyrimidin-4-amine ("104")

6-(4-(1-(2-(azetidin-1-yl)ethyl)-4-(2-(trifluoromethyl)pyridin-4-yl)-1H-imidazol-2-yl)piperidin-1-yl)-5-ethylpyrimidin-4-amine ("105")

5-(2-(1-(6-amino-5-ethylpyrimidin-4-yl)piperidin-4-yl)-1-(2-(azetidin-1-yl)ethyl)-1H-imidazol-4-yl)-2-fluorobenzamide ("106")

5-(2-(1-(6-amino-5-ethylpyrimidin-4-yl)piperidin-4-yl)-1-(2-(azetidin-1-yl)ethyl)-1H-imidazol-4-yl)-2-methoxybenzamide ("107")

6-(4-(1-(2-(azetidin-1-yl)ethyl)-4-(4-fluoro-3-methoxyphenyl)-1H-imidazol-2-yl)piperidin-1-yl)-5-ethylpyrimidin-4-amine ("108")

6-(4-(1-(2-(azetidin-1-yl)ethyl)-4-(4-fluoro-3-(trifluoromethyl)phenyl)-1H-imidazol-2-yl)piperidin-1-yl)-5-(isoxazol-4-yl)pyrimidin-4-amine ("109")

6-(4-(1-(2-(azetidin-1-yl)ethyl)-4-(4-fluoro-3-(trifluoromethyl)phenyl)-1H-imidazol-2-yl)piperidin-1-yl)-5-(1H-pyrrol-3-yl)pyrimidin- 4-amine ("110")

6-(4-(1-(2-(azetidin-1-yl)ethyl)-4-(2-methylpyridin-4-yl)-1H-imidazol-2-yl)piperidin-1-yl)-5-ethylpyrimidin-4-amine ("111")

6-(4-(1-(2-(azetidin-1-yl)ethyl)-4-(2-methoxypyridin-4-yl)-1H-imidazol-2-yl)piperidin-1-yl)-5-ethylpyrimidin-4-amine ("112")

6-(4-(1-(2-(azetidin-1-yl) ethyl)-4-(5-methylpyridin-3-yl)-1H-imidazol-2-yl)piperidin-1-yl)-5-ethylpyrimidin-4-amine ("113")

6-(4-(1-(2-(azetidin-1-yl)ethyl)-4-(4-fluoro-3-(trifluoromethyl)phenyl)-1H-imidazol-2-yl)piperidin-1-yl)-5-isopropylpyrimidin-4-amine ("114")

6-(4-(1-(2-(azetidin-1-yl)ethyl)-4-(2-(trifluoromethyl)pyridin-4-yl)-1H-imidazol-2-yl)piperidin-1-yl)-5-methoxypyrimidin-4-amine ("115")

6-(4-(1-(2-(azetidin-1-yl)ethyl)-4-(2-(trifluoromethyl)pyridin-4-yl)-1H-imidazol-2-yl)piperidin-1-yl)-5-ethoxypyrimidin-4-amine ("116")

6-(4-(1-(2-(azetidin-1-yl)ethyl)-4-(2-(trifluoromethyl)pyridin-4-yl)-1H-imidazol-2-yl)piperidin-1-yl)-5-isopropoxypyrimidin-4-amine ("117")

6-(4-(1-(2-(azetidin-1-yl)ethyl)-4-(2-(trifluoromethyl)pyridin-4-yl)-1H-imidazol-2-yl)piperidin-1-yl)-5-(2,2,2,-trifluoroethoxy)pyrimidin- 4-amine ("118")

6-(4-(1-(2-(azetidin-1-yl)ethyl)-4-(6-(trifluoromethyl)pyridin-2-yl)-1H-imidazol-2-yl)piperidin-1-yl)-5-ethylpyrimidin-4-amine ("119")

4-amino-6-(4-(1-(2-(azetidin-1-yl)ethyl)-4-(4-fluoro-3-methoxyphenyl)-1H-imidazol-2-yl)piperidin-1-yl)pyrimidine-5-carbonitrile ("120")

4-amino-6-(4-(1-(2-(azetidin-1-yl)ethyl)-4-(4-fluoro-3-methoxyphenyl)-1H-imidazol-2-yl)piperidin-1-yl)pyrimidine-5-carboxamide ("121")

4-amino-6-(4-(1-(2-(azetidin-1-yl)ethyl)-4-(4-fluoro-3-methylphenyl)-1H-imidazol-2-yl)piperidin-1-yl)pyrimidin-5-carbonitrile ("122")

6-(4-(1-(2-(azetidin-1-yl)ethyl)-4-(6-chloropyridin-2-yl)-1H-imidazol-2-yl)piperidin-1-yl)-5-ethylpyrimidin-4-amine ("123")

4-amino-6-(4-(1-(2-(azetidin-1-yl)ethyl)-4-(4-fluoro-3-methylphenyl)-1H-imidazol-2-yl)piperidin-1-yl)pyrimidine-5-carboxamide ("124")

4-amino-6-(4-(1-(2-(azetidin-1-yl)ethyl)-4-(2-(trifluoromethyl)pyridin-4-yl)-1H-imidazol-2-yl)piperidin-1-yl)pyrimidine-5-carbonitrile ("125")

6-(4-(1-(2-(azetidin-1-yl)ethyl)-4-2-(trifluoromethyl)pyridin-4-yl)-1H-imidazol-2-yl)piperidin-1-yl)-5-bromopyrimidin-4-amine ("126")

5-bromo-6-(4-(1-(2-((3-chloropropyl)amino)ethyl)-4-(2-(trifluoromethyl)pyridin-4-yl)-1H-imidazol-2-yl)piperidin-1-yl)pyrimidin-4-amine ("127")

4-amino-6-(4-(1-(2-aminoethyl)-4-(2-(trifluoromethyl)pyridin-4-yl)-1H-imidazol-2-yl)piperidin-1-yl)pyrimidine-5-carboxylic acid ("128")

4-amino-6-(4-(1-(2-(azetidin-1-yl)ethyl)-4-(furan-3-yl)-1H-imidazol-2-yl)piperidin-1-yl)pyrimidine-5-carbonitrile ("129")

4-amino-6-(4-(1-(2-(azetidin-1-yl)ethyl)-4-(thiophen-3-yl)-1H-imidazol-2-yl)piperidin-1-yl)pyrimidine-5-carbonitrile ("130")

4-amino-6-(4-(1-(2-(azetidin-1-yl)ethyl)-4-phenyl-1H-imidazol-2-yl)piperidin-1-yl)pyrimidine-5-carbonitrile ("131")

4-amino-6-(4-(1-(2-(azetidin-1-yl)ethyl)-4-(isoxazol-4-yl)-1H-imidazol-2-yl)piperidin-1-yl)pyrimidine-5-carbonitrile ("132")

4-amino-6-(4-(1-(2-(azetidin-1-yl)ethyl)-4-(furan-3-yl)-1H-imidazol-2-yl)piperidin-1-yl)pyrimidine-5-carboxamide ("133")

4-amino-6-(4-(1-(2-(azetidin-1-yl)ethyl)-4-(thiophen-3-yl)-1H-imidazol-2-yl)piperidin-1-yl)pyrimidine-5-carbonxamide ("134")

4-amino-6-(4-(1-(2-(azetidin-1-yl)ethyl)-4-(isoxazol-4-yl)-1H-imidazol-2-yl)piperidin-1-yl)pyrimidine-5-carboxamide ("135")

4-amino-6-(4-(1-(2-(azetidin-1-yl)ethyl)-4-phenyl-1H-imidazol-2-yl)piperidin-1-yl)pyrimidine-5-carboxamide ("136")

4-amino-6-(4-(4-(4-fluoro-3-(trifluoromethyl)phenyl)-1-(pyrrolidin-3-yl)-1H-imidazol-2-yl)piperidin-1-yl)pyrimidine-5-carbonitrile ("137")

4-amino-6(4-(4-(4-fluoro-3-(trifluoromethyl)phenyl)-1-(pyrrolidin-3-yl)-1H-imidazol-2-yl)piperidin-1-yl)pyrimidine-5-carboxamide ("138")

6-(4-(1-(2-aminoethyl)-4-(4-fluoro-3-(trifluorometlhy)phenyl)-1H-imidazol-2-yl)piperidin-1-yl)-5-ethylpyrimidin-4-amine ("139")

4-amino-6-(4-(1-(azetidin-3-ylmethyl)-4-(4-fluoro-3-(trifluoromethyl)phenyl)-1H-imidazol-2-yl)piperidin-1-yl)pyrimidine-5-carboxamide ("140")

4-amino-6-(4-(1-(azetidin-3-ylmethyl)-4-(4-fluoro-3-(trifluoromethyl)phenyl)-1H-imidazol-2-yl)piperidin-1-yl)pyrimidine-5-carbonitrile ("141")

4-amino-6-(4-(1-(azetidin-3-yl)-4-(4-fluoro-3-(trifluoromethyl)phenyl)-1H-imidazol-2-yl)piperidin-1-yl)pyrimidine-5-carbonitrile ("142")

4-amino-6-(4-(1-(azetidin-3-yl)-4-(4-fluoro-3-(trifluoromethyl)phenyl)-1H-imidazol-2-yl)piperidin-1-yl)pyrimidine-5-carboxamide ("143")

6-(4-(1-(2-(azetidin-1-yl)ethyl)-4-(2-(trifluoromethyl)pyridin-4-yl)-1H-imidazol-2-yl)piperidin-1-yl)-5-chloropyrimidin-4-amine ("144")

4-amino-6-(4-(1-(2-(azetidin-1-yl)ethyl)-4-(1H-pyrazol-4-yl)-1H-imidazol-2-yl)piperidin-1-yl)pyrimidine-5-carboxamide ("145")

(S)-4-amino-6-(4-(1-(azetidin-2-ylmethyl)-4-(4-fluoro-3-(trifluoromethyl)phenyl)-1H-imidazol-2-yl)piperidin-1-yl)pyrimidine-5-carbonitrile ("146")

4-amino-6-(4-(4-(4-fluoro-3-(trifluoromethyl)phenyl)-1-(pyrrolidin-2-ylmethyl)-1H-imidazol-2-yl)piperidin-1-yl)pyrimidine-5-carbonitrile ("147")

6-(4-(1-(azetidin-3-ylmethyl)-4-(4-fluoro-3-(trifluoromethyl)phenyl)-1H-imidazol-2-yl)piperidin-1-yl)-5-chloropyrimidin-4-amine ("148")

(S)-6-(4-(1-(azetidin-2-ylmethyl)-4-(4-fluoro-3-(trifluoromethyl)phenyl)-1H-imidazol-2-yl)piperidin-1-yl)-5-chloropyrimidin-4-amine ("149")

(S)-4-amino-6-(4-(1-(azetidin-2-ylmethly)-4-(4-fluoro-3-(trifluoromethly)phenyl)-1H-imidazol-2-yl)piperidin-1-yl)pyrimindine-5-carboxamide ("150")

6-(4-(1-(azetidin-3-ylmethyl)-4-(4-fluoro-3-(trifluoromethyl)phenyl)-1H-imidazol-2-yl)piperidin-1-yl)-5-ethylpyrimidin-4-amine ("151")

(S)-6-(4-(1-(azetidin-2-ylmethyl)-4-(4-fluoro-3-(trifluoromethyl)phenyl)-1H-imidazol-2-yl)piperidin-1-yl)-5-ethylpyrimidin-4-amine ("152")

4-amino-6-(4-(4-(4-fluoro-3-(trifluoromethyl)phenyl)-1-(pyrrolidin-2-ylmethyl)-1H-imidazol-2-yl)piperidin-1-yl)pyrimidine-5-carboxamide ("153")

4-amino-6-(4-(4-(4-fluoro-3-(trifluoromethyl)phenyl)-1-(piperidin-4-yl)-1H-imidazol-2-yl)piperidin-1-yl)pyrimidine-5-carboxamide ("154")

4-amino-6-(4-(4-(4-fluoro-3-(trifluoromethyl)phenyl)-1-(piperidin-4-yl)-1H-imidazol-2-yl)piperidin-1-yl)pyrimidine-5-carbonitrile ("155")

4-amino-6-(4-(4-(4-fluoro-3-(trifluoromethyl)phenyl)-1-((1-methylazetidin-3-yl)methyl)-1H-imidazol-2-yl)piperidin-1-yl)pyrimidine-5- carboxamide ("156")

5-ethyl-6-(4-(4-(4-fluoro-3-(trifluoromethyl)phenyl)-1-(piperidin-4-yl)-1H-imidazol-2-yl)piperidin-1-yl)pyrimidin-4-amine ("157")

4-amino-6-(4-(1-(2-aminoethyl)-4-(4-fluoro-3-(trifluoromethyl)phenyl)-1H-imidazol-2-yl)piperidin-1-yl)pyrimidine-5-carbonitrile ("158")

4-amino-6-(4-(1-(2-aminoethyl)-4-(4-fluoro-3-(trifluoromethyl)phenyl)-1H-imidazol-2-yl)piperidin-1-yl)pyrimindine-5-carboxamide ("159")

2-(2-(1-(6-amino-5-(1H-pyrazol-4-yl)pyrimindin-4-yl)piperidin-4-yl)-4-(4-fluoro-3-methylphenyl)-1H-imidazol-1-yl)ethanol ("160")

6-(4-(1-(2-(cyclopropylamino)ethyl)-4-(4-fluoro-3-methylphenyl)-1H-imidazol-2-yl)piperidin-1-yl)-5-(1H-pyrazol-4-yl)pyrimidin-4-amine ("161")

6-(4-(4-(4-fluoro-3-methylphenyl)-1-(2-(methylamino)ethyl)-1H-imidazol-2-yl)piperidin-1-yl)-5-(1H-pyrazol-4-yl)pyrimidin-4-amine ("162")

6-(4-(1-(2-(dimethylamino)ethyl)-4-(4-fluoro-3-methylphenyl)-1H-imidazol-2-yl)piperidin-1-yl)-5-(1H-pyrazol-4-yl)pyrimidin-4-amine ("163")

6-(4-(1-(2-(azetidin-1-yl)ethyl)-4-(4-fluoro-3-methylphenyl)-1H-imidazol-2-yl)piperidin-1-yl)-5-(1H-pyrazol-4-yl)pyrimidin-4- amine ("164")

6-(4-(1-(2-(tert-butylamino)ethyl)-4-(4-fluoro-3-methylphenyl)-1H-imidazol-2-yl)piperidin-1-yl)-5-(1H-pyrazol-4-yl)pyrimidin-4-amine ("165")

5-bromo-6-(4-(1-(2-(methylamino)ethyl)-4-(2-trifluoromethyl)pyridin-4-yl)-1H-imidazol-2-yl)piperidin-1-yl)pyrimidin-4-amine ("166")

6-(4-(1-(2-(methylamino)ethyl)-4-(2-(trifluoromethyl)pyridin-4-yl)-1H-imidazol-2-yl)piperidin-1-yl)pyrimidin-4-amine ("167")

6-(4-(1-(2-(azetidin-1-yl)ethyl)-4-(2-(trifluoromethyl)pyridin-4-yl)-1H-imidazol-2-yl)piperidin-1-yl)-5-(isoxazol-4-yl)pyrimidin-4- amine ("168")

4-amino-6-(4-(1-(2-(methylamino)ethyl)-4-(2-(trifluoromethyl)pyridin-4-yl)-1H-imidazol-2-yl)piperidin-1-yl)pyrimidine-5-carbonitrile ("169")

5-(4,5-dihydroisoxazol-4-yl)-6-(4-(1-(2-(methylamino)ethyl)-4-(2-(trifluoromethyl)pyridin-4-yl)-1H-imidazol-2-yl)piperidin-1-yl)pyrimdin-4-amine ("170")

5-ethyl-6-(4-(1-(2-(methylamino)ethyl)-4-(2-(trifluoromethyl)pyridin-4-yl)-1H-imidazol-2-yl)piperidin-1-yl)pyrimidin-4-amine ("171")

5-chloro-6-(4-(1-(2-(methylamino)ethyl)-4-(2-(trifluoromethyl)pyridin-4-yl)-1H-imidazol-2-yl)piperidin-1-yl)pyrimidin-4-amine ("172")

5-chloro-6-(4-(1-(2-(cyclopropylamino)ethyl)-4-(2-(trifluoromethyl)pyridin-4-yl)-1H-imidazol-2-yl)piperidin-1-yl)pyrimidin-4-amine ("173")

6-(4-(1-(2-(ethylamino)ethyl)-4-(4-(fluoro-3-(trifluoromethyl)phenyl)-1H-imidazol-2-yl)piperidin-1-yl)-5-isopropoxypyrimidin-4-amine ("174")

6-(4-(1-(azetidin-3-ylmethyl)-4-(4-fluoro-3-(trifluoromethyl)phenyl)-1H-imidazol-2-yl)piperidin-1-yl)-5-isopropoxypyrimidin-4-amine ("175")

6-(4-(1-(azetidin-3-ylmethyl)-4-(4-fluoro-3-(trifluoromethyl)phenyl)-1H-imidazol-2-yl)piperidin-1-yl)-5-ethoxypyrimidin-4-amine ("176")

6-(4-(1-(2-(azetidin-1-yl)ethyl)-4-(4-fluoro-3-(trifluoromethyl)phenyl)-1H-imidazol-2-yl)piperidin-1-yl)-5-ethoxypyrimidin-4-amine ("177")

6-(4-(1-(2-(azetidin-1-yl)ethyl)-4-(4-fluoro-3-methylphenyl)-1H-imidazol-2-yl)piperidin-1-yl)-5-isopropoxy-pyrimidin-4-amine ("178")

6-(4-(1-(2-(azetidin-1-yl)ethyl)-4-(2-isopropylpyridin-4-yl)-1H-imidazol-2-yl)piperidin-1-yl)-5-ethylpyrimidin-4-amine ("179")

6-(4-(1-(2-(azetidin-1-yl)ethyl)-4-(2-isopropylpyridin-4-yl)-1H-imidazol-2-yl)piperidin-1-yl)-5-chloropyrimidin-4-amine ("180")

6-(4-(1-(2-(azetidin-1-yl)ethyl)-4-(2-isopropylpyridin-4-yl)-1H-imidazol-2-yl)piperidin-1-yl)-5-bromopyrimidin-4-amine ("181")

6-(4-(1-(2-(azetidin-1-yl)ethyl)-4-(2-isopropylpyridin-4-yl)-1H-imidazol-2-yl)piperidin-1-yl)-5-vinylpyrimidin-4-amine ("182")

6-(4-(1-(azetidin-3-ylmethyl)-4-(4-fluoro-3-(trifluoromethyl)phenyl)-1H-imidazol-2-yl)piperidin-1-yl)-5-vinylpyrimidin-4-amine ("183")

6-(4-(1-(azetidin-3-ylmethyl)-4-(4-fluoro-3-methylphenyl)-1H-imidazol-2-yl)piperidin-1-yl)-5-methoxypyrimidin-4-amine ("184")

6-(4-(1-(azetidin-3-ylmethyl)-4-(4-fluoro-3-methylphenyl)-1H-imidazol-2-yl)piperidin-1-yl)-5-ethoxypyrimidin-4-amine ("185")

6-(4-(1-(azetidin-3-ylmethyl)-4-(4-fluoro-3-methylphenyl)-1H-imidazol-2-yl)piperidin-1-yl)-5-(2,2,2-trifluoroethoxy)pyrimidin-4-amine ("186")

6-(4-(1-(azetidin-3-ylmethyl)-4-(4-fluoro-3-methylphenyl)-1H-imidazol-2-yl)piperidin-1-yl)-5-isopropxypyrimidin-4-amine ("187")

6-(4-(1-(azetidin-3-ylmethyl)-4-(4-fluoro-3-methylphenyl)-1H-imidazol-2-yl)piperidin-1-yl)-5-ethylpyrimidin-4-amine ("188")

6-(4-(1-(azetidin-3-ylmethyl)-4-(4-fluoro-3-methylphenyl)-1H-imidazol-2-yl)piperidin-1-yl)-5-isopropylpyrimidin-4-amine ("189")

6-(4-(1-(2-(azetidin-1-yl)ethyl)-4-(4-fluoro-3-methylphenyl)-1H-imidazol-2-yl)piperidin-1-yl)-5-bromopyrimidin-4-amine ("190")

4-amino-6-(4-(1-(azetidin-3-ylmethyl)-4-(4-fluoro-3-methylphenyl)-1H-imidazol-2-yl)piperidin-1-yl)pyrimidine-5-carbonitrile ("191")

6-(4-(1-(2-(azetidin-1-yl)ethyl)-4-(2-(trifluoromethyl)pyridin-4-yl)-1H-imidazol-2-yl)piperidin-1-yl)-5-chloro-N-methylpyrimidin-4-amine ("192")

(6-{4-[1-Azetidin-3-ylmethyl-4-(4-fluoro-3-methyl-phenyl)-1H-imidazol-2-yl]-piperidin-1-yl}-5-chloro-pyrimidin-4-yl)-methyl-amine ("193")

6-(4-(1-(azetidin-3-ylmethyl)-4-(4-fluoro-3-methylphenyl)-1H-imidazol-2-yl)cyclohexyl)-5-isopropylpyrimidin-4-amine ("194")

5-Ethyl-6-{4-[4-(4-fluoro-phenyl)-1-(2-morpholin-4-yl-ethyl)-1H-imidazol-2-yl]-piperidin-1-yl}-pyrimidin-4-ylamine ("195")

6-{4-[4-(3,4-Difluoro-phenyl)-1-(2-morpholin-4-yl-ethyl)-1H-imidazol-2-yl]-piperidin-1-yl}-5-ethyl-pyrimidin-4-ylamine ("196")

5-Ethyl-6-(4-{4-(4-fluoro-phenyl)-1-[2-(2-oxa-6-aza-spiro[3.3]hept-6-yl)-ethyl]-1H-imidazol-2-yl)-piperidin-1-yl)- pyrimidin-4-ylamine ("197")

6-(4-{4-(3,4-Difluoro-phenyl)-1-[2-(2-oxa-6-aza-spiro[3.3]hept-6-yl)-ethyl]-1H-imidazol-2-yl}-piperidin-1-yl)-5-ethyl-pyrimidin-4-ylamine ("198")

6-(4-[4-(3,4-Difluoro-phenyl)-1-[2-(3-fluoro-azetidin-1-yl)-ethyl]-1H-imidazol-2-yl}-piperidin-1-yl)-5-ethyl-pyrimidin-4-ylamine ("199")

5-Ethyl-6-{4-[1-[2-(3-fluoro-azetidin-1-yl)-ethyl]-4-(4-fluoro-phenyl)-1H-imidazol-2-yl]-piperidin-1-yl}-pyrimidin-4-ylamine ("200")

5-Ethyl-6-(4-{4-(4-fluoro-phenyl)-1-[2-(2-oxa-6-aza-spiro[3.4]oct-6-yl)-ethyl]-1H-imidazol-2-yl}-piperidin-1-yl)-pyrimidin-4-ylamine ("201")

6-(4-{4-(3,4-Difluoro-phenyl)-1-[2-(2-oxa-6-aza-spiro[3.4]oct-6-yl)-ethyl]-1H-imidazol-2-yl}-piperidin-1-yl)-5-ethyl-pyrimidin-4-ylamine ("202")

6-(4-{4-(3,4-Difluoro-phenyl)-1-[2-(6-oxa-1-aza-spiro[3.3]hept-1-yl]-ethyl]-1H-imidazol-2-yl}-piperidin-1-yl)-5-ethyl-pyrimidin-4-ylamine ("203")

5-Ethyl-6-(4-{4-(4-fluoro-phenyl)-1-[2-(6-oxa-1-aza-spiro[3.3]hept-1-yl)-ethyl]-1H-imidazol-2-yl}-piperidin-1-yl)-pyrimidin-4-ylamine ("204")

4-Amino-6-{4-[1-(2-azetidin-1-yl-ethyl)-4-(5-chloro-6-fluoro-pyridin-3-yl)-1H-imidazol-2-yl]-piperidin-1-yl}-pyrimidine-5-carbonitrile ("205")

4-Amino-6-{4-[1-(2-azetidin-1-yl-ethyl)-4-(2-fluoro-pyridin-4-yl)-1H-imidazol-2-yl]-piperidin-1-yl}-pyrimidine-5-carbonitrile ("206")

4-Amino-6-{4-[1-(2-azetidin-1-yl-ethyl)-4-(1H-indazol-5-yl)-1H-imidazol-2-yl]-piperidin-1-yl}-pyrimidine-5-carbonitrile ("207")

6-{4-(4-fluoro-3-trifluoromethyl-phenyl)-1-2-pyrrolidin-1-yl-ethyl)-1H-imidazol-2-yl]-piperidin-1-yl}-5-ethyl-pyrimidin-4-ylamine ("208")

5-Chloro-6{4  -(4-fluoro-3-trifluoromethyl-phenyl)-1-2-pyrrolidin-1-yl-ethyl)-1H-imidazol-2-yl]-piperidin-1-yl}-pyrimidin-4-ylamine ("209")

5-Chloro-6{4-(4-hydroxy-3-trifluoromethyl-phenyl)-1-2-pyrrolidin-1-yl-ethyl)-1H-imidazol-2-yl]-piperidin-1-yl}-pyrimidin-4-ylamine ("210")

5-Fluoro-6{4-(4-fluoro-3-trifluoromethyl-phenyl)-1-2-pyrrolidin-1-yl-ethyl)-1H-imidazol-2-yl]-piperidin-1-yl}-pyrimidin-4-ylamine ("211")

6-{4-(4-fluoro-3-trifluoromethyl-phenyl)-1-2-piperidin-1-yl-ethyl)-1H-imidazol-2-yl]-piperidin-1-yl}-5-isopropylene-pyrimidin-4-ylamine ("212")

6-{4-(4-fluoro-3-trifluoromethyl-phenyl)-1-2-pyrrolidin-1-yl-ethyl)-1H-imidazol-2-yl]-piperidin-1-yl}-5-isopropylene-pyrimidin-4-ylamine ("213")

6-{4-(4-fluoro-3-trifluoromethyl-phenyl)-1-2-pyrrolidin-1-yl-ethyl)-1H-imidazol-2-yl]-piperidin-1-yl}-yrimidin-4-ylamine ("214")

6-{4-(4-fluoro-3-trifluoromethyl-phenyl)-1-2-pyrrolidin-1-yl-ethyl)-1H-imidazol-2-yl]-piperidin-1-yl}-5-methyl-pyrimidin-4-ylamine ("215")

5-Chloro-6{4-(4-fluoro-3-trifluoromethyl-phenyl)-1-2-piperidin-1-yl-ethyl)-1H-imidazol-2-yl]-piperidin-1-yl}-pyrimidin-4-ylamine ("216")

5-Bromo-6{4-(4-fluoro-3-trifluoromethyl-phenyl)-1-2-pyrrolidin-1-yl-ethyl)-1H-imidazol-2-yl]-azetidin-1-yl}-pyrimidin-4-ylamine ("217")

5-Chloro-6{4-(4-fluoro-3-trifluoromenthyl-phenyl)-1-2-pyrrolidin-1-yl-ethyl)-1H-imidazol-2-yl]-azetidin-1-yl}-pyrimidin-4-ylamine ("218")

5-(4-fluorophenyl)-6{4-(4-fluoro-3-trifluoromethyl-phenyl)-1-2-azetidin-1-yl-ethyl)-1H-imidazol-2-yl]-piperidin-1-yl}-pyrimidin-4-ylamine ("219")

5-vinyl-6{4-(4-fluoro-3-trifluoromethyl-phenyl)-1-2-azetidin-1-yl-ethyl)-1H-imidazol-2-yl]-piperidin-1-yl}-pyrimidin-4-ylamine ("220")

6{4-(4-fluoro-3-trifluoromenthyl-phenyl)-1-2-azetidin-1-yl-ethyl)-1H-imidazol-2-yl]-piperidin-1-yl}-pyrimidin-4-ylamine ("221")

5-(4-methyl carboxyesterphenyl)-6{4-(4-fluoro-3-trifluoromethyl-phenyl)-1-2-azetidin-1-yl-ethyl)-1H-imidazol-2-yl]-piperidin-1-yl}-pyrimidin-4-ylamine ("222")

5-(4-methyl carboxyesterphenyl)-6{4-(4-fluoro-3-trifluoromethyl-phenyl)-1-2-pyrrolidin-1-yl-ethyl)-1H-imidazol-2-yl]-piperidin-1-yl}-pyrimidin-4-ylamine ("223")

5-(4-carboxy acidphenyl)-6{4-(4-fluoro-3-trifluoromethyl-phenyl)-1-2-azetidin-1-yl-ethyl)-1H-imidazol-2-yl]-piperidin-1-yl}-pyrimidin-4-ylamine ("224")

5-(4-carboxy acid phenyl)-6{4-(4-fluoro-3-trifluoromethyl-phenyl)-1-2-pyrrolidin-1-yl-ethyl)-1H-imidazol-2-yl]-piperidin-1-yl}-pyrimidin-4-ylamine ("225")

5-Bromo-6{4-(3,4-difluorophenyl)-1-2-pyrrolidin-1-yl-ethyl)-1H-imidazol-2-yl]-piperidin-1-yl}-pyrimidin-4-ylamine ("226")

5-Bromo-6{4-(4-fluorophenyl)-1-2-pyrrolidin-1-yl-ethyl)-1H-imidazol-2-yl]-piperidin-1-yl}-pyrimidin-4-ylamine ("227")

5-Bromo-6{4-(3-fluorophenyl)-1-2-pyrrolidin-1-yl-ethyl)-1H-imidazol-2-yl]-piperidin-1-yl}-pyrimidin-4-ylamine ("228")

5-Bromo-6{4-(3-fluoro-4-trifluoromethyl-phenyl)-1-2-pyrrolidin-1-yl-ethyl)-1H-imidazol-2-yl]-piperidin-1-yl}-pyrimidin-4-ylamine ("229")

5-Ethyl-6{4-(4-fluoro-3-trifluoromethyl-phenyl)-1-2-azetidin-1-yl-ethyl)-1H-imidazol-2-yl]-piperidin-1-yl}-pyrimidin-4-ylamine ("230")

5-Ethyl-6{4-(3-fluorophenyl)-1-2-pyrrolidin-1-yl-ethyl)-1H-imidazol-2-yl]-piperidin-1-yl}-pyrimidin-4-ylamine ("231")

5-Ethyl-6{4-(4-fluorophenyl)-1-2-pyrrolidin-1-yl-ethyl)-1H-imidazol-2-yl]-piperidin-1-yl}-pyrimidin-4-ylamine ("232")

5-Ethyl-6{4-(3,4-difluorophenyl)-1-2-pyrrolidin-1-yl-ethyl)-1H-imidazol-2-yl]-piperidin-1-yl}-pyrimidin-4-ylamine ("233")

5-Ethyl-6{4-(3-fluoro-4-trifluoromethylphenyl)-1-2-pyrrolidin-1-yl-ethyl)-1H-imidazol-2-yl]-piperidin-1-yl}-pyrimidin-4-ylamine ("234")

5-Chloro-6{4-(3-fluoro-4-trifluoromethylphenyl)-1-2-pyrrolidin-1-yl-ethyl)-1H-imidazol-2-yl]-piperidin-1-yl}-pyrimidin-4-ylamine ("235")

5-Chloro-6{4-(3-fluoromethylphenyl)-1-2-pyrrolidin-1-yl-ethyl)-1H-imidazol-2-yl]-piperidin-1-yl}-pyrimidin-4-ylamine ("236")

5-Chloro-6{4-(4-fluoromethylphenyl)-1-2-pyrrolidin-1-yl-ethyl)-1H-imidazol-2-yl]-piperidin-1-yl}-pyrimidin-4-ylamine ("237")

5-Chloro-6{4-(3,4-difluoromethylphenyl)-1-2-pyrrolidin-1-yl-ethyl)-1H-imidazol-2-yl]-piperidin-1-yl}-pyrimidin-4-ylamine ("238")

5-Vinyl-6{4-(3-fluoro-4-trifluoromethylphenyl)-1-2-pyrrolidin-1-yl-ethyl)-1H-imidazol-2-yl]-piperidin-1-yl}-pyrimidin-4-ylamine ("239")

5-Vinyl-6{4-(3-fluorophenyl)-1-2-pyrrolidin-1-yl-ethyl)-1H-imidazol-2-yl]-piperidin-1-yl}-pyrimidin-4-ylamine ("240")

5-Vinyl-6{4-(4-fluorophenyl)-1-2-pyrrolidin-1-yl-ethyl)-1H-imidazol-2-yl]-piperidin-1-yl}-pyrimidin-4-ylamine ("241")

5-Vinyl-6{4-(3,4-difluorophenyl)-1-2-pyrrolidin-1-yl-ethyl)-1H-imidazol-2-yl]-piperidin-1-yl}-pyrimidin-4-ylamine ("242")

6{4-(3,4-difluorophenyl)-1-2-pyrrolidin-1-yl-ethyl)-1H-imidazol-2-yl]-piperidin-1-yl}-pyrimidin-4-ylamine ("243")

6{4-(3-fluorophenyl)-1-2-pyrrolidin-1-yl-ethyl)-1H-imidazol-2-yl]-piperidin-1-yl}-pyrimidin-4-ylamine ("244")

5-Ethyl-6{4-(3-fluoro-4-trifluoromethylphenyl)-1-2-((S)-3-fluoro-pyrrolidin-1-yl)-ethyl)-1H-imidazol-2-yl]-piperidin-1-yl}-pyrimidin-4- ylamine ("245")

5-Ethyl-6{4-(3-fluoro-4-trifluoromethylphenyl)-1-2-((R)-3-fluoro-pyrrolidin-1-yl)-ethyl)-1H-imidazol-2-yl]-piperidin-1-yl}-pyrimidin-4- ylamine ("246")

5-Ethyl-6{4-(3-fluoro-4-trifluoromethylphenyl)-1-2-(4,4-difluoro-piperidin-1-yl)-ethyl)-1H-imidazol-2-yl]-piperidin-1-yl}-pyrimidin-4- ylamine ("247")

5-Ethyl-6{4-(3-fluoro-4-trifluoromethylphenyl)-1-2-(3,3-difluoro-piperidin-1-yl)-ethyl)-1H-imidazol-2-yl]-piperidin-1-yl}-pyrimidin-4- ylamine ("248")

5-Ethyl-6{4-(3-fluoro-4-trifluoromethylphenyl)-1-2-(4-fluoro-piperidin-1-yl)-ethyl)-1H-imidazol-2-yl]-piperidin-1-yl}-pyrimidin-4-ylamine ("249")

5-Ethyl-6{4-(3-fluoro-4-trifluoromethylphenyl)-1-2-(3-fluoro-piperidin-1-yl)-ethyl)-1H-imidazol-2-yl]-piperidin-1-yl}-pyrimidin-4-ylamine ("250")

5-Ethyl-6{4-(3-fluoro-4-chlorophenyl)-1-2-(pyrrolidin-1-yl-ethyl)-1H-imidazol-2-yl]-piperidin-1-yl}-pyrimidin-4-ylamine ("251")

5-Ethyl-6{4-(4-fluoro-3-chlorophenyl)-1-2-(pyrrolidin-1-yl-ethyl)-1H-imidazol-2-yl]-piperidin-1-yl}-pyrimidin-4-ylamine ("252")

5-cyclobutyl-6{4-(3-fluoro-4-trifluoromethylphenyl)-1-2-(piperidin-1-yl-ethyl)-1H-imidazol-2-yl]-piperidin-1-yl}-pyrimidin-4-ylamine ("253")

5-cyclobutyl-6{4-(3-fluoro-4-trifluoromethylphenyl)-1-2-(pyrrolidin-1-yl-ethyl)-1H-imidazol-2-yl]-piperidin-1-yl}-pyrimidin-4-ylamine ("254")

5-cyclobutyl-6{4-(3,4-difluorophenyl)-1-2-(pyrrolidin-1-yl-ethyl)-1H-imidazol-2-yl]-piperidin-1-yl}-pyrimidin-4-ylamine ("255")

5-cyclobutyl-6{4-(4-fluorophenyl)-1-2-(pyrrolidin-1-yl-ethyl)-1H-imidazol-2-yl]-piperidin-1-yl}-pyrimidin-4-ylamine ("256")

5-cyclobutyl-6{4-(3-fluorophenyl)-1-2-(pyrrolidin-1-yl-ethyl)-1H-imidazol-2-yl]-piperidin-1-yl}-pyrimidin-4-ylamine ("257")

5-cyclobutyl-6{4-(3-fluoro-4-trifluoromethyl-phenyl)-1-2-(pyrrolidin-1-yl-ethyl)-1H-imidazol-2-yl]-piperidin-1-yl}-pyrimidin-4-ylamine ("258")

5-cyclobutyl-6{4-(4-trifluoromethyl-phenyl)-1-2-(pyrrolidin-1-yl-ethyl)-1H-imidazol-2-yl]-piperidin-1-yl}-pyrimidin-4-ylamine ("259")

5-cyclobutyl-6{4-(4-chloro-3-fluoro-phenyl)-1-2-pyrrolidin-1-yl-ethyl)-1H-imidazol-2-yl]-piperidin-1-yl}-pyrimidin-4-ylamine ("260")

5-cyclobutyl-6{4-(3-trifluoromethyl-phenyl)-1-2-(pyrrolidin-1-yl-ethyl)-1H-imidazol-2-yl]-piperidin-1-yl}-pyrimidin-4-ylamine ("261")

5-cyclobutyl-6{4-(3-chloro-4-fluoro-phenyl)-1-2-(pyrrolidin-1-yl-ethyl)-1H-imidazol-2-yl]-piperidin-1-yl}-pyrimidin-4-ylamine ("262")

5-cyclobutyl-6{4-(4-chloro-phenyl)-1-2-(pyrrolidin-1-yl-ethyl)-1H-imidazol-2-yl]-piperidin-1-yl}-pyrimidin-4-ylamine ("263")

5-cyclobutyl-6{4-(3-chloro-phenyl)-1-2-(pyrrolidin-1-yl-ethyl)-1H-imidazol-2-yl]-piperidin-1-yl}-pyrimidin-4-ylamine ("264")

5-Bromo-6{4-(4-trifluoromethyl-phenyl)-1-2-pyrrolidin-1-yl-ethyl)-1H-imidazol-2-yl]-piperidin-1-yl}-pyrimidin-4-ylamine ("265")

5-Bromo-6{4-(4-chloro-3-fluoro-phenyl)-1-2-pyrrolidin-1-yl-ethyl)-1H-imidazol-2-yl]-piperidin-1-yl}-pyrimidin-4-ylamine ("266")

5-Bromo-6{4-(3-trifluoromethyl-phenyl)-1-2-pyrrolidin-1-yl-ethyl)-1H-imidazol-2-yl]-piperidin-1-yl}-pyrimidin-4-ylamine ("267")

5-Bromo-6{4-(3-chloro-4-fluorophenyl)-1-2-pyrrolidin-1-yl-ethyl)-1H-imidazol-2-yl]-piperidin-1-yl}-pyrimidin-4-ylamine ("268")

5-vinyl-6{4-(4-trifluoromethyl-phenyl)-1-2-(pyrrolidin-1-yl-ethyl)-1H-imidazol-2-yl]-piperidin-1-yl}-pyrimidin-4-ylamine ("269")

-6{4-(4-trifluoromethyl-phenyl)-1-2-(pyrrolidin-1-yl-ethyl)-1H-imidazol-2-yl]-piperidin-1-yl}-pyrimidin-4-ylamine ("270")

5-Ethyl-6{4-(4-trifluoromethyl-phenyl)-1-2-(pyrrolidin-1-yl-ethyl)-1H-imidazol-2-yl]-piperidin-1-yl}-pyrimidin-4-ylamine ("271")

5-Ethyl-6{4-(3-trifluoromethyl-phenyl)-1-2-(pyrrolidin-1-yl-ethyl)-1H-imidazol-2-yl]-piperidin-1-yl}-pyrimidin-4-ylamine ("272")

5-Ethyl-6{4-(4-chloro-phenyl)-1-2-(pyrrolidin-1-yl-ethyl)-1H-imidazol-2-yl]-piperidin-1-yl}-pyrimidin-4-ylamine ("273")

5-Ethyl-6{4-(3-chloro-phenyl)-1-2-(pyrrolidin-1-yl-ethyl)-1H-imidazol-2-yl]-piperidin-1-yl}-pyrimidin-4-ylamine ("274")

5-Ethyl-6{4-(4-fluoro-4-trifluoromethyl-phenyl)-1-2-((3,3-difluoro-pyrrolidin-1-yl)-ethyl)-1H-imidazol-2-yl]-piperidin-1-yl}-pyrimidin-4-ylamine ("275")

5-Ethyl-6{4-(4-fluoro-3-trifluoromethyl-phenyl)-1-2-((piperidin-1-yl)-ethyl)-1H-imidazol-2-yl]-piperidin-1-yl}-pyrimidin-4-ylamine ("276")

5-Ethyl-6{4-(3-trifluoromethyl-phenyl)-1-2-(azetidin-1-yl-ethyl)-1H-imidazol-2-yl]-piperidin-1-yl}-pyrimidin-4-ylamine ("277")

5-Ethyl-6{4-(3-fluoro-phenyl)-1-2-(azetidin-1-yl-ethyl)-1H-imidazol-2-yl]-piperidin-1-yl}-pyrimidin-4-ylamine ("278")

5-Ethyl-6{4-(3-chloro-phenyl)-1-2-(azetidin-1-yl-ethyl)-1H-imidazol-2-yl]-piperidin-1-yl}-pyrimidin-4-ylamine ("279")

5-cyclobutyl-6{4-(3-fluoro-4-trifluoromethylphenyl)-1-2-(azetidin-1-yl-ethyl)-1H-imidazol-2-yl]-piperidin-1-yl}-pyrimidin-4-ylamine ("280")

5-Ethyl-6{4-(4-fluoro-3-chlorophenyl)-1-2-(azetidin-1-yl-ethyl)-1H-imidazol-2-yl]-piperidin-1-yl}-pyrimidin-4-ylamine ("281")

5-Ethyl-6{4-(3,4-difluorophenyl)-1-2-(azetidin-1-yl-ethyl)-1H-imidazol-2-yl]-piperidin-1-yl}-pyrimidin-4-ylamine ("282")

5-Nitro-6{4-(4-fluoro-3-trifluomethyl-phenyl)-1-2-(azetidin-1-yl-ethyl)-1H-imidazol-2-yl]-piperidin-1-yl}-pyrimidin-4-ylamine ("283")

5-Amino-6{4-(4-fluoro-3-trifluomethyl-phenyl)-1-2-(azetidin-1-yl-ethyl)-1H-imidazol-2-yl]-piperidin-1-yl}-pyrimidin-4-ylamine ("284")

5-Formyl-6{4-(4-fluoro-3-trifluomethyl-phenyl)-1-2-(azetidin-1-yl-ethyl)-1H-imidazol-2-yl]-piperidin-1-yl}-pyrimidin-4-ylamine ("285")

6{4-(4-fluoro-3-trifluomethyl-phenyl)-1-2-(pyrrolidin-1-yl-ethyl)-1H-imidazol-2-yl]-piperidin-1-yl}-pyrimidin-4-ylamine-5-carboxy acid ("286")

5-Formyl-6{4-(4-fluoro-3-trifluomethyl-phenyl)-1-2-(pyrrolidin-1-yl-ethyl)-1H-imidazol-2-yl]-piperidin-1-yl}-pyrimidin-4-ylamine ("287")

5-Ethylamide-6{4-(4-fluoro-3-trifluomethyl-phenyl)-1-2-(azetidin-1-yl-ethyl)-1H-imidazol-2-yl]-piperidin-1-yl}-pyrimidin-4-ylamine ("288")

5-Ethoxy-6{4-(3-chloro-4-fluorophenyl)-1-2-(pyrrolidin-1-yl-ethyl)-1H-imidazol-2-yl]-piperidin-1-yl}-pyrimidin-4-ylamine ("289")

5-isopropoxy-6{4-(3-chloro-4-fluorophenyl)-1-2-(pyrrolidin-1-yl-ethyl)-1H-imidazol-2-yl]-piperidin-1-yl}-pyrimidin-4-ylamine ("290")

5-Ethoxy-6{4-(4-fluoro-3-trifluomethyl-phenyl)-1-2-(N, N-dimethylamino-1-yl-ethyl)-1H-imidazol-2-yl]-piperidin-1-yl}-pyrimidin-4-ylamine ("291")

5-Isoprpoxy-6{4-(4-fluoro-3-trifluomethyl-phenyl)-1-2-(N,N-dimethylamino-1-yl-ethyl)-1H-imidazol-2-yl]-piperidin-1-yl}-pyrimidin-4-ylamine ("292")

5-Ethoxy-6{4-(4-fluoro-3-methyl-phenyl)-1-2-(N,N-dimethylamino-1-yl-ethyl)-1H-imidazol-2-yl]-piperidin-1-yl}-pyrimidin-4-ylamine ("293")

5-isopropoxy-6{4-(4-fluoro-3-methyl-phenyl)-1-2-(N,N-dimethylamino-1-yl-ethyl)-1H-imidazol-2-yl]-piperidin-1-yl}-pyrimidin-4-ylamine ("294")

5-Ethyl-6{4-(4-fluoro-3-methyl-phenyl)-1-2-(N,N-dimethylamino-1-yl-ethyl)-1H-imidazol-2-yl]-piperidin-1-yl}-pyrimidin-4-ylamine ("295")

5-Ethyl-6{4-(4-fluoro-3-methyl-phenyl)-1-2-(N,N-diethylamino-1-yl-ethyl)-1H-imidazol-2-yl]-piperidin-1-yl}-pyrimidin-4-ylamine ("296")

5-Ethyl-6{4-(4-fluoro-3-methyl-phenyl)-1-2-(pyrrolidin-1-yl-ethyl)-1H-imidazol-2-yl]-piperidin-1-yl}-pyrimidin-4-ylamine ("297")

5-Ethoxy-6{4-(4-fluoro-3-methyl-phenyl)-1-2-(pyrrolidin-1-yl-ethyl)-1H-imidazol-2-yl]-piperidin-1-yl}-pyrimidin-4-ylamine ("298")

5-Isopropoxy-6{4-(4-fluoro-3-methyl-phenyl)-1-2-(pyrrolidin-1-yl-ethyl)-1H-imidazol-2-yl]-piperidin-1-yl}-pyrimidin-4-ylamine ("299")

5-Ethyl-6{4-(4-fluoro-3-methyl-phenyl)-1-2-(N,N-isopropylethylamino-1-yl-ethyl)-1H-imidazol-2-yl]-piperidin-1-yl}-pyrimidin-4-ylamine ("300")

5-Ethoxy-6{4-(4-fluoro-3-methyl-phenyl)-1-2-(N,N-isopropylethylamino-1-yl-ethyl)-1H-imidazol-2-yl]-piperidin-1-yl}-pyrimidin-4-ylamine ("301")

5-Isopropoxy-6{4-(4-fluoro-3-methyl-phenyl)-1-2-(N,N-isopropylethylamino-1-yl-ethyl)-1H-imidazol-2-yl]-piperidin-1-yl}-pyrimidin-4-ylamine ("302")

5-Ethoxy-6{4-(4-fluoro-3-methyl-phenyl)-1-2-(N,N-diethylamino-1-yl-ethyl)-1H-imidazol-2-yl]-piperidin-1-yl}-pyrimidin-4-ylamine ("303")

5-Isopropoxy-6{4-(4-fluoro-3-methyl-phenyl)-1-2-(N,N-diethylamino-1-yl-ethyl)-1H-imidazol-2-yl]-piperidin-1-yl}-pyrimidin-4-ylamine ("304")

4-amino-6{4-(4-fluoro-3-trifluoromethyl-phenyl)-1-2-(pyrrolidin-1-yl-ethyl)-1H-imidazol-2-yl]-piperidin-1-yl}-pyrimidin-5-carbonitrile ("305")

4-amino-6{4-(3,4-difluorophenyl)-1-2-(pyrrolidin-1-yl-ethyl)-1H-imidazol-2-yl]-piperidin-1-yl}-pyrimidin-5-carbonitrile ("306")

4-amino-6{4-(3-chloro-4-fluorophenyl)-1-2-(pyrrolidin-1-yl-ethyl)-1H-imidazol-2-yl]-piperidin-1-yl}-pyrimidin-5-carbonitrile ("307")

4-amino-6{4-(4-fluorophenyl)-1-2-(pyrrolidin-1-yl-ethyl)-1H-imidazol-2-yl]-piperidin-1-yl}-pyrimidin-5-carbonitrile ("308")

4-amino-6{4-(3-fluorophenyl)-1-2-(pyrrolidin-1-yl-ethyl)-1H-imidazol-2-yl]-piperidin-1-yl}-pyrimidin-5-carbonitrile ("309")

4-amino-6{4-(3-trifluoromethyl-phenyl)-1-2-(pyrrolidin-1-yl-ethyl)-1H-imidazol-2-yl]-piperidin-1-yl}-pyrimidin-5-carbonitrile ("310")

4-amino-6{4-(3-chloro-phenyl)-1-2-(pyrrolidin-1-yl-ethyl)-1H-imidazol-2-yl]-piperidin-1-yl}-pyrimidin-5-carbonitrile ("311")

4-amino-6{4-(4-fluoro-3-trifluoromethyl-phenyl)-1-2-(piperidin-1-yl-ethyl)-1H-imidazol-2-yl]-piperidin-1-yl}-pyrimidin-5-carbonitrile ("312")

4-amino-6{4-(3,4-difluorophenyl)-1-2-(azetidin-1-yl-ethly)-1H-imidazol-2-yl]-piperidin-1-yl}-pyrimidin-5-carbonitrile ("313")

4-amino-6{4-(4-fluoro-3-difluoromethoxy-phenyl)-1-2-(azetidin-1-yl-ethyl)-1H-imidazol-2-yl]-piperidin-1-yl}-pyrimidin-5-carbonitrile ("314")

4-amino-6{4-(2-oxo-1,2-dihydro-pyridin-4-yl)-1-2-(azetidin-1-yl-ethyl)-1H-imidazol-2-yl]-piperidin-1-yl}-pyrimidin-5-carbonitrile ("315")

4-amino-6{4-(4-methyl-3-trifluoromethyl-phenyl)-1-2-(azetidin-1-yl-ethyl)-1H-imidazol-2-yl]-piperidin-1-yl}-pyrimidin-5-carbonitrile ("316")

4-amino-6{4 (2-isopropyl-pyridin-4-yl)-1-2-(azetidin-1-yl-ethyl)-1H-imidazol-2-yl]-piperidin-1-yl}-pyrimidin-5-carbonitrile ("317")

4-amino-6{4 (2-ethyl-pyridin-4-yl)-1-2-(azetidin-1-yl-ethyl)-1H-imidazol-2-yl]-piperidin-1-yl}-pyrimidin-5-carbonitrile ("318")

4-amino-6{4 (2-cyclopropyl-pyridin-4-yl)-1-2-(azetidin-1-yl-ethyl)-1H-imidazol-2-yl]-piperidin-1-yl}-pyrimidin-5-carbonitrile ("319")

4-amino-6{4-(4-methyl-3-fluoro-phenyl)-1-2-(azetidin-1-yl-ethyl)-1H-imidazol-2-yl]-piperidin-1-yl}-pyrimidin-5-carbonitrile ("320")

4-amino-6{4-(4-methoxy-3-fluoro-phenyl)-1-2-(azetidin-1-yl-ethyl)-1H-imidazol-2-yl]-piperidin-1-yl}-pyrimidin-5-carbonitrile ("321")

4-amino-6{4-(4-methyl-3-chloro-phenyl)-1-2-(azetidin-1-yl-ethyl)-1H-imidazol-2-yl]-piperidin-1-yl}-pyrimidin-5-carbonitrile ("322")

4-amino-6{4-(4-methoxy-3-chloro-phenyl)-1-2-(azetidin-1-yl-ethyl)-1H-imidazol-2-yl]-piperidin-1-yl}-pyrimidin-5-carbonitrile ("323")

4-amino-6{4-(3-methyl-4-fluoro-phenyl)-1-2-(pyrrolidin-1-yl-ethyl)-1H-imidazol-2-yl]-piperidin-1-yl}-pyrimidin-5-carbonitrile ("324")

4-amino-6{4-(3-methyl-4-fluoro-phenyl)-1-2-(N,N-dimethylamino)-1-yl-ethyl)-1H-imidazol-2-yl]-piperidin-1-yl}-pyrimidin-5-carbonitrile ("325")

4-amino-6{4-(3-methyl-4-fluoro-phenyl)-1-2-(N,N-diethylamino)-1-yl-ethyl)-1H-imidazol-2-yl]-piperidin-1-yl}-pyrimidin-5-carbonitrile ("326")

4-amino-6{4-(3-methyl-4-fluoro-phenyl)-1-2-(N,N-isoproplethylamino)-1-yl-ethyl)-1H-imidazol-2-yl]-piperidin-1-yl}-pyrimidin-5-carbonitrile ("327")

4-amino-6{4-(3,4-difluorophenyl)-1-2-(azetidin-1-yl-ethyl)-1H-imidazol-2-yl]-piperidin-1-yl}-pyrimidin-5-carboxylic acid amide ("328")

4-amino-6{4-(3,4-difluorophenyl)-1-2-(pyrrolidin-1-yl-ethyl)-1H-imidazol-2-yl]-piperidin-1-yl}-pyrimidin-5-carboxylic acid amide ("329")

4-amino-6{4-(3-chloro-4-fluorophenyl)-1-2-(pyrrolidin-1-yl-ethyl)-1H-imidazol-2-yl]-piperidin-1-yl}-pyrimidin-5-carboxylic acid amide ("330")

4-amino-6{4-(4-fluoro-3-trifluoromethylphenyl)-1-2-(pyrrolidin-1-yl-ethyl)-1H-imidazol-2-yl]-piperidin-1-yl}-pyrimidin-5-carboxylic acid amide ("331")

4-amino-6{4 (2-isopropyl-pyridin-4-yl)-1-2-(azetidin-1-yl-ethyl)-1H-imidazol-2-yl]-piperidin-1-yl}-pyrimidin-5-carboxylic acid amide ("332")

4-amino-6{4-(4-fluorophenyl)-1-2-(pyrrolidin-1-yl-ethyl)-1H-imidazol-2-yl]-piperidin-1-yl}-pyrimidin-5-carboxylic acid amide ("333")

4-amino-6{4-(3-fluorophenyl)-1-2-(pyrrolidin-1-yl-ethyl)-1H-imidazol-2-yl]-piperidin-1-yl}-pyrimidin-5-carboxylic acid amide ("334")

4-amino-6{4-(3-trifluoromethyl-phenyl)-1-2-(pyrrolidin-1-yl-ethyl)-1H-imidazol-2-yl]-piperidin-1-yl}-pyrimidin-5-carboxylic acid amide ("335")

4-amino-6{4-(3-chloro-phenyl)-1-2-(pyrrolidin-1-yl-ethyl)-1H-imidazol-2-yl]-piperidin-1-yl}-pyrimidin-5-carboxylic acid amide ("336")

4-amino-6{4-(4-fluoro-3-trifluoromethyl-phenyl)-1-2-(piperidin-1-yl-ethyl)-1H-imidazol-2-yl]-piperidin-1-yl}-pyrimidin-5-carboxylic acid amide ("337")

4-amino-6{4-(4-fluoro-3-difluoromethoxy-phenyl)-1-2-(azetidin-1-yl-ethyl)-1H-imidazol-2-yl]-piperidin-1-yl}-pyrimidin-5-carboxylic acid amide ("338")

4-amino-6{4-(2-oxo-pyridin-4-yl)-1-2-(azetidin-1-yl-ethyl)-1H-imidazol-2-yl]-piperidin-1-yl}-pyrimidin-5-carboxylic acid amide ("339")

4-amino-6{4-(4-methyl-3-trifluoromethyl-phenyl)-1-2-(azetidin-1-yl-ethyl)-1H-imidazol-2-yl]-piperidin-1-yl}-pyrimidin-5-carboxylic acid amide ("340")

4-amino-6{4 (2-ethyl-pyridin-4-yl)-1-2-(azetidin-1-yl-ethyl)-1H-imidazol-2-yl]-piperidin-1-yl}-pyrimidin-5-carboxylic acid amide ("341")

4-amino-6{4 (2-cylopropyl-pyridin-4-yl)-1-2-(azetidin-1-yl-ethyl)-1H-imidazol-2-yl]-piperidin-1-yl}-pyrimidin-5-carboxylic acid amide ("342")

4-amino-6{4 (2-tert-butyl-pyridin-4-yl)-1-2-(azetidin-1-yl-ethyl)-1H-imidazol-2-yl]-piperidin-1-yl}-pyrimidin-5-carboxylic acid amide ("343")

4-amino-6{4-(4-methyl-3-fluoro-phenyl)-1-2-(azetidin-1-yl-ethyl)-1H-imidazol-2-yl]-piperidin-1-yl}-pyrimidin-5-carboxylic acid amide ("344")

4-amino-6{4-(4-methoxy-3-fluoro-phenyl)-1-2-(azetidin-1-yl-ethyl)-1H-imidazol-2-yl]-piperidin-1-yl}-pyrimidin-5-carboxylic acid amide ("345")

4-amino-6{4-(3-chloro-4-methyl-phenyl)-1-2-(azetidin-1-yl-ethyl)-1H-imidazol-2-yl]-piperidin-1-yl}-pyrimidin-5-carboxylic acid amide ("346")

4-amino-6{4-(3-chloro-4-methoxy-phenyl)-1-2-(azetidin-1-yl-ethyl)-1H-imidazol-2-yl]-piperidin-1-yl}-pyrimidin-5-carboxylic acid amide ("347")

4-amino-6{4-(4-fluoro-3-methyl-phenyl)-1-2-(N,N-dimethylamino-ethyl)-1H-imidazol-2-yl]-piperidin-1-yl}-pyrimidin-5-carboxylic acid amide ("348")

4-amino-6{4-(4-fluoro-3-methyl-phenyl)-1-2-(N,N-diethylamino-ethyl)-1H-imidazol-2-yl]-piperidin-1-yl}-pyrimidin-5-carboxylic acid amide ("349")

4-amino-6{4-(4-fluoro-3-methyl-phenyl)-1-2-(pyrrolidin-1-yl-ethyl)-1H-imidazol-2-yl]-piperidin-1-yl}-pyrimidin-5-carboxylic acid amide ("350")

4-amino-6{4-(4-fluoro-3-methyl-phenyl)-1-2-(N,N-ethylisopropylamino-ethyl)-1H-imidazol-2-yl]-piperidin-1-yl}-pyrimidin-5-carboxylic acid amide ("351")

6-{4-[1-(2-Azetidin-1-yl-ethyl)-4-(2-dimethylamino-pyrimidin-5-yl)-1H-imidazol-2-yl]-piperidin-1-yl}-5-ethyl-pyrimidin-4-ylamine ("352")

4-Amino-6-{4-[1-(2-azetidin-1-yl-ethyl)-4-(2-fluoro-phenyl)-1H-imidazol-2-yl]-piperidin-1-yl}-pyrimidin-5-carbonitrile ("353")

3-[2-[1-(6-Amino-5-cyano-pyrimidin-4-yl)-piperidin-4-yl]-1-(2-azetidin-1-yl-ethyl)-1H-imidazol-4-yl]-benzenesulfonamide ("354")

4-Amino-6-{4-[1-(2-azetidin-1-yl-ethyl)-4-(3-methanesulfonyl-phenyl)-1H-imidazol-2-yl]-piperidin-1-yl}-pyrimidin-5-carbonitrile ("355")

4-Amino-6-{4-[1-(2-azetidin-1-yl-ethyl)-4-(3-methanesulfonyl-phenyl)-1H-imidazol-2-yl]-piperidin-1-yl}-pyrimidine-5-carboxylic acid amide ("356")

4-Amino-6-{4-[4-(4-fluoro-3-trifluoromethyl-phenyl)-1-(2-hydroxy-ethyl)-1H-imidazol-2-yl]-piperidin-1-yl}-pyrimidine-5-carbonitrile ("357")

4-Amino-6-{4-[1-[2-(cyclopropylmethyl-amino)-ethyl]-4-(4-fluoro-3-trifluoromethyl-phenyl)-1H-imidazol-2-yl]-piperidin-1-yl}-pyrimidine-5-carbonitrile ("358")

4-Amino-6-{4-[1-[2-(cyclopropylmethyl-amino)-ethyl]-4-(4-fluoro-3-trifluoromethyl-phenyl)-1H-imidazol-2-yl]-piperidin-1-yl}-pyrimidine-5-carboxylic acid amide ("359")

4-Amino-6-(4-{4-(4-fluoro-3-trifluoromethyl-phenyl)-1-[2-(isopropyl-methyl-amino)-ethyl]-1H-imidazol-2-yl}-piperidin-1-yl)-pyrimidine-5-carbonitrile ("360")

4-Amino-6-(4-{4-(4-fluoro-3-trifluoromethyl-phenyl)-1-[2-(isopropyl-methyl-amino)-ethyl]-1H-imidazol-2-yl}-piperidin-1-yl)-pyrimidine-5-carboxylic acid amide ("361")

4-Amino-6-{4-[1-{2-[(2-dimethylamino-ethyl)-methyl-amino]-ethyl}-4-(4-fluoro-3-trifluoromethyl-phenyl)-1H-imidazol-2-yl]-piperidin-1-yl}-pyrimidine-5-carbonitrile ("362")

4-Amino-6-[4-(4-(4-fluoro-3-trifluoromethyl-phenyl)-1-{2-[(2-methoxy-ethyl)-1-methyl-amino]-ethyl}-1H-imidazol-2-yl)-piperidin-1-yl]-pyrimidine-5-carbonitrile ("363")

4-Amino-6-(4-{4-(4-fluoro-3-trifluoromethyl-phenyl)-1-[2-(2-methoxy-ethylamino)-ethyl]-1H-imidazol-2-yl}-pyrimidin-1-yl)-pyrimidine-5-carbonitrile ("364")

4-Amino-6-{4-[1-{2-[(2-dimethylamino-ethyl)-methyl-amino]-ethyl}-4-4(4-fluoro-3-trifluoromethyl-phenyl)-1H-imidazol-2-yl]-piperidin-1-yl}-pyrimidine-5-carboxylic acid amide ("365")

4-Amino-6-[4-(4-(4-fluoro-3-trifluoromethyl-phenyl)-1-{2-[(2-methoxy-ethyl)-methyl-amino]-ethyl}-1H-imidazol-2-yl)-piperidin-1-yl]-pyrimidine-5-carboxylic acid amide ("366")

4-Amino-6-(4-{4-(4-fluoro-3-trifluoromethyl-phenyl)-1-[2-(2-methoxy-ethylamino)-ethyl]-1H-imidazol-2-yl}-piperidin-1-yl)-pyrimidine-5-carboxylic acid amide ("367")

4-Amino-6-{4-[1-[2-(benzyl-methyl-amino)-ethyl]-4-(4-fluoro-3-trifluoromethyl-phenyl)-1H-imidazol-2-yl]-piperidin-1-yl}-pyrimidine-5-carboxylic acid amide ("368")

4-Amino-6-{4-[4-(4-fluoro-3-trifluoromethyl-phenyl)-1-(2-isopropylamino-ethyl)-1H-imidazol-2-yl]-piperidin-1-yl}-pyrimidine-5- carbonitrile ("369")

4-Amino-6-{4-[4-(4-fluoro-3-trifluoromethyl-phenyl)-1-(2-isopropylamino-ethyl)-1H-imidazol-2-yl]-piperidin-1-yl}-pyrimidine-5- carboxylic acid amide ("370")

4-Amino-6-(4-{4-(4-fluoro-4-trifluoromethyl-phenyl)-1-[2-(2-methoxy-1-methyl-ethylamino)-ethyl]-1H-imidazol-2-yl}-piperidin-1-yl)-pyrimidine-5-carboxylic acid amide ("371")

4-Amino-6-{4-[4-(4-fluoro-3-trifluoromethyl-phenyl)-1-(2-isobutylamino-ethyl)-1H-imidazol-2-yl]-piperidin-1-yl}-pyrimidine-5- carbonitrile ("372")

4-Amino-6-{4-[4-(4-fluoro-3-trifluoromethyl-phenyl)-1-(2-isobutylamino-ethyl)-1H-imidazol-2-yl]-piperidin-1-yl}-pyrimidine-5-carboxylic acid amide ("373")

4-Amino-6-{4-[4-(4-fluoro-3-trifluoromethyl-phenyl)-1-(2-methylamino-ethyl)-1H-imidazol-2-yl]-piperidin-1-yl}-pyrimidine-5-carbonitrile ("374")

4-Amino-6-{4-[1-(2-tert-butylamino-ethyl)-4-(4-fluoro-3-trifluoromethyl-phenyl)-1H-imidazol-2-yl]-piperidin-1-yl}-pyrimidine-5- carbonitrile ("375")

4-Amino-6-{4-[4-(4-fluoro-3-trifluoromethyl-phenyl)-1-(2-methylamino-ethyl)-1H-imidazol-2-yl]-piperidin-1-yl}-pyrimidine-5-carboxylic acid amide ("376")

4-Amino-6-{4-[1-(2-tert-butylamino-ethyl)-4-(4-fluoro-3-trifluoromethyl-phenyl)-1H-imidazol-2-yl]-piperidin-1-yl}-pyrimidine-5- carboxylic acid amide ("377")

4-Amino-6-{4-[1-[2-(cyclopropylmethyl-amino)-ethyl]-4-(4-fluoro-3-methyl-phenyl)-1H-imidazol-2-yl]-piperidin-1-yl}-pyrimidine-5-carbonitrile ("378")

4-Amino-6-(4-{4-(4-fluoro-3-methyl-phenyl)-1-[2-(isopropyl-methyl-amino)-ethyl]-1H-imidazol-2-yl}-piperidin-1-yl)-pyrimidine-5- carbonitrile ("379")

4-Amino-6-{4-[4-(4-fluoro-3-methyl-phenyl)-1-(2-isopropylamino-ethyl)-1H-imidazol-2-yl]-piperidin-1-yl}-pyrimidine-5-carbonitrile ("380")

4-Amino-6-{4-[1-(2-cyclopentylamino-ethyl)-4-(4-fluoro-3-trifluoromethyl-phenyl)-1H-imidazol-2-yl]-piperidin-1-yl}-pyrimidine-5- carbonitrile ("381")

4-Amino-6-{4-[1-[2-(1,1-dimethyl-propylamino)-ethyl]-4-(4-fluoro-3-trifluoromethyl-phenyl)-1H-imidazol-2-yl]-piperidin-1-yl}-pyrimidine-5-carbonitrile ("382")

4-Amino-6-{4-[1-[2-(cyclopropylmethyl-amino)-ethyl]-4-(4-fluoro-3-methyl-phenyl)-1H-imidazol-2-yl]-piperidin-1-yl}-pyrimine-5- carboxylic acid amide ("383")

4-Amino-6-{4-[4-(4-fluoro-3-methyl-phenyl)-1-(2-hydroxy-ethyl)-1H-imidazol-2-yl]-piperidin-1-yl}-pyrimidine-5-carbonitrile ("384")

4-Amino-6-(4-{4-(4-fluoro-3-methyl-phenyl)-1-[2-(isopropyl-methyl-amino)-ethyl]-1H-imidazol-2-yl}-piperidin-1-yl)-pyrimidine-5- carboxylic acide amide ("385")

4-Amino-6-{4-[4-(4-fluoro-3-methyl-phenyl)-1-(2-isopropylamino-ethyl)-1H-imidazol-2-yl]-piperidin-1-yl}-pyrimidine-5-carboxylic acid amide ("386")

4-Amino-6-{4-[1-(2-cyclopentylamino-ethyl)-4-(4-fluoro-3-trifluoromethyl-phenyl)-1H-imidazol-2-yl]-piperidin-1-yl}-pyrimidine-5- carboxylic acid amide ("387")

4-Amino-6-{4-[1-[2-(1,1-dimethyl-propylamino)-ethyl]-4-(4-fluoro-3-trifluoromethyl-phenyl)-1H-imidazol-2-yl]-piperidin-1-yl}-pyrimidine-5-carboxylic acid amide ("388")

4-Amino-6-{4-[1-(2-cyclopentylamino-ethyl)-4-(4-fluoro-3-methyl-phenyl)-1H-imidazol-2-yl]-piperidin-1-yl}-pyrimidine-5-carbonitrile ("389")

4-Amino-6-{4-[4-(4-fluoro-3-methyl-phenyl)-1-(2-isobutylamino-ethyl)-1H-imidazol-2-yl]-piperidin-1-yl}-pyrimidine-5-carbonitrile ("390")

4-Amino-6-{4-[1-(2-cyclopentylamino-ethyl)-4-(4-fluoro-3-methyl-phenyl)-1H-imidazol-2-yl]-piperidin-1-yl}-pyrimidine-5-carboxylic acid amide ("391")

4-Amino-6-{4-[4-(4-fluoro-3-methyl-phenyl)-1-(2-isobutylamino-ethyl)-1H-imidazol-2-yl]-piperidin-1-yl}-pyrimidine-5-carboxylic acid amide ("392")

4-Amino-6-{4-[4-(4-fluoro-3-methyl-phenyl)-1-(2-hydroxy-ethyl)-1H-imidazol-2-yl]-piperidin-1-yl}-pyrimidine-5-carboxylic acid amide ("393")

4-Amino-6-{4-[4-(4-fluoro-3-methyl-phenyl)-1-(2-methylamino-ethyl)-1H-imidazol-2-yl]-piperidin-1-yl}-pyrimidine-5-carbonitrile ("394")

4-Amino-6-{4-[4-(4-fluoro-3-trifluoromethyl-phenyl)-1-(2-hydroxy-ethyl)-1H-imidazol-2-yl]-piperidin-1-yl}-pyrimidine-5-carboxylic acid amide ("395")

2-[2-[1-(6-Amino-5-ethoxy-pyrimidin-4-yl)-piperidin-4-yl]-4-(4-fluoro-3-methyl-phenyl)-imidazol-1-yl]-ethanol ("396")

4-Amino-6-{4-[4-(4-fluoro-3-methyl-phenyl)-1-(2-methylamino-ethyl)-1H-imidazol-2-yl]-piperidin-1-yl}-pyrimidine-5-carboxylic acid amide ("397")

5-Ethoxy-6-{4-[4-(4-fluoro-3-trifluoromethyl-phenyl)-1-(2-isopropylamino-ethyl)-1H-imidazol-2-yl]-piperidin-1-yl}-pyrimidin-4-ylamine ("398")

{3-[2-[1-(6-Amino-5-isopropyl-pyrimidin-4-yl)-piperidin-4-yl]-4-(4-fluoro-3-methyl-phenyl)-imidazol-1-ylmethyl]-azetidin-1-yl}- methanol ("399")

5-Ethyl-6-{4-[4-(4-fluoro-3-methyl-phenyl)-1-(1-methyl-azetidin-3-ylmethyl)-1H-imidazol-2-yl]-piperidin-1-yl}-pyrimidin-4-ylamine ("400")

and pharmaceutically acceptable salts, or solvates thereof.

5. A pharmaceutical composition comprising a compound according to claim 1, or a pharmaceutically acceptable salt, or solvate thereof, together with a pharmaceutically acceptable carrier.

6. A kit consisting of separate packs of
   a) an effective amount of a compound according to claim 1 or a pharmaceutically acceptable salt, or solvate thereof, and
   b) an effective amount of a further medicament active ingredient.

7. The compound according to claim 1, wherein
   $R^1$ is Hal, LA, O(LA), CN, $CONH_2$, or a monocyclic aliphatic or aromatic homo- or heterocycle having 0, 1 or 2 N or 0 atoms and 5 or 6 skeleton atoms,
   $R^2$ is $NH_2$, and
   $R^3$ is N,
   and pharmaceutically acceptable salts, solvates, or solvates of salts, thereof.

8. The compound according to claim 1, wherein
   $R^2$ is $NH_2$,
   $R^3$ is N, and
   $R^4$ is unbranched or branched, linear or monocyclic alkyl having 1, 2, 3, 4, 5, 6, 7, 8 or 9 C atoms, in which one or two $CH_2$ groups may be replaced by an —O—, —NH—, group, and/or in which one or two CH groups may be replaced by —N—,
   and pharmaceutically acceptable salts, solvates, or solvates of salts, thereof.

9. The compound according to claim 1, wherein
   $R^2$ is $NH_2$,
   $R^3$ is N, and
   $R^5$ is cyclohexyl, phenyl or pyridyl, which is unsubstituted or mono- or disubstituted by Hal or LA,
   and pharmaceutically acceptable salts, solvates, or solvates of salts, thereof.

10. The compound according to claim 1, wherein
    $R^1$ is Hal, LA, O(LA), CN, $CONH_2$, or a monocyclic aliphatic or aromatic homo- or heterocycle having 0, 1 or 2 N or 0 atoms and 5 or 6 skeleton atoms,
    $R^2$ is $NH_2$,
    $R^3$ is N, and
    $R^5$ is cyclohexyl, phenyl or pyridyl, which is unsubstituted or mono- or disubstituted by Hal or LA,
    and pharmaceutically acceptable salts, solvates, or solvates of salts, thereof.

11. The compound according to claim 1, wherein
    $R^1$ is Hal, LA, O(LA), CN, $CONH_2$, or a monocyclic aliphatic or aromatic homo- or heterocycle having 0, 1 or 2 N or 0 atoms and 5 or 6 skeleton atoms,
    $R^2$ is $NH_2$,
    $R^3$ is N, and
    $R^4$ is unbranched or branched, linear or monocyclic alkyl having 1, 2, 3, 4, 5, 6, 7, 8 or 9 C atoms, in which one or two CH$_2$ groups may be replaced by an by —O— or —NH—, and/or in which one or two CH groups may be replaced by —N—,
and pharmaceutically acceptable salts, solvates, or solvates of salts, thereof.

12. The compound according to claim 1, wherein
R$^2$ is NH$_2$,
R$^3$ is N,
R$^4$ is unbranched or branched, linear or monocyclic alkyl having 1, 2, 3, 4, 5, 6, 7, 8 or 9 C atoms, in which one or two CH$_2$ groups may be replaced by —O— or —NH—, and/or in which one or two CH groups may be replaced by —N—, and
R$^5$ is cyclohexyl, phenyl or pyridyl, which is unsubstituted or mono- or disubstituted by Hal or LA,
and pharmaceutically acceptable salts, solvates, or solvates of salts, thereof.

13. The compound according to claim 1, wherein
R$^1$ is Hal, LA, O(LA), CN, CONH$_2$, or a monocyclic aliphatic or aromatic homo- or heterocycle having 0, 1 or 2 N or 0 atoms and 5 or 6 skeleton atoms,
R$^2$ is NH$_2$,
R$^3$ is N,
R$^4$ is unbranched or branched, linear or monocyclic alkyl having 1, 2, 3, 4, 5, 6, 7, 8 or 9 C atoms, in which one or two CH$_2$ groups may be replaced by —O— or —NH—, and/or in which one or two CH groups may be replaced by —N—, and
R$^5$ is cyclohexyl, phenyl or pyridyl, which is unsubstituted or mono- or disubstituted by Hal or LA.
and pharmaceutically acceptable salts, solvates, or solvates of salts, thereof.

14. The compound according to claim 1, wherein
R$^1$ is Cl, CN, CONH$_2$, isopropyl, isopropyloxy, ethyl, ethenyl, ethyloxy,
R$^2$ is NH$_2$, and
R$^3$ is N,
and pharmaceutically acceptable salts, solvates, or solvates of salts, thereof.

15. The compound according to claim 1, wherein
R$^2$ is NH$_2$,
R$^3$ is N, and
R$^4$ is branched monocyclic alkyl having 5, 6 or 7 C atoms, of which 3 or 4 C atoms are ring atoms, and in which one CH$_2$ group may be replaced by —O— or —NH—, and/or in which one CH group may be replaced by —N—, or unbranched or branched linear alkyl having 5, 6 or 7 C atoms, in which one CH$_2$ group may be replaced by —O— or —NH—, and/or in which one CH group may be replaced by —N—,
and pharmaceutically acceptable salts, solvates, or solvates of salts, thereof.

16. The compound according to claim 1, wherein
R$^2$ is NH$_2$,
R$^3$ is N, and
R$^5$ is phenyl or pyridyl, which is para-substituted by Hal and/or meta-substituted by Hal or LA,
and pharmaceutically acceptable salts, solvates, or solvates of salts, thereof.

17. The compound according to claim 1, wherein
R$^2$ is NH$_2$,
and pharmaceutically acceptable salts, solvates, or solvates of salts, thereof.

18. The compound according to claim 1, wherein
R$^3$ is N,
and pharmaceutically acceptable salts, solvates, or solvates of salts, thereof.

19. The compound according to claim 1, wherein
R$^4$ is unbranched or branched, linear or monocyclic alkyl having 1, 2, 3, 4, 5, 6, 7, 8 or 9 C atoms, in which one or two CH$_2$ groups may be replaced by —O— or —NH—, and/or in which one or two CH groups may be replaced by —N—,
and pharmaceutically acceptable salts, solvates, or solvates of salts, thereof.

20. The compound according to claim 1, wherein
R$^5$ is cyclohexyl, phenyl or pyridyl, which is unsubstituted or mono- or disubstituted by Hal or LA,
and pharmaceutically acceptable salts, solvates, or solvates of salts, thereof.

21. The compound according to claim 1, wherein
R$^1$ is Cl, CN, CONH$_2$, isopropyl, isopropyloxy, ethyl, ethenyl, ethyloxy,
R$^2$ is NH$_2$,
R$^3$ is N,
R$^4$ is branched monocyclic alkyl having 5, 6 or 7 C atoms, of which 3 or 4 C atoms are ring atoms, and in which one CH$_2$ group may be replaced by —O— or —NH—, and/or in which one CH group may be replaced by —N—,
or unbranched or branched linear alkyl having 5, 6 or 7 C atoms, in which one CH$_2$ group may be replaced by —O— or —NH—, and/or in which one CH group may be replaced by —N—,
and pharmaceutically acceptable salts, solvates, or solvates of salts, thereof.

22. The compound according to claim 1, wherein
R$^1$ is Cl, CN, CONH$_2$, isopropyl, isopropyloxy, ethyl, ethenyl, ethyloxy,
R$^2$ is NH$_2$,
R$^3$ is N,
R$^5$ is phenyl or pyridyl, which is para-substituted by Hal and/or meta-substituted by Hal or LA,
and pharmaceutically acceptable salts, solvates, or solvates of salts, thereof.

23. The compound according to claim 1, wherein
R$^2$ is NH$_2$,
R$^3$ is N,
R$^4$ is branched monocyclic alkyl having 5, 6 or 7 C atoms, of which 3 or 4 C atoms are ring atoms, and in which one CH$_2$ group may be replaced by —O— or —NH—, and/or in which one CH group may be replaced by —N—,
or unbranched or branched linear alkyl having 5, 6 or 7 C atoms, in which one CH$_2$ group may be replaced by —O— or —NH—, and/or in which one CH group may be replaced by —N—,
R$^5$ is phenyl or pyridyl, which is para-substituted by Hal and/or meta-substituted by Hal or LA,
and pharmaceutically acceptable salts, solvates, or solvates of salts, thereof.

24. The compound according to claim 1, wherein
R$^1$ is Cl, CN, CONH$_2$, isopropyl, isopropyloxy, ethyl, ethenyl, ethyloxy,
R$^2$ is NH$_2$,
R$^3$ is N,
R$^4$ is branched monocyclic alkyl having 5, 6 or 7 C atoms, of which 3 or 4 C atoms are ring atoms, and in which one CH$_2$ group may be replaced by —O— or —NH—, and/or in which one CH group may be replaced by —N—,
or unbranched or branched linear alkyl having 5, 6 or 7 C atoms, in which one CH$_2$ group may be replaced by —O— or —NH—, and/or in which one CH group may be replaced by —N—,
R$^5$ is phenyl or pyridyl, which is para-substituted by Hal and/or meta-substituted by Hal or LA, and pharmaceutically acceptable salts, solvates, or solvates of salts, thereof.

25. The compound according to claim 1, selected from:

4-Amino-6-{4-[1-(2-azetidin-1-yl-ethyl)-4-(4-fluoro-3-trifluoromethyl-phenyl)-1H-imidazol-2-yl]-piperidin-1-yl}-pyrimidine-5-carboxylic acide amide;

6-(4-(1-(2-(azetidin-1-yl)ethyl)-4-(2-(trifluoromethyl)pyridin-4-yl)-1H-imidazol-2-yl)piperidin-1-yl)-5-chloropyrimidin-4-amine;

6-(4-(1-(2-(azetidin-1-yl)ethyl)-4-(4-fluoro-3-(trifluoromethyl)phenyl)-1H-imidazol-2-yl)piperidin-1-yl)-5-isopropoxypyrimidin-4-amine;

4-Amino-6-{4-[1-(2-azetidin-1-yl-ethyl)-4-(3-chloro-4-fluoro-phenyl)-1H-imidazol-2-yl]-piperidin-1-yl}-pyrimidine-5-carboxylic acid amide;

6-(4-(1-(2-aminoethyl)-4-(4-fluoro-3-(trifluoromethyl)phenyl)-1H-imidazol-2-yl)piperidin-1-yl)-5-ethylpyrimidin-4-amine;

4-Amino-6-(4-{4-(4-fluoro-3-trifluoromethyl-phenyl)-1-[2-(2-methoxy-ethylamino)-ethyl]-1H-imidazol-2-yl}-piperidin-1-yl)-pyrimidine-5-carbonitrile;

4-amino-6-(4-(1-(2-(azetidin-1-yl)ethyl)-4-(4-fluoro-3-methylphenyl)-1H-imidazol-2-yl)piperidin-1-yl)-pyrimidine-5-carboxamide;

4-Amino-6-{4-[1-(2-azetidin-1-yl-ethyl)-4-cyclohexyl-1H-imidazol-2-yl]-piperidin-1-yl}-pyrimidine-5-carbonitrile;

4-Amino-6-{4-[4-(4-fluoro-3-trifluoromethyl-phenyl)-1-(2-isopropylamino-ethyl)-1H-imidazol-2-yl]-piperidin-1-yl}-pyrimidine-5- carboxylic acid amide;

4-Amino-6-{4-[1-[2-(cyclopropylmethyl-amino)-ethyl]-4-(4-fluoro-3-methyl-phenyl)-1H-imidazol-2-yl]-piperidin-1-yl}-pyrimidine-5-carboxylic acid amide;

4-amino-6-(4-(4-(4-fluoro-3-(trifluoromethyl)phenyl)-1-(pyrrolidin-3-yl)-1H-imidazol-2-yl)piperidin-1-yl)pyrimidine-5-carboxyamide;

5-ethyl-6-(4-(4-(4-fluoro-3-(trifluoromethyl)phenyl)-1-(piperidin-4-yl)-1H-imidazol-2-yl)piperidin-1-yl)pyrimidin-4-amine;

4-Amino-6-{4-[1-(2-cyclopentylamino-ethyl)-4-(4-fluoro-3-methyl-phenyl)-1H-imidazol-2-yl]-piperidin-1-yl}-pyrimidine-5-carboxylic acid amide;

4-Amino-6-{4-[4-(4-fluoro-3-methyl-phenyl)-1-(2-methylamino-ethyl)-1H-imidazol-2-yl]-piperidin-1-yl}-pyrimidine-5-carboxylic acid amide;

5-Ethoxy-6-{4-[4-(4-fluoro-3-trifluoromethyl-phenyl)-1-(2-isopropylamino-ethyl)-1H-imidazol-2-yl]-piperidin-1-yl}-pyrimidin-4-ylamine;

5-chloro-6-(4-(1-(2-(cyclopropylamino)ethyl)-4-(2-(trifluoromethyl)pyridin-4-yl)-1H-imidazol-2-yl)piperidin-1-yl)pyrimidin-4-amine;

6-(4-(1-(2-ethylamino)ethyl)-4-(4-fluoro-3-(trifluoromethyl)phenyl)-1H-imidazol-2-yl)piperidin-1-yl)-5-isopropoxypyrimidin-4-amine;

6-(4-(1-(2-(dimethylamino)ethyl)-4-(4-fluoro-3-methylphenyl)-1H-imidazol-2-yl)piperidin-1-yl)-5-(1H-pyrazol-4-yl)pyrimidin-4-amine;

6-(4-(1-(2-(azetidin-1-yl)ethyl)-4-(2-isopropylpyridin-4-yl)-1H-imidazol-2-yl)piperidin-1-yl)-5-vinylpyrimidin-4-amine; and 6-(4-(1-(azetidin-3-ylmethyl)-4-(4-fluoro-3-methylphenyl)-1H-imidazol-2-yl)cyclohexyl)-5-isopropylpyrimidin-4-amine;

and pharmaceutically acceptable salts, or solvates thereof.

26. The compound of according to claim 1, selected from

4-Amino-6-{4-[1-(2-azetidin-1-yl-ethyl)-4-(4-fluoro-3-trifluoromethyl-phenyl)-1H-imidazol-2-yl]-piperidin-1-yl}-pyrimidine-5-carboxylic acid amide ("78");

4-amino-6-(4-(1-(2-(azetidin-1-yl)ethyl)-4-(4-fluoro-3-methylphenyl)-1H-imidazol-2-yl)piperidin-1-yl)pyrimidine-5-carboxamide ("124");

6-(4-(1-(2-(dimethylamino)ethyl)-4-(4-fluoro-3-methylphenyl)-1H-imidazol-2-yl)piperidin-1-yl)-5-(1H-pyrazol-4-yl)pyrimidin-4-amine ("163"); and 6-(4-(1-(2-(azetidin-1-yl)ethyl)-4-(2-isopropylpyridin-4-yl)-1H-imidazol-2-yl)piperidin-1-yl)-5-ethylpyrimidin-4-amine ("179");

and pharmaceutically acceptable salts, or solvates thereof.

* * * * *